United States Patent
LeClere

(10) Patent No.: US 11,352,637 B2
(45) Date of Patent: Jun. 7, 2022

(54) METHODS AND COMPOSITIONS FOR HERBICIDE TOLERANCE IN PLANTS

(71) Applicant: MONSANTO TECHNOLOGY LLC, St. Louis, MO (US)

(72) Inventor: Sherry L. LeClere, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/604,027

(22) PCT Filed: Apr. 13, 2018

(86) PCT No.: PCT/US2018/027565
§ 371 (c)(1),
(2) Date: Oct. 9, 2019

(87) PCT Pub. No.: WO2018/191663
PCT Pub. Date: Oct. 18, 2018

(65) Prior Publication Data
US 2020/0208169 A1 Jul. 2, 2020

Related U.S. Application Data

(60) Provisional application No. 62/485,751, filed on Apr. 14, 2017.

(51) Int. Cl.
*C12N 15/82* (2006.01)
*C12Q 1/6895* (2018.01)

(52) U.S. Cl.
CPC ..... *C12N 15/8274* (2013.01); *C12N 15/8294* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS 8,404,933 B2    3/2013  Chen et al.
8,535,893 B2    9/2013  Walsh et al.

FOREIGN PATENT DOCUMENTS

WO  WO 2007/053482   10/2007
WO     2010020654    2/2010
WO  WO 2014/132141   9/2014
WO  WO 2016/205711   12/2016

OTHER PUBLICATIONS

Song and Xu. "Ectopic Overexpression of an Auxin/Indole-3-Acetic Acid (Aux/IAA) Gene OsIAA4 in Rice Induces Morphological Changes and Reduces Responsiveness to Auxin". Int. J. Mol. Sci. 2013, 14(7), 13645-13656. (Year: 2013).*

(Continued)

*Primary Examiner* — Matthew R Keogh
*Assistant Examiner* — David R Byrnes
(74) *Attorney, Agent, or Firm* — Dentons US LLP; Amanda Carmany-Rampey

(57) ABSTRACT

Provided herein are novel methods and compositions for conferring tolerance to auxin herbicides to plants. Also provided are herbicide tolerant plants, seeds, cells, and plant parts containing modified AUX/IAA proteins, as well as methods of producing the same.

29 Claims, 13 Drawing Sheets

Specification includes a Sequence Listing.

(56) References Cited

OTHER PUBLICATIONS

Joseph, Dwayne. "Evaluation of 2,4-D and Dicamba Based Herbicide Programs for Weed Control in Tolerant Soybean". Thesis. Clemson University. (Year: 2014).*
Yang et al. "The IAA1 protein is encoded by AXR5 and is a substrate of SCFTIR1" The Plant Journal. 40: 772-782. (Year: 2004).*
Grossman. "Auxin Herbicide Action Lifting the Veil Step by Step". Plant Signaling and Behavior. (2)5: 421-423. (Year: 2007).*
Tatematsue et al. "MASSUGU2 Encodes Aux/IAA19, an Auxin-Regulated Protein That Functions Together with the Transcriptional Activator NPH4/ARF7 to Regulate Differential Growth Responses of Hypocotyl and Formation of Lateral Roots in *Arabidopsis thaliana*". The Plant Cell. 16: 379-393. (Year: 2004).*
Han et al. "The Effects of Amino Acid Replacements of Glycine 121 on Transmembrane Helix 3 of Rhodopsin". The Journal of Biological Chemistry. 271(50):32330-32336. (Year: 1996).*
Hong Yu, et al., "Mutations in the TIR1 Auxin Receptor That Increase Affinity for Auxin/Indole-3-Acetic Acid Proteins Result in Auxin Hypersensitivity", Plant Physiology, vol. 162, No. 1, Mar. 28, 2013 (Mar. 28, 2013), pp. 295-303.
Sarah Lee et al: "Defining Binding Efficiency and Specificity of Auxins for SCF TIR1/AFB-Aux/IAA Co-receptor Complex Formation", ACS Chemical Biology, vol. 9, No. 3, Dec. 23, 2013 (Dec. 23, 2013), pp. 673-682.
International Search Report for PCT/US18/027565, dated Aug. 7, 2018.
International Written Opinion for PCT/US18/027565, dated Aug. 29, 2018.
Kato et al., "Auxin-Mediated Transcriptional System with a Minimal Set of Components is critical for Morphogenesis through the Life Cycle in Marchantia polymorpha," *PLoS Genetics*, vol. 11, No. 6, e100535 pp. 1-26; 2015.
Kepinski et al. "Auxin-induced SCF$^{TIR1}$-Aux/IAA interaction involves stable modification of the SCF$^{TIR1}$ complex," *Proc. Natl. Acad. Sci. USA,* vol. 101, No. 33; pp. 12381-12386; 2004.
LeClere et al.,"Cross-resistance to dicamba, 2, 4-D, and fluroxypyr in *Kochia scoparia* is endowed by a mutation in an AUX/IAA gene," *Proc. Natl. Acad. Sci. USA;* vol. 115, No. 13., pp. 2911-2920; 2018.
Genbank "MF376150: Bassia scoparia AUX/IAA protein mutant form (IAA16) mRNA, IAA16R, allele, complete cds," NCBI GenBank, pp. 1-2; 2018. Retrieved from the internet: https://www.ncbi.nln.nih.gov/nuccora/MF376150; 2018.
Tan, et al., "Mechanism of auxin perception by the TIR1 ubiquitin ligase," Nature, 2007, 640-645, 446(7136).
Hamann, et al., "The *Arabidopsis* Bodenlos Gene Encodes an Auxin Response Protein Inhibiting Monopteros-Mediated Embryo Patterning," Genes Dev., 2002, 1610-1615, 16(13).
Howatt, et al., "Ethylene Effect on Kochia (*Kochia scoparia*) and Emission Following Dicamba Application," Weed Science, 2006, 31-37, 54(1).
Parry, et al., "Complex Regulation of the TIR1/AFB Family of Auxin Receptors," PNAS, 2009, 22540-22545, 106(52).
Preston, et al., "Inheritance of Resistance to the Auxinic Herbicide Dicamba in Kochia (*Kochia scoparia*)," Weed Science, 2009, 43-47, 57(1).
Rinaldi, et al., "A Gain-of-Function Mutation in IAA16 Confers Reduced Responses to Auxin and Abscisic Acid and Impedes Plant Growth and Fertility," Plant Mol Biol. 2012, 359-373, 79(4-5).
Rogg, et al., "A Gain-of-Function Mutation in IAA28 Suppresses Lateral Root Development," Plant Cell. 2001, 465-80, 13(3).
Rouse, et al., "Changes in Auxin Response From Mutations in an AUX/IAA Gene," Science, 1998, 1371-3, 279 (5355).
Sauer, et al., "Oligonucleotide-Mediated Genome Editing Provides Precision and Function to Engineered Nucleases and Antibiotics in Plants," Plant Physiol, 2016, 1917-1928, 170(4).
Uehara, et al., "Domain II Mutations in CRANE/IAA18 Suppress Lateral Root Formation and Affect Shoot Development in *Arabidopsis thaliana*," Plant Cell Physiol., 2008, 1025-38, 49(7).
Yang, et al., "The IAA1 Protein is Encoded by AXR5 and is a Substrate of SCF(TIR1)," Plant J., 2004, 772-82, 40(5).
Kepinski, et al., "The *Arabidopsis* F-box protein TIR1 is an auxin receptor," Nature, 2005, 446-451, 435(7041).
Dharmasiri et al., "The F-box protein TIR1 is an auxin receptor," Nature, 2005, 441-445, 435(7041).
Gleason, et al., "Mutant Analysis in *Arabidopsis* Provides Insight into the Molecular Mode of Action of the Auxinic Herbicide Dicamba," PLoS One, 2011, e17245, 6(3).
Villalobos et al., "A combinatorial TIR1/AFB-Aux/IAA co-receptor system for differential sensing of auxin," Nat Chem Biol., 2012, 477-85, 8(5).
Extended European Search Report for European Application No. 18784200.0, dated Mar. 15, 2021.

* cited by examiner

FIG. 4

```
SEQ_ID_1     ------------------------------M------------INF    4
SEQ_ID_11    ---------MTYQLQSVDK---EGLG--------TATC--         18
SEQ_ID_19    ----------MATMLTKEH---G--------------LNL         13
SEQ_ID_31    ----------MAG------------------------LGF          6
SEQ_ID_41    ----------MTSIMGTEDD---KYST----------INF         17
SEQ_ID_57    ---MILHNPINILRLPLLH---HHLQHQLLHNPSSLIHA          33
SEQ_ID_59    ----------MATT--------D--------------LGF          8
SEQ_ID_79    ----------MATT----T------D-----------LGF          9
SEQ_ID_97    ----------MHGE---ERE---KPD-----------LNL         13
SEQ_ID_103   MSKQLEHDYIGLSEVSSME---SSEKLTTDSEGSNGLNL          36
SEQ_ID_117   ----------MEAVGLNMPN---NQF-----------VSL         16
SEQ_ID_137   ----------MTSVLGAECD---KIR-----------LDY         16
SEQ_ID_139   ----------MTSVLGAECD---KIR-----------LDY         16
SEQ_ID_159   ----------MSPQLLGVQE---HIQGNT--SFPTSTCSM         25
SEQ_ID_165   MSVPLEHDYIGLSDASSLERSSESSNISSDSETNNVLNL          39
SEQ_ID_167   MSVPLEHDYIGLSEPSSMEKASESSNHSSESDKNNALNL          39
SEQ_ID_169   -------MSMSLKELDYIS---SSEAEMEKITHKQDLNL          29
SEQ_ID_179   ----------MSPPLLDVGE---VEESRSNVTLLASSNSM         27
SEQ_ID_197   ----------MTNVGDAERD---KYSL----------INF         17
SEQ_ID_217   ----------MLSN---ERD---KYT-----------IDF         13
SEQ_ID_262   ------------------------------M------------INF    4

SEQ_ID_1     EA----------TELRLGL------PGE-N----------H        18
SEQ_ID_11    ----------LKERNYLGL------SDCSSS---------V        34
SEQ_ID_19    KE----------TELCLGL------PGGGG----------G        28
SEQ_ID_31    EE----------TELRLGL------PGGSN---E------A        22
SEQ_ID_41    EE----------TELRLGL------PGANG----------         31
SEQ_ID_57    R------------------GL------PGSESPERED----H        47
SEQ_ID_59    EE----------TELRLGL------PGGGG----EV---V        25
SEQ_ID_79    EA----------TELRLGL------PGGGGGGEPAL---G        30
SEQ_ID_97    EA----------TELRLGL------PGG-----------          25
SEQ_ID_103   KA----------TELRLGL------PGSESPERIDSVGGL         60
SEQ_ID_117   KE----------TELCLGL------PGGGG----------G        31
SEQ_ID_137   EAE---------TELRLGL------PGANG----------N        32
SEQ_ID_139   EAE---------TELRLGL------PGA-G----------N        31
SEQ_ID_159   ESNYQKIPGLTERNYLGF------SDCSS----------V         49
SEQ_ID_165   KA----------TELRLGL------PGFAKNSEES----A         59
SEQ_ID_167   KA----------TELRLGL------PGLGQDLEEN----A         59
SEQ_ID_169   KA----------TELRLGL------PGSESPERNT----I         49
SEQ_ID_179   ESVSPNNLEFEERNYMGL------SDSSS----------E         51
SEQ_ID_197   EE----------TELRLGL------PGAGD----------H        32
SEQ_ID_217   EE----------TELRLGLGLGIGLAGAAD----------         33
SEQ_ID_262   EA----------TELRLGL------PGG-N----------H        18
```

FIG. 4
(CONTINUED)

```
SEQ_ID_1      GG-------GMAAKNNGKRGFSET-----VDLKLNLS--   43
SEQ_ID_11     DSST-VPNLVLDTDKKSSLNFKAT------ELRLGLPES   66
SEQ_ID_19     GGGG-GE--VETPRATGKRGFSET-----VDLKLNLHSK   59
SEQ_ID_31     EE----A--AAAVRSSGKRGYAET-----IDLVLKLEPA   50
SEQ_ID_41     ND-------GETTKNNGKRGFSET-----VNLKLNLS--   56
SEQ_ID_57     DQN---VLSLKSFVSGAKRGFSDALDGG-GNWVFSGGSG   82
SEQ_ID_59     GE----G--RSSVVSSGKRGFAET-----IDLKLKLEPA   53
SEQ_ID_79     GE----G--RSSSSASGKRGFAET-----IDLKLKLEPA   58
SEQ_ID_97     ---------SEGSEVVRKRGFSET-----VDLKLNLSGK   50
SEQ_ID_103    DKNGYPLGVLKNLVSGAKRGFSDAIDGGSGKWVFSGSGG   99
SEQ_ID_117    GG----D--QTSLKSSGKRGFSET-----VDLKLNLQSK   59
SEQ_ID_137    EV-------ESTNKNNGKRVFSET-----VDLKLNLSNS   59
SEQ_ID_139    EL-------ESSNKNNGKRVFSET-----VDLKLNLSNS   58
SEQ_ID_159    DSSN-VS--TISEVNKNSLNLKAT------ELRLGLP-G   78
SEQ_ID_165    TKF----AHVKNFMSGAKRGFSDVNIEGPGKWKMNGGSE   94
SEQ_ID_167    CKN----SPVKNFVSGAKRGFSDVNFDGSCKWGFNGGYE   94
SEQ_ID_169    NGGG--TAALKILVSGAKRVFSDTIKTSSGTWFGSDNGG   89
SEQ_ID_179    DSCM-TA--TKSDGNKPSLNLKAT------ELRLGLP-G   86
SEQ_ID_197    GE-------SPVKNSCGKRGFSET---ANVDLKLNLSPI   61
SEQ_ID_217    GD-------QLAKNNGKRGFSETEGDSSVDLKLNLSSS   65
SEQ_ID_262    GG-------EMAGKNNGKRGFSET-----VDLKLNLS--   43

SEQ_ID_1      ----------STAMDSV----------SELDLVN-----   57
SEQ_ID_11     SQ--------SPQRETD------FGLLSPRTPDEKLLFP  91
SEQ_ID_19     E-----------DLNEN---------LKNVSK------  71
SEQ_ID_31     S------AAAPPSEDGE-----QVADGVAEAQPSP----  74
SEQ_ID_41     ------------SKET----------VAEDSDK-----  67
SEQ_ID_57     GGT-------EGLFSPRRGGK-NNGGKDLSGSDSGSVL- 112
SEQ_ID_59     TPAAVL-KAAEADEHQDGVAAAKEDAGCVAAAEE-----  25
SEQ_ID_79     A-------VVEAEEEEE------DHGVAVALEK-----  30
SEQ_ID_97     E----------AGVDDN---------KVKSLQK-----  25
SEQ_ID_103    SETD--LTKGGGLFSPRGG---NGGGKHLGGSESN----  60
SEQ_ID_117    DGGGGGGVGVGVDLNEN----------VKNVSTNV----  31
SEQ_ID_137    KD--------STLMD-----------NINQVDN-----  73
SEQ_ID_139    KD--------STLMDNI---------NINQVDN-----  74
SEQ_ID_159    SQ--------SPERDQE------NSLTSSEKLDEKPLFP 103
SEQ_ID_165    ADL---GKTSSVLFSPRGG---INGGLEKNQVQQS---- 123
SEQ_ID_167    GDS---VKGSCSTTSVLFG---INSGKESKQTQQ----- 122
SEQ_ID_169    SEVD--FVRNSAFFSSSSSSP-RGENKNPSSVKDA---- 118
SEQ_ID_179    SE--------SPERDPD------NCLRSSSQLDEKPLFP 105
SEQ_ID_197    ND--------SASSSST----------IASVAEN-----  77
SEQ_ID_217    TT--------TTASTTT----------TNTTATKTTAEN  86
SEQ_ID_262    ----------STAMDSV----------SKVDLEN-----  57
```

FIG. 4
(CONTINUED)

```
SEQ_ID_1     -------------------MKEK----------------  61
SEQ_ID_11    LLPCKD----H-----ASGNKRGY---------------  106
SEQ_ID_19    --------------------EKTLL--------------  76
SEQ_ID_31    -------------AAADGQLKRSPSQSSVV---T------  92
SEQ_ID_41    -------------------MKEK-----------S-----  72
SEQ_ID_57    -----K--DGAARKPSVVQEKKPQVAAT---S--------  134
SEQ_ID_59    ----------AAVGGKMRSPSQSSVV---T------  104
SEQ_ID_79    -----------EEEAGKMRSPSQSSVA---AA------  97
SEQ_ID_97    ---------------EKSKSLLP------C--------  73
SEQ_ID_103   -----N--QHSSLGTPVKNDVVPQSPKP---M--------  151
SEQ_ID_117   -----------------DGEKSLCS--------------  92
SEQ_ID_137   -------------------MKEKKNNIVVP---S-------  85
SEQ_ID_139   -------------------MKEKKNNIVVP---S-------  86
SEQ_ID_159   LLPSSS----SSQKIISSGHKRVFTDTMDSSSE------  132
SEQ_ID_165   --------ISPSNVQPIEEKKKEHVS-------------  141
SEQ_ID_167   ----------PS-PLPLEEKKKASVTTE---N-------  140
SEQ_ID_169   -------VVSSSSKNYLHDKHSQISAS---N-------  139
SEQ_ID_179   LHPSSDGLYSSPQKTVVSGNKRGFSDAMNEFSEEKYHAN  144
SEQ_ID_197   -------------------KGKDTT-------T------  84
SEQ_ID_217   VKESKLDKSVNSGVDQKLKEKVAS-------T-------  111
SEQ_ID_262   -------------------MKEK----------------  61

SEQ_ID_1     ---------------------------------------  61
SEQ_ID_11    ---------------------------------------  106
SEQ_ID_19    ---------------------------------------  76
SEQ_ID_31    ---------------------------------------  92
SEQ_ID_41    ---------------------------------------  72
SEQ_ID_57    ---------------------------------------  134
SEQ_ID_59    ---------------------------------------  104
SEQ_ID_79    ---------------------------------------  97
SEQ_ID_97    ---------------------------------------  73
SEQ_ID_103   ---------------------------------------  151
SEQ_ID_117   ---------------------------------------  92
SEQ_ID_137   ---------------------------------------  85
SEQ_ID_139   ---------------------------------------  86
SEQ_ID_159   -------------------TKGVISSNSELPSIKC  148
SEQ_ID_165   ---------------------------------------  141
SEQ_ID_167   ---------------------------------------  140
SEQ_ID_169   ---------------------------------------  139
SEQ_ID_179   IGLKAGSLLENLGSQMGKVKEPTTQKAVQERPQENSESR  183
SEQ_ID_197   ---------------------------------------  84
SEQ_ID_217   ---------------------------------------  111
SEQ_ID_262   ---------------------------------------  61
```

FIG. 4
(CONTINUED)

```
SEQ_ID_1    --------V--VKPP-AKAQVV-GWPPV RSFRKNVMSGQ  88
SEQ_ID_11   ---LAKSGSN--NAPASKAQVV-GWPPI RSYRKNTMASS  139
SEQ_ID_19   ------KDP--AKPP-AKAQVV-GWPPV RSYRKNMMAVQ  105
SEQ_ID_31   -TPQPDADP--EKPRAPKAQAVX GWPPV RSVRRTLLAAA 128
SEQ_ID_41   -----STDP--AKPP-AKAQVV-GWPPV RSFRKNIMAVQ  102
SEQ_ID_57   -----SHGNGNI-APASKAQVV-GWPPI RSFRKNTMASH  166
SEQ_ID_59   -AAAVQADPA-EKPRAPKAQVV-GWPPV RSFRKNIMSVQ  140
SEQ_ID_79   -AAAVLADPA-EKPRAAKAQVV-GWPPV RSFRKNIMSVQ  133
SEQ_ID_97   -----GNDP--ARPP-AKAQVV-GWPPV RSFRKNMLAGO  103
SEQ_ID_103  -----HEKKPQISAPAAKAQVV-GWPPI RSFRKNSMASN  184
SEQ_ID_117  ------KDP--AKPP-AKAQVV-GWPPV RSYRKNVMAQK  121
SEQ_ID_137  -----SNDP--AKSP-AKAQVV-GWPPV RSFRKNVMAIQ  115
SEQ_ID_139  -----SNDP--AKPP-AKAQVV-GWPPV RSFRKNVMAIQ  116
SEQ_ID_159  STPISKVNNN-SNPPSSKAQVV-GWPPV RSFRKN-MLAV  184
SEQ_ID_165  ------RNV---APPSAKAQVV-GWPPI RSFRKNTMVTN  170
SEQ_ID_167  -----GRSR---TPPSAKAQVV-GWPPI RSFRKNTMTAN  170
SEQ_ID_169  -----GQDS----VAASKGQVV-GWPPI RSFRKNCMVVK  168
SEQ_ID_179  PSGNETANNN-TSTPVSKAQVV-GWPPI RSFRKN-TLAT  219
SEQ_ID_197  -----SATV--SPPPRAKAQVV-GWPPV RSFRKNIVNVH  115
SEQ_ID_217  -----TADP--AKPTPAKTQVV-GWPPV RAFRKNIVAAQ  142
SEQ_ID_262  --------V--VKPP-AKAQVV-GWPPV RSFRKNVMSGQ   88

SEQ_ID_1    KPTAGDATE-GTKNTS----------SSX----------  106
SEQ_ID_11   TSKNTNEV-----GLG----------PLF----------  153
SEQ_ID_19   KVSTEDVAE-KTTSST-------ANSGAF----------  126
SEQ_ID_31   ERGGAGAX-------------------------------  136
SEQ_ID_41   KASSEEEGG-SKKAGNSAAAITTTTAAAF----------  130
SEQ_ID_57   PPKNDDGDGKAEAKLG--------SGCLY----------  187
SEQ_ID_59   SDKGAGGSK-DADKLSPAA--AAGGGAAF----------  166
SEQ_ID_79   SDKGAAAAN--GDKSSP----AAGGGAAF----------  156
SEQ_ID_97   KGGSEEGE---KVSCN-----------AAF---------  119
SEQ_ID_103  LPKNDE---DAEGKLG--------SGCLY----------  202
SEQ_ID_117  NTSGGEGAE-K--GSS-------GSSAAF----------  140
SEQ_ID_137  KNTTGAGES-SGTGTG-----------AAF---------  133
SEQ_ID_139  KNTTGAGEI-SGTGTG-----------AAF---------  134
SEQ_ID_159  NSKNNDEVD-GKPGLS-----------ALF---------  202
SEQ_ID_165  LSKNAGDVATAEGNSGG-------GGCLY----------  192
SEQ_ID_167  LSKND-DANAAEENLG----------CLY----------  188
SEQ_ID_169  NTKNEE-------DTG---------SQCVY---------  182
SEQ_ID_179  TSKNNDEVD-GKAMAG-----------ALF---------  237
SEQ_ID_197  QKSNSETEV-DKSISG------GGGNGAF----------  137
SEQ_ID_217  KKTSDDQTD-QKASSN------AITSAAF----------  164
SEQ_ID_262  KPTTGDATE-QNDKTS---------GSSGATSSASACA  116
```

FIG. 4
(CONTINUED)

```
SEQ_ID_1     ----------IPYLRKIDLKLYKTYQDLSDAL-SKMFS  133
SEQ_ID_11    ----VKVSMDGAPYLRKVDLRTYTCYQHLSSALXEKMFS  188
SEQ_ID_19    ----VKVSMDGAPYLRKVDLTMYKSYKELSDAL-AKMFS  160
SEQ_ID_31    ----VKVSMDGAPYLRRVDMGTYKSYQELSKAL-EKMFS  170
SEQ_ID_41    ----VKVSMDGAPYLRKVDLKLYKSYQQLSDAL-SKMFS  164
SEQ_ID_57    ----VKVSMDGAPYLRKVDLKIYGSYKELSSAL-EKMFS  221
SEQ_ID_59    ----VKVSLDGAPYLRKVDLKMYKSYQELSKAL-ENMFS  200
SEQ_ID_79    ----VKVSLDGAPYLRKVDLKMYRSYQQLSKAL-ENMFS  190
SEQ_ID_97    ----VKVSMDGAPYLRKVDLKMYTSYQELSNAL-GNMFS  153
SEQ_ID_103   ----VKVSMDGAPYLRKVDLKLYSTYMELSSAL-EKMFS  236
SEQ_ID_117   ----VKVCMDGAPYLRKVDLKMYQSYQELSDAL-AKMFS  174
SEQ_ID_137   ----VKVSVDGAPYLRKVDLKMYKSYQQLSDAL-GKMFS  167
SEQ_ID_139   ----VKVSVDGAPYLRKVDLKMYKSYQQLSDAL-GKMFS  168
SEQ_ID_159   ----VKVSMDGAPYLRKVDLRGYSTYQELSSAL-EKMFS  236
SEQ_ID_165   ----VKVSMDGAPYLRKIDLKIYHNYAELSQAL-EKMFS  226
SEQ_ID_167   ----VKVSMDGAPYLRKVDLKTCKNYSQLSKAL-EKMFD  222
SEQ_ID_169   ----VKVSMDGAPYLRKVDLKIYKSYLDLSSAL-EKMFC  216
SEQ_ID_179   ----IKVSMDGAPYLRKVDLRNYSAYQELSSAL-EKMFS  271
SEQ_ID_197   ----VKVSMDGAPYLRKVDLKLYKSYQELSDAL-AKMFS  171
SEQ_ID_217   ----VKVSMDGAPYLRKVDLKLYKSYQDLSDAL-GKMFS  198
SEQ_ID_262   TVAYVKVSMDGAPYLRKIDLKLYKTYQDLSNAL-SKMFS  154

SEQ_ID_1     SFTIG----NYG-PQGM---KDFMNESRLIDLLNGSDYV  164
SEQ_ID_11    CFTLG----QCG-LHGAH-GRERMSEVKLKDLLHGSEFV  221
SEQ_ID_19    SFTMG----NYGXPRNG---IDFMNESKLMDLLNSSEYV  192
SEQ_ID_31    SFTIGNDCSQAQ-AQGM---TG-MNESKLVDLLSGSDYV  204
SEQ_ID_41    SFTIG----NCG-SHGM---KDFMNESKLIDLLNGSEYV  195
SEQ_ID_57    CFTIG----QCG-SHGVXPGGDGLSESRLIDLLHGSEYV  255
SEQ_ID_59    SFTIG----SCG-SQGM---NG-MNESKLVDLLNGSEYV  230
SEQ_ID_79    SFTIG----SCG-SQGM---NG-MNESKLVDLLNGSEYV  220
SEQ_ID_97    SFTIG----NYG-SQGM---KDFMNESKLMDLLNGFDHV  184
SEQ_ID_103   CFTIG----QCG-SNGV-PIRDGLSESRLMDLLHGSEYV  269
SEQ_ID_117   SFTMG----EYG-TQGM---IDFMNERKLMDLLNSSEFV  205
SEQ_ID_137   SFTIG----NCG-TQGF---KDFMNESKLIDLLNGSDYV  198
SEQ_ID_139   SFTIG----NCG-TQGF---KDFMNESKLIDLLNGSDYV  199
SEQ_ID_159   CFTIG----QCG-SQGGP-LRGSESESKLRDLLHGSEYV  269
SEQ_ID_165   CFTLG----QCT-SSGLR-RREGLSESNLKDLLHGSECV  259
SEQ_ID_167   RFTLG----QCT-SNGLR-GQEGLCESNLKDLLHHNESV  255
SEQ_ID_169   SFTLG-----------------LRES-PMDLLNGPEYV  236
SEQ_ID_179   CFTIG----QYG-AHGAL-GMEKMSESKLKDLLHGSEYV  304
SEQ_ID_197   SFTID----NCG-SQVT---KDFMNESKLIDLLHGSDYV  202
SEQ_ID_217   SFTIG----NYG-SQGM---KDFMNESKLIDLLNGSEYV  229
SEQ_ID_262   SFTIG----NYG-PQGM---KDFMNESKLIDLLNGSDYV  185
```

FIG. 4
(CONTINUED)

```
SEQ_ID_1    PTYEDKDGDWMLVGDVPWGMFVDSCKRIRIMKGSEAIGL  203
SEQ_ID_11   LTYEDKDGDWMLVGDVPWEIFTESCRKLKIMKGSDSIGL  260
SEQ_ID_19   PTYEDKDGDWMLVGDVPWEMFVGSCKRLRIMKGSEAIGL  231
SEQ_ID_31   PTYEDKDGDWMLVGDVPWEMFVASCKRLRIMKGSEAIGL  243
SEQ_ID_41   PTYEDKDGDWMLVGDVPWEMFVDSCKRLRIMKGSEAIGL  234
SEQ_ID_57   LTYEDKDGDWMLVGDVPWEMFTDSCKRLRIMKSTEAIGL  294
SEQ_ID_59   PTYEDKDGDWMLVGDVPWEMFVESCKRLRIMKGSEAIGL  269
SEQ_ID_79   PTYEDKDGDWMLVGDVPWEMFVESCKRLRIMKGSEAIGL  259
SEQ_ID_97   PTYEDKDGDWMLVGDVPWEMFVDSCKRLRIMKGKEAIGL  223
SEQ_ID_103  LTYEDKDGDWMLVGDVPWEMFTDSCKRMRIMKSSEAIGL  308
SEQ_ID_117  PTYEDKDGDWMLVGDVPWEMFVDSCKRLRIMKGSEAIGL  244
SEQ_ID_137  PTYEDKDGDWMLVGDVPWEMFVDSCKRLRIMKGSEAIGL  237
SEQ_ID_139  PTYEDKDGDWMLVGDVPWEMFVDSCKRLRIMKGSEAIGL  238
SEQ_ID_159  VTYEDKDGDWMLVGDVPWDMFIGSCKRLKIMKGSDAIGL  308
SEQ_ID_165  LTYEDKDGDWMLVGDVPWEMFIDSCKRLRIMKGSEAIGL  298
SEQ_ID_167  LTYEDKDGDWMLVGDVPWEMFIDSCKRLRIMKGSEAIGL  294
SEQ_ID_169  LTYEDKDGDLMLVGDVPWDMFTGSCKRMRIMKSSDATGL  275
SEQ_ID_179  LTYEDKDGDWMLVGDVPWEMFIDSCKRLRIMKSSDAIGL  343
SEQ_ID_197  PTYEDKDGDWMLVGDVPWEMFVQSCKRLRIMKGSEAIGL  241
SEQ_ID_217  PTYEDKDGDWMLVGDVPWEMFVGSCKRLRIMKGSEAIGL  268
SEQ_ID_262  PTYEDKDGDWMLVGDVPWEMFVDSCKRIRIMKGSEAIGL  224

SEQ_ID_1    APRALEKCKNRS       215
SEQ_ID_11   APSAVEKSKNKD       272
SEQ_ID_19   APRAMEKCKSRS       243
SEQ_ID_31   APRAMEKCKSRS       255
SEQ_ID_41   APRAVEKCKNRS       246
SEQ_ID_57   APRAMEKCKNRT       306
SEQ_ID_59   APRAMEKCKNRS       281
SEQ_ID_79   APRAMEKCKNRS       271
SEQ_ID_97   APRAMEKCKNRS       235
SEQ_ID_103  APRAMEKCKSRN       320
SEQ_ID_117  APRAMEKCKSRS       256
SEQ_ID_137  APRAVEKCKNRS       250
SEQ_ID_139  APRAVEKCKNRS       250
SEQ_ID_159  APRASVKSNNRN       320
SEQ_ID_165  APRAMDKCKNKN       310
SEQ_ID_167  APRSMEKSKNQIRGV    309
SEQ_ID_169  APRAMEKGKVRN       287
SEQ_ID_179  APRAVEKCRNRS       355
SEQ_ID_197  APRAVEKCKNRS       253
SEQ_ID_217  APRAVEKCKNRS       280
SEQ_ID_262  APRALEKCKNRS       236
```

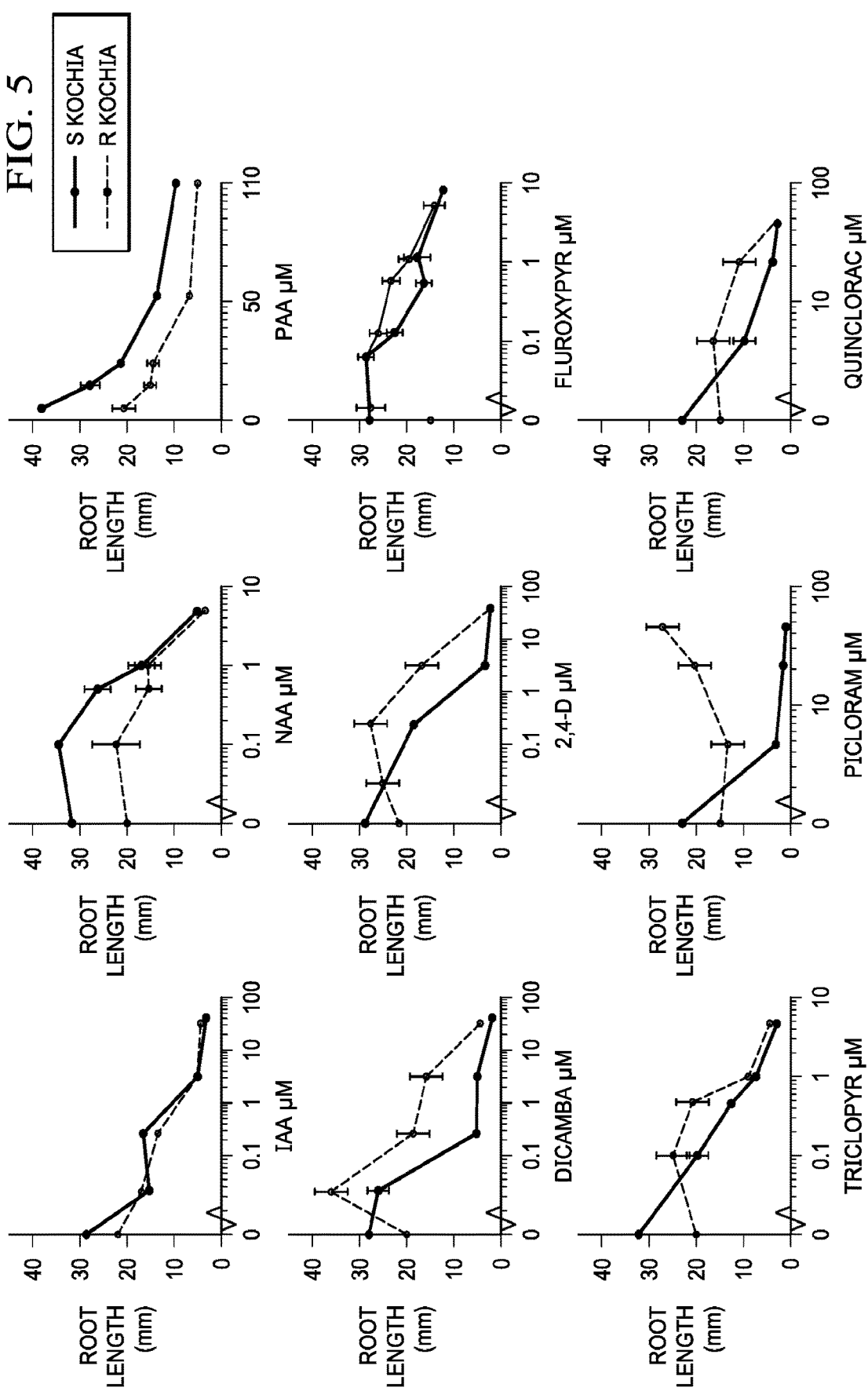

METHODS AND COMPOSITIONS FOR HERBICIDE TOLERANCE IN PLANTS

REFERENCE TO RELATED APPLICATION

This application is a 371 National Stage application of International Application No. PCT/US2018/027565, filed Apr. 13, 2018, which claims the benefit of U.S. Provisional Application No. 62/485,751, filed Apr. 14, 2017, which are herein incorporated by reference in their entireties.

FIELD OF THE INVENTION

The present invention relates to the field of biotechnology. More specifically, the invention relates to compositions and methods for producing crop plants that are resistant to auxin herbicides. In particular, the invention relates to plants, plant issues and plant seeds that contain altered KsIAA16 genes and proteins that provide resistance to auxin herbicide compared to unaltered KsIAA16 genes and proteins.

INCORPORATION OF SEQUENCE LISTING

A sequence listing contained in the file named "MONS406WO_ST25-sub.txt" which is 468 kilobytes measured in MS-Windows®) and created on Nov. 28, 2021, comprises 293 nucleotide sequences, is filed electronically herewith and incorporated by reference in its entirety.

BACKGROUND

Weeds are plants that compete with cultivated plants in an agronomic environment and cost farmers billions of dollars annually in crop losses and the expense of efforts to keep weeds under control. Weeds also serve as hosts for crop diseases and insect pests. The losses caused by weeds in agricultural production environments include decreases in crop yield, reduced crop quality, increased irrigation costs, increased harvesting costs, reduced land value, injury to livestock, and crop damage from insects and diseases harbored by the weeds. The principal means by which weeds cause these effects are: 1) competing with crop plants for water, nutrients, sunlight and other essentials for growth and development, 2) production of toxic or irritant chemicals that cause human or animal health problem, 3) production of immense quantities of seed or vegetative reproductive parts or both that contaminate agricultural products and perpetuate the species in agricultural lands, and 4) production on agricultural and nonagricultural lands of vast amounts of vegetation that must be disposed of.

Chemical herbicides are often used to control the growth and spread of weeds. Chemical herbicides are active at one or more target sites within a plant where they interrupt normal plant functions. Auxin is a central regulator in plant growth and development, and has been implicated in numerous developmental and response pathways, including cell division and elongation, plant patterning, root growth, vascular development, leaf shape, phototropism, and gravitropism. Because this plant hormone is key to so many critical plant pathways, perturbation of auxin levels or response often leads to plant death. This has led to the identification and commercialization of a number of compounds that can mimic the function of the naturally-occurring active auxin is indole-3-acetic acid (IAA), making them effective herbicides. These auxin herbicides include compounds such as 3,6-dichloro-2-methoxybenzoic acid (dicamba), and 2,4-dichlorophenoxyacetic acid (2,4-D). There is a need for crop plants that are resistant to auxin herbicides.

SUMMARY

In one aspect, a modified plant or seed is provided, wherein the modified plant or seed is sensitive to at least one endogenous auxin, and wherein the modified plant or seed exhibits tolerance to at least one synthetic auxin herbicide. The endogenous auxin may be selected from the group consisting of IAA and NAA, and the synthetic auxin herbicide may be selected from the group consisting of dicamba, 2,4-D, picloram, triclopyr, quinclorac and fluroxypyr. In some embodiments, the modified plant or seed comprises at least one modification in an endogenous gene encoding an AUX/IAA protein, wherein said at least one modification confers tolerance to an auxin herbicide as compared to a control plant without said at least one modification. In further embodiments, the modification results in an AUX/IAA polypeptide comprising a modified degron domain that comprises the motif $X_1WPPX_2$ (SEQ ID NO: 293), wherein $X_1$ has been modified relative to a wild type AUX/IAA polypeptide, to be asparagine (N), isoleucine (I), or leucine (L) relative to a wild type AUX/IAA polypeptide and wherein $X_2$ is isoleucine (I), valine (V), leucine (L), or methionine (M). In yet further embodiments the modification results in an AUX/IAA polypeptide comprising an amino acid sequence at least 90% identical to SEQ ID NO: 219, wherein the modified plant or seed is not a *Kochia scoparia* plant or seed. The modification may result in an AUX/IAA polypeptide comprising an amino acid sequence of SEQ ID NO: 219, wherein the modified plant or seed is not a *Kochia scoparia* plant or seed. In certain embodiments, said modified plant or seed is a crop plant or crop seed, for example a monocot crop plant selected from the group consisting of maize, sorghum, wheat, canola, soy, and cotton, grapes, tomato, potato, lettuce, broccoli, cucumber, peanut, melon, leeks, onion, rice, and barley, or a dicot crop plant selected from the group consisting of soybean, alfalfa, sunflower, cotton, canola, and sugar beet. Said modification may result in increased tolerance to an auxin herbicide as compared to a control plant or seed lacking said modification.

In another aspect, a method of generating a modified plant is provided, comprising the steps of: (a.) introducing a modification in a AUX/IAA gene of a plant cell; (b.) identifying and selecting one or more plant cells of step (a.) comprising said modification in a degron domain of AUX/IAA; and c. regenerating at least one plant from at least one or more cells selected in step (b).

In a further aspect, a modified DNA molecule is provided that encodes a modified auxin/indole-3-acetic acid (AUX/IAA) polypeptide, wherein said AUX/IAA polypeptide comprises a modified degron domain that comprises the motif $X_1WPPX_2$, wherein $X_1$ has been modified to be asparagine (N), isoleucine (I), or leucine (L) relative to a wild type AUX/IAA polypeptide and wherein $X_2$ is isoleucine (I), valine (V), leucine (L), or methionine (M). In some embodiments, $X_1$ has been modified from glycine to asparagine. In further embodiments, the modified AUX/IAA polypeptide comprises a polypeptide sequence selected from the group consisting of: (a.) a sequence having at least 90% sequence identity to SEQ ID NOs: 2n−1, wherein n=1-110, or wherein any of SEQ ID NOs: 247-284; and (b.) a fragment of the sequence of (a.) having auxin/indole-3-acetic acid binding activity. In certain embodiments, the modified AUX/IAA polypeptide comprises a polynucleotide sequence having at least 95% sequence identity to SEQ ID NO: 220 or the sequence of SEQ ID NO: 220.

In yet a further aspect, a DNA construct is provided comprising a modified DNA molecule provided herein operably linked to a heterologous promoter. The promoter may be an inducible promoter or a native auxin/indole-3-acetic acid gene promoter in the genome of a plant.

In another aspect, a recombinant plant, plant part, cell, or seed comprising a modified DNA molecule provided herein is provided. A plant genome comprising a modified DNA molecule provided herein is further provided.

In a further aspect, a method is provided for conferring auxin herbicide tolerance to a plant comprising expressing in said plant a modified DNA molecule described herein. Said method may comprise transforming said plant or a progenitor thereof with the modified DNA molecule. In some embodiments, the auxin herbicide is selected from the group consisting of dicamba, 2,4-D, picloram, triclopyr, quinclorac and fluroxypyr.

In another aspect, a method for producing an auxin herbicide tolerant plant is provided comprising: modifying an AUX/IAA polypeptide of said plant to alter residue $X_1$ in a degron domain that comprises the motif $X_1WPPX_2$ relative to SEQ ID NO: 217, wherein $X_2$ is an isoleucine, valine, leucine, or methionine. In certain embodiments, $X_1$ is modified from glycine to asparagine, isoleucine, or leucine. In further embodiments, modifying comprises site-specific mutagenesis. In some embodiments, the degron domain is modified by a base editing enzyme.

Plants produced by the methods described herein are further provided.

In yet a further aspect, methods are provided for detecting a plant exhibiting sensitivity at least one endogenous auxin and tolerance to at least one auxin herbicide, comprising the steps of: a. obtaining a genomic DNA sample from said plant; b. amplifying said DNA sample using a first primer and a second primer to produce an amplicon; c. detecting in said amplicon a polynucleotide sequence encoding the motif $X_1WPPX_2$ within SEQ ID NO: 219. In some embodiments, said first primer has a sequence of SEQ ID NO: 221 and said second primer has a sequence of SEQ ID NO: 222. Detecting may comprise restriction fragment length polymorphism (RFLP) analysis. In other embodiments, said first primer has a sequence of SEQ ID NO: 223 and said second primer has a sequence of SEQ ID NO: 224. Detecting may further comprise using a probe selected from the group consisting of SEQ ID NO: 225, SEQ ID NO: 226, or combinations thereof.

BRIEF DESCRIPTION OF THE DRAWINGS

FIG. 4: Shows a multiple sequence alignment of representative members of the phylogenetic tree of FIG. 2, with degron motif indicated by the boxed amino acids.

FIG. 5: Shows root elongation response of seedlings of the resistant (R) and sensitive (S) *Kochia* biotypes in the presence and absence of natural and synthetic auxins.

DETAILED DESCRIPTION

Figure 1:
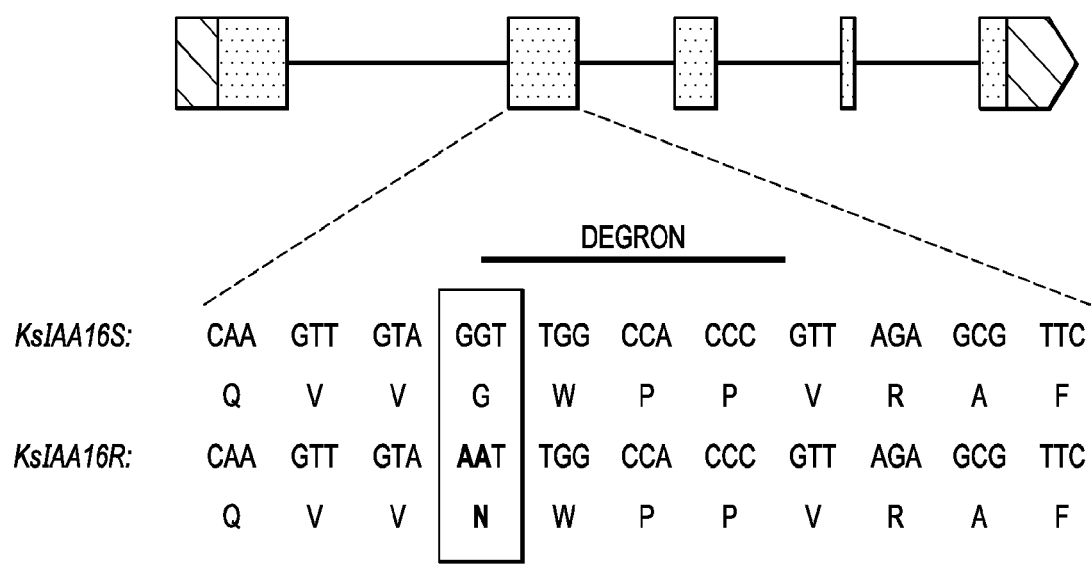
FIG. 1: Shows the gene structure of KsIAA16 wherein nucleotide and amino acid differences between sensitive (S) and resistant (R) alleles are indicated. Shown are nucleotide positions 370 to 402 of SEQ ID NO:218 and amino acid positions 124 to 134 of SEQ ID NO:217 (KsIAA16S), as well as nucleotide positions 370 to 402 of SEQ ID NO:220 and amino acid positions 124 to 134 of SEQ ID NO:219 (KsIAA16R).

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

The plant hormone auxin serves as a central regulator of genes involved numerous plant growth, developmental, and response pathways. The naturally occurring active auxin is indole-3-acetic acid (IAA), but many other compounds have been found to mimic the function of IAA when applied to plants. This has led to the identification and commercialization of a number of compounds that function as effective herbicides.

While corn and other monocotyledonous crops are naturally tolerant to low levels of synthetic auxin herbicides, dicotyledonous crops such as soybean and cotton are highly sensitive. Efforts to develop auxin herbicide tolerant varieties have been focused on the heterologous expression of enzymes that inactivate the auxin herbicide, thereby rendering otherwise sensitive plants tolerant to the herbicide. For example, dicamba tolerant soybean plants have been produced to comprise a gene from *Stenotrophomonas maltophilia* that encodes for dicamba monooxygenase (DMO), an enzyme that inactivates dicamba by converting it to the non-herbicidal 3,6-dicholorosalicylic acid.

While this approach has been successful, recent advances in genome editing techniques have been of great interest in the development crops with improved traits. With regard to the trait of auxin herbicide tolerance, genome editing can be used to generate specific mutations that alter the mechanism of auxin perception in a plant, such that the plant is resistant to the effect of synthetic auxins, including auxin herbicides, but is still sensitive to endogenous auxins. This modification in auxin perception would potentially not result in any significant fitness penalties. Not wishing to be bound by a particular theory, a plant that is tolerant due to altered auxin perception would not need to expend resources to highly express any metabolic proteins for herbicide detoxification, which in turn, would leave the plant more resources to commit to other growth properties.

In order to utilize genome editing techniques to modify auxin perception in tolerant plants, specific mutations that confer the desired auxin perception phenotype must be identified. A great deal of work has been done to identify and characterize mutations that result in altered auxin perception in the model plant *Arabidopsis thaliana*, however none of the known mutations resulted in resistance to synthetic auxins, while maintaining sensitivity to endogenous IAA. As a result, most known mutations were found to result in plant growth defects in *Arabidopsis*.

Auxin herbicide resistant field isolates potentially provide a distinct set of examples where plants have an altered auxin perception yet maintain sufficient fitness to propagate under harsher conditions than what is typically provided by controlled environments. Efforts to identify the genetic basis of auxin herbicide resistance in any field-derived weed species have been previously hindered by the low frequency of resistance alleles and slow spread of auxin herbicide resistant weeds.

One weed of particular agricultural importance is *Kochia scoparia* L. Schrad, a robust dicotyledonous weed species. Despite the problematic rise and spread of dicamba resistant *Kochia*, the genetic basis for this resistance has not been reported. The present disclosure shows for the first time the genetic basis for the dicamba resistant phenotype exhibited by a *Kochia* biotype from Western Nebraska. Surprisingly, the present inventors have shown that the dicamba resistance in this *Kochia* biotype is due to a two nucleotide base change resulting in a glycine to asparagine amino acid change within the highly conserved "GWPPV/I" motif located in the degron domain of a auxin/indole-3-acetic acid (AUX/IAA) protein most closely resembling IAA16 in *Arabidopsis*. Additionally, it was demonstrated that the mutant IAA16 protein from the resistant *Kochia* biotype appeared to have altered auxin perception.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., F1, F2, F3, F4, F5, F6, F7, etc. A plant cell is a biological cell of a plant, taken from a plant or derived through culture from a cell taken from a plant.

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one aspect, a modified plant provided herein comprises no non-plant genetic material or sequences. In yet another aspect, a modified plant provided herein comprises no interspecies genetic material or sequences.

As used herein, an "endogenous gene" or a "native copy" of a gene refers to a gene that originates from within a given organism, cell, tissue, genome, or chromosome. An "endogenous gene" or a "native copy" of a gene is a gene that was not previously modified by human action. Similarly, an "endogenous protein" refers to a protein encoded by an endogenous gene.

As used herein, "synthetic auxin herbicide" or "auxin herbicide" means any herbicide that exerts herbicidal activity through mimicking an endogenous plant auxin or inhibit the movement of auxinic compounds out of cells. Examples of synthetic auxin herbicides include benzoic acids, phenoxycarboxylic acids, pyridine carboxylic acids, quinoline carboxylic acids, semi-carbasones, Diflufenzopyr, 2,4-D, 2,4-DB, MCPA, MCPB, Mecoprop, Dicamba, Clopyralid, Fluroxypyr, Picloram, Triclopyr, Aminopyralid, Aminocyclopyrachlor, and Quinclorac.

In one aspect, the present disclosure provides a non-transgenic plant comprising a synthetic mutation in a degron domain of an AUX/IAA protein. In one aspect, the present disclosure provides a non-transgenic plant comprising a synthetic mutation in a degron domain of an IAA16 protein. As used herein, the term "synthetic mutation" refers to non-spontaneous mutation and occurs as a result genome modification, for example by a site-specific genome modification enzyme.

Several embodiments relate to a modified auxin/indole-3-acetic acid (AUX/IAA) polypeptide, said AUX/IAA polypeptide comprising a modified degron domain that comprises the motif $X_1WPPX_2$, wherein $X_1$ has been modified from glycine to asparagine, isoleucine or leucine, and wherein $X_2$ is isoleucine, valine, leucine or methionine. Several embodiments relate to a nucleic acid sequence encoding a modified auxin/indole-3-acetic acid (AUX/IAA) polypeptide, said AUX/IAA polypeptide comprising a modified degron domain that comprises the motif $X_1WPPX_2$, wherein $X_1$ has been modified from glycine to asparagine, isoleucine or leucine, and wherein $X_2$ is isoleucine, valine, leucine or methionine. Several embodiments relate to a plant, plant part, plant cell, or plant seed comprising a nucleic acid sequence encoding a modified auxin/indole-3-acetic acid (AUX/IAA) polypeptide and/or a modified auxin/indole-3-acetic acid (AUX/IAA) polypeptide, said AUX/IAA polypeptide comprising a modified degron domain that comprises the motif $X_1WPPX_2$, wherein $X_1$ has been modified from glycine to asparagine, isoleucine or leucine, and wherein $X_2$ is isoleucine, valine, leucine or methionine. In some embodiments, a plant, plant part, plant cell, or plant seed comprising a modified auxin/indole-3-acetic acid (AUX/IAA) polypeptide, said AUX/IAA polypeptide comprising a modified degron domain that comprises the motif $X_1WPPX_2$, wherein $X_1$ has been modified from glycine to asparagine, isoleucine, or leucine, and wherein $X_2$ is isoleucine, valine, leucine or methionine is resistant to the effect of synthetic auxins, including auxin herbicides, but is still sensitive to endogenous auxins.

In one aspect, a modification to a nucleic acid molecule encoding a protein results in at least 1, at least 2, at least 3, at least 4, at least 5, at least 6, at least 7, at least 8, at least 9, at least 10, at least 15, at least 20, at least 25, at least 30, at least 40, at least 50, at least 75, or at least 100 missense mutations as compared to an endogenous protein. In another aspect, a modification to a nucleic acid molecule encoding a AUX/IAA protein results in at least 1, at least 2, at least 3, at least 4, at least 5, at least 6, at least 7, at least 8, at least 9, at least 10, at least 15, at least 20, at least 25, at least 30, at least 40, at least 50, at least 75, or at least 100 missense mutations as compared to an unmodified sequence. As used herein, a "missense mutation" refers to a single nucleotide change that results in a codon that codes for a different amino acid. For example, the codon "CGU" encodes an arginine amino acid. If a missense mutation changes the G to a U, producing a "CUU" codon, the codon now encodes a leucine amino acid. Missense mutations can be caused by an insertion, deletion, substitution, or inversion.

In further embodiments, methods of designing and producing crop plants that exhibit tolerance to auxin herbicides are provided. In some embodiments, methods of designing plants that exhibit tolerance to auxin herbicides by modifying the genome of a plant cell to alter a gene involved auxin herbicide tolerance as described herein is provided. Genome modification can be accomplished through targeted mutagenesis as described herein.

Several embodiments relate to a modified auxin/indole-3-acetic acid (AUX/IAA) polypeptide capable of providing auxin resistance to a plant. Several embodiments relate to nucleic acid sequences encoding modified auxin/indole-3-acetic acid (AUX/IAA) polypeptides, as well as compositions and methods of using modified polypeptides. In some embodiments, nucleic acid sequences encoding modified auxin/indole-3-acetic acid (AUX/IAA) polypeptides provide for tolerance to auxin herbicide in plants comprising the recombinant DNA molecules.

Several embodiments relate to nucleic acid molecules, polynucleotides, polypeptides, proteins, cells, seeds, or plants that are the result of genetic engineering and as such would not normally be found in nature and are created by human intervention. Several embodiments relate to a plant genome comprising a DNA sequence that does not naturally occur in such plant genome and as such is the result of human intervention. In some embodiments, a DNA sequence provided herein encodes a modified AUX/IAA polypeptide comprising a modified degron domain. In certain embodiments, modified AUX/IAA polypeptides comprising an alteration relative to the polypeptide encoded by KsIAA16S (SEQ ID NO: 218) in a degron domain comprising the motif $X_1WPPX_2$ are provided. In some embodiments, recombinant polypeptides comprising modified degron domains comprising the motif $X_1WPPX_2$, wherein $X_1$ has been modified from glycine to a different amino acid, for example to a hydrophilic amino acid such as arginine, asparagine, aspartate, glutamate, glutamine, lysine, serine, or threonine, and $X_2$ is a hydrophobic amino acid such a leucine or isoleucine are provided. In some embodiments, a recombinant polypeptide comprising a modified degron domain comprising the motif $X_1WPPX_2$, wherein $X_1$ has been modified from glycine to asparagine, isoleucine, or leucine, and $X_2$ is isoleucine, valine, leucine, or methionine is provided. In some embodiments, polypeptides comprising a polypeptide sequence wherein any one of SEQ ID NOs: 2n-1, wherein n=1-110, or wherein any of SEQ ID NOs: 247-284 has been altered to have a modified degron domain comprising the motif $X_1WPPX_2$, for example wherein $X_1$ has been modified from glycine to asparagine, isoleucine or leucine, and $X_2$ is isoleucine, valine, leucine or methionine are provided.

Several embodiments relate to polynucleotides encoding polypeptide sequences capable of conferring to a plant altered auxin perception, for example polypeptides wherein any one of SEQ ID NOs: 2n-1, wherein n=1-110, or wherein any of SEQ ID NOs: 247-284 have been altered to have a modified degron domain comprising the motif $X_1WPPX_2$, for example wherein $X_1$ has been modified from glycine to asparagine, isoleucine, or leucine, and $X_2$ is isoleucine, valine, leucine, or methionine. In some embodiments, polynucleotides comprising the polynucleotide sequence of SEQ ID NO: 220 (KsIAA16R). In some embodiments, plants, plant parts, plant cells, or seeds comprising polynucleotide or polypeptide sequences described herein are provided.

In some embodiments, nucleic acid molecules may be synthesized and modified by methods known in the art, either completely or in part, where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). In some embodiments, nucleic acid molecules having at least 85%, at least 90%, at least 91%, at least 92%, at least 93%, at least 94%, at least 95%, at least 96%, at least 97%, at least 98%, at least 99%, at least 99.5%, or 100% sequence identity to a polynucleotide sequence of SEQ ID NOs: 2n-1, wherein n=1-110 and capable of conferring to a plant altered auxin perception which confers tolerance to auxin herbicides are provided.

Several embodiments relate to polypeptide sequences having at least 85%, at least 90%, at least 91%, at least 92%, at least 93%, at least 94%, at least 95%, at least 96%, at least 97%, at least 98%, at least 99%, at least 99.5%, or 100% sequence identity to a polypeptide sequence of SEQ ID NOs: 2n-1, wherein n=1-110, and capable of conferring to a plant altered auxin perception which confers tolerance to auxin herbicides.

In some embodiments, fragments of a polynucleotide or polypeptide sequence capable of conferring to a plant altered auxin perception which confers tolerance to auxin herbicides are provided. In specific embodiments, fragments of any one of SEQ ID NOs: 2n-1, wherein n=1-110 comprising at least about 50, 95, 150, 250, 500, 750, or at least about 1000 contiguous nucleotides, or longer, of any one of SEQ ID NOs: 2n-1, wherein n=1-110, and capable of conferring to a plant altered auxin perception which confers tolerance to auxin herbicides are provided.

The AUX/IAA family of proteins contains four conserved domains, wherein domain II constitutes a 17 amino acid sequence that functions as a degron domain that confers auxin-dependent degradation. In particular, this degron domain contains the motif "GWPPV/I", which is strictly conserved among all AUX/IAA proteins. In some embodiments, polynucleotides encoding an AUX/IAA polypeptide comprising a fragment or variant of the amino acid sequences provided herein and comprising a modified degron domain that comprises the motif $X_1WPPX_2$, wherein modification of the degron domain provides a polypeptide capable of conferring to a plant altered auxin perception which confers tolerance to synthetic auxin herbicides are provided. In certain embodiments, polypeptides encoded by polynucleotides comprise a fragment or variant of the amino acid sequences provided herein and comprise a modified degron domain that comprises the motif $X_1WPPX_2$ wherein $X_1$ has been modified from glycine to asparagine, isoleucine, or leucine, and wherein $X_2$ is isoleucine, valine, leucine or methionine.

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of by Title 37 of the United States Code of Federal Regulations § 1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a polynucleotide, or fragment thereof, as disclosed herein. For example, polymerase chain reaction (PCR) technology can be used to amplify a particular starting polynucleotide molecule and/or to produce variants of the original molecule. Polynucleotide molecules, or fragment thereof, can also be obtained by other techniques, such as by directly synthesizing the fragment by chemical means, as is commonly practiced by using an automated oligonucleotide synthesizer. A polynucleotide can be single-stranded (ss) or double-stranded (ds). "Double-stranded" refers to the base-pairing that occurs between sufficiently complementary, anti-parallel nucleic acid strands to form a double-stranded nucleic acid structure, generally under physiologically relevant conditions. Embodiments of the method include those wherein the polynucleotide is at least one selected from the group consisting of sense single-stranded DNA (ssDNA), sense single-stranded RNA (ssRNA), double-stranded RNA (dsRNA), double-stranded DNA (dsDNA), a double-stranded DNA/RNA hybrid, anti-sense ssDNA, or anti-sense ssRNA; a mixture of polynucleotides of any of these types can be used.

As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar Inc., Madison, Wis.), and MUSCLE (version 3.6) (Edgar, "MUSCLE: multiple sequence alignment with high accuracy and high throughput" Nucleic Acids Research 32(5):1792-7 (2004)) for instance with default parameters. An "identity fraction" for aligned segments of a test sequence and a reference sequence is the number of identical components that are shared by the two aligned sequences divided by the total number of components in the portion of the reference sequence segment being aligned, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

As used herein, the term "protein-coding polynucleotide molecule" refers to a polynucleotide molecule comprising a nucleotide sequence that encodes a protein. A "protein-coding sequence" means a polynucleotide sequence that encodes a protein. Such a polynucleotide is at least one selected from the group consisting of sense single-stranded DNA (ssDNA), sense single-stranded RNA (ssRNA), double-stranded RNA (dsRNA), double-stranded DNA (dsDNA), a double-stranded DNA/RNA hybrid, anti-sense ssDNA, or anti-sense ssRNA; or a mixture of polynucleotides of any of these types.

A "sequence" means a sequential arrangement of nucleotides or amino acids. The boundaries of a protein-coding sequence may be determined by a translation start codon at the 5'-terminus and a translation stop codon at the 3'-terminus. In some embodiments, a protein-coding molecule may comprise a DNA sequence encoding a protein sequence. In some embodiments, a protein-coding molecule may comprise a RNA sequence encoding a protein sequence. As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which are ultimately folded into proteins.

Because of the degeneracy of the genetic code, a variety of different polynucleotide sequences can encode polypeptides, such as the altered polypeptides disclosed herein. A table showing all possible triplet codons (and where U also replaces T) and the amino acid encoded by each codon is described in Lewin (1985). In addition, it is well within the capability of one of skill in the art to create alternative polynucleotide sequences encoding the same, or essentially the same, altered polypeptides as described herein. These variant or alternative polynucleotide sequences are within the scope of the embodiments described herein. As used herein, references to "essentially the same" sequence refers to sequences which encode amino acid substitutions, deletions, additions, or insertions which do not materially alter the functional activity of the polypeptide encoded by the polynucleotides of the embodiments described herein. Allelic variants of the nucleotide sequences encoding a wild type or altered polypeptide are also encompassed within the scope of the embodiments described herein. Substitution of amino acids other than those specifically exemplified or naturally present in a wild type or altered AUX/IAA polypeptide are also contemplated within the scope of the embodiments described herein, so long as the polypeptide having the substitution still retains substantially the same functional activity (e.g., selective auxin perception) described herein.

I. Genome Editing

Targeted modification of plant genomes through the use of genome editing methods can be used to create improved plant lines through modification of plant genomic DNA. In addition, genome editing methods can enable targeted insertion of one or more nucleic acids of interest into a plant genome. Examples methods for introducing donor polynucleotides into a plant genome or modifying genomic DNA of a plant include the use of sequence specific nucleases, such as zinc-finger nucleases, engineered or native meganucleases, TALE-endonucleases, or an RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system). Several embodiments relate to methods of genome editing is using single-stranded oligonucleotides to introduce precise base pair modifications in a plant genome, as described by Sauer et al (Plant Physiol. 2016 April; 170(4): 1917-1928). Methods of genome editing to modify, delete, or insert nucleic acid sequences into genomic DNA are known in the art.

Several embodiments relate to a CRISPR/Cas9 system used to modify or replace an existing coding sequence within a plant genome, such as a sequence encoding an AUX/IAA polypeptide. Several embodiments relate to a CRISPR/Cpf1 system used to modify or replace an existing coding sequence within a plant genome, such as a sequence encoding an AUX/IAA polypeptide. Several embodiments relate to a Cas9-cytidine deaminase used to modify an existing coding sequence within a plant genome, such as a sequence encoding an AUX/IAA polypeptide. Several embodiments relate to a Cpf1-cytidine deaminase used to modify an existing coding sequence within a plant genome, such as a sequence encoding an AUX/IAA polypeptide. In further embodiments, transcription activator-like effectors (TALEs) are used for modification or replacement of an existing coding sequence within a plant genome, such as a sequence encoding an AUX/IAA polypeptide. In some embodiments, an existing AUX/IAA polypeptide coding sequence within a plant genome is modified by non-templated genome editing with a sequence specific nuclease. In some embodiments, an existing AUX/IAA polypeptide coding sequence within a plant genome is modified by templated genome editing with a sequence specific nuclease. In some embodiments, a sequence specific nuclease and a donor nucleic acid encoding a modified degron domain is introduced into a plant cell. In some embodiments the modified degron domain encodes a X1WPPX2 motif capable of conferring to a plant tolerance to auxin herbicides. In some embodiments, X1 has been modified from glycine to asparagine, isoleucine, or leucine. In some embodiments, X2 is isoleucine, valine, leucine or methionine. Modification or replacement of an endogenous AUX/IAA-encoding sequence according to the methods provided herein results in expression of a polypeptide comprising a modified degron domain comprising the motif $X_1WPPX_2$, for example wherein one or more of $X_1$ and $X_2$ has been altered. Several embodiments therefore relate to providing a sequence specific nuclease capable of recognizing a specific nucleotide sequence of interest, such as an AUX/IAA sequence, within a genome of a plant to allow for alteration of the AUX/IAA sequence by non-templated editing or integration of a donor nucleic acid at that site.

Modifications to an AUX/IAA-encoding sequence, for example a sequence provided herein as one of SEQ ID NOs: 2n-1, wherein n=1-110, may result in a sequence encoding a polypeptide comprising a modified degron domain comprising the motif $X_1WPPX_2$ as described herein, capable of conferring to a plant altered auxin perception which confers tolerance to auxin herbicides. In some embodiments, $X_1$ has been modified from glycine to asparagine, isoleucine, or leucine. In some embodiments, $X_2$ is isoleucine, valine, leucine or methionine.

In an aspect, a "modification" comprises the insertion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In another aspect, a "modification" comprises the deletion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In a further aspect, a "modification" comprises the inversion of at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the substitution of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the substitution of an "A" for a "C", "G" or "T" in a nucleic acid sequence. In some embodiments, a "modification" comprises the substitution of a "C" for an "A", "G" or "T" in a nucleic acid sequence. In some embodiments, a "modification" comprises the substitution of a "G" for an "A", "C" or "T" in a nucleic acid sequence. In some embodiments, a "modification" comprises the substitution of a "T" for an "A", "C" or "G" in a nucleic acid sequence. In some embodiments, a "modification" comprises the substitution of a "C" for a "U" in a nucleic acid sequence. In some embodiments, a "modification" comprises the substitution of a "G" for an "A" in a nucleic acid sequence. In some embodiments, a "modification" comprises the substitution of an "A" for a "G" in a nucleic acid sequence. In some embodiments, a "modification" comprises the substitution of a "T" for a "C" in a nucleic acid sequence.

In some embodiments, a recombinant DNA construct, such as a transgene or expression cassette comprising nucleic acid sequence encoding an AUX/IAA protein is provided. In some embodiments, the AUX/IAA protein is an IAA16 homolog. In some embodiments, the nucleic acid sequence encodes an AUX/IAA protein comprising a modified degron domain. In some embodiments, the modified degron domain comprises a $X_1WPPX_2$ motif capable of conferring to a plant tolerance to auxin herbicides. In some embodiments, $X_1$ has been modified from glycine to asparagine, isoleucine, or leucine. In some embodiments, $X_2$ is isoleucine, valine, leucine or methionine. In some embodiments, the transgene or expression cassette comprises a promoter derived from an endogenous promoter of an IAA gene operably linked to the AUX/IAA-encoding sequence. In some embodiments, the transgene or expression cassette, may be inserted or integrated into a locus within the genome of a plant or plant cell. In some embodiments, the transgene or expression cassette, may be inserted or integrated into a specific site or locus within the genome of a plant or plant cell via site-directed integration. In some embodiments, a recombinant DNA construct comprises a nucleotide sequence encoding a polypeptide wherein any one of SEQ ID NOs: 2n-1, wherein n=1-110 have been altered to have a modified degron domain comprising the motif $X_1WPPX_2$, or a sequence encoding a fragment of such a polypeptide. In some embodiments, a recombinant DNA construct may further comprise one or two homology arms flanking an insertion sequence (i.e., the sequence, transgene, cassette, etc., to be inserted into the plant genome).

Several embodiments relate to a recombinant DNA construct comprising an expression cassette(s) encoding a site-specific nuclease and/or any associated protein(s) to carry out genome modification. These nuclease expressing cassette(s) may be present in the same molecule or vector as a donor template for templated editing or an expression cassette comprising nucleic acid sequence encoding an AUX/IAA protein as described herein (in cis) or on a separate molecule or vector (in trans). Several methods for site-directed integration are known in the art involving different sequence-specific nucleases (or complexes of proteins and/or guide RNA) that cut the genomic DNA to produce a double strand break (DSB) or nick at a desired genomic site or locus. As understood in the art, during the process of repairing the DSB or nick introduced by the nuclease enzyme, the donor template DNA, transgene, or expression cassette may become integrated into the genome at the site of the DSB or nick. The presence of the homology arm(s) in the DNA to be integrated may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9, CasX, CasY or Cpf1). For methods using RNA-guided site-specific nucleases (e.g., Cas9, CasX, CasY or Cpf1), the recombinant DNA construct(s) may also comprise a sequence encoding one or more guide RNAs to direct the nuclease to the desired site within the plant genome. In some embodiments, one or more guide RNAs may be provided on a separate molecule or vector (in trans).

II. Site-Specific Genome Modification Enzymes

As used herein, the term "double-strand break inducing agent" refers to any agent that can induce a double-strand break (DSB) in a DNA molecule. In some embodiments, the double-strand break inducing agent is a site-specific genome modification enzyme.

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

Several embodiments relate to promoting recombination by providing a site-specific genome modification enzyme, for example, a sequence-specific nuclease, to a plant cell. In some embodiments, recombination is promoted by providing a single-strand break inducing agent. In some embodiments, recombination is promoted by providing a double-strand break inducing agent. In some embodiments, recombination is promoted by providing a strand separation inducing reagent. In one aspect, the site-specific genome modification enzyme is selected from an endonuclease, a recombinase, a transposase, a deaminase, a helicase or any combination thereof. In some embodiments, recombination occurs between B chromosomes. In some embodiments, recombination occurs between a B chromosome and an A chromosome.

Several embodiments relate to promoting integration of one or more DNAs of interest by providing a site-specific genome modification enzyme. In some embodiments, integration of one or more DNAs of interest is promoted by providing a single-strand break inducing agent. In some embodiments, integration of one or more DNAs of interest is promoted by providing a double-strand break inducing agent. In some embodiments, integration of one or more DNAs of interest is promoted by providing a strand separation inducing reagent. In one aspect, the site-specific genome modification enzyme is selected from an endonuclease, a recombinase, a transposase, a helicase or any combination thereof.

In one aspect, the endonuclease is selected from a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), an RNA-guided nuclease, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, Mad7, homologs thereof, or modified versions thereof).

In some embodiments, the site-specific genome modification enzyme is a dCas9-Fok1 fusion protein. In another aspect, the site-specific genome modification enzyme is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

In some embodiments, the site-specific genome modification enzyme is a dCas9-cytosine deaminase fusion protein. In another aspect, the site-specific genome modification enzyme is a dCas9-adenine deaminase fusion protein. In some embodiments, one or more of a dCas9-cytosine deaminase fusion protein and a dCas9-adenine deaminase fusion protein are utilized to modify a nucleic acid sequence encoding the degron domain of an AUX/IAA protein. In some embodiments, a nucleic acid sequence encoding a degron domain is modified to encode a degron domain comprising the motif $X_1WPPX_2$, wherein $X_1$ has been modified from glycine to asparagine, isoleucine, or leucine, and $X_2$ is isoleucine, or valine, leucine, or methionine. In some embodiments, the AUX/IAA protein is an ortholog of KsIAA16.

In some embodiments, the site-specific genome modification enzyme is a dCpf1-cytosine deaminase fusion protein. In another aspect, the site-specific genome modification enzyme is a dCpf1-adenine deaminase fusion protein. In some embodiments, one or more of a dCpf1-cytosine deaminase fusion protein and a dCpf1-adenine deaminase fusion protein are utilized to modify a nucleic acid sequence encoding the degron domain of an AUX/IAA protein. In some embodiments, a nucleic acid sequence encoding a degron domain is modified to encode a degron domain comprising the motif X1WPPX2, wherein X1 has been modified from glycine to asparagine, isoleucine, or leucine, and X2 is isoleucine, or valine, leucine, or methionine. In some embodiments, the AUX/IAA protein is an ortholog of KsIAA16.

In some embodiments, the site-specific genome modification enzyme is a recombinase. Non-limiting examples of recombinases include a tyrosine recombinase attached to a DNA recognition motif provided herein is selected from the group consisting of a Cre recombinase, a Gin recombinase, a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), RNA-guided nucleases (non-limiting examples of RNA-guided nucleases include the CRISPR associated nucleases, such as Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, Mad7, homologs thereof, or modified versions thereof) and engineered RNA-guided nucleases (RGNs), induce a genome modification such as a double-stranded DNA break (DSB) or single-strand DNA break at the target site of a genomic sequence. In some embodiments, breaks or nicks in the target DNA sequence are repaired by the natural processes of homologous recombination (HR) or non-homologous end-joining (NHEJ). In some embodiments, sequence modifications occur at or near the cleaved or nicked sites, which can include deletions or insertions that result in modification of the nucleic acid sequence, or integration of exogenous nucleic acids by homologous recombination or NHEJ.

Any of the DNA of interest provided herein can be integrated into a target site of a chromosome sequence by introducing the DNA of interest and the provided site-specific genome modification enzymes. Any method provided herein can utilize any site-specific genome modification enzyme provided herein.

Several embodiments relate to a method and/or a composition provided herein comprising at least one, at least two, at least three, at least four, at least five, at least six, at least seven, at least eight, at least nine, or at least ten site-specific genome modification enzymes. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific genome modification enzymes.

In one aspect, a targeted genome modification as described herein comprises the use of a recombinase. In an aspect, a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA binding domain. The Flp-FRT site-directed recombination system comes from the 2μ plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

In some embodiments, a targeted genome modification as described herein comprises the use of a zinc-finger nuclease (ZFN). ZFNs are synthetic proteins consisting of an engineered zinc finger DNA-binding domain fused to the cleavage domain of the FokI restriction nuclease. ZFNs can be designed to cleave almost any long stretch of double-stranded DNA for modification of the zinc finger DNA-binding domain. ZFNs form dimers from monomers composed of a non-specific DNA cleavage domain of FokI nuclease fused to a zinc finger array engineered to bind a target DNA sequence. The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art. The FokI nuclease domain requires dimerization to cleave DNA and therefore two ZFNs with their C-terminal regions are needed to bind opposite DNA strands of the cleavage site (separated by 5-7 nt). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

Several embodiments relate to a method and/or composition provided herein comprising one or more, two or more, three or more, four or more, or five or more ZFNs directed to a target sequence in a gene encoding an AUX/IAA protein. In another aspect, a ZFN provided herein is capable of generating a targeted DSB. In one aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or Agrobacterium-mediated transformation).

Several embodiments relate to generating a modification as described herein using a meganuclease. Meganucleases, which are commonly identified in microbes, are unique enzymes with high activity and long recognition sequences (>14 nt) resulting in site-specific digestion of target DNA. Engineered versions of naturally occurring meganucleases typically have extended DNA recognition sequences (for example, 14 to 40 nt). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In one aspect, a method and/or composition provided herein comprises one or more, two or more, three or more, four or more, or five or more meganucleases directed to a target sequence in a gene encoding an AUX/IAA protein. In some embodiments, a meganuclease provided herein is capable of generating a targeted DSB. In some embodiments, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or Agrobacterium-mediated transformation).

In some embodiments, a targeted genome modification as described herein comprises the use of a transcription activator-like effector nuclease (TALEN). TALENs are artificial restriction enzymes generated by fusing the transcription activator-like effector (TALE) DNA binding domain to a nuclease domain. In one aspect, the nuclease is selected from a group consisting of PvuII, MutH, TevI and FokI, AlwI, MlyI, SbfI, SdaI, StsI, CleDORF, Clo051, Pept071. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site. Transcription activator-like effectors (TALEs) can be engineered to bind practically any DNA sequence, such as a target sequence in a nucleic acid encoding an AUX/IAA protein. TALE proteins are DNA-binding domains derived from various plant bacterial pathogens of the genus Xanthomonas. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

In one aspect, a method and/or composition provided herein comprises one or more, two or more, three or more, four or more, or five or more TALENs. In another aspect, a TALEN provided herein is capable of generating a targeted DSB in a target sequence in a nucleic acid encoding an AUX/IAA protein. In one aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or Agrobacterium-mediated transformation).

In some embodiments, a targeted genome modification as described herein comprises the use of at least one, at least two, at least three, at least four, at least five, at least six, at least seven, at least eight, at least nine, or at least ten RNA-guided nucleases. In some embodiments, a CRISPR/Cas9 system, a CRISPR/Cpf1 system, a CRISPR/CasX system, or a CRISPR/CasY system are alternatives may be used to generate modifications to a nucleic acid encoding an AUX/IAA protein. The CRISPR systems are based on RNA-guided engineered nucleases that use complementary base pairing to recognize DNA sequences at target sites. The CRISPR (clustered regularly interspaced short palindromic repeats)/Cas (CRISPR-associated) system is an alternative to synthetic proteins whose DNA-binding domains enable them to modify genomic DNA at specific sequences (e.g., ZFN and TALEN). CRISPR/Cas systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5'-NGG-3' but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA. Specificity of the CRISPR/Cas system is based on an RNA-guide that use complementary base pairing to recognize target DNA sequences. In some embodiments, the site-specific genome modification enzyme is a CRISPR/Cas system. In an aspect, a site-specific genome modification enzyme provided herein can comprise any RNA-guided Cas nuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, Mad7, homologs thereof, or modified versions thereof); and, optionally, the guide RNA necessary for targeting the respective nucleases.

Several embodiments relate to plant cells, plant tissue, plant seed and plants produced by the methods disclosed herein. Plants may be monocots or dicots, and may include, for example, rice, wheat, barley, oats, rye, sorghum, maize, grapes, tomatoes, potatoes, lettuce, broccoli, cucumber, peanut, melon, leeks, onion, soybean, alfalfa, sunflower, cotton, canola, and sugar beet plants.

III. Expression Constructs

Polynucleotides as described herein can be provided in an expression construct. Expression constructs generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, "operably linked" means two DNA molecules linked in manner so that one may affect the function of the other. Operably-linked DNA molecules may be part of a single contiguous molecule and may or may not be adjacent. For example, a promoter is operably linked with a polypeptide-encoding DNA molecule in a DNA construct where the two DNA molecules are so arranged that the promoter may affect the expression of the DNA molecule.

As used herein, the term "heterologous" refers to the relationship between two or more items derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell, seed, or organism into which it is inserted when it would not naturally occur in that particular cell, seed, or organism.

An expression construct can comprise a promoter sequence operably linked to a polynucleotide sequence encoding a modified polypeptide as described herein. Promoters can be incorporated into a polynucleotide using standard techniques known in the art. Multiple copies of promoters or multiple promoters can be used in an expression construct as described herein. In some embodiments, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

Embodiments relate to a recombinant DNA molecule encoding a modified AUX/IAA polypeptide, said AUX/IAA polypeptide comprising a modified degron domain that comprises the motif $X_1WPPX_2$, wherein $X_1$ has been modified from glycine to asparagine, and wherein $X_2$ is isoleucine or valine, wherein the recombinant DNA molecule is further defined as operably linked to a heterologous regulatory element. In specific embodiments, the heterologous regulatory element is a promoter functional in a plant cell. In further embodiments, the promoter is an inducible promoter.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, zein promoters including maize zein promoters, prolifera promoter, Ap3 promoter, heat shock promoters, T-DNA 1'- or 2'-promoter of *A. tumefaciens*, polygalacturonase promoter, chalcone synthase A (CHS-A) promoter from *petunia*, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs described herein.

Expression constructs may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides described herein. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

IV. Transformation Methods

Several embodiments relate to plant cells, plant tissues, plants, and seeds that comprise a recombinant DNA as described herein. In some embodiments, the recombinant DNA encodes a sequence-specific enzyme. In some embodiments, cells, tissues, plants, and seeds comprising the recombinant DNA molecules exhibit tolerance to auxin herbicides. In some embodiments, the recombinant DNA encoding a sequence-specific enzyme is bred out of plants exhibiting tolerance to auxin herbicides.

Suitable methods for transformation of host plant cells include virtually any method by which DNA or RNA can be introduced into a cell (for example, where a recombinant DNA construct is stably integrated into a plant chromosome or where a recombinant DNA construct or an RNA is transiently provided to a plant cell) and are well known in the art. Two effective methods for cell transformation are *Agrobacterium*-mediated transformation and microprojectile bombardment-mediated transformation. Microprojectile bombardment methods are illustrated, for example, in U.S. Pat. Nos. 5,550,318; 5,538,880; 6,160,208; and 6,399,861. *Agrobacterium*-mediated transformation methods are described, for example in U.S. Pat. No. 5,591,616, which is incorporated herein by reference in its entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores and pollen. Callus can be initiated from tissue sources including, but not limited to, immature or mature embryos, hypocotyls, seedling apical meristems, microspores and the like. Cells containing a transgenic nucleus are grown into transgenic plants.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Several embodiments relate to methods and constructs for regenerating a plant from a cell with modified genomic DNA resulting from genome editing. The regenerated plant can then be used to propagate additional plants.

Several embodiments relate to a method of introducing an allelic variant of a gene encoding an AUX/IAA protein comprising: (a) introducing at least one modification to an endogenous AUX/IAA gene in at least one plant cell, thereby generating said allelic variant; (b) identifying and selecting at least one plant cell of step (a) comprising said allelic variant that exhibits tolerance to an auxin herbicide; and (c) regenerating a plant from the at least one plant cell selected in step (b). Several embodiments relate to a method of introducing an allelic variant of a gene encoding an AUX/IAA protein comprising: (a) introducing at least one modification to an endogenous AUX/IAA gene in at least one plant cell, thereby generating said allelic variant; (b) identifying and selecting at least one plant cell of step (a) comprising said allelic variant that exhibits tolerance to an auxin herbicide; (c) identifying and selecting at least one plant cell of step (b) that exhibits sensitivity to an endogenous auxin IAA; and (d) regenerating a plant from the at least one plant cell selected in step (c). In an aspect, the method comprises introducing a modification in a sequence encoding a degron domain of an AUX/IAA protein. In some embodiments the modified degron domain encodes a X1WPPX2 motif capable of conferring to a plant tolerance to auxin herbicides. In some embodiments, X1 has been modified from glycine to asparagine, isoleucine, or leucine. In some embodiments, X2 is isoleucine, valine, leucine or methionine. In another aspect, the method of introducing comprises introducing a recombinant DNA vector comprising a polynucleotide sequence specific enzyme direct to a target sequence in a nucleic acid encoding an AUX/IAA protein.

V. Auxin Herbicides and Plants with Auxin Herbicide Tolerance

Several embodiments relate to plant cells, plant tissues, plants, and seeds that comprise an AUX/IAA protein comprising a modified degron domain. In some embodiments, the modified degron domain comprises a X1WPPX2 motif capable of conferring tolerance to synthetic auxin herbicides to plant cells, plant tissues, plants, and seeds. In some embodiments, X1 has been modified from glycine to asparagine, isoleucine, or leucine. In some embodiments, X2 is isoleucine, valine, leucine or methionine. Plants may be monocots or dicots, and may include, for example, rice, wheat, barley, oats, rye, sorghum, maize, grapes, tomatoes, potatoes, lettuce, broccoli, cucumber, peanut, melon, pepper, carrot, squash, onion, soybean, alfalfa, sunflower, cotton, canola, and sugar beet plants.

Synthetic auxin herbicides are also called auxinic, growth regulator herbicides, or Group O or Group 4 herbicides, based on their mode of action. The mode of action of the synthetic auxin herbicides is that they appear to affect cell wall plasticity and nucleic acid metabolism, which can lead to uncontrolled cell division and growth. The group of synthetic auxin herbicides includes four chemical families: phenoxy, carboxylic acid (or pyridine), benzoic acid, and the newest family quinoline carboxylic acids.

The phenoxy herbicides are most common and have been used as herbicides since the 1940s when (2,4-dichlorophenoxy) acetic acid (2,4-D) was discovered. Other examples include 4-(2,4-dichlorophenoxy) butyric acid (2,4-DB), 2-(2,4-dichlorophenoxy) propanoic acid (2, 4-DP), (2,4,5-trichlorophenoxy)acetic acid (2,4,5-T), 2-(2,4,5-Trichlorophenoxy) Propionic Acid (2,4,5-TP), 2-(2,4-dichloro-3-methylphenoxy)-N-phenylpropanamide (clomeprop), (4-chloro-2-methylphenoxy) acetic acid (MCPA), 4-(4-chloro-o-tolyloxy) butyric acid (MCPB), and 2-(4-chloro-2-methylphenoxy) propanoic acid (MCPP).

The next largest chemical family is the carboxylic acid herbicides, also called pyridine herbicides. Examples include 3,6-dichloro-2-pyridinecarboxylic acid (Clopyralid), 4-amino-3,5,6-trichloro-2-pyridinecarboxylic acid (picloram), (2,4,5-trichlorophenoxy) acetic acid (triclopyr), and 4-amino-3,5-dichloro-6-fluoro-2-pyridyloxyacetic acid (fluroxypyr). The third chemical family is the benzoic acids, examples of which include 3,6-dichloro-o-anisic acid (dicamba) and 3-amino-2,5-dichlorobenzoic acid (choramben). The fourth and newest chemical family of the auxinic herbicides is the quinaline carboxylic acid family, which includes 7-chloro-3-methyl-8-quinolinecarboxylic acid (quinmerac) and 3,7-dichloro-8-quinolinecarboxylic acid (quinclorac). This latter is unique in that it also will control some grass weeds, unlike the other auxin-like herbicides which essentially control only broadleaf or dicotyledonous plants.

Synthetic auxin herbicides may be applied to a plant growth area comprising the plants and seeds provided by the compositions and methods described herein as a method for controlling weeds. Plants and seeds provided by the compositions and methods described herein comprise a synthetic auxin herbicide tolerance trait and as such are tolerant to the application of one or more auxin herbicides. The herbicide application may be the recommended commercial rate (1×) or any fraction or multiple thereof, such as twice the recommended commercial rate (2×). Auxin herbicide rates may be expressed as acid equivalent per pound per acre (lb ae/acre) or acid equivalent per gram per hectare (g ae/ha) or as pounds active ingredient per acre (lb ai/acre) or grams active ingredient per hectare (g ai/ha), depending on the herbicide and the formulation. The plant growth area may or may not comprise weed plants at the time of herbicide application.

Herbicide applications may be sequentially or tank mixed with one, two, or a combination of several auxin herbicides or any other compatible herbicide. Multiple applications of one herbicide or of two or more herbicides, in combination or alone, may be used over a growing season to areas comprising plants expressing a modified AUX/IAA protein as described herein for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, "tolerance" or "herbicide tolerance" means a plant, seed, or cell's ability to resist the toxic effects of an herbicide when applied. The herbicide tolerance of a plant, seed, plant tissue, plant part, or cell may be measured by comparing the plant, seed, plant tissue, plant part, or cell to a suitable control. For example, the herbicide tolerance may be measured or assessed by applying an herbicide to a plant comprising a recombinant DNA molecule encoding a modified polypeptide capable of conferring herbicide tolerance (the test plant) and a plant not comprising the recombinant DNA molecule encoding the modified polypeptide capable of conferring herbicide tolerance (the control plant) and then comparing the plant injury of the two plants, where herbicide tolerance of the test plant is indicated by a decreased injury rate as compared to the injury rate of the control plant. An herbicide tolerant plant, seed, plant tissue, plant part, or cells exhibits a decreased response to the toxic effects of an herbicide when compared to a control plant, seed, plant tissue, plant part, or cell. As used herein, an "herbicide tolerance trait" is a transgenic trait imparting improved herbicide tolerance to a plant as compared to the wild-type plant.

As used herein, the term "comprising" means "including but not limited to".

Having described several embodiments in detail, it will be apparent that modifications, variations, and equivalent embodiments are possible. Furthermore, it should be appreciated that the examples in the present disclosure are provided as non-limiting examples.

Examples

Example 1: Identification of Genetic Differences Between Dicamba-Resistant and Dicamba-Sensitive *Kochia scoparia* Biotypes A dicamba resistant *Kochia* biotype which exhibits a nearly 30-fold increase in dicamba resistance believed to be conferred by a dominant or semi-dominant single genetic locus was obtained. Transcriptome sequencing of cDNA isolated from aerial tissues of vegetative-stage plants of the dicamba resistant *Kochia* biotype (R) and a dicamba sensitive *Kochia* biotype (S) allowed identification of putative *Kochia* orthologs of *Arabidopsis* genes known to be involved in auxin synthesis, transport and regulatory response. Comparators included one AUX1/LAX transporter, one ABP homolog, several multi-drug resistance-like proteins (MRP), four TIR/AFB co-receptors, and ten AUX/IAA proteins.

Leaf tissue was harvested separately from greenhouse-grown S and R *Kochia* biotypes and frozen on liquid nitrogen. Total RNA was isolated from three biological replicates for each tissue using TRIzol (Invitrogen) according to the manufacturer's protocol. RNA quantity was determined with a Nanodrop 8000 spectrophotometer and integrity assessed by BioAnalyzer assay with RIN greater than 6. Two mg of total RNA was used for sequencing library preparation with Illumina TruSeq RNA Sample Prep Kit V2 following manufacturer's protocol. qPCR (SYBR PCR Master Mix, Applied Biosystems) was utilized to quantify sequencing libraries. Sequencing was performed with HiSeq2000 sequencing using 50 base pair reads, as described previously (Rice et al., 2014). Paired end reads were used to build *Kochia* transcriptome assemblies for R (82,123,945 pairs) and S (68,928,684 pairs) biotypes. Reads were first quality trimmed using FASTX toolkit (version 0.0.13, minimum 50% of bases with quality score>=30) and then assembled using Trinity (version r2013_08_14, default settings, minimum transcript length=300) (Grabherr et al., Nat Biotechnol. 2011 29(7):644-52.).

Figure 2:
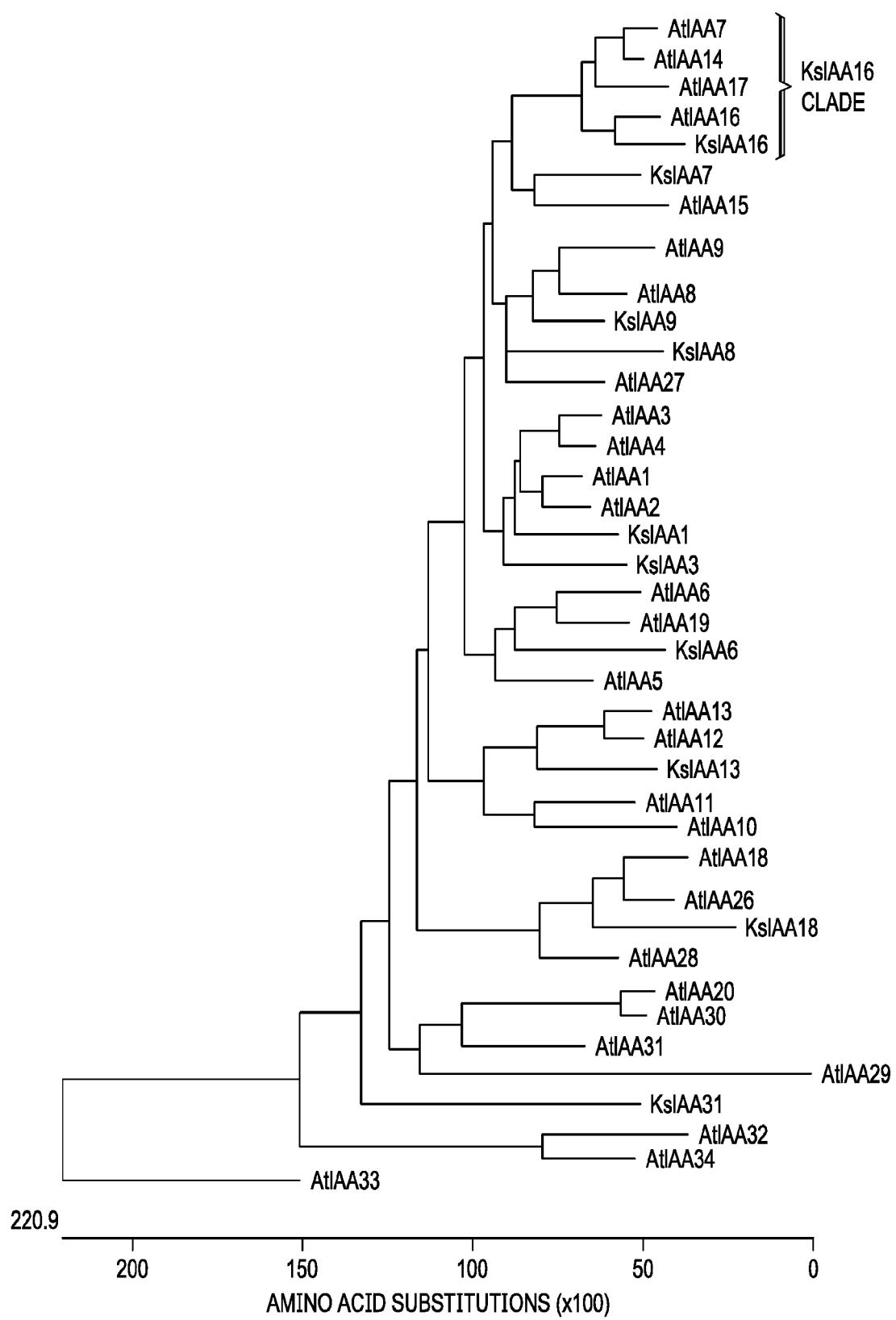
FIG. 2: Shows a phylogenetic tree containing *Arabidopsis* AUX/IAA proteins as well as putative orthologous *Kochia* AUX/IAA proteins identified in transcriptome sequences. The members of this phylogenetic tree are: AtIAA1, (SEQ ID NO: 247); AtIAA2, (SEQ ID NO: 248); AtIAA3, (SEQ ID NO: 249); AtIAA4, (SEQ ID NO: 250); AtIAA5, (SEQ ID NO: 251); AtIAA6, (SEQ ID NO: 252); AtIAA7, (SEQ ID NO: 253); AtIAA8, (SEQ ID NO: 254); AtIAA9, (SEQ ID NO: 255); AtIAA10, (SEQ ID NO: 256); AtIAA11, (SEQ ID NO: 257); AtIAA12, (SEQ ID NO: 258); AtIAA13, (SEQ ID NO: 259); AtIAA14, (SEQ ID NO: 260); AtIAA15, (SEQ ID NO: 261); AtIAA16, (SEQ ID NO: 262); AtIAA17, (SEQ ID NO: 263); AtIAA18, (SEQ ID NO: 264); AtIAA19, (SEQ ID NO: 265); AtIAA20, (SEQ ID NO: 266); AtIAA26, (SEQ ID NO: 267); AtIAA27, (SEQ ID NO: 268); AtIAA28, (SEQ ID NO: 269); AtIAA29, (SEQ ID NO: 270); AtIAA30, (SEQ ID NO: 271); AtIAA31, (SEQ ID NO: 272); AtIAA32, (SEQ ID NO: 273); AtIAA33, (SEQ ID NO: 274); AtIAA34, (SEQ ID NO: 275); KsIAA1, (SEQ ID NO: 276); KsIAA3, (SEQ ID NO: 277); KsIAA6, (SEQ ID NO: 278); KsIAA7, (SEQ ID NO: 279); KsIAA8, (SEQ ID NO: 280); KsIAA9, (SEQ ID NO: 281); KsIAA13, (SEQ ID NO: 282); KsIAA18, (SEQ ID NO: 283); KsIAA31, (SEQ ID NO: 284).
Figure 3:
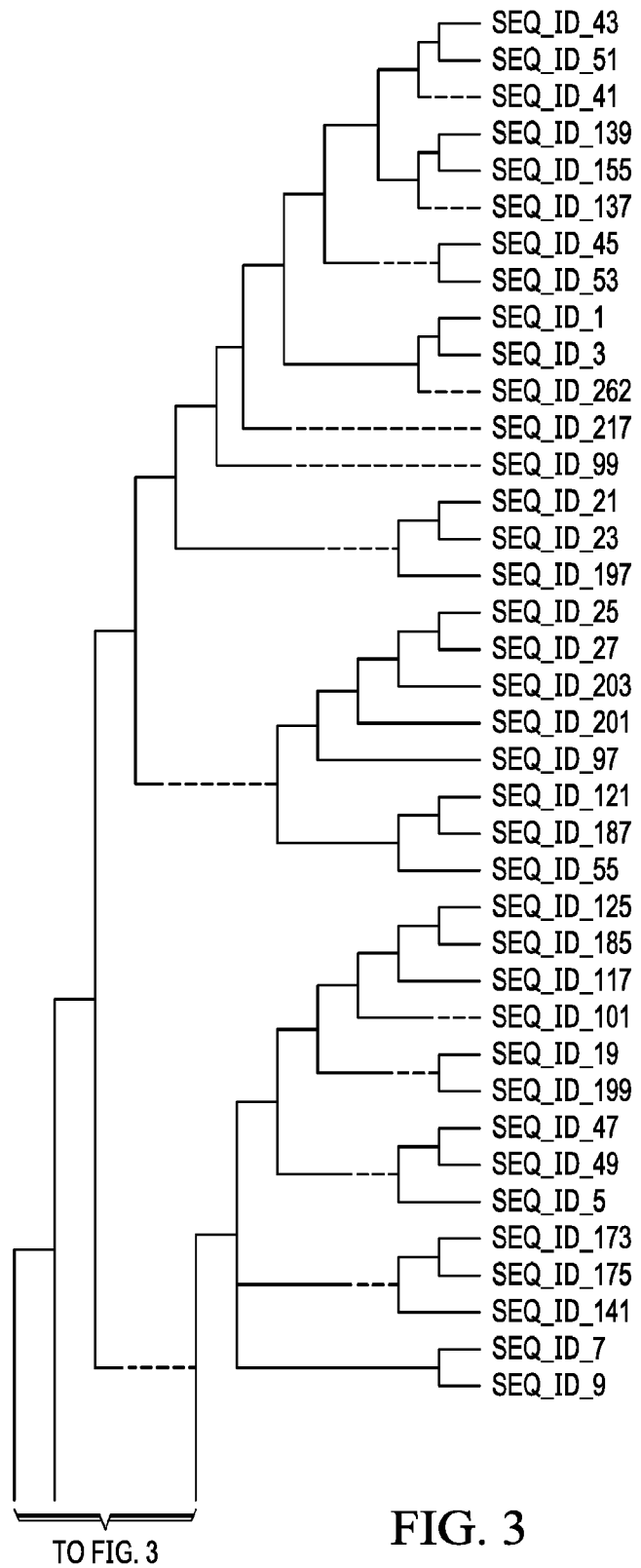
FIG. 3: Shows a phylogenetic tree of orthologs of the KsIAA16 clade from amino acid sequences from *Brassica napus, Glycine max, Triticum aestivum, Gossypium hirsutum, Sorghum bicolor, Zea mays, Vitis vinifera, Cucumis melo, Solanum tuberosum, Solanum lycopersicum, Lactuca sativa, Cucumis sativus, Medicago truncatula*, and *Helianthus annuus*.
Figure 3:
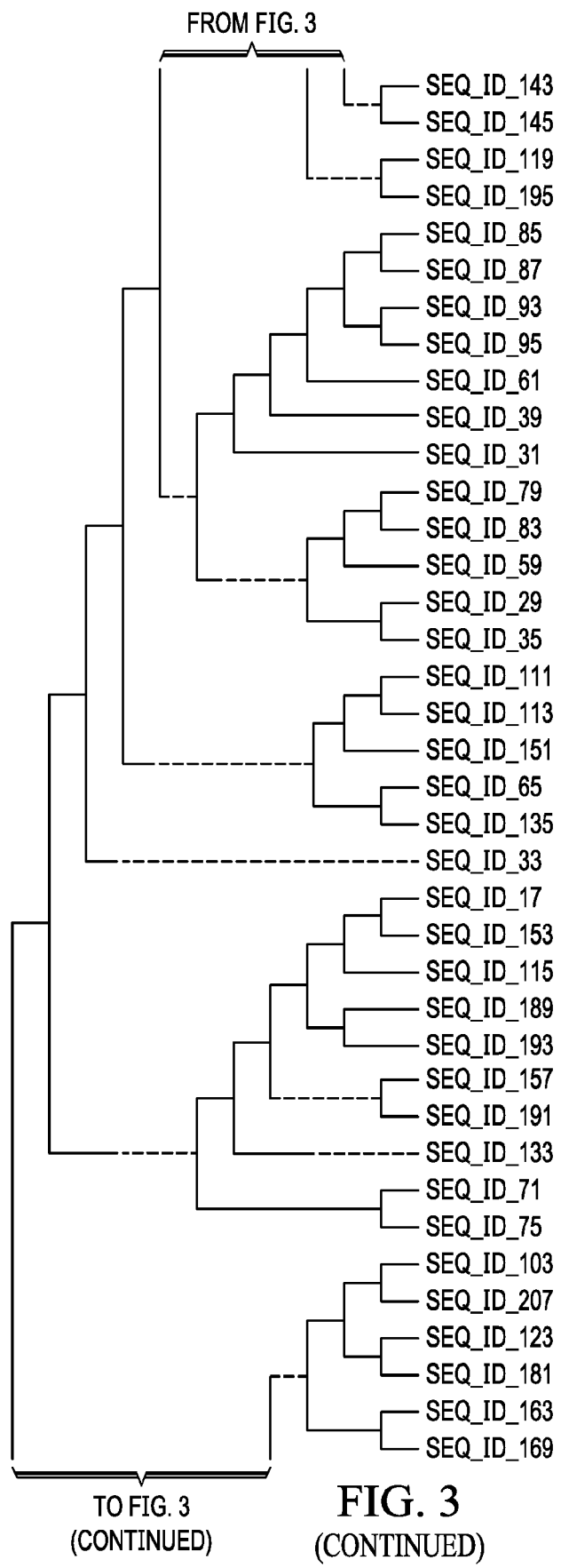
Figure 3:
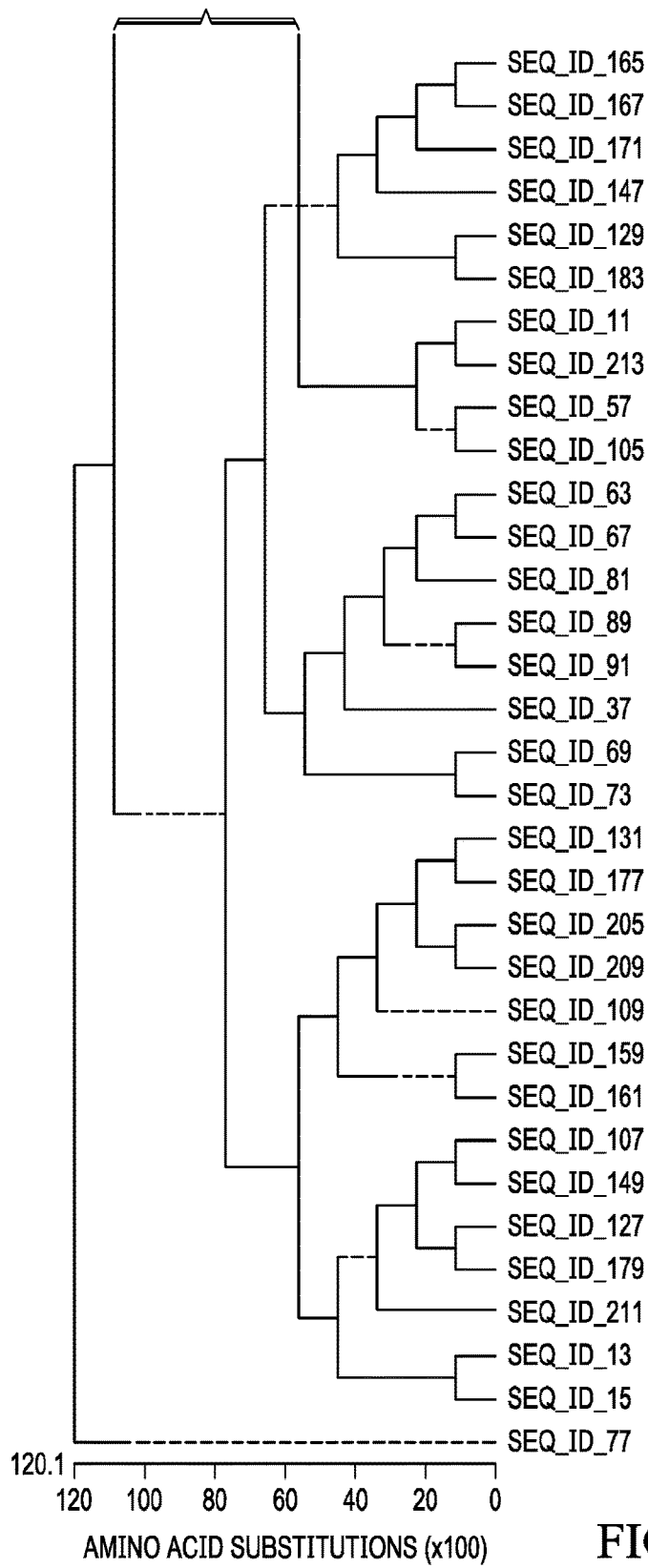

A significant difference between the *Kochia* R and S transcripts was observed. The R biotype exhibited a GG to AA nucleotide change compared to the sequence of transcripts from the S biotype. The GG to AA nucleotide change results in a glycine (G) to asparagine (N) amino acid substitution (FIG. 1). The protein (KsIAA16; SEQ ID NO:217) comprising this amino acid substitution (SEQ ID NO:219) is most closely related to the *Arabidopsis* AUX/IAA protein At.IAA16 (SEQ ID NO:262), which falls into the same clade as At.IAA7 (SEQ ID NO:253), At.IAA14 (SEQ ID NO:260), and At.IAA17 (SEQ ID NO:263) (FIG. 2). The observed amino acid change occurs within a highly conserved degron region (GWPPV/I) (FIG. 1). Changes within this five amino acid degron region have been reported to increase stability of AUX/IAA proteins, and result in dominant auxin resistance in a number of *Arabidopsis* mutants including axr5 (IAA1) (Yang et al., 2004), shy2 (IAA3) (Tian and Reed, 1999), axr2 (IAA7, (SEQ ID NO:247)) (Nagpal et al., 2000), slr (IAA14, (SEQ ID NO:260)) (Fukaki et al., 2002), axr3 (IAA17, (SEQ ID NO:263)) (Rouse et al., 1998), crane (IAA18, (SEQ ID NO:264)) (Uehara et al., 2008), bodenlos (IAA12, (SEQ ID NO:258)) (Hamann et al., 2002), msg2 (IAA19, (SEQ ID NO:265)) (Tatematsu et al., 2004), iaa16 (SEQ ID NO:262) (Rinaldi et al., 2012), and iaa28 (SEQ ID NO:269) (Rogg et al., 2001), as shown in Table 1. These findings indicate that the observed GG to AA nucleotide change, resulting in a glycine (G) to asparagine (N) amino acid substitution in KsIAA16 is likely the basis of the observed dicamba resistance in this *Kochia* biotype.

TABLE 1

Amino acid sequences within the degron domain of *Arabidopsis* gain-of-function AUX/IAA mutants

| Mutant (protein) | wild-type protein | Observed sequence in degron region | | | | |
|---|---|---|---|---|---|---|
| Consensus: | SEQ ID: | G | W | P | P | V/I |
| crane1 (IAA18) | 264 | R | W | P | P | V |
| crane2 (IAA18) | 264 | E | W | P | P | V |
| axr5-1 (IAA1) | 247 | G | W | P | S | V |
| shy2-1 (IAA3) | 249 | G | W | S | P | V |
| shy2-3 (IAA3) | 249 | E | W | P | P | V |
| shy2-6 (IAA3) | 249 | G | W | P | L | V |
| axr2-1 (IAA7) | 253 | G | W | S | P | V |
| bdl (IAA12) | 258 | G | W | S | P | I |
| slr1-1 (IAA14) | 260 | G | W | P | S | V |
| slr1-2 (IAA14) | 260 | G | W | S | P | V |
| slr1-3 (IAA14) | 260 | G | W | A | P | V |
| axr3-1 (IAA17) | 263 | G | W | P | L | V |
| axr3-3 (IAA17) | 263 | G | W | P | P | G |
| axr3-101 (IAA17) | 263 | E | W | P | P | V |
| msg2-1 (IAA19) | 265 | G | W | P | S | V |
| msg2-2 (IAA19) | 265 | R | W | P | P | V |
| msg2-3 (IAA19) | 265 | G | W | P | L | V |
| msg2-4 (IAA19) | 265 | G | W | L | P | V |
| iaa28-1 | 269 | G | W | L | P | V |
| iaa16-1 | 262 | G | W | L | P | V |

Whereas mutations in the highly conserved GWPPV degron sequence have been previously reported to provide resistance to the endogenous auxin compound indole-3-acetic acid (IAA), these mutations have not been observed to impart resistance (e.g., decreased binding affinity) to herbicidal auxin compounds while remaining sensitive (e.g., still capable of binding) to the endogenous auxin IAA. Degron sequence mutants identified in *Arabidopsis* exhibit a significantly altered ability to perceive endogenous IAA resulting in deleterious phenotypes and undesirable off-types.

Example 2: Sequence-Based Identification of TIR/AFB Homologs from *Kochia*

A number of auxin perception pathways have been identified in plants. One of the most well-studied pathways involves the SCF ubiquitin ligase-catalyzed degradation of AUX/IAA transcriptional repressors, which is mediated by the TIR1/AFB family of F-box proteins. In the presence of auxin, TIR1, a subunit of the SCF complex, acts as an auxin receptor. Once TIR1 has bound auxin, it is able to bind members of the AUX/IAA protein family with a high affinity, thereby forming a complex between the two proteins and promoting ubiquitination of the AUX/IAA protein, tagging it for degradation. When AUX/IAA protein is bound to an auxin-bound TIR1 protein, the "GWPPV/I" motif in the degron region of the AUX/IAA protein is believed to be positioned to cover the entire auxin molecule. It has been observed that mutations in the degron motif result in stabilization of the AUX/IAA protein, which in turn leads to a reduced auxin response and a variety of growth defects in plant model systems.

Because AUX/IAA proteins act as auxin co-receptors in concert with TIR/AFB proteins, the identification of putative homologs of TIR/AFB proteins from *Kochia* was undertaken to determine if the KsIAA16 protein interacts with TIR/AFB proteins in the presence of auxins. Such an interaction would indicate that KsIAA16 is an auxin co-receptor.

A BLAST analysis of the *Kochia* transcriptome dataset was performed using known *Arabidopsis* TIR/AFB proteins as the query sequence. Using this approach, four TIR/AFB orthologs were identified in *Kochia*. Proteins were aligned with orthologs TIR1, AFB1, AFB2, AFB3, AFB4, and AFB5 from *Arabidopsis* as well as AFB6 orthologs from *Phoenix dactylifera* L. (date palm) and *Pinus taeda* L. (loblolly pine) (Parry et al., 2009). Alignments were performed using the Clustal W method in MegAlign software (DNASTAR, Madison, Wis.). The results indicated that *Kochia* contains one ortholog from each known clade of the *Arabidopsis* TIR/AFB family.

Example 3: *Kochia* Auxin Response Factors and Auxin Interaction Assay

Yeast two-hybrid (Y2H) studies were conducted using the Matchmaker® Gold Yeast Two-Hybrid System: vectors, transformation protocols and yeast strains (Clonetech Laboratories, Inc.). The coding sequences for the KsIAA16R (SEQ ID NO: 220), KsIAA16S (SEQ ID NO: 218), KsTIR1 (SEQ ID NO: 285), KsAFB6 (SEQ ID NO: 287), KsAFB2 (SEQ ID NO: 289), and KsAFB5 (SEQ ID NO: 291) were PCR amplified using primers specified in Table 2.

TABLE 2

Primer sequences used in Y2H vector construction

| Primer name | SEQ ID NO: | Sequence |
|---|---|---|
| KsIAA16-F | 227 | ATGTTGAGTAACGAGAGAGACAAG |
| KsIAA16-R | 228 | TCAGCTTCTGTTCTTGCACTTCTC |
| KsTIR1-F | 229 | CACCATGGAGCAACACCAACCCCAG |
| KsTIR1-R | 230 | CTTCTTAGCAATCAGCTCAAG |
| KsAFB2-F | 231 | CACCATGAATTATTTCCCAGAAGAAG |
| KsAFB2-R | 232 | CTACAAGGTCCATACGAATTCTG |
| KsAFB6-F | 233 | CACCATGGGTTCAAAAAAGTGCAAAAATTC |
| KsAFB6-R | 234 | TCATAGCGTCAGAACAAAAGGAG |
| KsAFB5-F | 235 | CACCATGAGAGAGGGCACCGATAACAG |
| KsAFB5-R | 236 | CTACAATATCCTCACATGTTC |
| Y2H_KsIAA16-F | 237 | TACGACGTACCAGATTACGCTCATATGTTGAGTAACGAGAGAGACAAG |
| Y2H_KsIAA16-R | 238 | AGCTCGAGCTCGATGGATCCCGAGAAGTGCAAGAACAGAAGCTGA |
| Y2H_TIR1-F | 239 | CTGATCTCAGAGGAGGACCTGCATATGGAGCAACACCAACCCCAG |
| Y2H_TIR1-R | 240 | GGCCGCTGCAGGTCGACGGATCCCTTATTCAGTGCACAACGGTGATGC |
| Y2H_AFB2-F | 241 | CTGATCTCAGAGGAGGACCTGCATATGAATTATTTCCCAGAAGAAG |
| Y2H_AFB2-R | 242 | GGCCGCTGCAGGTCGACGGATCCCTACAAGGTCCATACGAATTCTG |

TABLE 2-continued

Primer sequences used in Y2H vector construction

| Primer name | SEQ ID NO: | Sequence |
|---|---|---|
| Y2H_AFB5-F | 243 | CTGATCTCAGAGGAGGACCTGCATATGAGAGAGGGCACCGATAACAG |
| Y2H_AFB5-R | 244 | GGCCGCTGCAGGTCGACGGATCCCCTACAATATCCTCACATGTTC |
| Y2H_AFB6-F | 245 | CTGATCTCAGAGGAGGACCTGCATATGGGTTCAAAAAAGTGCAAAAATTC |
| Y2H_AFB6-R | 246 | GGCCGCTGCAGGTCGACGGATCCCTCATAGCGTCAGAACAAAAGGAG |

PCR products were gel purified and recombined into NdeI/NotI digested pGADT7 or pGBKT7 vectors using the In-Fusion® cloning system (Clonetech Laboratories, Inc.). The pGBKT7 vector contained the GAL4 DNA binding domain, rendering the fusions as the "bait," whereas the "prey" were the fusions containing the pGADT7 vector, which contained the GAL4 activation domain. All vectors were first sequence verified and then the listed vector combinations were co-transformed into the yeast strain, Y2HGold. The vector combinations were as follows: pGADT7-T+pGBKT7 empty (negative control), pGADT7-T+pGBKT7-Lam (weak interaction control), pGADT7-T+pGBKT7-53 (strong interaction control), pGBKT7 empty was co-transformed with pGADT&KsIAA16 constructs as a negative control, and pGADT7-T was co-transformed with each pGDKT7TIR/AFB construct as a negative control. Transformants were plated on SC-Trp-Leu plates to select for those containing both plasmids. Four healthy colonies were selected at random and resuspended into 300 µL of 0.1% agar in water. Five µL of this dilution was replica spotted onto each plate. Plates were incubated at 30° C. for 3 days prior to evaluation of colony growth.

This method enabled the study of the binding/interaction of the *Kochia* R and S alleles of KsIAA16 with each of the *Kochia* TIR/AFB homologs (KsTIR1 (SEQ ID NO: 285), and KsAFB6 (SEQ ID NO: 287)) in the absence or presence of 100 µM or 500 µM exogenous concentrations of IAA, NAA, dicamba, and 2,4-D, picloram, triclopyr, quinclorac, fluroxypyr or phenylacetic acid (PAA). All combinations of bait and prey vectors displayed good growth in the absence of selection, which indicated that transcript expression did not have any inherent negative effects on yeast growth. The results obtained from the Y2H assays are shown in Table 3 and Table 4.

TABLE 3

Y2H assay results testing KsIAA16S and KsIAA16R binding with KsTIR1

| | Ability to bind in combination with KsTIR1 | | | |
|---|---|---|---|---|
| allele: | KsIAA16S | | KsIAA16R | |
| auxin: | [100 mM] | [500 mM] | [100 mM] | [500 mM] |
| no auxin | — | | — | |
| IAA | +++ | +++ | ++ | +++ |
| NAA | +++ | +++ | +++ | +++ |
| Dicamba | +++ | +++ | − | − |
| 2,4-D | + | +++ | − | − |

TABLE 3-continued

Y2H assay results testing KsIAA16S
and KsIAA16R binding with KsTIR1

| allele: | Ability to bind in combination with KsTIR1 | | | |
|---|---|---|---|---|
| | KsIAA16S | | KsIAA16R | |
| auxin: | [100 mM] | [500 mM] | [100 mM] | [500 mM] |
| Picloram | − | − | − | − |
| Triclopyr | − | ++ | − | − |
| Quinclorac | − | − | − | − |
| Fluroxypyr | − | − | − | − |
| PAA | − | − | − | − |

TABLE 4

Y2H assay results testing KsIAA16S
and KsIAA16R binding with KsAFB6

| allele: | Ability to bind in combination with KsAFB6 | | | |
|---|---|---|---|---|
| | KsIAA16S | | KsIAA16R | |
| auxin: | [100mM] | [500mM] | [100mM] | [500mM] |
| no auxin | — | | — | |
| IAA | +++ | +++ | − | ++ |
| NAA | +++ | +++ | − | ++ |
| Dicamba | − | − | − | − |
| 2,4-D | − | +++ | − | − |
| Picloram | − | +++ | − | − |
| Triclopyr | +++ | +++ | − | − |
| Quinclorac | − | +++ | − | − |
| Fluroxyp yr | − | − | − | − |
| PAA | − | − | − | − |

In the absence of auxin, little to no growth was observed for both the R and S alleles of KsIAA16 with the KsTIR1 and KsAFB6 orthologs, indicating the proteins do not interact in the absence of auxin. KsIAA16S exhibited interaction with KsTIR1 in the presence of both 100 μM and 500 μM IAA, 2-(1-naphthyl) acetic acid (NAA), dicamba, and 2,4-D, as well as 500 μM triclopyr, but KsIAA16R only exhibited interaction with KsTIR1 in the presence of 100 μM and 500 μM IAA and NAA. KsIAA16R exhibited a decreased ability to interact with KsTIR1 in the presence of dicamba and 2,4-D. Not wishing to be bound by a particular theory, a decreased interaction KsIAA16R of with KsTIR1 in the presence of dicamba and 2,4-D resulting in increased stability of KsIAA16R in the presence of dicamba and 2,4-D would explain the resistance to these compounds observed in the dicamba resistant *Kochia* biotype. Similarly, KsIAA16S was observed to interact with KsAFB6 in the presence of 100 μM and 500 μM IAA, NAA, and triclopyr and 500 μM 2,4-D, picloram and quinclorac, but an interaction between KsIAA16R and KsAFB6 was only observed in the presence of the highest concentration of IAA and NAA tested (500 μM). This indicates that KsIAA16R has a reduced ability to interact with KsAFB6 in the presence of IAA and NAA, as only the higher concentration could facilitate binding, and an interaction between KsIAA16R and KsAFB6 was not observed in the presence of triclopyr, 2,4-D, quinclorac, or picloram at the concentrations tested. No interaction in the presence of PAA or fluroxypyr was observed with any of the protein combinations tested. Not wishing to be bound by a particular theory, the lack of observed Y2H interaction in the presence of fluroxypyr may be due to either an unstable interaction that prevents detection in the yeast system, or may be due to lack of metabolism of the fluroxypyr methylheptyl ester, which plants and bacteria are reported to cleave and release as free acid. These findings indicate that KsIAA16 functions as an auxin co-receptor in concert with KsTIR1 and/or KsAFB6, and that the combination of KsIAA16 with KsTIR1 and/or KsAFB6 is responsible, at least in part, for the perception of each of these auxin herbicides. Furthermore, this is the first reported characterization of an AFB6 homolog, as this clade has been lost from several of the more studied species including *Arabidopsis*, rice, sorghum, and maize (Hayashi, 2012; Mironova et al., 2010; Parry et al., 2009). Not wishing to be bound by a particular theory, these findings indicate that KsAFB6 can function as an auxin co-receptor, and in concert with KsIAA16, KsAFB6 is capable of interacting in the presence of several tested auxin herbicides.

Example 4: Characterization of Auxin-Mediated
Root Elongation Response in Dicamba-Resistant
and Dicamba-Sensitive *Kochia*

The root elongation response of seedlings from the R and S *Kochia* biotypes was tested to determine if the R biotype response was consistent with the Y2H findings. For root elongation studies, plant nutrient media was used, with 0.5% sucrose. Seeds were surface sterilized in 30% bleach with 0.1% Triton-X100 for 10 to 30 minutes, then rinsed twice in sterile water and resuspended in 0.1% agar for plating. Root lengths were measured to the nearest millimeter, and the average root length of 12 individuals was calculated unless otherwise noted. The root elongation data, shown in FIG. 5, show that the R *Kochia* biotype remained sensitive to root elongation inhibition by IAA and NAA, but was resistant to inhibition by dicamba, and 2,4-D. Additionally it was observed that the R biotype displayed a short root phenotype in the absence of auxin. These findings are consistent with the observed Y2H results showing that at the concentrations tested, IAA and NAA can facilitate some interaction of KsIAA16R with KsTIR1 and/or KsAFB6, but dicamba, 2,4-D, picloram, triclopyr, quinclorac, and fluroxypyr cannot. It appeared that the native auxin PAA also had an effect on root elongation. The observation outlined herein, in addition with the Y2H results, provide further support for the hypothesis that the auxin resistance observed in this *Kochia* biotype is due to the mutation in KsIAA16R.

Example 5: Development of Molecular Markers for
the KsIAA16R Allele

Based on the identified base pair substitutions in KsIAA16 between the S and R *Kochia* biotypes, a restriction fragment length polymorphism (RFLP) assay and a Taqman® assay were developed for the purposes of genotyping.

For the RFLP assay, forward primer (SEQ ID NO: 221) and reverse primer (SEQ ID NO: 222) were designed to amplify a 146 bp product from genomic DNA of both resistant and susceptible plants. The mutation identified in the R biotype was found to generate an additional MluCI restriction site in the KsIAA16R allele. This allowed for the R and S alleles to be distinguished when digested products are run on a 4% agarose gel, given that the S allele product has only two MluCI restriction endonuclease cleavage sites and generates fragments of 120, 19, and 7 base pairs following digestion, whereas the R allele has three cleavage sites and generates fragments of 90, 30, 19, and 7 base pairs.

For the Taqman® assay, the forward primer (SEQ ID NO: 223) and the reverse primer (SEQ ID NO: 224) were designed to amplify the genomic DNA of both KsIAA16 alleles. The VIC-labeled probe (SEQ ID NO: 225) was designed to detect the R allele, and the FAM-labeled probe (SEQ ID NO: 226) was designed to detect the S allele. Each PCR reaction was performed using Taqman assay mix and TaqMan® universal master mix II in a 20 µL final volume in a 96-well plate. Assays were performed according to manufacturer conditions on a ViiA7 System (Applied Biosystems) using standard Taqman genotyping assay conditions of 95° C. for 15 sec, 60° C. for 60 sec with a plate read every cycle for 40 cycles. Allele calls were designated by the ViiA7 software, and known homozygous Kochia R and S genomic DNA, as well as no-DNA controls, were included in each experiment. These markers can be used for both detection of the R allele in individuals from field populations as well as to determine the genotypes of plants resulting from crossing events to allow determination of segregation patterns and for fitness studies.

Example 6: Segregation Patterns of the Dicamba Resistance Trait in Kochia

To determine whether the KsIAA16R allele co-segregates with the dicamba resistance phenotype, spray tests were performed on Kochia populations comprising S and R plants. Crosses between S and R individuals were performed, utilizing the S biotype as the female and the R biotype as the male in order to identify individuals resulting from cross pollination. Because of the anatomy of Kochia reproductive organs, preventing some self-pollination is difficult, however, utilization of the Taqman® genotyping assay enabled distinction between progeny were heterozygous for KsIAA16 (R/S) versus progeny resulting from simple pollination (S/S). Several verified heterozygous $F_1$ plants were selected for F2 seed production. In addition, a subset of S/S and R/S individuals from the $F_1$ generation was subjected to dicamba sprays to ensure that the marker could effectively identify the R allele. A perfect correlation was observed between plants that were determined to be heterozygous for the R allele and plants that showed resistance to dicamba in the $F_1$ spray test. This result indicates dicamba resistance is a dominant or semi-dominant trait.

To determine whether the KsIAA16R allele co-segregates with the dicamba resistance phenotype, 720 $F_2$ progeny from verified heterozygous $F_1$ parental plants were sampled and genotyped, and tolerance to a dicamba spray concentration double the typical dicamba field use rate (1120 g/ha) was determined. Plant identity was maintained throughout the experiment, and genotype and percent visible dicamba injury was determined for each of the F2 progeny. The average injury per genotype was about 80% for S/S, about 40% for R/S, and about 20% for R/R. Based on the Taqman genotyping assay, 234 homozygous sensitive plants (S/S), 371 heterozygous plants (R/S), and 105 homozygous resistant plants (R/R), were identified. Fourteen plants returned an undetermined genotype, thus representing a 2% PCR reaction failure rate. These genotype numbers are significantly different (1:1.6:0.4) than the expected Mendelian 1:2:1 segregation pattern (P<0.05), indicating that germination and/or seedling establishment may be impacted by the resistance allele. A strong correlation was found between the genotype results and the observed dicamba injury, with a mean injury rating of 82.3% for S/S individuals, 35.9% for R/S individuals, and 24.6% for R/R individuals. Statistical analysis of these data using ANOVA indicated with high certainty that the dicamba resistance phenotype is associated with the presence of the KsIAA16R allele (p<0.0001), and Cramer-von Mises statistical analysis showed the trait to be semi-dominant.

Example 7: Expression and Testing of KsIAA16 in Arabidopsis thaliana

To determine if the presence of the KsIAA16R allele alone was necessary and sufficient to confer dicamba resistance, several transgene expression constructs were generated for study of KsIAA16 in Arabidopsis. Agrobacterium tumefaciens was used to introduce the binary vectors in the plants using the floral dip method (Clough and Bent, 1998). Vectors contained either the ethanol inducible alcA promoter elements (Salter et al., 1998), the constitutive CaMV35S promoter, or the native Arabidopsis IAA16 promoter (AtIAA16P) driving either KsIAA16R (SEQ ID NO: 220) or KsIAA16S (SEQ ID NO: 218). GUS reporter constructs contained a 2.5 kb genomic DNA fragment from directly upstream of KsIAA16, which is expected to contain most of the promoter elements as well as the 5'UTR, driving uidA. All constructs contained either a Spectinomycin resistance gene (SPEC) or a glufosinate resistance gene (BAR) in the T-DNA region to serve as the selectable marker. For all constructs, T1 seed was harvested, surface sterilized, and plated on the appropriate selective media to identify independent T1 transformants. Single seed decent and segregation on selective media was used to estimate transgene insertion number and identify homozygous lines. For induction of the P-Alc promoter, ethanol was added to a final concentration of 0.01% just before plates were poured, and plates were used immediately. All plates were grown in a Percival growth chamber (Percival Scientific, Inc.) at 22° C. with 16 hour day/8 hour night light cycle and a light intensity of 200 mol/min/m$^2$. Relative humidity was maintained at 50%. GUS assays were performed according to standard protocols. Briefly, a 20 mg/mL X-Gluc (GoldBio, St. Louis, Mo.) stock in dimethylformamide was diluted into 50 mM phosphate buffer, pH 7.0, to a final concentration of 1 mg/mL. This solution was added to plant tissues, and samples were placed under vacuum for 5 minutes to ensure penetration of the solution into the tissues. Samples were covered in foil to prevent light entry and place at 37° C. for 24 hours to allow color development. Staining solution was removed and chlorophyll was cleared by incubating samples in 50% ethanol for several hours. For seedling arrest counts, seedlings that displayed radical protrusion, but whose root never reached a length of more than 2-3 mm at 8 days after plating were considered arrested.

A large percentage of seedlings from lines carrying the 35S:KsIAA16 constructs and the P-Alc:KsIAA16 constructs appeared to arrest shortly after germination, potentially due to high levels of constitutive/basal expression (Table 5). Induction of expression from the P-Alc promoter using 0.01% ethanol increased arrest rates slightly, but not significantly. There was no difference in the 35S:KsIAA16 line in the presence or absence of ethanol.

TABLE 5

Transgenic Arabidopsis seedling arrest data

| Construct | % Arrested Seedlings Uninduced | % Arrested Seedlings Induced |
| --- | --- | --- |
| None (non-transgenic WT) | 1.62 ± 0.94 | 4.15 ± 0.19 |
| P-Alc:KsIAA16S | 57.2 ± 10.7 | 76.4 ± 9.83 |
| P-Alc:KsIAA16R | 34.3 ± 15.4 | 46.1 ± 10.5 |

TABLE 5-continued

Transgenic *Arabidopsis* seedling arrest data

| Construct | % Arrested Seedlings Uninduced | % Arrested Seedlings Induced |
|---|---|---|
| 35S:KsIAA16S | 78.2 ± 4.73 | 77.2 ± 6.11 |
| 35S:KsIAA16R | 45.4 ± 14.4 | 42.6 ± 11.7 |

Lines carrying AtIAA16P:KsIAA16 constructs did not appear to have significant amounts of seedling arrest, and thus were used for further study. As shown in Table 6, four independent transformant lines carrying AtIAA16P:KsIAA16R showed resistance to dicamba in a root elongation inhibition assay, whereas only one of the four lines carrying AtIAA16P:KsIAA16S showed very slight resistance. Several lines from both constructs also showed slight resistance to root inhibition by IAA. Taken together, these data support the hypothesis that the KsIAA16R allele functions in *Arabidopsis* similar to the way it functions in *Kochia*. In addition it appears that the putative overexpression of the KsIAA16S allele can sometimes cause resistance to exogenous auxins, albeit to a lesser extent. Not wishing to be bound by a particular theory, this may be due to an increased amount of total AUX/IAA protein present as compared to that in a wild-type plant, as slightly increased resistance to IAA in root elongation assays has been previously reported to result from the heterologous expression of the wild-type AUX/IAA gene PtrIAA14 (Liu et al., 2015). In aggregate, these results suggest that the expression pattern/magnitude of the KsIAA16 transgene affects auxin perception, since only those with the endogenous promoter of the closest *Arabidopsis* homolog (AtAA16P) produced plants with minimal off-types.

TABLE 6

Root Length (in mm) of T2 transgenics on plant nutrient plus IAA or dicamba

| Construct Line: | No auxin | +5 μM IAA | +5 μM Dicamba |
|---|---|---|---|
| non-transgenic WT | 26.67 ± 0.96 | 5.83 ± 0.24 | 9.08 ± 0.66 |
| AtIAA16P:KsIAA16S_T2-1 | 28.0 ± 0.88 | 7.0 ± 0.77 | 13.50 ± 1.01 |
| AtIAA16P:KsIAA16S_T2-2 | 27.67 ± 1.67 | 9.5 ± 0.84 | 11.42 ± 1.28 |
| AtIAA16P:KsIAA16S_T2-3 | 30.58 ± 2.14 | 5.67 ± 0.54 | 14.17 ± 0.9 |
| AtIAA16P:KsIAA16S_T2-4 | 28.92 ± 1.1 | 5 ± 0.34 | 10.67 ± 0.72 |
| AtIAA16P:KsIAA16R_T2-1 | 30.83 ± 1.87 | 12.17 ± 1.01 | 12.42 ± 1.27 |
| AtIAA16P:KsIAA16R_T2-2 | 29 ± 1.8 | 18.17 ± 3.09 | 15.5 ± 1.45 |
| AtIAA16P:KsIAA16R_T2-3 | 36.92 ± 1.91 | 22.75 ± 2.09 | 15.58 ± 1.57 |
| AtIAA16P:KsIAA16R_T2-4 | 38.25 ± 2.11 | 27.25 ± 1.88 | 17.5 ± 2.12 |

To understand the expression patterns of KsIAA16 and how spatiotemporal expression compares with the observed *Kochia* resistance phenotypes, northern analysis of *Kochia* tissue was performed. Additionally a KsIAA16 promoter (P):β-glucuronidase (GUS) reporter construct was generated and transformed in *Arabidopsis* to allow visualization of KsIAA16 expression in a heterologous system. Visualization of expression patterns of the KsIAA16P:GUS construct in *Arabidopsis* by X-gluc staining indicated that the reporter was not expressed in dry or imbibed seed, but was strongly expressed at or just after germination. Expression appeared broadly throughout most tissues, with the highest levels apparent in vasculature tissues and lateral root primordial. Expression remained strong throughout development, with diffuse staining apparent throughout all leaves and in inflorescence tissues and appearing strongest in vascular tissues. Staining was also apparent in the pollen and carpels in flowers, the septum of young siliques, and the abscission zones of mature siliques. Northern blot analysis of *Kochia* tissues from both sensitive and resistant lines showed that endogenous alleles of the KsIAA16 transcript were transcribed in all tissues analyzed. This broad expression pattern for KsIAA16 may explain the strong resistance to foliar dicamba sprays.

Example 8: Modification of AUX/IAA Genes in Crop Plants

Based on the identified base pair substitutions that result in a glycine to asparagine amino acid change within the degron domain of the KsIAA16 protein, corresponding base pair substitutions can be made in IAA16 orthologs of crops plants, such as maize, sorghum, wheat, canola, soy, cotton, grapes, tomato, potato, lettuce, broccoli, cucumber, peanut, melon, leeks, onion, rice, barley, or other orthologs identified herein. These sequences may be modified using targeted genome editing (e.g., single-stranded oligonucleotide-mediated genome editing, meganucleases, zinc finger nucleases, TALENs, or RNA-guided nuclease (e.g., CRISPR technology).

TABLE 7

Orthologs of the KsIAA16 clade

| Designation | SEQ ID NO | DNA/PRT | Species |
|---|---|---|---|
| MRT3708_6332P.5 | 1 | PRT | *Brassica napus* |
| MRT3708_6332C.5 | 2 | DNA | *Brassica napus* |
| MRT3708_5638P.5 | 3 | PRT | *Brassica napus* |
| MRT3708_5638C.5 | 4 | DNA | *Brassica napus* |
| MRT3708_56595P.2 | 5 | PRT | *Brassica napus* |
| MRT3708_56595C.2 | 6 | DNA | *Brassica napus* |
| MRT3708_12408P.4 | 7 | PRT | *Brassica napus* |
| MRT3708_12408C.4 | 8 | DNA | *Brassica napus* |
| MRT3708_40183P.1 | 9 | PRT | *Brassica napus* |
| MRT3708_40183C.1 | 10 | DNA | *Brassica napus* |
| MRT3708_19539P.5 | 11 | PRT | *Brassica napus* |
| MRT3708_19539C.5 | 12 | DNA | *Brassica napus* |
| MRT3708_62039P.1 | 13 | PRT | *Brassica napus* |
| MRT3708_62039C.1 | 14 | DNA | *Brassica napus* |
| MRT3708_38282P.2 | 15 | PRT | *Brassica napus* |
| MRT3708_38282C.2 | 16 | DNA | *Brassica napus* |
| MRT3708_11965P.4 | 17 | PRT | *Brassica napus* |
| MRT3708_11965C.4 | 18 | DNA | *Brassica napus* |
| MRT3847_266780P.5 | 19 | PRT | *Glycine max* |
| MRT3847_266780C.5 | 20 | DNA | *Glycine max* |
| MRT3847_64144P.5 | 21 | PRT | *Glycine max* |
| MRT3847_64144C | 22 | DNA | *Glycine max* |
| MRT3847_57460P.4 | 23 | PRT | *Glycine max* |
| MRT3847_57460C | 24 | DNA | *Glycine max* |
| MRT3847_273343P.3 | 25 | PRT | *Glycine max* |
| MRT3847_273343C | 26 | DNA | *Glycine max* |
| MRT3847_343242P.1 | 27 | PRT | *Glycine max* |
| MRT3847_343242C | 28 | DNA | *Glycine max* |
| MRT4565_269292P.2 | 29 | PRT | *Triticum aestivum* |
| MRT4565_269292C | 30 | DNA | *Triticum aestivum* |
| MRT4565_281861P.1 | 31 | PRT | *Triticum aestivum* |
| MRT4565_281861C | 32 | DNA | *Triticum aestivum* |
| MRT4565_280751P | 33 | PRT | *Triticum aestivum* |
| MRT4565_280751C | 34 | DNA | *Triticum aestivum* |

TABLE 7-continued Orthologs of the KsIAA16 clade

| Designation | SEQ ID NO | DNA/PRT | Species |
|---|---|---|---|
| MRT4565_221930P.2 | 35 | PRT | Triticum aestivum |
| MRT4565_221930C | 36 | DNA | Triticum aestivum |
| MRT4565_291685P.1 | 37 | PRT | Triticum aestivum |
| MRT4565_291685C | 38 | DNA | Triticum aestivum |
| MRT4565_219014P.2 | 39 | PRT | Triticum aestivum |
| MRT4565_219014C | 40 | DNA | Triticum aestivum |
| MRT3635_87572P.1 | 41 | PRT | Gossypium hirsutum |
| MRT3635_87572C | 42 | DNA | Gossypium hirsutum |
| MRT3635_79125P.1 | 43 | PRT | Gossypium hirsutum |
| MRT3635_79125C | 44 | DNA | Gossypium hirsutum |
| MRT3635_25740P.3 | 45 | PRT | Gossypium hirsutum |
| MRT3635_25740C | 46 | DNA | Gossypium hirsutum |
| MRT3635_4714P.2 | 47 | PRT | Gossypium hirsutum |
| MRT3635_4714C | 48 | DNA | Gossypium hirsutum |
| MRT3635_86248P.1 | 49 | PRT | Gossypium hirsutum |
| MRT3635_86248C | 50 | DNA | Gossypium hirsutum |
| MRT3635_90266P.1 | 51 | PRT | Gossypium hirsutum |
| MRT3635_90266C | 52 | DNA | Gossypium hirsutum |
| MRT3635_81130P.1 | 53 | PRT | Gossypium hirsutum |
| MRT3635_81130C | 54 | DNA | Gossypium hirsutum |
| MRT3635_11021P.3 | 55 | PRT | Gossypium hirsutum |
| MRT3635_11021C | 56 | DNA | Gossypium hirsutum |
| MRT3635_21712P.3 | 57 | PRT | Gossypium hirsutum |
| MRT3635_21712C | 58 | DNA | Gossypium hirsutum |
| MRT4558_20126P.2 | 59 | PRT | Sorghum bicolor |
| MRT4558_20126C | 60 | DNA | Sorghum bicolor |
| MRT4558_15323P.2 | 61 | PRT | Sorghum bicolor |
| MRT4558_15323C | 62 | DNA | Sorghum bicolor |
| MRT4558_11520P.3 | 63 | PRT | Sorghum bicolor |
| MRT4558_11520C | 64 | DNA | Sorghum bicolor |
| MRT4558_39366P.1 | 65 | PRT | Sorghum bicolor |
| MRT4558_39366C | 66 | DNA | Sorghum bicolor |
| MRT4558_41876P.2 | 67 | PRT | Sorghum bicolor |
| MRT4558_41876C | 68 | DNA | Sorghum bicolor |
| MRT4558_19650P.2 | 69 | PRT | Sorghum bicolor |
| MRT4558_19650C | 70 | DNA | Sorghum bicolor |
| MRT4558_17725P.2 | 71 | PRT | Sorghum bicolor |
| MRT4558_17725C | 72 | DNA | Sorghum bicolor |
| MRT4558_31221P.1 | 73 | PRT | Sorghum bicolor |
| MRT4558_31221C | 74 | DNA | Sorghum bicolor |
| MRT4558_18424P.2 | 75 | PRT | Sorghum bicolor |
| MRT4558_18424C | 76 | DNA | Sorghum bicolor |
| MRT4558_25019P.2 | 77 | PRT | Sorghum bicolor |
| MRT4558_25019C | 78 | DNA | Sorghum bicolor |
| Zm_B73_CR03.G1573030.2 | 79 | PRT | Zea mays |
| Zm_B73_CR03.G1573030.2 | 80 | DNA | Zea mays |
| Zm_B73_CR06.G1567330.4 | 81 | PRT | Zea mays |
| Zm_B73_CR06.G1567330.4 | 82 | DNA | Zea mays |
| Zm_B73_CR03.G1573030.3 | 83 | PRT | Zea mays |
| Zm_B73_CR03.G1573030.3 | 84 | DNA | Zea mays |
| Zm_B73_CR05.G107360.1 | 85 | PRT | Zea mays |
| Zm_B73_CR05.G107360.1 | 86 | DNA | Zea mays |
| Zm_B73_CR05.G107360.4 | 87 | PRT | Zea mays |
| Zm_B73_CR05.G107360.4 | 88 | DNA | Zea mays |
| Zm_B73_CR08.G1372595.4 | 89 | PRT | Zea mays |
| Zm_B73_CR08.G1372595.4 | 90 | DNA | Zea mays |
| Zm_B73_CR08.G1372595.2 | 91 | PRT | Zea mays |
| Zm_B73_CR08.G1372595.2 | 92 | DNA | Zea mays |
| Zm_B73_CR05.G107360.3 | 93 | PRT | Zea mays |
| Zm_B73_CR05.G107360.3 | 94 | DNA | Zea mays |
| Zm_B73_CR05.G107360.6 | 95 | PRT | Zea mays |
| Zm_B73_CR05.G107360.6 | 96 | DNA | Zea mays |
| Grape_G23841001 | 97 | PRT | Vitis vinifera |
| Vv_pn_G23841001.cds | 98 | DNA | Vitis vinifera |
| Grape_G07456001 | 99 | PRT | Vitis vinifera |
| Vv_pn_G07456001.cds | 100 | DNA | Vitis vinifera |
| Grape_G20121001 | 101 | PRT | Vitis vinifera |
| Vv_pn_G20121001.cds | 102 | DNA | Vitis vinifera |
| Grape_G16706001 | 103 | PRT | Vitis vinifera |
| Vv_pn_G16706001.cds | 104 | DNA | Vitis vinifera |
| Grape_G34355001 | 105 | PRT | Vitis vinifera |
| Vv_pn_G34355001.cds | 106 | DNA | Vitis vinifera |
| Grape_G15048001 | 107 | PRT | Vitis vinifera |
| Vv_pn_G15048001.cds | 108 | DNA | Vitis vinifera |
| Grape_G13515001 | 109 | PRT | Vitis vinifera |
| Vv_pn_G13515001.cds | 110 | DNA | Vitis vinifera |
| Grape_G16808001 | 111 | PRT | Vitis vinifera |
| Vv_pn_G16808001.cds | 112 | DNA | Vitis vinifera |
| Grape_G34468001 | 113 | PRT | Vitis vinifera |
| Vv_pn_G34468001.cds | 114 | DNA | Vitis vinifera |
| Grape_G23840001 | 115 | PRT | Vitis vinifera |
| Vv_pn_G23840001.cds | 116 | DNA | Vitis vinifera |
| Melon_CR05.G1184860.1 | 117 | PRT | Cucumis melo |
| CumMe_WSH_CR05.G1184860.1.cds | 118 | DNA | Cucumis melo |
| Melon_CR05.G8296840.1 | 119 | PRT | Cucumis melo |
| CumMe_WSH_CR05.G8296840.1.cds | 120 | DNA | Cucumis melo |
| Melon_CR01.G21880170 | 121 | PRT | Cucumis melo |
| CumMe_WSH_CR01.G21880170.1.cds | 122 | DNA | Cucumis melo |
| Melon_CR02.G13303860.1 | 123 | PRT | Cucumis melo |
| CumMe_WSH_CR02.G13303860.1.cds | 124 | DNA | Cucumis melo |
| Melon_CR04.G42703650.1 | 125 | PRT | Cucumis melo |
| CumMe_WSH_CR04.G42703650.1.cds | 126 | DNA | Cucumis melo |
| Melon_CR03.G513090.1 | 127 | PRT | Cucumis melo |
| _WSH_CR03.G513090.1.cds | 128 | DNA | Cucumis melo |
| Melon_CR01.G27930430.1 | 129 | PRT | Cucumis melo |
| CumMe_WSH_CR01.G27930430.1.cds | 130 | DNA | Cucumis melo |
| Melon_CR08.G2010270.1 | 131 | PRT | Cucumis melo |
| CumMe_WSH_CR08.G2010270.1.cds | 132 | DNA | Cucumis melo |
| Melon_CR01.G21857860.1 | 133 | PRT | Cucumis melo |
| CumMe_WSH_CR01.G21857860.1.cds | 134 | DNA | Cucumis melo |
| Melon_CR05.G1129600.1 | 135 | PRT | Cucumis melo |
| CumMe_WSH_CR05.G1129600.1.cds | 136 | DNA | Cucumis melo |
| solanum_tuberosum_NM_001288469 | 137 | PRT | Solanum tuberosum |

TABLE 7-continued

Orthologs of the KsIAA16 clade

| Designation | SEQ ID NO | DNA/PRT | Species |
|---|---|---|---|
| solanum_tuberosum_NM_001288469 | 138 | DNA | Solanum tuberosum |
| Tomato_H1706_CR01.G10036700.2.pep | 139 | PRT | Solanum lycopersicum |
| S1_H1706_CR01.G10036700.2.cds | 140 | DNA | Solanum lycopersicum |
| Tomato_H1706_CR09.G9206940.1.pep | 141 | PRT | Solanum lycopersicum |
| S1_H1706_CR09.G9206940.1.cds | 142 | DNA | Solanum lycopersicum |
| Tomato_H1706_CR06.G6397690.1.pep | 143 | PRT | Solanum lycopersicum |
| S1_H1706_CR06.G6397690.1.cds | 144 | DNA | Solanum lycopersicum |
| Tomato_H1706_CR06.G1533090.1.pep | 145 | PRT | Solanum lycopersicum |
| S1_H1706_CR06.G1533090.1.cds | 146 | DNA | Solanum lycopersicum |
| Tomato_H1706_CR03.G6662920.1.pep | 147 | PRT | Solanum lycopersicum |
| S1_H1706_CR03.G6662920.1.cds | 148 | DNA | Solanum lycopersicum |
| Tomato_H1706_CR04.G9333290.1.pep | 149 | PRT | Solanum lycopersicum |
| S1_H1706_CR04.G9333290.1.cds | 150 | DNA | Solanum lycopersicum |
| Tomato_H1706_CR03.G6654390.1.pep | 151 | PRT | Solanum lycopersicum |
| S1_H1706_CR03.G6654390.1.cds | 152 | DNA | Solanum lycopersicum |
| Tomato_H1706_CR09.G9201650.1.pep | 153 | PRT | Solanum lycopersicum |
| S1_H1706_CR09.G9201650.1.cds | 154 | DNA | Solanum lycopersicum |
| Tomato_H1706_CR01.G10036700.1.pep | 155 | PRT | Solanum lycopersicum |
| S1_H1706_CR01.G10036700.1.cds | 156 | DNA | Solanum lycopersicum |
| Tomato_H1706_UN.G146.1.pep | 157 | PRT | Solanum lycopersicum |
| S1_H1706_UN.G146.1.cds | 158 | DNA | Solanum lycopersicum |
| Ls_CR03.G18217910.3.pep | 159 | PRT | Lactuca sativa |
| Ls_CR03.G18217910.3.cds | 160 | DNA | Lactuca sativa |
| Ls_CR04.G10487150.1.pep | 161 | PRT | Lactuca sativa |
| Ls_CR04.G10487150.1.cds | 162 | DNA | Lactuca sativa |
| Ls_CR00.G117220650.1.pep | 163 | PRT | Lactuca sativa |
| Ls_CR00.G117220650.1.cds | 164 | DNA | Lactuca sativa |
| Ls_CR04.G31733300.1. | 165 | PRT | Lactuca sativa |
| Ls_CR04.G31733300.1.cds | 166 | DNA | Lactuca sativa |
| Ls_CR05.G19800880.1.pep | 167 | PRT | Lactuca sativa |
| Ls_CR05.G19800880.1.cds | 168 | DNA | Lactuca sativa |
| Ls_CR07.G13339890.1.pep | 169 | PRT | Lactuca sativa |
| Ls_CR07.G13339890.1.cds | 170 | DNA | Lactuca sativa |
| Ls_CR01.G11430140.2.pep | 171 | PRT | Lactuca sativa |
| Ls_CR01.G11430140.2.cds | 172 | DNA | Lactuca sativa |
| Ls_CR03.G4757280.1.pep | 173 | PRT | Lactuca sativa |
| Ls_CR03.G4757280.1.cds | 174 | DNA | Lactuca sativa |
| Ls_CR00.G147430470.1.pep | 175 | PRT | Lactuca sativa |
| Ls_CR00.G147430470.1.cds | 176 | DNA | Lactuca sativa |
| CumSa_CL_CR06.G5192480.1.pep | 177 | PRT | Cucumis sativus |
| CumSa_CL_CR06.G5192480.1.cds | 178 | DNA | Cucumis sativus |
| CumSa_CL_CR02.G3923960.1.pep | 179 | PRT | Cucumis sativus |
| CumSa_CL_CR02.G3923960.1.cds | 180 | DNA | Cucumis sativus |
| CumSa_CL_SF1059.G337640.1.pep | 181 | PRT | Cucumis sativus |
| CumSa_CL_SF1059.G337640.1.cds | 182 | DNA | Cucumis sativus |
| CumSa_CL_CR07.G4126220.1.pep | 183 | PRT | Cucumis sativus |
| CumSa_CL_CR07.G4126220.1.cds | 184 | DNA | Cucumis sativus |
| CumSa_CL_CR03.G1762590.1.pep | 185 | PRT | Cucumis sativus |
| CumSa_CL_CR03.G1762590.1.cds | 186 | DNA | Cucumis sativus |
| CumSa_CL_CR07.G3464540.1.pep | 187 | PRT | Cucumis sativus |
| CumSa_CL_CR07.G3464540.1.cds | 188 | DNA | Cucumis sativus |
| CumSa_CL_CR02.G279760.1.pep | 189 | PRT | Cucumis sativus |
| CumSa_CL_CR02.G279760.1.cds | 190 | DNA | Cucumis sativus |
| CumSa_CL_CR02.G2168140.1.pep | 191 | PRT | Cucumis sativus |
| CumSa_CL_CR02.G2168140.1.cds | 192 | DNA | Cucumis sativus |
| CumSa_CL_CR03.G1764230.1.pep [ | 193 | PRT | Cucumis sativus |
| CumSa_CL_CR03.G1764230.1.cds | 194 | DNA | Cucumis sativus |
| CumSa_CL_SF18540.G80440.1.pep | 195 | PRT | Cucumis sativus |
| CumSa_CL_SF18540.G80440.1.cds | 196 | DNA | Cucumis sativus |
| MRT3880_29642P | 197 | PRT | Medicago truncatula |
| MRT3880_29642C | 198 | DNA | Medicago truncatula |
| MRT3880_23017P.2 | 199 | PRT | Medicago truncatula |
| MRT3880_23017C | 200 | DNA | Medicago truncatula |
| MRT3880_21535P.1 | 201 | PRT | Medicago truncatula |
| MRT3880_21535C | 202 | DNA | Medicago truncatula |
| MRT3880_5928P.1 | 203 | PRT | Medicago truncatula |
| MRT3880_5928C | 204 | DNA | Medicago truncatula |
| MRT3880_30136P.2 | 205 | PRT | Medicago truncatula |
| MRT3880_30136C | 206 | DNA | Medicago truncatula |
| MRT3880_5412P.2 | 207 | PRT | Medicago truncatula |
| MRT3880_5412c | 208 | DNA | Medicago truncatula |
| MRT3880_34104P.1 | 209 | PRT | Medicago truncatula |
| MRT3880_34104c | 210 | DNA | Medicago truncatula |
| MRT3880_60998P.1 | 211 | PRT | Medicago truncatula |
| MRT3880_60998c | 212 | DNA | Medicago truncatula |
| MRT3880_8385P.2 | 213 | PRT | Medicago truncatula |
| MRT3880_8385C | 214 | DNA | Medicago truncatula |
| HaIAA27 | 215 | PRT | Helianthus annuus |
| FR669188.1 | 216 | DNA | Helianthus annuus |
| KsIAA16S | 217 | PRT | Kochia scoparia |
| KsIAA16S | 218 | DNA | Kochia scoparia |
| KSIAA16R | 219 | PRT | Kochia scoparia |
| KSIAA16R | 220 | DNA | Kochia scoparia |

Precise genome editing can be accomplished as described (Sauer, et al. (2016)). Single-stranded oligonucleotides are used to engineer the GG to AA nucleotide change in the degron motif of the AUX/IAA 16 ortholog of the desired plant species. Selection for the introduced mutation is by molecular analysis, genome sequence confirmation of the nucleotide changes, and auxin sensitivity assays.

Alternatively, one or more site-specific nucleases, for example zinc finger nucleases, TALENs, or RNA-guided nucleases (e.g., CRISPR-Cas9, CRISPR-Cpf1, CRISPR-CasX, etc.) are introduced into a plant cell, along with a template comprising an exon encoding the mutated degron motif (GG to AA nucleotide change). The site-specific nuclease induces a double-strand break (DSB) in the chromosome around the exon of the AUX/IAA16 ortholog encoding the degron motif. Through homologous recombination, the template replaces the endogenous exon encoding the wild type degron motif. Plants carrying the mutated degron motif are selected using standard molecular analysis and auxin sensitivity assays.

Alternatively, one or more site-specific nucleases, for example zinc finger nucleases, TALENs, or RNA-guided nucleases (e.g., CRISPR) are introduced into a plant cell, with a template comprising an exon encoding the mutated degron motif (GG to AA nucleotide change). The site-specific nucleases induce two double-strand break (DSB) in the chromosome, one DSB 5'- and one DSB 3' of the exon of the AUX/IAA16 ortholog encoding the degron motif. Through non-homologous end joining, the template replaces the endogenous exon encoding the wild type degron motif. Plants carrying the mutated degron motif are selected using standard molecular analysis and auxin sensitivity assays.

Alternatively, a base editing enzyme (e.g., Cas9-cytidine deaminase, Cpf1-cytidine deaminase, etc.) are introduced into a plant cell. The base editing enzyme catalyzes C-to-T base conversions in the exon of the AUX/IAA16 ortholog encoding the degron motif resulting in glycine (G) to asparagine (N) amino acid substitution in the degron motif. Plants carrying the mutated degron motif are selected using standard molecular analysis and auxin sensitivity assays.

Example 9. Cross-Resistance of *Kochia* R-Biotype to 2,4-D and Fluroxypyr

Figure 6A:
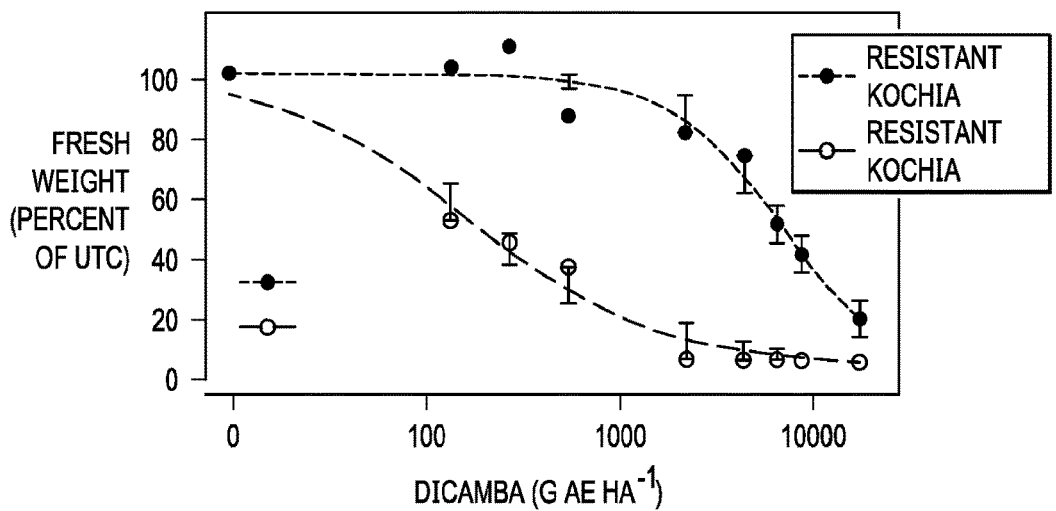
FIG. 6: Shows fresh weight (percentage of Untreated Control) for Dicamba (Panel A), 2,4-D (Panel B) and Fluroxypyr (Panel C).
Figure 6B:
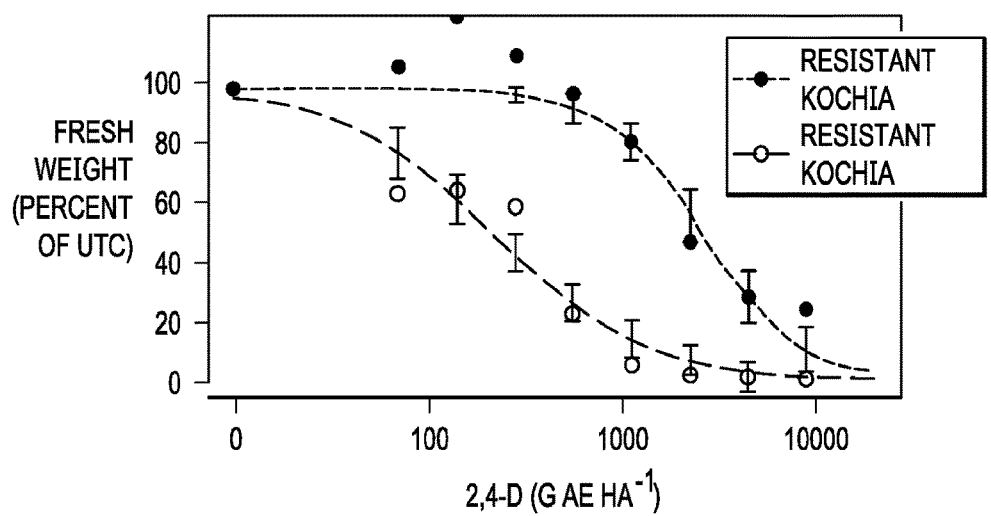
Figure 6C:
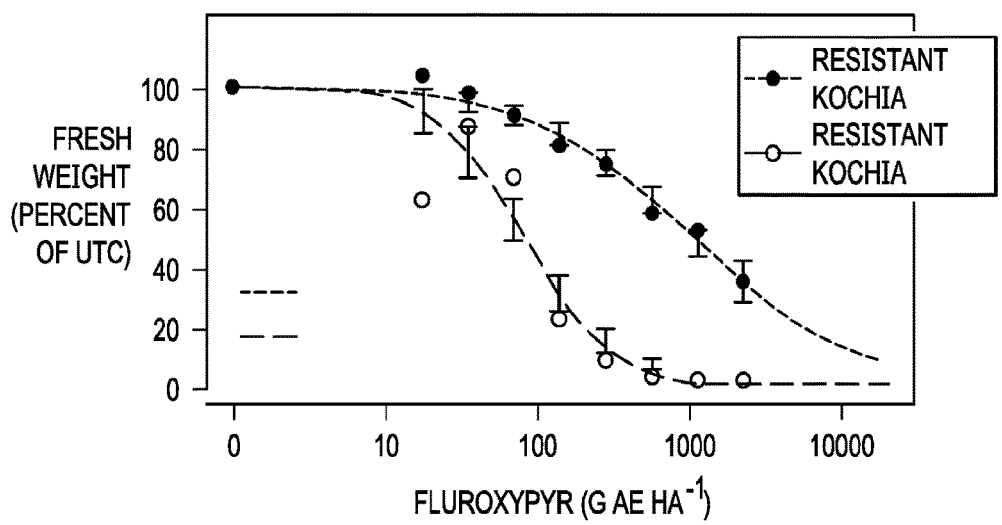

To elucidate whether the *Kochia* R-biotype is cross resistant to 2,4-D or fluroxypyr, greenhouse grown 10 to 15 cm tall *Kochia* plants were sprayed with either Dicamba at 0, 140, 280, 560, 2240, 4480, 6720, 8960, or 17920 g a.e.ha$^{-1}$; 2,4-D at 0, 70, 140, 280, 560, 1120, 2240, 4480, 6720, 8960 g a.e.ha$^{-1}$ or fluroxypyr at 0, 17.5, 35, 70, 140, 280, 420, 560, 1120, 2240 g a.e.ha$^{-1}$ with a track sprayer. Fresh weights were determined at 21 DAT and used to calculate dose response curves using "R" software. The curves for R *Kochia* (filled circles) and S *Kochia* (open circles) are shown in FIG. 6 for Dicamba in Panel A, 2,4-D in Panel B, and Fluroxypyr in Panel C. Visible injury at 14 days after treatment (DAT) for R and S biotypes was observed for all treatments (not shown).

---

What is claimed is:

1. A modified plant or seed, wherein the modified plant or seed is sensitive to at least one auxin selected from the group consisting of IAA and NAA, and wherein the modified plant or seed exhibits tolerance to at least one auxin herbicide selected from the group consisting of dicamba, 2,4-D, picloram, triclopyr, quinclorac and fluroxypyr, compared to a control plant not comprising the modification, wherein said modification results in an AUX/IAA polypeptide comprising a modified degron domain that comprises the motif $X_1WPPX_2$ (SEQ ID NO: 293), wherein $X_1$ has been modified relative to a wild type AUX/IAA polypeptide, to be asparagine (N), and wherein $X_2$ is isoleucine (I), valine (V), or leucine (L), and wherein said modification results in an AUX/IAA polypeptide comprising an amino acid sequence having at least 90% sequence identity to SEQ ID NO: 219.

2. The modified plant or seed of claim 1, wherein modification results in: i) an AUX/IAA polypeptide comprising the amino acid sequence of SEQ ID NO: 219, or ii) increased tolerance to an auxin herbicide as compared to a control plant or seed lacking said modification.

3. The modified plant or seed of claim 1, wherein said modified plant or seed is a crop plant or crop seed.

4. The modified plant or seed of claim 3, wherein said crop plant is a monocot or dicot crop plant.

5. The modified plant or seed of claim 4, wherein said crop plant is selected from the group consisting of maize, sorghum, wheat, canola, soy, -cotton, grapes, tomato, potato, lettuce, broccoli, cucumber, peanut, melon, leeks, onion, rice, and barley.

6. The modified plant or seed of claim 4, wherein said crop plant is selected from the group consisting of soybean, alfalfa, sunflower, cotton, canola, and sugar beet.

7. A method of generating a modified plant comprising the steps of: a. introducing a modification in a AUX/IAA gene of a plant cell, wherein said modification results in an AUX/IAA polypeptide comprising a modified degron domain that comprises the motif $X_1WPPX_2$ (SEQ ID NO: 293), wherein X: has been modified relative to a wild type AUX/IAA polypeptide, to be asparagine and wherein $X_2$ is isoleucine (I), valine (V), or leucine (L), and wherein said modification results in an AUX/IAA polypeptide comprising an amino acid sequence having at least 90% sequence identity to SEQ ID NO: 219; b. identifying and selecting one or more plant cells of step (a) comprising said modification in a degron domain of AUX/IAA; and c. regenerating at least one plant from at least one or more cells selected in step (b).

8. A modified DNA molecule encoding a modified auxin/indole-3-acetic acid (AUX/IAA) polypeptide capable of conferring tolerance to at least one auxin herbicide selected from the group consisting of dicamba, 2,4-D, picloram, triclopyr, quinclorac and fluroxypyr, compared to a control plant not comprising the modification, wherein said AUX/IAA polypeptide comprises a modified degron domain that comprises the motif $X_1WPPX_2$ (SEQ ID NO: 293), wherein $X_1$ has been modified to be asparagine (N) relative to a wild type AUX/IAA polypeptide and wherein $X_2$ is isoleucine (I), valine (V), or leucine (L), and wherein said modification results in an AUX/IAA polypeptide comprising an amino acid sequence having at least 90% sequence identity to SEQ ID NO: 219.

9. The modified DNA molecule of claim 8, wherein: i) said modified AUX/IAA polypeptide comprises the amino acid sequence of SEQ ID NO: 219; or ii) said modification results in increased tolerance to an auxin herbicide in a plant as compared to a control plant or seed lacking said modification.

10. The modified DNA molecule of claim 9, wherein said modified DNA molecule comprises:
  i) a polynucleotide sequence having at least 95% sequence identity to SEQ ID NO: 220, or
  ii) the polynucleotide sequence of SEQ ID NO: 220.

11. A DNA construct comprising the modified DNA molecule of claim 8 operably linked to a heterologous promoter.

12. The DNA construct of claim 11, wherein the promoter is defined as an inducible promoter or a native auxin/indole-3-acetic acid gene promoter.

13. A recombinant plant, plant part, cell, seed or plant genome comprising the modified DNA molecule of claim 8.

14. A method for conferring auxin herbicide tolerance to a plant comprising expressing in said plant the modified DNA molecule of claim 8.

15. The method of claim 14, further defined as comprising transforming said plant or a progenitor thereof with the modified DNA molecule of claim 8.

16. A method for producing an auxin herbicide tolerant plant wherein the plant is sensitive to at least one auxin selected from the group consisting of IAA and NAA, and wherein the modified plant or seed exhibits tolerance to at least one auxin herbicide selected from the group consisting of dicamba, 2,4-D, picloram, triclopyr, quinclorac and fluroxypyr, compared to a control plant not comprising the modification, wherein said modification results in an AUX/IAA polypeptide comprising a modified degron domain that comprises the motif $X_1WPPX_2$ (SEQ ID NO: 293) comprising:
  modifying an AUX/IAA polypeptide of said plant to comprise a modified degron domain that comprises the motif $X_1WPPX_2$ (SEQ ID NO: 293), wherein Xi has been modified relative to a wild type AUX/IAA polypeptide, to be asparagine (N), and wherein $X_2$ is isoleucine (1), valine (V), or leucine (L), and wherein said modification results in an AUX/IAA polypeptide comprising an amino acid sequence having at least 90% sequence identity to SEQ ID NO: 219.

17. The method of claim 16, wherein said modifying comprises site-specific mutagenesis.

18. The modified plant or seed of claim 1, wherein $X_2$ is isoleucine (I).

19. The modified plant or seed of claim 1, wherein $X_2$ is valine (V).

20. The modified plant or seed of claim 1, wherein $X_2$ is leucine (L).

21. The method of claim 7, wherein $X_2$ is isoleucine (I).

22. The method of claim 7, wherein $X_2$ is valine (V).

23. The method of claim 7, wherein $X_2$ is leucine (L).

24. The modified DNA molecule of claim 8, wherein $X_2$ is isoleucine (I).

25. The modified DNA molecule of claim 8, wherein $X_2$ is valine (V).

26. The modified DNA molecule of claim 8, wherein $X_2$ is leucine (L).

27. The method of claim 16, wherein $X_2$ is isoleucine (I).

28. The method of claim 16, wherein $X_2$ is valine (V).

29. The method of claim 16, wherein $X_2$ is leucine (L).

* * * * *

SEQUENCE LISTING

```
<160> NUMBER OF SEQ ID NOS: 293

<210> SEQ ID NO 1
<211> LENGTH: 215
<212> TYPE: PRT
<213> ORGANISM: Brassica napus
<220> FEATURE:
<221> NAME/KEY: misc_feature
<222> LOCATION: (106)..(106)
<223> OTHER INFORMATION: Xaa can be any naturally occurring amino acid

<400> SEQUENCE: 1

Met Ile Asn Phe Glu Ala Thr Glu Leu Arg Leu Gly Leu Pro Gly Glu
1               5                   10                  15

Asn His Gly Gly Gly Met Ala Ala Lys Asn Asn Gly Lys Arg Gly Phe
            20                  25                  30

Ser Glu Thr Val Asp Leu Lys Leu Asn Leu Ser Ser Thr Ala Met Asp
        35                  40                  45

Ser Val Ser Glu Leu Asp Leu Val Asn Met Lys Glu Lys Val Val Lys
    50                  55                  60

Pro Pro Ala Lys Ala Gln Val Val Gly Trp Pro Pro Val Arg Ser Phe
65                  70                  75                  80

Arg Lys Asn Val Met Ser Gly Gln Lys Pro Thr Ala Gly Asp Ala Thr
                85                  90                  95

Glu Gly Thr Lys Asn Thr Ser Ser Ser Xaa Ile Pro Tyr Leu Arg Lys
            100                 105                 110

Ile Asp Leu Lys Leu Tyr Lys Thr Tyr Gln Asp Leu Ser Asp Ala Leu
        115                 120                 125

Ser Lys Met Phe Ser Ser Phe Thr Ile Gly Asn Tyr Gly Pro Gln Gly
    130                 135                 140

Met Lys Asp Phe Met Asn Glu Ser Arg Leu Ile Asp Leu Leu Asn Gly
145                 150                 155                 160

Ser Asp Tyr Val Pro Thr Tyr Glu Asp Lys Asp Gly Asp Trp Met Leu
                165                 170                 175

Val Gly Asp Val Pro Trp Gly Met Phe Val Asp Ser Cys Lys Arg Ile
            180                 185                 190

Arg Ile Met Lys Gly Ser Glu Ala Ile Gly Leu Ala Pro Arg Ala Leu
        195                 200                 205
```

Glu Lys Cys Lys Asn Arg Ser
            210                 215

<210> SEQ ID NO 2
<211> LENGTH: 648
<212> TYPE: DNA
<213> ORGANISM: Brassica napus
<220> FEATURE:
<221> NAME/KEY: misc_feature
<222> LOCATION: (191)..(191)
<223> OTHER INFORMATION: n is a, c, g, or t

<400> SEQUENCE: 2

```
atgattaatt ttgaggcaac ggagctgagg ttagggctgc cgggtgagaa tcacggagga      60
ggcatggctg cgaaaaacaa cggcaaaaga ggattctctg agaccgttga tctcaaattg     120
aatctttctt ctacggctat ggattcagtt tctgaacttg atttagtgaa tatgaaggag     180
aaggtcgtaa naaccaccgg ccaaggcaca agttgtggga tggccaccgg tacgatcttt     240
ccggaagaac gtcatgtcag gccaaaagcc aaccgctgga gatgccaccg aaggaaccaa     300
aaacacttcc agcagctgat accgtaccta agaaaaattg atttgaaact ttacaaaaca     360
tatcaagacc tctccgacgc cttaagcaaa atgttcagct cttttaccat aggcaactat     420
ggaccacaag gaatgaaaga ttttatgaac gagagtaggt tgatcgatct tttgaacgga     480
tcagattacg ttccaactta tgaagataaa gatggagact ggatgcttgt aggagacgta     540
ccgtggggga tgtttgttga ttcatgcaaa cgcataagaa taatgaaggg atcagaagca     600
atcggacttg ctccaagggc attagaaaag tgcaagaaca gaagctga                 648
```

<210> SEQ ID NO 3
<211> LENGTH: 231
<212> TYPE: PRT
<213> ORGANISM: Brassica napus

<400> SEQUENCE: 3

Met Ile Asn Phe Glu Ala Thr Glu Leu Arg Val Asp Pro Arg Val Arg
1               5                   10                  15

Asn His Gly Gly Asp Met Ala Met Lys Asn Asn Gly Lys Arg Gly Phe
            20                  25                  30

Ser Glu Thr Val Asp Leu Lys Leu Asn Leu Ser Ser Thr Ala Leu Asp
        35                  40                  45

Ser Val Ser Gly Val Asp Leu Glu Asn Met Lys Glu Lys Val Val Lys
    50                  55                  60

Pro Pro Ala Lys Ala Gln Val Val Gly Trp Pro Val Arg Ser Phe
65                  70                  75                  80

Arg Lys Asn Val Met Ser Gly Gln Lys Pro Thr Ala Gly Asp Ala Ala
                85                  90                  95

Glu Gly Thr Glu Lys Thr Ser Ser Ser Asn Ala Ala Thr Ser Ser Ala
            100                 105                 110

Ala Ala Tyr Val Lys Val Ser Met Asp Gly Ala Pro Tyr Leu Arg Lys
        115                 120                 125

Ile Asp Leu Lys Leu Tyr Lys Thr Tyr Gln Asp Leu Ser Asp Ala Leu
    130                 135                 140

Ser Lys Met Phe Ser Ser Phe Thr Leu Gly Asn Tyr Gly Pro Gln Gly
145                 150                 155                 160

Met Lys Asp Phe Met Asn Glu Ser Arg Leu Ile Asp Leu Leu Asn Gly
                165                 170                 175

```
Ser Asp Tyr Val Pro Thr Tyr Glu Asp Lys Asp Gly Asp Trp Met Leu
            180                 185                 190

Val Gly Asp Val Pro Trp Gly Met Phe Val Asp Ser Cys Lys Arg Ile
        195                 200                 205

Arg Ile Met Lys Gly Ser Glu Ala Ile Val Arg Ala Pro Arg Ala Leu
    210                 215                 220

Glu Lys Cys Lys Asn Arg Ser
225                 230

<210> SEQ ID NO 4
<211> LENGTH: 696
<212> TYPE: DNA
<213> ORGANISM: Brassica napus

<400> SEQUENCE: 4
atgatcaatt ttgaggcgac ggagctgagg gtcgacccac gcgtccgcaa tcacggagga      60
gacatggcca tgaaaaataa tgggaaacga ggattttctg agaccgttga tctcaaactg     120
aatctttcat ccacggcttt ggattcggtt tccggagttg atttagagaa tatgaaggag     180
aaggtcgtaa aaccaccagc caaggcacaa gttgtgggat ggccaccggt acgatctttc     240
cggaagaacg tcatgtcagg ccaaaagcca accgctggga tgccgccga aggaacggaa      300 aagacttcca gcagcaacgc agccacttcc tctgccgcag cttacgtgaa agttagcatg     360
gacggcgcac cgtacctaag aaaaattgat ttgaaacttt acaaaacata tcaagacctc     420
tccgacgcct taagcaaaat gttcagctct tttaccctag caactatgg accacaagga      480 atgaaagatt ttatgaacga gagtaggttg atcgatcttt tgaacggatc agattacgtt     540
ccaacttatg aagataaaga tggagactgg atgcttgtag agacgtacc gtggggatg      600 tttgttgatt catgcaaacg cataagaata atgaagggat cagaagcaat cgtccgtgct     660
ccaagggcat tagaaaagtg caagaacaga agctga                              696

<210> SEQ ID NO 5
<211> LENGTH: 240
<212> TYPE: PRT
<213> ORGANISM: Brassica napus
<220> FEATURE:
<221> NAME/KEY: misc_feature
<222> LOCATION: (152)..(152)
<223> OTHER INFORMATION: Xaa can be any naturally occurring amino acid

<400> SEQUENCE: 5

Met Ile Gly Gln Leu Met Asn Leu Lys Ala Thr Glu Leu Cys Leu Gly
1               5                   10                  15

Leu Pro Gly Gly Ala Glu Ala Val Glu Ser Pro Ala Lys Ser Ala Val
            20                  25                  30

Gly Asn Lys Arg Gly Phe Ser Glu Thr Val Asp Leu Met Leu Asn Leu
        35                  40                  45

Gln Cys Asn Lys Glu Glu Thr Val Asp Leu Asn Asn Ala Thr Ala Ser
    50                  55                  60

Lys Glu Lys Thr Leu Leu Lys Asp Pro Ala Lys Pro Ala Lys Ala
65                  70                  75                  80

Gln Val Val Gly Trp Pro Pro Val Arg Asn Tyr Arg Lys Asn Met Met
                85                  90                  95

Thr Gln Gln Lys Thr Ser Gly Glu Glu Ala Ser Ser Glu Lys Ala
            100                 105                 110

Gly Asn Gly Gly Gly Ala Ala Ala Leu Val Lys Val Ser Met Asp
        115                 120                 125
```

Gly Ala Pro Tyr Leu Arg Lys Val Asp Leu Lys Met Tyr Lys Ser Tyr
            130                 135                 140

Gln Asp Leu Ser Asp Ala Leu Xaa Ala Lys Met Phe Ser Ser Phe Thr
145                 150                 155                 160

Met Gly Asn Tyr Gly Ala Gln Gly Met Ile Asp Phe Met Asn Glu Ser
                165                 170                 175

Lys Leu Met Asp Leu Leu Asn Ser Ser Asp Tyr Val Pro Ser Tyr Glu
            180                 185                 190

Asp Lys Asp Ser Asp Trp Met Leu Val Gly Asp Val Pro Trp Glu Met
                195                 200                 205

Phe Val Asp Ser Cys Lys Arg Leu Arg Ile Met Lys Gly Ala Glu Ala
            210                 215                 220

Ile Gly Leu Ala Pro Arg Ala Met Glu Lys Tyr Cys Lys Asn Arg Ser
225                 230                 235                 240

<210> SEQ ID NO 6
<211> LENGTH: 720
<212> TYPE: DNA
<213> ORGANISM: Brassica napus
<220> FEATURE:
<221> NAME/KEY: misc_feature
<222> LOCATION: (457)..(457)
<223> OTHER INFORMATION: n is a, c, g, or t

<400> SEQUENCE: 6
atgatcggac agcttatgaa cctcaaggcg acggagctct gtctcggcct ccccggcggc      60
gctgaagccg tcgagagtcc ggccaaatcg gcggtgggga caagagagg cttctccgag      120 accgtggatc tcatgctcaa tcttcagtgc aacaaagaag aaaccgtcga tcttaacaac      180
gccacagctt ccaaagagaa gactctcctc aaagaccctg ctaagcctcc tgctaaagcc      240
caagtggtgg gatggccacc tgtgaggaac tacaggaaga acatgatgac tcagcagaag      300
acaagcggcg aggaggaggc cagcagcgag aaggctggaa atggtggagg agctgccgct      360
gcattggtga aggtatccat ggacggagct ccttacctaa ggaaagtgga ccttaagatg      420
tacaaaagct atcaggatct ctctgatgct ttgggcnaaa tgttcagctc ctttactatg      480
ggaaactatg gagcacaagg aatgatagat ttcatgaacg agagcaagct aatggatctg      540
cttaatagtt ctgattacgt tccaagctac gaggacaaag atagcgattg gatgctcgtc      600
ggggatgtcc catgggaaat gtttgtcgac tcatgcaaac gtttgcgcat tatgaaggga      660
gctgaagcaa ttggacttgc tccgagagca atggagaagt actgcaagaa cagatcctga      720

<210> SEQ ID NO 7
<211> LENGTH: 228
<212> TYPE: PRT
<213> ORGANISM: Brassica napus

<400> SEQUENCE: 7

Met Met Gly Thr Val Glu Leu Asn Leu Arg Asp Thr Glu Leu Cys Leu
1               5                   10                  15

Gly Leu Pro Gly Gly Glu Thr Gly Ala Pro Val Thr Gly Thr Lys Arg
            20                  25                  30

Gly Phe Ser Glu Thr Val Asp Leu Lys Leu Asn Leu Asn Asn Glu Pro
        35                  40                  45

Glu Ile Asn Glu Gly Ser Lys Pro His Asp Val Thr Ser Val Ser
    50                  55                  60

Lys Glu Lys Ser Ser Ser Pro Lys Asp Pro Ala Lys Pro Pro Ala Lys

```
                65                  70                  75                  80
Ala Gln Val Val Gly Trp Pro Pro Val Arg Ser Tyr Arg Lys Asn Val
                        85                  90                  95

Met Gly Ser Tyr Gln Lys Pro Ser Gly Gly Thr Glu Thr Ala Ala Phe
                    100                 105                 110

Val Lys Val Ser Met Asp Gly Ala Pro Tyr Leu Arg Lys Val Asp Leu
                115                 120                 125

Lys Met Tyr Lys Ser Tyr Asp Glu Leu Ser Asn Ala Leu Ser Asn Met
            130                 135                 140

Phe Ser Ser Phe Thr Met Gly Lys Tyr Gly Gly Glu Gly Met Ile
145                 150                 155                 160

Asp Phe Met Asn Glu Arg Asn Met Ala Leu Val Thr Thr Trp Asp Tyr
                165                 170                 175

Val Pro Ser Tyr Glu Asp Lys Asp Gly Asp Trp Met Leu Val Gly Asp
            180                 185                 190

Val Pro Trp Pro Met Phe Val Asp Thr Cys Lys Arg Leu Arg Leu Met
        195                 200                 205

Lys Gly Ser Asp Ala Ile Gly Leu Ala Pro Arg Ala Met Glu Lys Cys
    210                 215                 220

Lys Thr Arg Ala
225

<210> SEQ ID NO 8
<211> LENGTH: 687
<212> TYPE: DNA
<213> ORGANISM: Brassica napus

<400> SEQUENCE: 8
atgatgggca ctgtcgagct gaatctgaga gacactgagc tgtgtcttgg tcttcccggc       60
ggagaaacgg gggctccggt gactggaacc aagagagggt tctcggagac agttgatttg      120
aagctcaatc tgaacaatga acctgaaatc aatgaaggat ctaagcctca tgacgtcgtg      180
acttctgttt ccaaggaaaa gagttcatct cccaaagatc ccgccaagcc tcctgccaag      240
gcacaagttg tgggatggcc acctgtgagg tcataccgga agaacgtgat gggttcgtac      300
caaaaaccaa gcggtggcac ggagacggct gcgtttgtga aggtgtcgat ggacggagca      360
ccgtacttga ggaaagtcga cttgaagatg tataagagct acgatgaact ctctaatgct      420
ttgtccaaca tgttcagctc ttttaccatg ggaaaatatg gaggagaaga aggaatgata      480
gacttcatga atgagaggaa catggcttta gtgactactt gggattatgt tccctcttat      540
gaagacaaag acggtgactg gatgctcgtc ggcgacgtcc cttggccaat gttcgttgat      600
acatgcaagc gtttacgtct catgaaagga tccgacgcca ttggtctcgc tccgagagca      660
atggagaagt gcaagaccag agcttga                                          687

<210> SEQ ID NO 9
<211> LENGTH: 204
<212> TYPE: PRT
<213> ORGANISM: Brassica napus

<400> SEQUENCE: 9

Met Met Asp Asn Ile Asp Leu Asn Leu Gln Glu Thr Glu Leu Cys Leu
1               5                   10                  15

Gly Leu Pro Gly Gly Met Thr Gly Thr Lys Arg Gly Phe Ser Glu Thr
            20                  25                  30

Val Asp Leu Lys Leu Asn Leu Asn Asn Glu Pro Glu Ser Lys Glu Val
```

```
                35                  40                  45
Ser Lys Thr His Asp Val Val Ile Ser Val Ser Lys Gln Lys Asn Lys
 50                  55                  60

Cys Pro Lys Asp Pro Thr Lys Pro Pro Ala Lys Ala Gln Val Val Gly
 65                  70                  75                  80

Trp Pro Pro Val Arg Ser Tyr Arg Lys Asn Val Met Gly Ser Cys Gln
                 85                  90                  95

Lys Ser Asn Asp Val Thr Glu Thr Ala Val Phe Val Lys Val Ser Met
                100                 105                 110

Asp Gly Ala Pro Tyr Leu Arg Lys Val Asp Leu Lys Met Tyr Lys Ser
            115                 120                 125

Tyr Asp Glu Leu Ser Asn Ala Leu Ser Asn Met Phe Gly Ser Phe Thr
130                 135                 140

Met Gly Lys Asn Gly Gly Glu Glu Gly Met Ile Asp Phe Met Asn Glu
145                 150                 155                 160

Arg Lys Val Arg Asp Leu Val Asn Ser Trp Asp Tyr Val Pro Ser Tyr
                165                 170                 175

Glu Asp Gln Asp Gly Asp Trp Met Leu Val Gly Asp Val Pro Leu Ala
            180                 185                 190

Met Phe Val Asp Thr Cys Lys Arg Leu Arg Leu Met
        195                 200

<210> SEQ ID NO 10
<211> LENGTH: 612
<212> TYPE: DNA
<213> ORGANISM: Brassica napus

<400> SEQUENCE: 10
atgatggaca atatcgacct gaatcttcag gaaactgagc tgtgtcttgg tcttcccggt        60
ggaatgaccg gaaccaagag aggattctcg gagacggttg atctgaaact caatctgaac       120
aatgaacctg aaagcaagga gtttctaag actcatgacg tcgtgatttc tgtttctaaa        180
caaaagaata atgtcccaa agatcctacc aagccccctg ccaaggcaca gttgtggga         240 tggccaccgg tgagatcata ccggaagaac gtgatgggtt cttgccaaaa atcaaacgat       300
gtcacggaga cggcggtgtt tgtaaaggtt tcgatggacg gagcacctta cttgagaaaa       360
gtcgacttaa agatgtataa agctacgac gaactctcta atgctttgtc aacatgttc         420 ggttctttta ccatgggaaa aaatggagga gaagaaggaa tgatagactt catgaatgag       480
cggaaagtta gggatttagt gaacagctgg gactatgttc cctcttacga agaccaagac       540
ggtgactgga tgctcgtcgg cgacgtccct ttggccatgt tcgttgatac atgcaagcgt       600
ttacgtctca tg                                                          612

<210> SEQ ID NO 11
<211> LENGTH: 272
<212> TYPE: PRT
<213> ORGANISM: Brassica napus
<220> FEATURE:
<221> NAME/KEY: misc_feature
<222> LOCATION: (183)..(183)
<223> OTHER INFORMATION: Xaa can be any naturally occurring amino acid

<400> SEQUENCE: 11

Met Thr Tyr Gln Leu Gln Ser Val Asp Lys Glu Gly Leu Gly Thr Ala
 1               5                  10                  15

Thr Cys Leu Lys Glu Arg Asn Tyr Leu Gly Leu Ser Asp Cys Ser Ser
                20                  25                  30
```

Ser Val Asp Ser Ser Thr Val Pro Asn Leu Val Leu Asp Thr Asp Lys
                 35                  40                  45

Lys Ser Ser Leu Asn Phe Lys Ala Thr Glu Leu Arg Leu Gly Leu Pro
 50                  55                  60

Glu Ser Ser Gln Ser Pro Gln Arg Glu Thr Asp Phe Gly Leu Leu Ser
 65                  70                  75                  80

Pro Arg Thr Pro Asp Glu Lys Leu Leu Phe Pro Leu Leu Pro Cys Lys
                 85                  90                  95

Asp His Ala Ser Gly Asn Lys Arg Gly Tyr Leu Ala Lys Ser Gly Ser
                100                 105                 110

Asn Asn Ala Pro Ala Ser Lys Ala Gln Val Val Gly Trp Pro Pro Ile
                115                 120                 125

Arg Ser Tyr Arg Lys Asn Thr Met Ala Ser Ser Thr Ser Lys Asn Thr
                130                 135                 140

Asn Glu Val Gly Leu Gly Pro Leu Phe Val Lys Val Ser Met Asp Gly
145                 150                 155                 160

Ala Pro Tyr Leu Arg Lys Val Asp Leu Arg Thr Tyr Thr Cys Tyr Gln
                165                 170                 175

His Leu Ser Ser Ala Leu Xaa Glu Lys Met Phe Ser Cys Phe Thr Leu
                180                 185                 190

Gly Gln Cys Gly Leu His Gly Ala His Gly Arg Glu Arg Met Ser Glu
                195                 200                 205

Val Lys Leu Lys Asp Leu Leu His Gly Ser Glu Phe Val Leu Thr Tyr
                210                 215                 220

Glu Asp Lys Asp Gly Asp Trp Met Leu Val Gly Asp Val Pro Trp Glu
225                 230                 235                 240

Ile Phe Thr Glu Ser Cys Arg Lys Leu Lys Ile Met Lys Gly Ser Asp
                245                 250                 255

Ser Ile Gly Leu Ala Pro Ser Ala Val Glu Lys Ser Lys Asn Lys Asp
                260                 265                 270

<210> SEQ ID NO 12
<211> LENGTH: 816
<212> TYPE: DNA
<213> ORGANISM: Brassica napus
<220> FEATURE:
<221> NAME/KEY: misc_feature
<222> LOCATION: (547)..(547)
<223> OTHER INFORMATION: n is a, c, g, or t

<400> SEQUENCE: 12
atgacttatc aattgcaaag tgtggacaag gagggtttgg gtacagcaac ttgtctgaag      60
gaacgcaact acttgggttt gtctgattgc tcctcctctg ttgacagctc aaccgttccc     120
aatcttgttc tagatactga caagaagagc agtctcaact tcaaagctac agagctaagg     180
ctaggtcttc cagaatcgtc tcagtctccc cagagagaaa ctgacttcgg tttgctgagt     240
ccaagaacgc ctgacgagaa acttctcttc ccgctgcttc cttgtaaaga ccatgcttca     300
ggcaacaaaa gaggatatct tgctaagagt ggctccaaca atgcacctgc ttccaaggcg     360
caggttgttg gttggcctcc aatcagatct acaggaagac acacaatggc ttcttctact     420
tccaagaaca ctaatgaggt tggtcttggt cctctgtttg tgaaggtgag catggatggt     480
gctccctatc tgaggaaagt ggatttgaga acctacactt gctatcaaca cttgtcttcg     540
gcacttngag aaatgttcag ctgcttcact cttggtcaat gtgggcttca tggagctcat     600
gggagggaaa gaatgagtga ggtgaagctg aaggatcttc ttcatggatc agagtttgtg     660

```
cttacttatg aagataaaga cggtgactgg atgctcgttg agatgtccc ctgggagata    720 tttactgaat catgtaggaa actgaagatc atgaagggct ctgattctat tggtttagct    780
ccaagtgcag tggagaaatc taagaacaaa gattga                              816
```

```
<210> SEQ ID NO 13
<211> LENGTH: 217
<212> TYPE: PRT
<213> ORGANISM: Brassica napus
<220> FEATURE:
<221> NAME/KEY: misc_feature
<222> LOCATION: (90)..(90)
<223> OTHER INFORMATION: Xaa can be any naturally occurring amino acid

<400> SEQUENCE: 13
```

Val Ala Gln Arg Leu Asp Pro Thr Thr Cys Ala Arg Thr Ser Arg Pro
1               5                   10                  15

Arg Ser Val Pro Leu Arg Ser Asn Leu Lys Pro Gln Arg Glu Tyr Thr
            20                  25                  30

Glu Val Lys Arg His Gln Asn Thr Gln Ser Thr Arg Glu Arg Thr Pro
        35                  40                  45

Leu Asn Ser Tyr Leu Arg Ile Phe Asp His Lys Lys Gly Thr Asp Leu
    50                  55                  60

Gly Trp Pro Pro Val Arg Ser Phe Arg Lys Asn Thr Leu Ala Thr Thr
65                  70                  75                  80

Cys Asn Asn Ser Asp Glu Val Asp Gly Xaa Pro Gly Ser Ala Ala Phe
                85                  90                  95

Phe Val Lys Val Ser Met Asp Gly Ala Pro Tyr Leu Arg Lys Val Asp
            100                 105                 110

Leu Lys Ser Tyr Thr Asn Tyr Gly Glu Leu Ser Ser Ala Leu Glu Lys
        115                 120                 125

Met Phe Thr Thr Phe Thr Leu Gly Gln Cys Gly Ser Asn Gly Ala Ala
    130                 135                 140

Gly Lys Asp Met Leu Arg Glu Thr Lys Leu Lys Asp Phe Leu Asn Gly
145                 150                 155                 160

Lys Asp Tyr Val Leu Thr Tyr Glu Asp Lys Asp Gly Asp Trp Met Leu
                165                 170                 175

Val Gly Asp Val Pro Trp Glu Met Phe Ile Asp Val Cys Lys Lys Leu
            180                 185                 190

Lys Ile Met Lys Gly Ala Asp Ala Ile Gly Leu Thr Ser Ala Pro Arg
        195                 200                 205

Gly Met Glu Lys Ser Lys Met Arg Ala
    210                 215

```
<210> SEQ ID NO 14
<211> LENGTH: 654
<212> TYPE: DNA
<213> ORGANISM: Brassica napus
<220> FEATURE:
<221> NAME/KEY: misc_feature
<222> LOCATION: (269)..(269)
<223> OTHER INFORMATION: n is a, c, g, or t

<400> SEQUENCE: 14
gtggcccaac gtcttgatcc tacgacgtgt gcgagaacct cgagacccag gtccgttccc    60
ctccggagca atctgaaacc acaacgagag tacaccgaag tgaaacgtca tcaaaacact    120
caatccactc gtgagcgcac cccccttaac tcctatctca gaattttcga ccacaaaaag    180
```

```
ggcacagatc ttggttggcc tccagtgaga tctttcagga agaacacatt ggcgaccacg      240
tgtaacaaca gtgatgaagt tgatgggtng ccaggttctg cggccttctt tgtgaaggtc      300
agcatggatg gtgctcctta tctgaggaaa gttgacctga gagctacac taactacggg       360 gagctttctt cagccttgga gaaaatgttc acaaccttca ctctcggtca atgcggatct      420
aatggagctg cagggaagga tatgctcaga gagaccaaac tcaaggattt tctgaatgga      480
aaagactatg tactcaccta tgaggacaag gatggtgact ggatgcttgt tggagatgtt      540
ccatgggaga tgtttattga tgtgtgcaag aagctgaaga taatgaaagg cgctgatgcc      600
attgggttaa cttcagctcc gagaggaatg gagaaatcga agatgagagc ttaa            654
```

<210> SEQ ID NO 15
<211> LENGTH: 332
<212> TYPE: PRT
<213> ORGANISM: Brassica napus

<400> SEQUENCE: 15

```
Met Ser Pro Glu Glu Leu Gln Ser Asn Gly Ser Val Ala Ser Ser
1               5                   10                  15

Thr Arg Asn Ile Val Gly Val Leu Lys Glu His Asn Tyr Leu Gly Leu
            20                  25                  30

Ser Asp Cys Ser Ser Val Gly Ser Asn Leu Ser Gly Leu Ala Asp
        35                  40                  45

Asp Asp Lys Ala Thr Ile Ser Leu Lys Ala Thr Glu Leu Thr Leu Gly
    50                  55                  60

Leu Pro Gly Ser Gln Ser Pro Ala Arg Asp Thr Glu Leu Asn Leu Leu
65                  70                  75                  80

Gly Pro Ala Lys Leu Asp Glu Lys Pro Phe Phe Pro Leu Leu Pro Ser
                85                  90                  95

Lys Asp Glu Met Cys Ser Ser Ser His Lys Asn Ile Ala Ser Gly
            100                 105                 110

Asn Lys Arg Gly Phe Ser Asp Thr Met Asp Lys Val Pro Leu Tyr Thr
        115                 120                 125

Glu Lys Asn Trp Met Phe Pro Glu Ala Val Val Ala Thr Gln Ser Val
130                 135                 140

Ile Lys Lys Glu Val Ala Gln Asn Leu Pro Lys Gly Lys Leu Ser Thr
145                 150                 155                 160

Thr Asn Asn Ser Ser Ser Pro Ala Ala Lys Ala Gln Ile Val Gly
                165                 170                 175

Trp Pro Pro Val Arg Ser Tyr Arg Lys Asn Thr Leu Ala Thr Thr Cys
            180                 185                 190

Lys Asn Ser Asp Glu Val Asp Gly Lys Pro Gly Ser Gly Pro Leu Phe
        195                 200                 205

Val Lys Val Ser Met Asp Gly Ala Pro Tyr Leu Arg Lys Val Asp Leu
210                 215                 220

Arg Ser Tyr Thr Asn Tyr Gly Glu Leu Ser Ala Ala Leu Glu Lys Met
225                 230                 235                 240

Phe Thr Thr Phe Thr Leu Gly Gln Cys Gly Thr Ser Gly Ala Thr Gly
                245                 250                 255

Lys Asp Val Arg Asn Glu Thr Lys Leu Lys Asp Leu Leu Asn Gly Lys
            260                 265                 270

Asp Tyr Val Leu Thr Tyr Glu Asp Lys Asp Gly Asp Trp Met Leu Val
        275                 280                 285

Gly Asp Phe Ser Trp Glu Ile Phe Ile Gly Val Cys Lys Lys Leu Lys
```

```
        290                 295                 300
Ile Met Lys Gly Cys Asp Ala Ile Gly Leu Ala Ala Pro Ala Pro
305                 310                 315                 320

Ala Pro Arg Ala Met Glu Lys Ser Lys Met Arg Ala
                325                 330
```

<210> SEQ ID NO 16
<211> LENGTH: 999
<212> TYPE: DNA
<213> ORGANISM: Brassica napus

<400> SEQUENCE: 16

```
atgtcaccgg aagaggagct gcagagcaat ggctctgtgg caagttctac caggaacatt    60
gtaggagtac tcaaggagca taactacttg gtctctctg attgttcctc tgttggaagc   120
tcaaatctct ccggccttgc agatgatgac aaagccacta tcagcctcaa ggccactgag   180
ctcacacttg gccttcctgg atcacagtct cctgctagag acactgagct caacttactt   240
ggccctgcta agctcgatga aaaccttttc tttcctttgc ttccttccaa agatgagatg   300
tgctcctcct cctcccacaa gaacattgcc tctgggaata aagaggcttc tctgacact    360
atggataaag ttcctctttta tactgagaaa aactggatgt ttcctgaagc cgtggtagcc   420
acccaatctg ttatcaagaa ggaagtggca cagaacttac taaaggaaa gctgagcact    480
acaaacaaca gctctagccc acctgcagcc aaggcacaga ttgttggttg gcctccagtg   540
aggtcctaca ggaagaacac attggccacc acttgtaaga acagtgatga agttgatggg   600
aagcctggtt ctgggccccct ctttgtgaag gtcagcatgg atggtgctcc ttatctgagg   660
aaagttgacc tgaggagcta cactaactac ggggagcttt ctgcagcctt ggagaaaatg   720
ttcaccactt tcactcttgg tcaatgtgga actagcggag ctacagggaa agatgtgcgt   780
aatgagacca aactcaagga tcttctgaat ggaaaagact atgtgctcac ttatgaggac   840
aaggatgggg actggatgct tgttggcgac ttttcatggg agatatttat tggtgtctgc   900
aagaagctca agataatgaa aggctgtgat gcgattgggt tagctgcagc tccagctcca   960
gcaccgagag caatggagaa atcgaagatg agagcttaa                          999
```

<210> SEQ ID NO 17
<211> LENGTH: 191
<212> TYPE: PRT
<213> ORGANISM: Brassica napus

<400> SEQUENCE: 17

```
Met Glu Asn Val Gly Val Cys Asp Glu Phe Val Asn Leu Lys Ala Thr
1               5                   10                  15

Glu Leu Arg Leu Gly Leu Pro Gly Thr Glu Asp Gly Gly Glu Glu Glu
            20                  25                  30

Arg Gln Lys Val Ser Cys Cys Lys Ser Asn Lys Arg Ala Phe Pro Glu
        35                  40                  45

Thr Glu Lys Asp Ile Glu Ser Thr Gly Thr Ser Glu Phe Leu Leu His
    50                  55                  60

Ser Lys Ala Gln Ile Val Gly Trp Pro Pro Val Arg Ser Tyr Arg Lys
65                  70                  75                  80

Asn Asn Ile Gln Thr Lys Lys Asn Glu Ser Glu Gly Gln Gly Met Tyr
                85                  90                  95

Val Lys Val Ser Met Asp Gly Ala Pro Tyr Leu Arg Lys Ile Asp Leu
            100                 105                 110
```

```
Thr Val Tyr Lys Gln Tyr Pro Glu Leu Met Lys Ser Leu Glu Asn Met
        115                 120                 125

Phe Lys Phe Ser Val Gly Lys Tyr Cys Glu Arg Glu Gly Tyr Lys Asp
    130                 135                 140

Ser Glu Phe Val Pro Thr Tyr Glu Asp Lys Asp Gly Asp Trp Met Leu
145                 150                 155                 160

Val Gly Asp Val Pro Trp Glu Met Phe Val Ser Ser Cys Lys Arg Leu
                165                 170                 175

Arg Ile Met Lys Gly Ser Glu Ala Lys Gly Leu Gly Cys Gly Val
            180                 185                 190

<210> SEQ ID NO 18
<211> LENGTH: 576
<212> TYPE: DNA
<213> ORGANISM: Brassica napus

<400> SEQUENCE: 18
atggaaaacg ttggtgtttg tgatgagttt gttaacctaa aggcaacaga gctgagacta      60
ggattaccag gaacagaaga tggaggtgaa gaggagagac aaaaggtttc ttgctgtaaa     120
agcaacaaaa gagcctttcc tgaaactgag aaagatattg agtcgaccgg aacgtccgaa     180 ttttgttgc attcaaaggc tcagattgtt ggatggccac ctgtaagatc ttacaggaag     240
aacaatattc agacgaagaa gaatgaatct gaaggtcaag gaatgtatgt gaaagtaagt     300
atggatggtg ctccctatct gaggaagata gatctaacgg tgtataagca atatccagaa     360
ttgatgaaat cgcttgaaaa catgtttaaa ttctctgtgg gaaaatattg tgagagagaa     420
ggatataaag actcagagtt tgtgcctact tatgaagaca agatggtgac tggatgcttg     480
gttggagatg ttccttggga gatgtttgtt tcgtcttgta agaggctaag gatcatgaaa     540
ggatcagaag ctaaaggtct cggttgtggt gtttaa                              576

<210> SEQ ID NO 19
<211> LENGTH: 243
<212> TYPE: PRT
<213> ORGANISM: Glycine max
<220> FEATURE:
<221> NAME/KEY: misc_feature
<222> LOCATION: (169)..(169)
<223> OTHER INFORMATION: Xaa can be any naturally occurring amino acid

<400> SEQUENCE: 19

Met Ala Thr Met Leu Thr Lys Glu His Gly Leu Asn Leu Lys Glu Thr
1               5                   10                  15

Glu Leu Cys Leu Gly Leu Pro Gly Gly Gly Gly Gly Gly Gly Gly Gly
            20                  25                  30

Gly Glu Val Glu Thr Pro Arg Ala Thr Gly Lys Arg Gly Phe Ser Glu
        35                  40                  45

Thr Val Asp Leu Lys Leu Asn Leu His Ser Lys Glu Asp Leu Asn Glu
    50                  55                  60

Asn Leu Lys Asn Val Ser Lys Glu Lys Thr Leu Leu Lys Asp Pro Ala
65                  70                  75                  80

Lys Pro Pro Ala Lys Ala Gln Val Val Gly Trp Pro Pro Val Arg Ser
                85                  90                  95

Tyr Arg Lys Asn Met Met Ala Val Gln Lys Val Ser Thr Glu Asp Val
            100                 105                 110

Ala Glu Lys Thr Thr Ser Ser Thr Ala Asn Ser Gly Ala Phe Val Lys
        115                 120                 125
```

Val Ser Met Asp Gly Ala Pro Tyr Leu Arg Lys Val Asp Leu Thr Met
    130                 135                 140

Tyr Lys Ser Tyr Lys Glu Leu Ser Asp Ala Leu Ala Lys Met Phe Ser
145                 150                 155                 160

Ser Phe Thr Met Gly Asn Tyr Gly Xaa Pro Arg Asn Gly Ile Asp Phe
                165                 170                 175

Met Asn Glu Ser Lys Leu Met Asp Leu Leu Asn Ser Ser Glu Tyr Val
            180                 185                 190

Pro Thr Tyr Glu Asp Lys Asp Gly Asp Trp Met Leu Val Gly Asp Val
        195                 200                 205

Pro Trp Glu Met Phe Val Gly Ser Cys Lys Arg Leu Arg Ile Met Lys
    210                 215                 220

Gly Ser Glu Ala Ile Gly Leu Ala Pro Arg Ala Met Glu Lys Cys Lys
225                 230                 235                 240

Ser Arg Ser

<210> SEQ ID NO 20
<211> LENGTH: 732
<212> TYPE: DNA
<213> ORGANISM: Glycine max
<220> FEATURE:
<221> NAME/KEY: misc_feature
<222> LOCATION: (505)..(505)
<223> OTHER INFORMATION: n is a, c, g, or t

<400> SEQUENCE: 20
atggcaacta tgctgacaaa ggagcatggt ctgaacctca aggagaccga gctttgcctc      60
ggtttgcctg gtggggagg cggcggcggc ggcggcggcg aggtggaaac tccaagggcc     120
actgggaaga gagggttctc tgagactgtt gatctgaaac ttaatcttca ttccaaggaa    180
gatctgaatg agaatctgaa gaatgtctca aggagaagaa ccctccttaa ggatcctgcc    240
aagccaccgg ctaaggctca agtggttggt tggccaccag tgaggtcata caggaagaac    300
atgatggcag tacaaaaggt tagcactgag gatgtggcag agaagacaac aagcagcact    360
gctaattctg gggcatttgt caaggttttc catggatggag caccttacct gcgcaaggtg    420
gacctcacaa tgtacaaaag ctacaaagag ttatctgatg ccttggccaa aatgttcagc    480
tccttcacca tgggtaacta tgggngccca aggaatggaa tagacttcat gaatgagagc    540
aagttgatgg atcttcttaa cagctctgag tatgtgccaa cctatgaaga taaggatggt    600
gactggatgc tcgtgggtga tgtcccatgg gagatgtttg ttgggtcatg caagcgcctg    660
cgaataatga aggggtcaga agcgattggc cttgcgccaa gagcaatgga aaatgcaaa     720 agcagaagct ga                                                       732

<210> SEQ ID NO 21
<211> LENGTH: 243
<212> TYPE: PRT
<213> ORGANISM: Glycine max

<400> SEQUENCE: 21

Met Glu Ala Glu Arg Asp Lys Tyr Lys Met Ile Asn Phe Glu Glu Thr
1               5                   10                  15

Glu Leu Arg Leu Gly Leu Pro Leu Ser Gly Asn Glu Thr Leu Lys Thr
            20                  25                  30

Thr Cys Ser Thr Gly Lys Arg Val Phe Ser Asp Thr Ala Val Asp Leu
        35                  40                  45

Lys Leu Asn Leu Ser Ser Thr Ser Asn Ser Ala Ser Ser Asp Leu Thr
    50                  55                  60

Lys Glu Lys Asn Ile Thr Ala Ala Ala Pro Pro Ala Asn Asp Pro Ala
65                  70                  75                  80

Lys Pro Pro Ala Lys Ala Gln Val Val Gly Trp Pro Pro Val Arg Ser
            85                  90                  95

Phe Arg Lys Asn Ile Val Gln Arg Ser Asn Asn Glu Gly Glu Lys
            100                 105                 110

Ala Ala Thr Ser Ser Asn Asn Val Asn Thr Gly Ala Ala Phe Val
            115                 120                 125

Lys Val Ser Met Asp Gly Ala Pro Tyr Leu Arg Lys Val Asp Leu Lys
            130                 135                 140

Leu Tyr Lys Ser Tyr Gln Glu Leu Leu Asp Ala Leu Ala Lys Met Phe
145                 150                 155                 160

Ser Ser Phe Thr Ile Asp Lys Cys Gly Ser Gln Gly Met Lys Asp Phe
                165                 170                 175

Met Asn Glu Ser Lys Leu Ile Asp Leu Leu Asn Gly Ser Asp Tyr Val
            180                 185                 190

Pro Thr Tyr Glu Asp Lys Asp Ala Asp Trp Met Leu Val Gly Asp Val
            195                 200                 205

Pro Trp Glu Met Phe Val Glu Ser Cys Lys Arg Leu Arg Ile Met Lys
210                 215                 220

Gly Ser Glu Ala Ile Gly Leu Ala Pro Arg Ala Val Glu Lys Cys Lys
225                 230                 235                 240

Asn Arg Ser

<210> SEQ ID NO 22
<211> LENGTH: 732
<212> TYPE: DNA
<213> ORGANISM: Glycine max

<400> SEQUENCE: 22
atggaggcag agcgagacaa gtacaagatg atcaactttg aagaaaccga gttacgactc      60
ggcctcccac tcagtggaaa cgagacgctc aaaaccactt gcagcactgg aagagggtt     120
ttttcggata ctgccgtgga tttgaagctt aacctttcct caacctcaaa cagtgcttct    180
tctgacctga ctaaagagaa gaacatcact gctgctgcac ctcctgctaa cgacccagca    240
aagccacctg caaaggcaca agtggtgggg tggccaccag tgaggtcttt cagaaagaac    300
attgttcaaa ggagtaacaa caatgagggc gaaaaagccg ccacaagtag tagcaacaat    360
gtgaacacgg gagcagcttt cgtgaaggtg agcatggatg gtgctcctta tttacgcaag    420
gtggatttga gttgtacaa gagctaccaa gagttgttgg atgcgctggc taaaatgttc    480
agttcattca ccattgacaa gtgtggatcc caaggcatga agacttcat gaacgagagc    540
aaattgattg atcttctcaa cggctctgat tacgtaccaa cctatgaaga caaagatgct    600
gactggatgc tcgttggtga cgtaccgtgg gaaatgttcg tggaatcatg caagcgcctg    660
cgtataatga aggatctga ggcaatcggg ctagcaccaa gagcagtgga aaagtgcaag    720
aacagaagct ag                                                       732

<210> SEQ ID NO 23
<211> LENGTH: 227
<212> TYPE: PRT
<213> ORGANISM: Glycine max

<400> SEQUENCE: 23

Met Ile Asn Phe Glu Glu Thr Glu Leu Arg Leu Gly Leu Pro Gly Asn
1               5                   10                  15

Asp Ser Ala Leu Lys Gly Ser Ala Ala Lys Arg Gly Phe Ser Glu Thr
        20                  25                  30

Ala Ser Val Asp Leu Lys Leu Asn Leu Ser Ser Cys Ile Asn Asp Ser
        35                  40                  45

Ala Ser Asp Ser Pro Ser Met Ser Thr Glu Lys Pro Lys Glu Asn
50                  55                  60

Lys Thr Thr Thr Ala Glu Pro Pro Ala Asn Asp Pro Ala Lys Pro
65                  70                  75                  80

Pro Ala Lys Ala Gln Val Val Gly Trp Pro Pro Val Arg Ser Phe Arg
                85                  90                  95

Lys Asn Ile Val Gln Arg Asn Ser Asn Glu Glu Glu Ala Glu Lys Ser
                100                 105                 110

Thr Lys Asn Ala Phe Val Lys Val Ser Met Asp Gly Ala Pro Tyr Leu
            115                 120                 125

Arg Lys Val Asp Ile Lys Leu Tyr Lys Ser Tyr Gln Glu Leu Ser Asp
        130                 135                 140

Ala Leu Ala Lys Met Phe Ser Ser Phe Thr Ile Glu Lys Cys Gly Ser
145                 150                 155                 160

Gln Gly Met Lys Asp Phe Met Asn Glu Thr Asn Gly Ser Asp Tyr Val
                165                 170                 175

Pro Thr Tyr Glu Asp Lys Asp Gly Asp Trp Met Leu Val Gly Asp Val
            180                 185                 190

Pro Trp Glu Met Phe Val Glu Ser Cys Lys Arg Leu Arg Ile Met Lys
        195                 200                 205

Gly Ser Glu Ala Ile Gly Leu Ala Pro Arg Ala Val Glu Lys Cys Lys
    210                 215                 220

Asn Arg Ser
225

<210> SEQ ID NO 24
<211> LENGTH: 684
<212> TYPE: DNA
<213> ORGANISM: Glycine max

<400> SEQUENCE: 24
atgattaact tcgaagaaac cgagttgcga ctcggcctcc ctggcaacga ctcagcactc      60
aagggaagtg ctgccaagag aggcttctct gaaactgctt ctgttgattt gaagcttaat     120 cttcttctt gcattaacga ctctgcctcg gattcaccct catctgtgtc tacagagaag      180
cccaaagaga caagactac cactgctgaa cctcctccag ctaatgatcc agcaaaacca      240
cctgcaaagg cacaagtggt gggttggcca ccagttaggt catttagaaa gaacatagtt     300
caaaggaaca gcaatgaaga agaggcagag aagagcacga gaatgctttc gtgaaggtg      360 agcatggatg gtgcaccgta tctacgaaag gtggacataa agttgtacaa gagctaccag     420
gagctgtcag atgcgctggc taagatgttc agttccttca cgattgaaaa gtgtgggtcc     480
caagggatga aggactttat gaatgagacc aatggctctg actatgtacc cacatatgaa     540
gacaaggacg gagactggat gctcgtcggt gatgtgccct gggagatgtt cgttgaatca     600
tgcaagcgtc ttcgcataat gaaaggctcc gaggcaatcg tcttgcgcc aagagccgtg      660 gaaaagtgca agaacagaag ctga                                             684

<210> SEQ ID NO 25
<211> LENGTH: 246
<212> TYPE: PRT

<213> ORGANISM: Glycine max

<400> SEQUENCE: 25

```
Met Val Phe Glu Glu Thr Glu Leu Arg Leu Gly Leu Gly Leu Cys Leu
1               5                   10                  15
Pro Gly Asn Gly Thr Thr Ala Thr Thr Glu Ala Ala Ala Glu Leu
            20                  25                  30
Gly Val Arg Lys Arg Gly Phe Ser Glu Thr Glu Thr Asp Glu Thr Ala
        35                  40                  45
Thr Val Asp Leu Met Leu Asn Leu Ser Pro Lys Glu Ala Ala Ala
    50                  55                  60
Asp Gly Ala Asp Pro Arg Glu Lys Pro Lys Thr Ser Pro Lys Glu Lys
65                  70                  75                  80
Thr Leu Leu Pro Asp Pro Ala Lys Pro Ala Lys Ala Gln Val
                85                  90                  95
Val Gly Trp Pro Pro Val Arg Ser Phe Arg Lys Asn Met Phe Ala Ala
            100                 105                 110
Gln Lys Ser Ser Gly Gly Glu Glu Ser Glu Lys Ser Pro Asn Ala
            115                 120                 125
Ser Phe Val Lys Val Ser Met Asp Gly Ala Pro Tyr Leu Arg Lys Val
    130                 135                 140
Asp Leu Lys Met Tyr Lys Ser Tyr Pro Glu Leu Ser Asp Ala Leu Gly
145                 150                 155                 160
Lys Met Phe Ser Ser Leu Thr Ile Gly Asn Cys Glu Ser Gln Gly Phe
                165                 170                 175
Lys Asp Phe Met Asn Glu Ser Lys Leu Met Asp Leu Leu Asn Ser Ser
            180                 185                 190
Asp Tyr Val Pro Thr Tyr Glu Asp Arg Asp Gly Asp Trp Met Leu Val
        195                 200                 205
Gly Asp Val Pro Trp Glu Met Phe Val Glu Ser Cys Lys Arg Leu Arg
    210                 215                 220
Ile Met Lys Gly Lys Glu Ala Ile Gly Leu Ala Pro Arg Ala Val Glu
225                 230                 235                 240
Lys Cys Lys Asn Arg Ser
                245
```

<210> SEQ ID NO 26
<211> LENGTH: 741
<212> TYPE: DNA
<213> ORGANISM: Glycine max

<400> SEQUENCE: 26

```
atggtgtttg aggaaactga gctgaggctg ggactgggac tatgtctccc tggaaatgga      60
accacggcaa caactgaagc tgctgctgcg aattaggag tgaggaagag agggttctct     120
gagactgaaa ctgatgaaac agccaccgtt gatttgatgc ttaacctctc acccaaggaa    180
gctgctgctg ctgatggtgc agatccacgt gagaagccaa agacttcgcc gaaggagaag    240
acccttctgc ttcccgatcc cgccaagcct cctgccaagg cgcaagtggt gggatggcca    300
cccgtgaggt ctttccggaa gaacatgttc gcagcccaaa agagcagcgg cggagaggaa    360
agcgaaaaga gcagccctaa tgcaagcttt gtcaaagtta gcatggatgg agcaccttac    420
ctccgcaaag ttgacttgaa gatgtacaag agttacccag agctctctga tgccttgggc    480
aaaatgtttta gctccctcac cattggaaat tgtgaatccc aaggcttcaa ggatttcatg    540
aatgagagca agttgatgga tcttttgaac agctccgact atgtcccgac ctatgaagac    600
```

```
agggatggcg actggatgct tgtcggtgat gtgccatggg agatgtttgt tgaatcatgc      660
aagcgtttac gtatcatgaa aggaaaggaa gctattggac tggcaccaag agccgtggag      720
aaatgcaaga acaggagcta g                                                741
```

<210> SEQ ID NO 27
<211> LENGTH: 253
<212> TYPE: PRT
<213> ORGANISM: Glycine max

<400> SEQUENCE: 27

```
Met Glu Val Gly Leu Lys Lys Glu Asn Met Gly Phe Glu Glu Thr Glu
1               5                   10                  15

Leu Arg Leu Gly Leu Pro Gly Asn Gly Gly Thr Glu Glu Val Leu Ile
            20                  25                  30

Arg Lys Arg Gly Phe Ser Glu Thr Glu Thr Gly His Glu Asp Glu Ser
        35                  40                  45

Ala Thr Thr Val Asp Leu Met Leu Asn Leu Ser Ser Lys Glu Ala Ala
    50                  55                  60

Thr Thr Ala Ala Ala Ala Asp Pro Thr Asp Lys His Lys Thr Leu
65                  70                  75                  80

Pro Lys Glu Lys Thr Leu Leu Pro Ala Asp Pro Ala Lys Pro Pro Ala
                85                  90                  95

Lys Thr Gln Val Val Gly Trp Pro Pro Val Arg Ser Phe Arg Lys Asn
            100                 105                 110

Met Leu Ala Val Gln Lys Ser Val Gly Glu Glu Asn Glu Lys Asn Ser
        115                 120                 125

Ser Ser Pro Asn Ala Ser Phe Val Lys Val Ser Met Asp Gly Ala Pro
    130                 135                 140

Tyr Leu Arg Lys Val Asp Leu Lys Met Tyr Lys Ser Tyr Arg Glu Leu
145                 150                 155                 160

Ser Asp Ser Leu Gly Lys Met Phe Ser Ser Phe Thr Ile Gly Asn Cys
                165                 170                 175

Glu Ser Gln Gly Met Lys Asp Phe Met Asn Glu Ser Lys Leu Asn Asp
            180                 185                 190

Leu Leu Asn Ser Ser Asp Tyr Val Pro Thr Tyr Glu Asp Lys Asp Gly
        195                 200                 205

Asp Trp Met Leu Val Gly Asp Val Pro Trp Glu Met Phe Val Glu Ser
    210                 215                 220

Cys Lys Arg Leu Arg Ile Met Lys Gly Lys Glu Ala Ile Gly Leu Gly
225                 230                 235                 240

Leu Ala Pro Arg Ala Met Ala Lys Ser Lys Asn Arg Ser
                245                 250
```

<210> SEQ ID NO 28
<211> LENGTH: 762
<212> TYPE: DNA
<213> ORGANISM: Glycine max

<400> SEQUENCE: 28

```
atggaggttg gcctcaagaa ggagaacatg gggtttgagg aaactgagtt aaggcttgga      60
ctgcctggaa acggaggcac tgaagaagtg ctcatcagga gaggggtttt ctctgagact      120
gaaactggtc atgaagatga gtctgccacc actgtggatt tgatgcttaa tctttcttct      180
aaggaggccg caaccactgc tgctgctgct gcagatccaa ctgataagca caagactttg      240
```

-continued

```
cctaaggaga agacccttct gccagcagat cctgctaagc ctccagccaa gacgcaggtg      300
gtgggttggc cacctgtgcg gtccttccgg aagaacatgt tagctgtaca aaagagcgtc      360
ggagaagaga acgagaagaa cagcagcagc cctaatgcaa gctttgtcaa agttagcatg      420
gatggagcac ttacctccg caaagtggac ttgaagatgt acaagagtta ccgagagctc       480
tctgattctt taggcaaaat gttcagctcc ttcaccattg gcaattgtga atcccaagga      540
atgaaggatt tcatgaatga gagcaagctg aatgatcttt tgaacagctc tgattatgtc      600
ccaacctatg aggacaagga tggtgactgg atgcttgtcg gtgatgtccc atgggagatg      660
tttgttgaat catgcaagcg tttacgcatc atgaaaggaa aggaggctat tggtcttggt      720
cttgcaccaa gagccatggc aaaatccaag aacaggagct ag                         762
```

<210> SEQ ID NO 29
<211> LENGTH: 523
<212> TYPE: PRT
<213> ORGANISM: Triticum aestivum

<400> SEQUENCE: 29

```
Met Ala Gly Leu Gly Phe Glu Glu Thr Glu Leu Arg Leu Gly Leu Pro
1               5                   10                  15

Gly Gly Gly Asn Glu Ala Glu Ala Ala Ala Val Arg Ser Ser
            20                  25                  30

Gly Lys Arg Gly Tyr Ala Glu Thr Ile Asp Leu Val Leu Lys Leu Glu
        35                  40                  45

Pro Ala Ser Ala Ala Ala Pro Pro Ser Gly Asp Asp Glu Glu Val Ala
    50                  55                  60

Asp Gly Val Ala Glu Ala Gln Pro Pro Ser Pro Ala Ala Val Asp Gly
65                  70                  75                  80

Gln Leu Lys Arg Ser Pro Ser Gln Ser Ser Val Val Thr Thr Ala Gln
                85                  90                  95

Pro Asp Ala Asp Pro Glu Lys Pro Arg Ala Pro Lys Ala Gln Ala Val
            100                 105                 110

Gly Trp Pro Pro Val Arg Ser Phe Arg Arg Asn Met Leu Ala Ala Ala
        115                 120                 125

Leu Val Lys Val Ser Met Asp Gly Ala Pro Tyr Leu Arg Lys Val Asp
    130                 135                 140

Met Gly Thr Tyr Lys Ser Tyr Gln Glu Leu Glu Lys Met Phe Ser Ser
145                 150                 155                 160

Phe Thr Ile Gly Asn Thr Pro Thr Gln Gly Met Thr Gly Met Asn Glu
                165                 170                 175

Ser Lys Leu Val Asp Leu Leu Ser Gly Ser Asp Tyr Val Pro Thr Tyr
            180                 185                 190

Gln Ala Arg Thr Ala Thr Gly Cys Ser Tyr Gly Arg Pro Leu His Ala
        195                 200                 205

Arg Pro Leu Lys Trp Ser Thr Lys Asp Thr Asp Lys Pro Cys Trp Gln
    210                 215                 220

Ser Leu Phe Ala Leu Gln Pro Leu Gln Asn Ser Gln Thr Glu Pro Gln
225                 230                 235                 240

Lys Leu Ala Glu Lys Arg Arg Lys Glu Arg Ser Lys Pro Ser Ser Ser
                245                 250                 255

Ser Ser Gly Arg Arg Arg Arg Ser Glu Glu Leu Ser Gln Leu Ala Met
            260                 265                 270

Ala Ala Asp Leu Gly Phe Glu Ala Thr Glu Leu Arg Leu Gly Leu Pro
        275                 280                 285
```

```
Gly Gly Gly Glu Gly Glu Ala Arg Ser Ser Gly Lys Arg Gly Phe
        290                 295                 300

Ala Glu Thr Ile Asp Leu Lys Leu Lys Leu Glu Pro Ala Gly Glu Glu
305                 310                 315                 320

Ala Pro Ala Glu Glu Asp Arg Ala Asp Val Ala Val Val Ala Ala Ala
                325                 330                 335

Ala Ala Glu Asn Gln Glu Glu Thr Ala Thr Asp Ala Gly Gly Gly Lys
            340                 345                 350

Met Lys Arg Ser Pro Ser Gln Ser Ser Val Val Thr Thr Ala Ala Leu
        355                 360                 365

Pro Asp Pro Ala Glu Lys Pro Arg Ala Pro Lys Ala Gln Val Val Gly
    370                 375                 380

Trp Pro Pro Val Arg Ser Phe Arg Lys Asn Ile Leu Ala Glu Lys Ser
385                 390                 395                 400

Ser Pro Ala Ala Ala Ala Phe Val Lys Val Ser Met Asp Gly Ala
                405                 410                 415

Pro Tyr Leu Arg Lys Val Asp Leu Asn Met Tyr Lys Thr Tyr Gln Asp
            420                 425                 430

Leu Ser Lys Ala Leu Glu Lys Met Phe Ser Ser Phe Thr Ile Gly Asn
        435                 440                 445

Cys Gly Thr Pro Gly Met Asn Gly Met Asn Glu Ser Lys Leu Met Asp
    450                 455                 460

Leu Leu Asn Gly Ser Glu Tyr Val Pro Thr Tyr Glu Asp Lys Asp Gly
465                 470                 475                 480

Asp Trp Met Leu Val Gly Asp Val Pro Trp Glu Met Phe Val Glu Ser
                485                 490                 495

Cys Lys Arg Leu Arg Ile Met Lys Gly Ser Glu Ala Ile Gly Leu Ala
            500                 505                 510

Pro Arg Ala Met Glu Lys Cys Lys Asn Arg Ser
        515                 520

<210> SEQ ID NO 30
<211> LENGTH: 1572
<212> TYPE: DNA
<213> ORGANISM: Triticum aestivum

<400> SEQUENCE: 30
atggcgggcc tcgggttcga ggagacggag ctccggctcg gcctgccagg cggcggcaac    60
gaggccgagg aggcggccgc cgcggtgagg agctccggca agaggggcta cgccgagacc   120
atcgacctcg tgctgaagct ggagcctgcg tcggcggccg cgccgccgtc tggggacgac   180
gaggaagtgg ccgacggtgt cgcggaggcg cagccgccgt ctccggctgc tgtcgacggg   240
cagttgaagc ggtcgccgag ccagagcagc gtggtcacca ccgcgcagcc ggacgcggac   300
cccgagaagc cgcgcgcgcc caaggcgcag gcggtggggt ggccgccggt gcggtcgttc   360
cggaggaaca tgctggcggc ggcgctggtg aaggtgagca tggacggcgc gccctacctg   420
cgcaaggtgg acatgggcac ctacaagagc taccaggagc tggagaagat gttcagctcc   480
ttcaccatcg gcaacactcc gactcagggg atgacgggca tgaacgagag caagctggtg   540
gacctgctca gcggctccga ctacgtgccc acctaccagg cacggacggc gactggatgc   600
tcgtacggac gtccccctcca cgctcgtccc ctgaagtgga gcacgaagga cactgacaag   660
ccctgttggc agtcgctttt cgcattgcag cctctgcaaa acagccaaac cgaaccccaa   720
aagctcgccg agaaacgcag aaaggagcga agcaaaccaa gcagcagcag cagcggaaga   780
```

```
agaagaagaa gcgaggagct gagccagcta gcaatggcgg cggacctggg cttcgaggcg     840
accgagctcc ggctcggcct gcccggcggc ggcgaggggg aggcgaggag ctcctccggc     900
aagaggggct tcgccgagac catcgacctg aagctcaagc tggagccggc cggcgaggag     960 gcgccgccg aggaggatcg ggccgacgtg gccgtggtcg ccgccgcggc ggcagagaac     1020
caggaggaga cggcgaccga cgccggcgga gggaagatga agaggtcgcc gagccagagc     1080
agcgtcgtca ccaccgccgc gctgcccgac cccgccgaga agccgcgcgc tcccaaggcg     1140
caggtggtgg ggtggcctcc ggtccggtcg ttccggaaga acatcctggc ggagaagtcg     1200
tcgccggcgg cagcggcggc gttcgtcaag gtgagcatgg acggcgcgcc ctacctgcgc     1260
aaggtggacc tcaacatgta caagacctac caggacctct ccaaggccct cgagaagatg     1320
ttcagctcct tcaccatcgg aaactgtgga actccaggga tgaacggcat gaacgagagc     1380
aagctgatgg atcttctcaa cggatccgag tatgttccga cgtacgagga caaggacggc     1440
gactggatgc tcgtcggcga cgtcccatgg gagatgttcg tcgagtcatg caagcgcctt     1500
cggataatga agggatcaga agctattggc cttgcaccaa gggcgatgga gaaatgcaag     1560
aacaggagct ga                                                        1572

<210> SEQ ID NO 31
<211> LENGTH: 255
<212> TYPE: PRT
<213> ORGANISM: Triticum aestivum
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid

<400> SEQUENCE: 31

Met Ala Gly Leu Gly Phe Glu Glu Thr Glu Leu Arg Leu Gly Leu Pro
1               5                   10                  15

Gly Gly Ser Asn Glu Ala Glu Glu Ala Ala Ala Val Arg Ser Ser
            20                  25                  30

Gly Lys Arg Gly Tyr Ala Glu Thr Ile Asp Leu Val Leu Lys Leu Glu
        35                  40                  45

Pro Ala Ser Ala Ala Ala Pro Ser Glu Asp Gly Glu Gln Val Ala
    50                  55                  60

Asp Gly Val Ala Glu Ala Gln Pro Ser Pro Ala Ala Asp Gly Gln
65                  70                  75                  80

Leu Lys Arg Ser Pro Ser Gln Ser Ser Val Val Thr Thr Pro Gln Pro
                85                  90                  95

Asp Ala Asp Pro Glu Lys Pro Arg Ala Pro Lys Ala Gln Ala Val Xaa
            100                 105                 110

Gly Trp Pro Pro Val Arg Ser Val Arg Arg Thr Leu Leu Ala Ala Ala
        115                 120                 125

Glu Arg Gly Gly Ala Gly Ala Xaa Val Lys Val Ser Met Asp Gly Ala
130                 135                 140

Pro Tyr Leu Arg Arg Val Asp Met Gly Thr Tyr Lys Ser Tyr Gln Glu
145                 150                 155                 160

Leu Ser Lys Ala Leu Glu Lys Met Phe Ser Ser Phe Thr Ile Gly Asn
                165                 170                 175

Asp Cys Ser Gln Ala Gln Ala Gln Gly Met Thr Gly Met Asn Glu Ser
```

```
                    180                 185                 190
Lys Leu Val Asp Leu Leu Ser Gly Ser Asp Tyr Val Pro Thr Tyr Glu
            195                 200                 205

Asp Lys Asp Gly Asp Trp Met Leu Val Gly Asp Val Pro Trp Glu Met
        210                 215                 220

Phe Val Ala Ser Cys Lys Arg Leu Arg Ile Met Lys Gly Ser Glu Ala
225                 230                 235                 240

Ile Gly Leu Ala Pro Arg Ala Met Glu Lys Cys Lys Ser Arg Ser
                245                 250                 255

<210> SEQ ID NO 32
<211> LENGTH: 765
<212> TYPE: DNA
<213> ORGANISM: Triticum aestivum

<400> SEQUENCE: 32
atggcgggcc tcgggttcga ggagaccgag ctccggctcg gcctgccagg cggcagcaac      60
gaggccgagg aggcggccgc cgcggtgagg agctccggca agaggggcta cgccgagacc     120
atcgacctcg tgctgaagct ggagccggcg tcggcggccg cgccgccgtc cgaggacggc     180
gagcaagtgg ccgacggcgt cgcggaggcg cagccgtctc cggctgctgc cgacgggcag     240
ttgaagcggt cgccgagcca gagcagcgtg gtcaccaccc cgcagccgga cgcggacccc     300
gagaagccgc cgcgcgccaa ggcgcaggcg gtggggttgg ccgccggtgc ggtcggtccg     360
ccggaccctg ctggcggcgg cggagagagg ggggccggc gcctggtgaa ggtgagcatg     420
gacggcgcgc cctacctgcg cagggtggac atgggcacct acaagagcta ccaggagctg     480
tccaaggccc tggagaagat gttcagctcc ttcaccatcg caacgactg ctctcaggct     540 caggctcagg ggatgacggg catgaacgag agcaagctgg tggacctgct cagcggctcc     600
gactacgtgc ccacctacga ggacaaggac ggcgactgga tgctcgtcgg cgacgtcccc     660
tgggagatgt tcgtggcgtc gtgcaagcgc ctccggataa tgaagggatc agaagccatc     720
ggcctcgcgc aagggcaat ggagaaatgc aagagcagga gctga                      765

<210> SEQ ID NO 33
<211> LENGTH: 228
<212> TYPE: PRT
<213> ORGANISM: Triticum aestivum
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 33

Lys Lys Asp Glu Gly Asp Pro Ser Leu Gly Gly Ala Trp Leu Gly Gly
1               5                   10                  15

Arg Cys Gly Gly Leu Pro Gly Xaa Lys Gly Gly Arg Arg Asn Xaa Glu
            20                  25                  30

Lys Gly Phe Ser Asp Arg Cys Leu Ser Ser Val Glu Pro Pro Glu Glu
        35                  40                  45

Gly Pro Pro Lys Arg Leu Ala Lys Val Ala Trp Phe Pro Pro Ala Ala
    50                  55                  60

Gly Thr Gly Arg Asn Gly Ala Arg Thr Arg Arg Cys Pro Ile Pro Pro
65                  70                  75                  80
```

Gly Asn Arg Val Gln Gly Ser Gly Gly Trp Pro Pro Val Arg Ser Phe
                 85                  90                  95

Arg Lys Asn Ile Leu Ala Glu Lys Ser Ser Pro Ala Ala Ala Ala
            100                 105                 110

Phe Val Lys Val Ser Met Asp Gly Ala Pro Tyr Leu Arg Lys Val Asp
            115                 120                 125

Leu Asn Met Tyr Lys Thr Tyr Gln Asp Leu Ser Lys Ala Leu Glu Lys
        130                 135                 140

Met Phe Ser Ser Phe Thr Ile Gly Asn Cys Gly Thr Pro Gly Met Asn
145                 150                 155                 160

Gly Met Asn Glu Ser Lys Leu Met Asp Leu Leu Asn Gly Ser Glu Tyr
                165                 170                 175

Val Pro Thr Tyr Glu Asp Lys Asp Gly Asp Trp Met Leu Val Gly Asp
            180                 185                 190

Val Pro Trp Glu Met Phe Val Glu Ser Cys Lys Arg Leu Arg Ile Met
        195                 200                 205

Lys Gly Ser Glu Ala Ile Gly Leu Ala Pro Arg Ala Met Glu Lys Cys
210                 215                 220

Lys Asn Arg Ser
225

<210> SEQ ID NO 34
<211> LENGTH: 687
<212> TYPE: DNA
<213> ORGANISM: Triticum aestivum
<220> FEATURE:
<221> NAME/KEY: misc_feature
<222> LOCATION: (70)..(72)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t

<400> SEQUENCE: 34
aaaaaagatg agggtgaccc ctcactagga ggggcttggt tgggggggccg ttgcggtggg    60 ctccccgggn nnaagggggg aaggaggaat anagaaaagg ggttttcgga ccgttgccta   120
agttcagtgg agccgccgga ggagggcccg ccgaagagat tggccaaagt ggcctggttc   180 cccccgccg caggaaccgg aaggaacggg gccagaaccc ggcggtgtcc gatcccccg    240 ggaaaccggg tccagggcag tggtgggtgg cctccggtcc ggtcgttccg gaagaacatc   300
ctggcggaga agtcgtcgcc ggcggcagcc gcggcgttcg tcaaggtgag catggacggc   360
gcgccctacc tgcgcaaggt ggacctcaac atgtacaaga cctaccagga cctctccaag   420
gccctcgaga gatgttcag ctccttcacc atcggaaact gtggaactcc agggatgaac   480
ggcatgaacg agagcaagct gatggatctt ctcaacggat ccgagtatgt tccgacgtac   540
gaggacaagg acggcgactg gatgctcgtc ggcgacgtcc catgggagat gttcgtcgag   600
tcatgcaagc gccttcggat aatgaaggga tcagaagcta ttggccttgc accaagggcg   660
atggagaaat gcaagaacag gagctga                                      687

<210> SEQ ID NO 35
<211> LENGTH: 267
<212> TYPE: PRT
<213> ORGANISM: Triticum aestivum
<220> FEATURE:
<221> NAME/KEY: misc_feature
<222> LOCATION: (181)..(181)
<223> OTHER INFORMATION: Xaa can be any naturally occurring amino acid

```
<220> FEATURE:
<221> NAME/KEY: misc_feature
<222> LOCATION: (241)..(241)
<223> OTHER INFORMATION: Xaa can be any naturally occurring amino acid

<400> SEQUENCE: 35
```

Met Ala Ala Asp Leu Gly Phe Asp Ala Thr Glu Leu Arg Leu Gly Leu
1               5                   10                  15

Pro Gly Gly Glu Gly Glu Ala Arg Ser Ser Gly Lys Arg Gly
            20                  25                  30

Phe Ala Glu Thr Ile Asp Leu Lys Leu Lys Leu Glu Pro Ala Gly Glu
                35                  40                  45

Glu Ala Pro Ala Glu Glu Asp Arg Ala Asp Val Ala Val Ala Ala
    50                  55                  60

Ala Ala Ala Glu Asn Gln Glu Glu Thr Ala Thr Asp Ala Gly Gly Gly
65                  70                  75                  80

Lys Met Lys Arg Ser Pro Ser Gln Ser Ser Val Val Thr Ser Ala Ala
                85                  90                  95

Leu Pro Asp Pro Ala Glu Lys Pro Arg Ala Pro Lys Ala Gln Val Val
                100                 105                 110

Gly Trp Pro Pro Val Arg Ser Phe Arg Lys Asn Ile Leu Ala Glu Lys
            115                 120                 125

Ser Ser Pro Ala Ala Ala Ala Phe Val Lys Val Ser Met Asp Gly
130                 135                 140

Ala Pro Tyr Leu Arg Lys Val Asp Leu Asn Met Tyr Lys Ser Tyr Gln
145                 150                 155                 160

Asp Leu Ser Asn Ala Leu Glu Asn Met Ser Ser Phe Thr Ile Gly
                165                 170                 175

Asn Cys Gly Thr Xaa Gly Met Asn Gly Met Asn Glu Ser Glu Leu Met
                180                 185                 190

Asp Leu Leu Ile Gly Ser Glu Tyr Val Pro Thr Tyr Glu Asp Lys Asp
                195                 200                 205

Gly Asp Cys Met Leu Val Gly Asp Val Pro Cys Glu Met Phe Val Lys
    210                 215                 220

Ser Cys Arg Pro Leu Arg Ile Met Asn Ala Ser Gln Ala Ile Gly Leu
225                 230                 235                 240

Xaa Pro Met Ala Met Glu Glu Leu Gln Asn Arg Pro Leu Gly Gly
                245                 250                 255

Ala Pro Asn Val Phe Pro Glu Ser Lys Asn Arg
            260                 265

```
<210> SEQ ID NO 36
<211> LENGTH: 549
<212> TYPE: DNA
<213> ORGANISM: Triticum aestivum

<400> SEQUENCE: 36
```
atggcagcgg acctgggctt cgacgcgacc gagctccggc tcggcctgcc cggcggcggc        60 gaggggagg cgaggagctc ctccggcaag aggggcttcg ccgagaccat cgacctgaag       120
ctgaagctgg agccggccgg cgaggaggcg ccggccgagg aggatcgggc cgacgtggcc      180
gtggtcgccg ccgcggcggc agagaaccag gaggagacgg cgacggacgc cggcggggggg    240 aagatgaaga ggtcgccgag ccagagcagc gtcgtcacct ccgccgcgct gcccgacccc      300
gccgagaagc cgcgcgcgcc caaggcgcag gtggtggggt ggcctccggt ccggtcgttc      360
cggaagaaca tcctggcgga gaagtcgtcg ccggcggcgg cggcggcgtt cgtcaaggtg     420
agcatggacg gcgcgcccta cctgcgcaag gtggacctca acatgtacaa gagctaccag    480
gacctctcca acgccctcga gaacatgtcc agctccttca ccatcggaaa ctgtggaact    540
cagggatga                                                            549

<210> SEQ ID NO 37
<211> LENGTH: 240
<212> TYPE: PRT
<213> ORGANISM: Triticum aestivum

<400> SEQUENCE: 37

Met Ala Pro Pro Gln Glu Arg Asp Tyr Ile Gly Leu Ser Pro Ala Ala
1               5                   10                  15

Ala Ala Ala Ala Thr Glu Leu Arg Leu Gly Leu Pro Gly Thr Glu Asp
                20                  25                  30

Ala Ala Gly Asp Gly Gly Ala Ala Ser Glu Ala Pro Leu Thr Leu
            35                  40                  45

Glu Leu Leu Ser Lys Gly Ala Lys Arg Gly Phe Ala Gly Ala Val
    50                  55                  60

Ala Glu Glu Glu Asp Glu Lys Lys Lys Ala Gln Pro Ala Ala Lys
65                  70                  75                  80

Ala Gln Val Val Gly Trp Pro Pro Ile Arg Ser Tyr Arg Lys Asn Thr
                85                  90                  95

Met Ala Thr Asn Leu Ser Ala Pro Arg Ser Lys Asp Glu Ala Glu Ala
                100                 105                 110

Lys Gln Ala Pro Ala Pro Gly Cys Leu Tyr Val Lys Val Ser Met Asp
            115                 120                 125

Gly Ala Pro Tyr Leu Arg Lys Val Asp Leu Lys Met Tyr Lys Asn Tyr
        130                 135                 140

Lys Asp Leu Ser Leu Glu Leu Glu Lys Lys Phe Ser Gly Phe Thr Val
145                 150                 155                 160

Gly His Gly Glu Ser Thr Gly Lys Ser Gly Arg Asp Gly Leu Ser Asp
                165                 170                 175

Cys Arg Leu Met Asp Leu Lys Ser Gly Thr Glu Leu Val Leu Thr Tyr
            180                 185                 190

Glu Asp Lys Asp Gly Asp Trp Met Leu Val Gly Asp Val Pro Trp Arg
        195                 200                 205

Met Phe Thr Asp Ser Cys Arg Arg Met Arg Ile Met Lys Gly Ser Asp
    210                 215                 220

Ala Val Gly Leu Ala Pro Arg Ala Ala Glu Lys Ser Lys Asn Gln Lys
225                 230                 235                 240

<210> SEQ ID NO 38
<211> LENGTH: 723
<212> TYPE: DNA
<213> ORGANISM: Triticum aestivum

<400> SEQUENCE: 38
atggcgccac cacaggagcg ggactacatc gggctgtcgc cggcagcggc ggcggcggcc     60
acggagctgc gcctggggct cccggggacg gaggacgctg ccggggacgg cgtggagcg    120 gcgtcggagg cgccgctgac actggagctc ctgtccaagg gcggggcgaa acgcgggttc    180
gcgggcgcgg tggcggagga ggaggacgag aagaagaagg cgcagccgcc ggccgccaag    240
gcacaggtgg taggatggcc accaatccgc agttacagga gaacaccat ggcgacgaac    300 ttatctgctc ccagaagcaa agacgaggcc gaggcgaagc aggcaccggc accaggctgc    360

```
ctttatgtca aggttagcat ggatggtgct ccttacctca ggaaggtgga tctcaagatg    420
tataagaact ataaggacct ctcgctggag ctggagaaaa agttcagcgg ctttactgtt    480
ggtcatggtg aatcgactgg aaaatcggga agagatggat tatctgattg ccggctgatg    540
gaccttaaaa gcggcactga acttgtgctc acttatgagg ataaggatgg tgattggatg    600
cttgttggtg atgttccatg gcgaatgttc acagacagct gtaggaggat gaggatcatg    660
aaggggtcag atgcagtggg cctcgctccg agggccgccg agaagagtaa gaaccagaag    720
tag                                                                  723
```

<210> SEQ ID NO 39
<211> LENGTH: 233
<212> TYPE: PRT
<213> ORGANISM: Triticum aestivum
<220> FEATURE:
<221> NAME/KEY: misc_feature
<222> LOCATION: (92)..(92)
<223> OTHER INFORMATION: Xaa can be any naturally occurring amino acid

<400> SEQUENCE: 39

```
Met Ala Gly Ala Asp Val Asp Val Gly Thr Glu Leu Arg Leu Gly Leu
1               5                   10                  15

Pro Gly Gly Gly Ala Glu Ala Ala Lys Ala Gly Lys Arg Gly Tyr Glu
            20                  25                  30

Asp Thr Ile Asp Leu Lys Leu Thr Leu Pro Thr Gly Met Gln Glu
        35                  40                  45

Asp Ser Ala Gly Lys Pro Glu Pro Ala Ala Asp Lys Ala Lys Arg Pro
    50                  55                  60

Ala Glu Ala Ala Ala Ala Asp Pro Glu Lys Pro Pro Ala Pro Lys Ala
65                  70                  75                  80

Gln Ala Val Gly Trp Pro Pro Val Arg Ser Tyr Xaa Arg Arg Asn Ala
                85                  90                  95

Met Thr Val Gln Ser Val Lys Ile Lys Lys Glu Glu Thr Glu Lys
            100                 105                 110

Gln Gln Pro Ala Gly Ala Ala Ala Gly Ala Asn Gly Ser Asn Phe Val
        115                 120                 125

Lys Val Ser Met Asp Gly Ala Pro Tyr Leu Arg Lys Val Asp Leu Lys
    130                 135                 140

Met Tyr Asn Thr Tyr Lys Asp Leu Ser Ile Ala Leu Gln Lys Met Phe
145                 150                 155                 160

Ser Thr Phe Thr Ala Thr Gly Asn Glu Gly Lys Met Val Glu Ala Val
                165                 170                 175

Asn Gly Ser Asp Val Val Thr Thr Tyr Glu Asp Lys Asp Gly Asp Trp
            180                 185                 190

Met Leu Val Gly Asp Val Pro Trp Glu Met Phe Val Ala Ser Cys Lys
        195                 200                 205

Arg Leu Arg Ile Met Lys Gly Ser Glu Ala Ile Gly Leu Ala Pro Arg
    210                 215                 220

Ala Lys Asp Lys Tyr Lys Asn Lys Ser
225                 230
```

<210> SEQ ID NO 40
<211> LENGTH: 504
<212> TYPE: DNA
<213> ORGANISM: Triticum aestivum

<400> SEQUENCE: 40

```
atggctggcg ccgacgtcga cgtcgggacg gagctcaggc tcgggctgcc cggggcggc      60 gccgaggcgg ccaaggccgg gaagaggggc tatgaggaca ccattgactt gaagctcacg     120
cttcccaccg gcggcatgca ggaagactcc gcaggcaagc cggagccggc cgccgacaag    180
gccaagaggc ccgcagaggc cgcggctgcc gaccccgaga agccacctgc tcccaaggca    240
caggctgtgg gttggccacc agtccggtcg tacccgcagg aacgccatga ccgtccagtc    300
ggtcaagatc aagaaggagg aggagaccga gaagcagcag cctgctggcg ccgctgctgg    360
cgccaacggc tccaactttg tcaaggtgag catggacggc gcgccctacc tgcgcaaggt    420
ggatctgaag atgtacaaca cctacaagga cctctccatt gctctgcaga agatgttcag    480
caccttcacc gcaactggga atga                                            504
```

<210> SEQ ID NO 41
<211> LENGTH: 246
<212> TYPE: PRT
<213> ORGANISM: Gossypium hirsutum

<400> SEQUENCE: 41

```
Met Thr Ser Ile Met Gly Thr Glu Asp Asp Lys Tyr Ser Thr Ile Asn
1               5                   10                  15

Phe Glu Glu Thr Glu Leu Arg Leu Gly Leu Pro Gly Ala Asn Gly Asn
                20                  25                  30

Asp Gly Glu Thr Thr Lys Asn Asn Gly Lys Arg Gly Phe Ser Glu Thr
            35                  40                  45

Val Asn Leu Lys Leu Asn Leu Ser Ser Lys Glu Thr Val Ala Glu Asp
        50                  55                  60

Ser Asp Lys Met Lys Glu Lys Ser Ser Thr Asp Pro Ala Lys Pro Pro
65                  70                  75                  80

Ala Lys Ala Gln Val Val Gly Trp Pro Pro Val Arg Ser Phe Arg Lys
                85                  90                  95

Asn Ile Met Ala Val Gln Lys Ala Ser Ser Glu Glu Gly Gly Ser
            100                 105                 110

Lys Lys Ala Gly Asn Ser Ala Ala Ala Ile Thr Thr Thr Ala Ala
        115                 120                 125

Ala Phe Val Lys Val Ser Met Asp Gly Ala Pro Tyr Leu Arg Lys Val
    130                 135                 140

Asp Leu Lys Leu Tyr Lys Ser Tyr Gln Gln Leu Ser Asp Ala Leu Ser
145                 150                 155                 160

Lys Met Phe Ser Ser Phe Thr Ile Gly Asn Cys Gly Ser His Gly Met
                165                 170                 175

Lys Asp Phe Met Asn Glu Ser Lys Leu Ile Asp Leu Leu Asn Gly Ser
            180                 185                 190

Glu Tyr Val Pro Thr Tyr Glu Asp Lys Asp Gly Asp Trp Met Leu Val
        195                 200                 205

Gly Asp Val Pro Trp Glu Met Phe Val Asp Ser Cys Lys Arg Leu Arg
    210                 215                 220

Ile Met Lys Gly Ser Glu Ala Ile Gly Leu Ala Pro Arg Ala Val Glu
225                 230                 235                 240

Lys Cys Lys Asn Arg Ser
                245
```

<210> SEQ ID NO 42
<211> LENGTH: 741
<212> TYPE: DNA

<213> ORGANISM: Gossypium hirsutum

<400> SEQUENCE: 42

```
atgactagca ttatgggcac agaggatgat aagtatagca cgattaactt cgaagagacg      60
gagttgcgtt tagggttgcc cggcgccaat ggaaacgacg gtgaaactac caaaaacaac     120
ggaaaacgag ggttctcaga gaccgttaat ttgaagctta acctttcatc aaaggagact     180
gtagccgagg attccgacaa gatgaaggag aagagctcaa ctgaccctgc aaagccacct     240
gccaaggcac aagtggtggg atggccacca gtcaggtcat tccggaagaa catcatggcc     300
gtccaaaaag ccagttccga ggaggaaggt ggcagcaaga aggccggaaa cagtgcagcc     360
gccattacta ccaccacggc tgcggcgttt gttaaggtca gcatggacgg tgcaccttat     420
ctacgcaaag tggacttgaa actatacaag agttaccaac aactctctga tgccttgagc     480
aaaatgttca gctccttcac tattggtaac tgtgggtctc atggaatgaa agatttcatg     540
aatgagagca aattgataga ccttttgaat ggttctgagt atgttcctac ttatgaagac     600
aaagatggag attggatgct tgttggagat gttccatggg agatgtttgt tgattcgtgc     660
aaacgcttac gaattatgaa aggatctgag gcaattggac ttgcaccaag agcagtagag     720
aagtgcaaga acagaagcta a                                               741
```

<210> SEQ ID NO 43
<211> LENGTH: 246
<212> TYPE: PRT
<213> ORGANISM: Gossypium hirsutum

<400> SEQUENCE: 43

```
Met Thr Ser Ile Met Gly Thr Glu Asp Asp Lys Tyr Ser Thr Ile Asn
 1               5                  10                  15

Phe Glu Glu Thr Glu Leu Arg Leu Gly Leu Pro Gly Ala Asn Gly Asn
             20                  25                  30

Glu Gly Glu Thr Thr Lys Asn Asn Gly Lys Arg Gly Phe Ser Glu Thr
         35                  40                  45

Val Asn Leu Lys Leu Asn Leu Ser Ser Lys Glu Thr Val Ala Glu Asp
     50                  55                  60

Ser Asp Lys Met Lys Glu Lys Ser Ser Thr Asp Thr Ala Lys Pro Pro
 65                  70                  75                  80

Ala Lys Ala Gln Val Val Gly Trp Pro Pro Val Arg Ser Phe Arg Lys
                 85                  90                  95

Asn Ile Met Ala Val Gln Lys Ala Ser Ser Glu Glu Glu Gly Gly Ser
            100                 105                 110

Lys Lys Ala Gly Asn Ser Ala Ala Ala Thr Thr Thr Thr Ala Ala
        115                 120                 125

Ala Phe Val Lys Val Ser Met Asp Gly Ala Pro Tyr Leu Arg Lys Val
    130                 135                 140

Asp Leu Lys Leu Tyr Lys Ser Tyr Gln Gln Leu Ser Asp Ala Leu Ser
145                 150                 155                 160

Lys Met Phe Ser Ser Phe Thr Ile Gly Asn Cys Gly Ser His Gly Met
                165                 170                 175

Lys Asp Phe Met Asn Glu Ser Lys Leu Ile Asp Leu Leu Asn Gly Ser
            180                 185                 190

Glu Tyr Val Pro Thr Tyr Glu Asp Arg Asp Gly Asp Trp Met Leu Val
        195                 200                 205

Gly Asp Val Pro Trp Glu Met Phe Val Asp Ser Cys Lys Arg Leu Arg
    210                 215                 220
```

Ile Met Lys Gly Ser Glu Ala Ile Gly Leu Ala Pro Arg Ala Val Glu
225                 230                 235                 240

Lys Cys Lys Asn Arg Gly
            245

<210> SEQ ID NO 44
<211> LENGTH: 741
<212> TYPE: DNA
<213> ORGANISM: Gossypium hirsutum

<400> SEQUENCE: 44

```
atgactagca ttatgggcac ggaggatgat aagtatagca cgattaactt cgaagagacg      60
gagttgcgtt tagggttgcc cggcgccaat ggaaacgaag gtgaaactac caaaaacaac     120
ggaaaacgag ggttctcgga gaccgttaat ttgaagctta acctttcatc aaaggagact     180
gtagccgagg attccgataa gatgaaggag aagagctcaa ctgacactgc aaagccacct     240
gccaaggcac aagtggtggg atggccacca gtcaggtcat tccggaagaa cataatggcc     300
gtccaaaaag ccagttccga ggaggaaggt ggcagcaaga aggccggaaa cagtgcagcc     360
gccactacta ccaccacagc tgcggcgttt gttaaggtca gcatggacgg tgcaccttat     420
ctacggaaag tggacttgaa actatacaag agttaccaac aactctctga tgccttaagc     480
aaaatgttca gctccttcac tattggtaac tgtgggtcac atggaatgaa agatttcatg     540
aacgagagca aattgataga ccttttgaat ggttctgagt atgttcctac ttacgaagac     600
agagatggag attggatgct tgttggtgat gttccatggg agatgttcgt tgattcatgc     660
aaacgcttac gaattatgaa aggatctgag gcaattggac ttgcaccaag agcagtagag     720
aagtgcaaga acagaggcta a                                              741
```

<210> SEQ ID NO 45
<211> LENGTH: 243
<212> TYPE: PRT
<213> ORGANISM: Gossypium hirsutum

<400> SEQUENCE: 45

Met Thr Ser Ile Met Ala Pro Glu Arg Asp Lys Tyr Ser Met Ile Asn
1               5                   10                  15

Phe Glu Glu Thr Glu Leu Arg Leu Gly Leu Pro Thr Gly Ile Glu Asn
                20                  25                  30

Asp Asn Glu Thr Ala Lys Asn Asn Gly Lys Arg Gly Tyr Ser Asp Met
            35                  40                  45

Val Asp Leu Lys Leu Asn Leu Ser Thr Thr Lys Glu Ala Ser Val Asp
        50                  55                  60

Glu Ala Glu Lys Met Lys Glu Lys Asn Thr Ala Lys Pro Pro Ala Lys
65                  70                  75                  80

Ala Gln Val Val Gly Trp Pro Pro Val Arg Ser Phe Arg Lys Asn Ile
                85                  90                  95

Met Thr Val Gln Lys Asn Ser Ser Asp Asn Lys Gly Glu Lys Thr Gly
                100                 105                 110

Ser Gly Asn Thr Ile Asn Thr Ala Leu Pro Ala Ala Phe Val Lys Val
            115                 120                 125

Ser Met Asp Gly Ala Pro Tyr Leu Arg Lys Val Asp Leu Lys Leu Tyr
        130                 135                 140

Lys Ser Tyr Gln Glu Leu Ser Asp Ala Leu Gly Lys Met Phe Ser Ser
145                 150                 155                 160

Phe Thr Ile Gly Asn Cys Gly Gly Ser Gln Gly Met Lys Asp Phe Met
            165                 170                 175

Asn Glu Ser Lys Leu Ile Asp Leu Leu Asn Gly Ser Glu Tyr Val Pro
        180                 185                 190

Thr Tyr Glu Asp Lys Asp Gly Asp Trp Met Leu Val Gly Asp Val Pro
    195                 200                 205

Trp Glu Met Phe Val Asp Ser Cys Lys Arg Leu Arg Ile Met Lys Gly
210                 215                 220

Ser Glu Ala Ile Gly Leu Ala Pro Arg Ala Val Asp Ser Cys Glu Lys
225                 230                 235                 240

Gly Arg Arg

<210> SEQ ID NO 46
<211> LENGTH: 732
<212> TYPE: DNA
<213> ORGANISM: Gossypium hirsutum

<400> SEQUENCE: 46

```
atgactagca ttatggctcc agagcgtgac aagtatagca tgattaattt cgaagagacg      60
gagttacgtt taggattacc cacaggcatt gaaaatgata atgaaaccgc caaaaataat     120
gggaaaagag ggtattcgga tatggttgat ttgaagctta acctttcaac aacaaaggaa     180
gcatcggtgg atgaagctga aagatgaag gagaaaaaca ctgcaaagcc ccctgctaag     240
gcacaagtag taggatggcc accggtcagg tcctttcgga aaacatcat gaccgttcag      300
aagaacagct ccgacaacaa gggtgagaaa accggcagtg aaacaccat taacaccgcc      360
ttaccggcgg cgtttgttaa ggtcagcatg gatggtgcac cctatctacg caaggtggac     420
ttgaaattat acaagagtta ccaagaacta tcggatgcct taggcaaaat gtttagctcc     480
ttcactattg gtaactgtgg gggttcacaa ggaatgaaag atttcatgaa tgaaagcaaa     540
ttaatagatc tcttgaacgg gtctgaatat gttcctactt atgaagacaa agatggagat     600
tggatgcttg ttggtgatgt cccatgggaa atgtttgtcg attcatgcaa gcgtttacga     660
atcatgaaag gatcagaagc cattggactt gctccaagag cagtggactc gtgcgagaaa     720
ggtcgacgat ag                                                         732
```

<210> SEQ ID NO 47
<211> LENGTH: 256
<212> TYPE: PRT
<213> ORGANISM: Gossypium hirsutum

<400> SEQUENCE: 47

Met Glu Val Gly Arg Lys Met Ala Asn Met Leu Gly Thr Glu His Asp
1               5                   10                  15

Leu Asn Phe Lys Glu Thr Glu Leu Cys Leu Gly Leu Pro Gly Gly Ile
            20                  25                  30

Ala Val Val Ala Ala Gly Asn Glu Thr Glu Ser Ser Ser Pro Lys
        35                  40                  45

Thr Asn Gly Lys Arg Gly Phe Ser Glu Thr Val Asp Leu Lys Leu Asn
    50                  55                  60

Leu Gln Ser Lys Glu Ser Thr Met Asp Leu Asn Lys Asn Leu Asp Asp
65                  70                  75                  80

Asn Gly Ser Lys Glu Lys Ser Gly Ser Ala Lys Asp Pro Ala Lys Pro
                85                  90                  95

Pro Ala Lys Ala Gln Val Val Gly Trp Pro Pro Val Arg Ser Tyr Arg
            100                 105                 110

Lys Asn Ile Met Ala Asn Gln Lys Asn Ser Ser Glu Glu Ser Gly Asn
            115                 120                 125

Ser Gly Ala Ala Leu Val Lys Val Ser Met Asp Gly Ala Pro Tyr Leu
        130                 135                 140

Arg Lys Val Asp Leu Lys Met Tyr Lys Ser Tyr Gln Glu Leu Ser Asp
145                 150                 155                 160

Ala Leu Ala Lys Met Phe Ser Ser Phe Thr Met Gly Asn Tyr Gly Pro
                165                 170                 175

Gln Gly Met Ile Asp Phe Met Asn Glu Ser Lys Leu Met Asp Leu Leu
            180                 185                 190

Asn Ser Ser Asp Tyr Val Pro Ser Tyr Glu Asp Lys Asp Gly Asp Trp
        195                 200                 205

Met Leu Val Gly Asp Val Pro Trp Gln Met Phe Val Asp Ser Cys Lys
    210                 215                 220

Arg Leu Arg Ile Met Lys Gly Ser Glu Ala Ile Gly Leu Ala Pro Arg
225                 230                 235                 240

Ala Met Glu Lys Cys Lys Ser Arg Ala Leu Lys Thr Arg Ser Trp Asn
                245                 250                 255

<210> SEQ ID NO 48
<211> LENGTH: 771
<212> TYPE: DNA
<213> ORGANISM: Gossypium hirsutum

<400> SEQUENCE: 48
atggaagttg gtcgaaaaat ggctaacatg cttggaaccg agcatgattt gaacttcaaa      60
gagaccgaac tgtgtcttgg tttgcccggt ggaatcgctg ttgttgctgc aggtaatgaa     120
acggaaagtt cttcttcccc aaagactaat ggcaagagag gcttctctga gactgttgat     180
ttgaagctta atcttcaatc caagaatcct accatggatc taaacaagaa ccttgatgac     240
aacggttcta aggaaaaatc aggttctgcc aaagatcctg caaaacctcc tgccaaggca     300
caagtggtgg gttggccacc agttcgatca tataggaaga acataatggc taaccagaag     360
aacagcagtg aagaaagtgg aatagtggt gcagctttgg tgaaagtgag tatggatggt      420
gcaccatatc tgagaaaagt tgatttgaag atgtataaga gttaccaaga gttatccgat     480
gccttggcta agatgtttag ctcttttcact atgggtaatt atggacctca aggaatgata     540
gatttcatga atgaaagcaa gttgatggat cttctcaaca gttctgatta tgtgccaagt     600
tatgaagata agatggcga ttggatgcta gttggtgatg tcccatggca gatgtttgtt      660
gactcatgca agcgcttacg cataatgaaa ggatccgaag cattggtct cgcaccaaga      720 gcaatggaga aatgcaagag cagagcccta aaaacaagat cctggaattg a              771

<210> SEQ ID NO 49
<211> LENGTH: 178
<212> TYPE: PRT
<213> ORGANISM: Gossypium hirsutum

<400> SEQUENCE: 49

Met Asp Leu Asn Lys Asn Leu Asp Asp Asn Gly Ser Lys Glu Lys Ser
1               5                   10                  15

Gly Ser Ala Lys Asp Pro Ala Lys Pro Ala Lys Ala Gln Val Val
            20                  25                  30

Gly Trp Pro Pro Val Arg Ser Tyr Arg Lys Asn Ile Met Ala Asn Gln
        35                  40                  45

Lys Asn Ser Ser Glu Glu Ser Gly Asn Ser Gly Ala Ala Leu Val Lys
    50                  55                  60

Val Ser Met Asp Gly Ala Pro Tyr Leu Arg Lys Val Asp Leu Lys Met
65                  70                  75                  80

Tyr Lys Ser Tyr Gln Glu Leu Ser Asp Ala Leu Ala Lys Met Phe Ser
                85                  90                  95

Ser Phe Thr Met Gly Asn Tyr Gly Pro Gln Gly Met Ile Asp Phe Met
            100                 105                 110

Asn Glu Ser Lys Leu Met Asp Leu Asn Ser Ser Asp Tyr Val Pro
            115                 120                 125

Ser Tyr Glu Asp Lys Asp Asp Trp Met Leu Val Gly Asp Val Pro
        130                 135                 140

Trp Gln Met Phe Val Asp Ser Cys Lys Arg Leu Arg Ile Met Lys Gly
145                 150                 155                 160

Ser Glu Ala Ile Gly Leu Ala Pro Arg Ala Met Glu Lys Cys Lys Ser
                165                 170                 175

Arg Ala

<210> SEQ ID NO 50
<211> LENGTH: 537
<212> TYPE: DNA
<213> ORGANISM: Gossypium hirsutum

<400> SEQUENCE: 50
atggatctaa acaagaacct tgatgacaac ggttctaagg aaaaatcagg ttccgccaaa      60
gatcctgcaa aacctcctgc caaggcacaa gtggtgggtt ggccaccagt tcgatcatat     120
aggaagaaca taatggctaa ccagaagaac agcagtgaag aaagtgggaa tagtggtgca     180
gctttggtga agtgagcat ggatggtgca ccatatctga aaaagttga tttgaagatg      240 tataagagtt accaagagtt atccgatgcc ttggctaaga tgtttagctc tttcactatg     300
ggtaattatg gacctcaagg aatgatagat ttcatgaatg aaagcaagtt gatggatctt     360
ctcaacagtt ctgattatgt gccaagttat gaagataaag atgacgattg gatgctagtt     420
ggtgatgtcc catggcagat gttttgttgac tcatgcaagc gcttacgcat aatgaaagga     480
tccgaagcaa ttggtctcgc accaagagca atggagaaat gcaagagcag agcctaa        537

<210> SEQ ID NO 51
<211> LENGTH: 250
<212> TYPE: PRT
<213> ORGANISM: Gossypium hirsutum
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid

<400> SEQUENCE: 51

Met Thr Ser Ile Met Gly Thr Glu Asp Asp Lys Tyr Ser Thr Ile Asn
1               5                   10                  15

Phe Glu Glu Thr Glu Leu Arg Leu Gly Leu Pro Gly Ala Asn Gly Asn
                20                  25                  30

Glu Gly Glu Thr Thr Lys Asn Asn Gly Lys Arg Gly Phe Ser Glu Thr
            35                  40                  45

Val Asn Leu Lys Leu Asn Leu Ser Ser Lys Glu Thr Val Ala Glu Asp
        50                  55                  60

```
Ser Asp Asn Met Lys Glu Lys Ser Thr Asp Thr Ala Lys Pro Pro
 65                  70                  75                  80

Ala Lys Ala Gln Val Gly Trp Pro Val Arg Ser Phe Arg Lys
             85                  90                  95

Asn Ile Met Ala Val Gln Lys Ala Ser Ser Glu Glu Gly Gly Ser
            100                 105                 110

Lys Lys Ala Gly Asn Ser Ala Ala Ala Thr Thr Thr Thr Ala Ala
            115                 120                 125

Ala Phe Val Lys Val Ser Met Asp Gly Ala Pro Tyr Leu Arg Lys Val
130                 135                 140

Asp Leu Lys Leu Tyr Lys Ser Tyr Gln Gln Leu Ser Asp Ala Leu Ser
145                 150                 155                 160

Lys Met Phe Ser Ser Phe Thr Ile Gly Asn Cys Gly Ser His Gly Met
                165                 170                 175

Lys Asp Phe Met Asn Glu Ser Lys Leu Ile Asp Leu Leu Asn Gly Ser
            180                 185                 190

Glu Tyr Val Pro Thr Tyr Glu Asp Arg Asp Gly Asp Xaa Met Leu Val
            195                 200                 205

Gly Asp Val Pro Trp Lys Met Ser Phe Ile His Ala Asn Ala Tyr Gln
210                 215                 220

Phe Glu Lys Ile Leu Arg Xaa Ile Gly Leu Ser Pro Arg Ala Val Glu
225                 230                 235                 240

Lys Val Gln Asn Gln Arg Leu Gly Arg Phe
                245                 250

<210> SEQ ID NO 52
<211> LENGTH: 555
<212> TYPE: DNA
<213> ORGANISM: Gossypium hirsutum

<400> SEQUENCE: 52
atgactagca ttatgggcac ggaggatgat aagtatagca cgattaactt cgaagagacg      60
gagttgcgtt tagggttgcc cggcgccaat ggaaacgaag gtgaaactac caaaacaac     120 ggaaaacgag ggttctcgga gaccgttaat ttgaagctta cctttcatc aaaggagact     180 gtagccgagg attccgataa catgaaggag aagagctcaa ctgacactgc aaagccacct     240
gccaaggcac aagtggtggg atggccacca gtcaggtcat tccggaagaa cataatggcc     300
gtccaaaaag ccagttccga ggaggaaggt ggcagcaaga aggccggaaa cagtgcagcc     360
gccactacta ccaccacagc tgcggcgttt gttaaggtca gcatggacgg tgcaccttat     420
ctacggaaag tggacttgaa actatacaag agttaccaac aactctctga tgccttaagc     480
aaaatgttca gctccttcac tattggttac tgtgggtcac atcgaacccc aaagattcaa     540
tattggttta ggtaa                                                     555

<210> SEQ ID NO 53
<211> LENGTH: 222
<212> TYPE: PRT
<213> ORGANISM: Gossypium hirsutum

<400> SEQUENCE: 53

Met Thr Ser Ile Met Asp Ala Glu His Asp Lys Tyr Ser Met Ile Asn
  1               5                  10                  15

Phe Glu Glu Thr Glu Leu Arg Leu Gly Leu Pro Thr Gly Ile Glu Asn
             20                  25                  30
```

```
Asp Asn Glu Thr Ala Lys Asn Gly Lys Arg Gly Tyr Ser Asp Met
         35                  40                  45

Val Asp Leu Lys Leu Asn Leu Ser Thr Thr Lys Glu Ala Ser Val Asp
 50                  55                  60

Glu Ala Glu Lys Met Lys Glu Lys Asn Thr Ala Lys Pro Pro Ala Lys
 65                  70                  75                  80

Ala Gln Val Val Gly Trp Pro Pro Val Arg Ser Phe Arg Lys Asn Ile
                 85                  90                  95

Met Thr Gly Gln Lys Asn Ser Ser Asp Asn Lys Gly Glu Lys Thr Gly
            100                 105                 110

Ser Gly Asn Thr Ile Asn Thr Ala Val Pro Ala Ala Phe Val Lys Val
            115                 120                 125

Ser Met Asp Gly Ala Pro Tyr Leu Arg Lys Val Asp Leu Lys Leu Tyr
130                 135                 140

Lys Ser Tyr Gln Glu Leu Ser Asp Ala Leu Gly Lys Met Phe Ser Ser
145                 150                 155                 160

Phe Thr Ile Gly Asn Cys Gly Gly Ser Gln Gly Met Lys Asp Phe Met
                165                 170                 175

Asn Glu Gly Lys Leu Ile Asp Leu Leu Asn Gly Ser Glu Tyr Val Pro
            180                 185                 190

Thr Tyr Glu Asp Lys Asp Gly Asp Trp Met Leu Ile Gly Asp Val Pro
            195                 200                 205

Trp Glu Met Phe Val His Phe Trp Gln Ala Phe Thr Lys His
            210                 215                 220

<210> SEQ ID NO 54
<211> LENGTH: 669
<212> TYPE: DNA
<213> ORGANISM: Gossypium hirsutum

<400> SEQUENCE: 54
atgactagca ttatggatgc agaacatgac aagtatagca tgattaattt cgaagagacg    60
gagttacgtt taggattacc cacaggcatt gaaaatgata atgaaaccgc caaaataat   120 gggaaaagag ggtattcgga tatggttgat ttgaagctta acctttcaac aacaaaggaa   180
gcatcggtgg atgaagctga aagatgaag gagaaaaaca ctgcaaagcc ccctgctaag   240
gcacaagtag taggatggcc accggtcagg tcctttcgga aaaacatcat gaccggtcag   300
aagaacagct ccgacaacaa gggtgagaaa accggcagtg gcaacaccat taacactgcc   360
gtacccgcgg cgtttgttaa ggtcagcatg gatggtgcac cctatctacg caaggtggac   420
ttgaaattat acaagagtta ccaagaacta tcggatgcct aggcaaaat gtttagctcc   480 ttcactattg gtaactgtgg gggttcacaa ggaatgaaag atttcatgaa tgaaggcaaa   540
ttaatagatc tcttgaatgg gtctgaatat gttcctactt atgaagacaa agatggagat   600
tggatgctta ttggtgatgt cccatgggag atgtttgtcc atttctggca agcgtttaca   660
aaacattga                                                          669

<210> SEQ ID NO 55
<211> LENGTH: 253
<212> TYPE: PRT
<213> ORGANISM: Gossypium hirsutum

<400> SEQUENCE: 55

Met Glu Val Gly Leu Lys Met Thr Met Lys Gly Gly Gly Gly Asp His
  1               5                  10                  15
```

Val Gly Gly Cys Asp Lys Glu Lys Met Gly Phe Glu Glu Thr Glu Leu
                20                  25                  30

Arg Leu Gly Leu Pro Gly Gly Gly Gly Gly Asp Gly Glu Val
            35                  40                  45

Val Arg Lys Arg Gly Phe Ser Glu Thr Val Asp Leu Lys Leu Asn Leu
 50                  55                  60

Ser Ser Lys Gln Asp Thr Ser Gly Ile Asp Pro Asn Asp Glu Lys Val
 65                  70                  75                  80

Lys Gly Leu His Gln Glu Lys Asn Leu Leu Ser Ala Ile Asp Ala
                85                  90                  95

Ala Lys Pro Pro Ala Lys Ala Gln Val Val Gly Trp Pro Pro Val Arg
                100                 105                 110

Ser Phe Arg Lys Asn Met Leu Ala Thr Thr Thr Gln Lys Ser Ser Ser
            115                 120                 125

Glu Glu Ser Gly Glu Lys Ala Ala Leu Val Lys Val Ser Met Asp Gly
            130                 135                 140

Ala Pro Tyr Leu Arg Lys Val Asp Leu Arg Met Tyr Thr Ser Tyr His
145                 150                 155                 160

Gln Leu Ser Asp Ala Leu Ala Lys Met Phe Ser Ser Phe Thr Ile Gly
                165                 170                 175

Asn Cys Gly Ser Gln Gly Ile Lys Asp Phe Met Asn Glu Ser Lys Leu
                180                 185                 190

Met Asp Leu Leu Asn Gly Ser Asp Tyr Val Pro Thr Tyr Glu Asp Lys
            195                 200                 205

Asp Gly Asp Trp Met Leu Val Gly Asp Val Pro Trp Glu Met Phe Val
210                 215                 220

Glu Ser Cys Lys Arg Leu Arg Ile Met Lys Gly Thr Glu Ala Ile Gly
225                 230                 235                 240

Leu Ala Pro Lys Ala Val Glu Lys Cys Lys Lys Arg Ser
            245                 250

<210> SEQ ID NO 56
<211> LENGTH: 762
<212> TYPE: DNA
<213> ORGANISM: Gossypium hirsutum

<400> SEQUENCE: 56
atggaagttg gcttaaagat gacgatgaaa ggaggcggag gagatcatgt tggaggttgc      60
gacaaagaga gatggggtt tgaagagact gagctgaggc tagggttgcc tggtggtggt     120
ggtggtggtg gtgacggtga agttgtgagg aaaagaggct tctctgaaac tgttgatttg     180
aagcttaacc tttcctccaa gcaagacacc tctgggatcg atcccaatga tgagaaagtg     240
aaaggcttgc accaggagaa gaatcttctc ctttctgcca ttgatgctgc taagcctcct     300
gccaaagcgc aagttgtggg atggccaccg gtccgatcat tccgaaagaa catgttagcc     360
accaccacac agaagagcag cagcgaggag agcggcgaga aggcggcgct ggtgaaggtg     420
agcatggacg gtgcacctta cctccgtaag gtggacttga ggatgtacac aagttaccac     480
caactctccg atgctttagc caaaatgttc agttctttta ctatcggaaa ttgtggatct     540
caaggaatta aggatttcat gaatgagagt aagctgatga tctccttaa tggctctgat     600 tatgttccta cctatgagga caaggatggt gactggatgc ttgttggtga cgtcccttgg     660
gagatgttcg tcgaatcatg caaaaggtta cgcataatga aggaacaga agcaatcgga     720 cttgcaccaa aagctgtgga gaaatgcaag aagagaagct ga                       762

```
<210> SEQ ID NO 57
<211> LENGTH: 306
<212> TYPE: PRT
<213> ORGANISM: Gossypium hirsutum
<220> FEATURE:
<221> NAME/KEY: misc_feature
<222> LOCATION: (234)..(234)
<223> OTHER INFORMATION: Xaa can be any naturally occurring amino acid

<400> SEQUENCE: 57

Met Ile Leu His Asn Pro Ile Asn Ile Leu Arg Leu Pro Leu Leu His
1               5                   10                  15

His His Leu Gln His Gln Leu Leu His Asn Pro Ser Ser Leu Ile His
            20                  25                  30

Ala Arg Gly Leu Pro Gly Ser Glu Ser Pro Glu Arg Glu Asp His Asp
        35                  40                  45

Gln Asn Val Leu Ser Leu Lys Ser Phe Val Ser Gly Ala Lys Arg Gly
    50                  55                  60

Phe Ser Asp Ala Leu Asp Gly Gly Asn Trp Val Phe Ser Gly Gly
65                  70                  75                  80

Ser Gly Gly Gly Thr Glu Gly Leu Phe Ser Pro Arg Arg Gly Gly Lys
                85                  90                  95

Asn Asn Gly Gly Lys Asp Leu Ser Gly Ser Asp Ser Gly Ser Val Leu
            100                 105                 110

Lys Asp Gly Ala Ala Arg Lys Pro Ser Val Val Gln Glu Lys Lys Pro
        115                 120                 125

Gln Val Ala Ala Thr Ser Ser His Gly Asn Gly Asn Ile Ala Pro Ala
    130                 135                 140

Ser Lys Ala Gln Val Val Gly Trp Pro Pro Ile Arg Ser Phe Arg Lys
145                 150                 155                 160

Asn Thr Met Ala Ser His Pro Pro Lys Asn Asp Gly Asp Gly Lys
                165                 170                 175

Ala Glu Ala Lys Leu Gly Ser Gly Cys Leu Tyr Val Lys Val Ser Met
            180                 185                 190

Asp Gly Ala Pro Tyr Leu Arg Lys Val Asp Leu Lys Ile Tyr Gly Ser
        195                 200                 205

Tyr Lys Glu Leu Ser Ser Ala Leu Glu Lys Met Phe Ser Cys Phe Thr
    210                 215                 220

Ile Gly Gln Cys Gly Ser His Gly Val Xaa Pro Gly Gly Asp Gly Leu
225                 230                 235                 240

Ser Glu Ser Arg Leu Ile Asp Leu Leu His Gly Ser Glu Tyr Val Leu
                245                 250                 255

Thr Tyr Glu Asp Lys Asp Gly Asp Trp Met Leu Val Gly Asp Val Pro
            260                 265                 270

Trp Glu Met Phe Thr Asp Ser Cys Lys Arg Leu Arg Ile Met Lys Ser
        275                 280                 285

Thr Glu Ala Ile Gly Leu Ala Pro Arg Ala Met Glu Lys Cys Lys Asn
    290                 295                 300

Arg Thr
305

<210> SEQ ID NO 58
<211> LENGTH: 711
<212> TYPE: DNA
<213> ORGANISM: Gossypium hirsutum

<400> SEQUENCE: 58
```

```
atgattttgc ataatcccat caatattctt cgccttcctc ttcttcatca ccaccttcag      60
caccaacttc ttcataatcc ctcgagccta attcatgcac gaggtttacc cgggtccgag     120
tcaccggaga gggaggatca tgaccaaaac gtgctttcac tgaagagttt tgtgtcaggg     180
gcaaaaagag gttttctga cgcactcgat ggtggcggta attgggtttt ctccggcggc      240
agtggtggag gaactgaagg gttgttttct cctagacgtg gcggtaaaaa taatggagga     300
aaagatcttt ctgggtcgga ttcgggttcg gttttgaaag atggagcagc tcggaagcca     360
tcggtggttc aagagaagaa gcctcaggta gctgctacca gtagccatgg aaatgggaat     420
attgctccag cttcaaaggc acaggtagtt ggatggccac caattcggtc tttccgaaag     480
aatacgatgg cttctcaccc tccgaagaat gatgatggtg atggtaaggc agaggccaag     540
ttaggatcag gatgtctgta tgtcaaagtt agtatggatg gtgctccata cctgaggaaa     600
gttgatctca aaatctatgg cagctacaaa gaactctcct cggcactgga aagatgttc      660 agttgcttta caattggtca gtgtggttct catggagttt cctggcggtg a             711
```

<210> SEQ ID NO 59
<211> LENGTH: 281
<212> TYPE: PRT
<213> ORGANISM: Sorghum bicolor

<400> SEQUENCE: 59

```
Met Ala Thr Thr Asp Leu Gly Phe Glu Glu Thr Glu Leu Arg Leu Gly
1               5                   10                  15

Leu Pro Gly Gly Gly Gly Glu Val Val Gly Glu Gly Arg Ser Ser Val
            20                  25                  30

Val Ser Ser Gly Lys Arg Gly Phe Ala Glu Thr Ile Asp Leu Lys Leu
        35                  40                  45

Lys Leu Glu Pro Ala Thr Pro Ala Ala Val Leu Lys Ala Ala Glu Ala
    50                  55                  60

Asp Glu His Gln Asp Gly Val Ala Ala Ala Lys Glu Asp Ala Gly Cys
65                  70                  75                  80

Val Ala Ala Ala Glu Glu Ala Ala Val Gly Gly Lys Met Lys Arg Ser
                85                  90                  95

Pro Ser Gln Ser Ser Val Val Thr Ala Ala Ala Val Gln Ala Asp Pro
            100                 105                 110

Ala Glu Lys Pro Arg Ala Pro Lys Ala Gln Val Val Gly Trp Pro Pro
        115                 120                 125

Val Arg Ser Phe Arg Lys Asn Ile Met Ser Val Gln Ser Asp Lys Gly
    130                 135                 140

Ala Gly Gly Ser Lys Asp Ala Asp Lys Ser Ser Pro Ala Ala Ala Ala
145                 150                 155                 160

Gly Gly Gly Ala Ala Phe Val Lys Val Ser Leu Asp Gly Ala Pro Tyr
                165                 170                 175

Leu Arg Lys Val Asp Leu Lys Met Tyr Lys Ser Tyr Gln Glu Leu Ser
            180                 185                 190

Lys Ala Leu Glu Lys Met Phe Ser Ser Phe Thr Ile Gly Ser Cys Gly
        195                 200                 205

Ser Gln Gly Met Asn Gly Met Asn Glu Ser Lys Leu Val Asp Leu Leu
    210                 215                 220

Asn Gly Ser Glu Tyr Val Pro Thr Tyr Glu Asp Lys Asp Gly Asp Trp
225                 230                 235                 240

Met Leu Val Gly Asp Val Pro Trp Glu Met Phe Val Glu Ser Cys Lys
```

```
                    245                 250                 255
Arg Leu Arg Ile Met Lys Gly Ser Glu Ala Ile Gly Leu Ala Pro Arg
            260                 265                 270

Ala Met Glu Lys Cys Lys Asn Arg Ser
        275                 280

<210> SEQ ID NO 60
<211> LENGTH: 846
<212> TYPE: DNA
<213> ORGANISM: Sorghum bicolor

<400> SEQUENCE: 60
atggcgacga cggacctggg gttcgaggag acggagctcc gtctgggcct gcccggcggc     60
gggggagagg tggtcggcga agggaggagc tctgtcgtct cctccgggaa gaggggcttc    120
gcagagacca tcgacctcaa gctgaagctg agccggcga ctcccgcggc cgtattgaag     180
gcggcggagg cggacgagca tcaggacggt gttgccgccg ccaaggaaga cgccggctgc    240
gtggccgccg cggaggaggc cgccgtcggc gggaagatga agaggtcccc gagccagagc    300
agcgtcgtca ccgccgccgc cgtgcaggct gaccccgccg agaagccgcg cgcccccaag    360
gctcaggtgg tgggatggcc accggtccgg tcgttccgga gaacatcat gtccgtgcag     420 tccgacaagg gcgccggcgg cagcaaagac gccgacaagt cctcgccggc ggcggcagct    480
ggcggtggtg cggcgttcgt gaaggtgagc ttggacggcg cgccgtacct gcgcaaggtg    540
gacctcaaga tgtacaagag ctaccaggag ctgtccaagg cgctcgagaa gatgttcagc    600
tccttcacca tttggaagctg tgggtctcaa gggatgaacg gcatgaacga gagcaagctg    660
gtggatctgc tcaacggctc cgagtacgtg ccgacctacg aggacaagga cggcgactgg    720
atgctcgtcg gcgacgtgcc gtgggagatg ttcgtcgagt catgcaagcg ccttcggatc    780
atgaaaggat cagaagccat tggcctcgca ccaagggcca tggagaaatg caagaacaga    840
agctga                                                                846

<210> SEQ ID NO 61
<211> LENGTH: 235
<212> TYPE: PRT
<213> ORGANISM: Sorghum bicolor

<400> SEQUENCE: 61

Met Ala Gly Ala Asp Val Asp Val Gly Thr Glu Leu Arg Leu Gly Leu
1               5                   10                  15

Pro Gly Gly Gly Ala Glu Ala Ala Lys Ala Ala Lys Arg Gly Phe Glu
            20                  25                  30

Asp Thr Ile Asp Leu Lys Leu Lys Leu Pro Thr Ala Gly Met Glu Glu
        35                  40                  45

Ala Ala Ala Ala Lys Pro Glu Pro Ala Ala Glu Lys Ala Lys Arg Pro
    50                  55                  60

Ala Glu Ala Pro Ala Ala Asp Ala Glu Lys Pro Pro Ala Pro Lys Ala
65                  70                  75                  80

Gln Ala Val Gly Trp Pro Pro Val Arg Ser Tyr Arg Arg Asn Val Met
                85                  90                  95

Thr Val Gln Ser Val Lys Ser Lys Glu Glu Pro Glu Lys Gln
            100                 105                 110

Gln Ser Ala Ala Ala Asn Ala Ser Gly Asn Ser Ser Ala Phe Val Lys
        115                 120                 125

Val Ser Met Asp Gly Ala Pro Tyr Leu Arg Lys Val Asp Leu Lys Met
```

```
                130             135             140
Tyr Asn Ser Tyr Lys Asp Leu Ser Ile Ala Leu Lys Lys Met Phe Ser
145                 150                 155                 160

Thr Phe Thr Thr Ser Gly Asn Asn Met Asn Glu Gly Lys Leu Val Asp
                165                 170                 175

Pro Val Ser Gly Ala Asp Val Val Thr Thr Tyr Glu Asp Lys Asp Gly
            180                 185                 190

Asp Trp Met Leu Val Gly Asp Val Pro Trp Glu Met Phe Val Glu Ser
        195                 200                 205

Cys Lys Arg Leu Arg Ile Met Lys Ser Ser Glu Ala Ile Gly Leu Ala
    210                 215                 220

Pro Arg Thr Lys Asp Lys Cys Lys Asn Lys Ser
225                 230                 235
```

<210> SEQ ID NO 62
<211> LENGTH: 708
<212> TYPE: DNA
<213> ORGANISM: Sorghum bicolor

<400> SEQUENCE: 62

```
atggctggcg ccgacgtcga cgtcgggacg gagctccggc tcggcctgcc gggaggaggc      60
gccgaggcgg ccaaggccgc gaagaggggc ttcgaggaca ccatcgacct caagctgaag     120
ctgcccaccg ccggcatgga ggaagctgcc gccgccaagc cggagccggc agccgagaag     180
gccaagaggc ccgccgaggc gccggcagct gatgccgaga agccacctgc acccaaggca     240
caagctgtgg gttggccacc agtccgatca taccgcagga acgtcatgac cgtccagtct     300
gtgaagagca agaaggaaga ggaacctgag aagcagcagt cggccgctgc caacgccagc     360
ggcaacagct ccgccttcgt gaaggtcagc atggacggcg cgccctacct gcgcaaggtg     420
gacctgaaga tgtacaacag ctacaaggac ctctctattg ctctgaagaa gatgttcagc     480
accttcacca catctgggaa caacatgaat gaggggaaat tggttgatcc agtcagcggt     540
gctgatgtgg tcactactta cgaagacaag gacggcgact ggatgcttgt tggtgacgtc     600
ccatgggaga tgtttgtcga gtcatgcaag cgtctgagga tcatgaagag ttctgaagcc     660
ataggtcttg caccaagaac gaaggacaag tgcaagaaca agagctga                 708
```

<210> SEQ ID NO 63
<211> LENGTH: 249
<212> TYPE: PRT
<213> ORGANISM: Sorghum bicolor

<400> SEQUENCE: 63

```
Met Ser Pro Pro Leu Glu Leu Asp Tyr Ile Gly Leu Ser Pro Gln Pro
1               5                   10                  15

Ala Ala Ala Ala Ala Ala Asp Ala Asp Asp Leu Lys Gly Thr
                20                  25                  30

Glu Leu Arg Leu Gly Leu Pro Gly Ser Gly Ser Pro Asp Arg Arg Val
            35                  40                  45

Ala Ala Ala Thr Ala Thr Thr Leu Glu Leu Pro Ala Lys Gly Ala
        50                  55                  60

Lys Arg Gly Phe Ser Asp Glu Ala Pro Pro Ser Pro Ala Ala Ala
65                  70                  75                  80

Ala Gly Lys Gly Lys Lys Val Ala Glu Glu Asp Asp Lys Lys
            85                  90                  95

Val Ala Ala Thr Pro Gln Pro Ala Ala Lys Ala Gln Val Val Gly Trp
```

100                 105                 110
Pro Pro Ile Arg Ser Tyr Arg Lys Asn Thr Met Ala Thr Thr Gln Leu
            115                 120                 125

Lys Gly Ser Lys Glu Asp Thr Glu Ala Lys Gln Gly Gln Gly Phe Leu
    130                 135                 140

Tyr Val Lys Val Ser Met Asp Gly Ala Pro Tyr Leu Arg Lys Ile Asp
145                 150                 155                 160

Leu Lys Thr Tyr Lys Asn Tyr Lys Asp Leu Ser Thr Ala Leu Glu Lys
                165                 170                 175

Met Phe Ser Gly Phe Ser Thr Gly Lys Asp Gly Leu Ser Glu Tyr Arg
            180                 185                 190

Lys Asp Gly Glu Tyr Val Leu Thr Tyr Glu Asp Lys Asp Gly Asp Trp
        195                 200                 205

Met Leu Val Gly Asp Val Pro Trp Glu Met Phe Ala Asp Ser Cys Arg
    210                 215                 220

Arg Leu Arg Ile Met Lys Gly Ser Asp Ala Ile Gly Leu Ala Pro Arg
225                 230                 235                 240

Ala Ala Asp Lys Ser Lys Asn Arg Asn
                245

<210> SEQ ID NO 64
<211> LENGTH: 750
<212> TYPE: DNA
<213> ORGANISM: Sorghum bicolor

<400> SEQUENCE: 64
atgtcgcccc cactcgagct cgactacata ggcctctcgc cgcagccggc cgccgccgcc      60
gccgccgccg atgccgacga cgacctgaag ggtaccgagc tccgcctcgg tctgccaggg     120
tccgggtcgc cggaccgccg tgtcgcggct gccaccgcta ccaccctgga gctgctcccg     180
gccaagggcg ccaagcgcgg gttttctgac gaggcgcccc cgccatctcc cgctgccgct     240
gccgggaagg gaaagaaggt ggcggaagag gaggacgacg acaagaaggt tgcagcgacg     300
ccgcagccgg ccgcaaaagc tcaggtggtg ggatggccac caatccgcag ctaccgcaag     360
aacacgatgg ctaccaccca gctgaagggt agcaaggagg atactgaggc caagcagggc     420
cagggattcc tgtacgtcaa ggtcagcatg gatggcgcgc cgtacctgag gaagattgac     480
ctcaagactt acaagaacta caaggacctg tctactgcgc ttgagaagat gttcagtggc     540
ttcagtactg gcaaggatgg cttatctgag taccgcaagg atggtgaata tgttttgact     600
tatgaggaca aggatggaga ttggatgctt gtcggcgatg taccatggga gatgttcgct     660
gactcttgcc gcaggctcag gatcatgaaa ggatcagatg caattggact tgctccaagg     720
gcagctgata agtccaagaa ccgcaactag                                      750

<210> SEQ ID NO 65
<211> LENGTH: 220
<212> TYPE: PRT
<213> ORGANISM: Sorghum bicolor

<400> SEQUENCE: 65

Met Ser Val Glu Thr Glu Arg Ser Ser Thr Glu Ser Ser Ala Ala Ser
1               5                  10                  15

Gly Leu Asp Phe Glu Asp Thr Ala Leu Thr Leu Thr Leu Arg Leu Pro
            20                  25                  30

Gly Ser Ala Pro Ala Pro Ala Val Ala Ala Ser Leu Ser Ser Ser
        35                  40                  45

Ser Ser Ser Ala Phe Pro Asp Ala Asp Arg Lys Arg Ala Ser Ser Asp
            50                  55                  60

Ala Asn Pro Asp Arg Ser Ser Pro Leu Ala Ala Ser Ser Asp Ala Ala
 65                  70                  75                  80

Pro Ala Pro Lys Ala Arg Val Val Gly Trp Pro Pro Val Arg Ser Tyr
                85                  90                  95

Arg Lys Asn Ala Leu Ala Asp Val Ala Gly Ser Ser Lys Ala Asn Gln
            100                 105                 110

Ala Ala Lys Phe Val Lys Val Ala Val Asp Gly Ala Pro Tyr Leu Arg
            115                 120                 125

Lys Val Asp Leu Gln Ala Tyr Ala Gly Tyr Asp Gln Leu Leu Arg Ala
130                 135                 140

Leu Gln Asp Lys Phe Phe Ser His Phe Thr Ile Arg Lys Phe Ala Asp
145                 150                 155                 160

Asp Glu Arg Lys Leu Val Asp Ala Val Asn Gly Thr Glu Tyr Val Pro
                165                 170                 175

Thr Tyr Glu Asp Lys Asp Gly Asp Trp Met Leu Val Gly Asp Val Pro
            180                 185                 190

Trp Lys Met Phe Val Glu Thr Cys Gln Arg Leu Arg Leu Met Lys Gly
            195                 200                 205

Ser Glu Ala Val Asn Leu Ala Pro Arg Ala Ala Arg
210                 215                 220

<210> SEQ ID NO 66
<211> LENGTH: 663
<212> TYPE: DNA
<213> ORGANISM: Sorghum bicolor

<400> SEQUENCE: 66
atgtcggtgg agacggagcg gagctccacc gagtcctccg cggcctccgg gctcgacttc     60
gaggacaccg cgctcacgct caccctccgc ctcccgggct ccgcccccgc ccccgctgcc    120
gtcgcggcct ccttgtcctc gtcctcgtcc tccgccttcc ccgacgccga ccgcaagcgc    180
gcctcctccg acgccaaccc cgaccgctcc tccccgctcg ccgcttcctc cgacgctgca    240
ccggcaccca aggcgcgggt ggtggggtgg ccgccggtga ggtcgtaccg caagaacgcg    300
ctcgccgacg tcgcgggatc cagcaaggca aaccaggccg ccaagttcgt caaggtggcc    360
gtcgacggcg cgccctacct gcggaaagtg gacctccagg cgtacgccgg ctacgaccag    420
ctcctccgcg cgctccagga caagttcttc tcccacttca ccatcaggaa gttcgccgac    480
gacgagagga agctggtgga cgcggtgaac gggacggagt acgtgcccac gtacgaggac    540
aaggatggcg actggatgct cgtcggcgac gtccccctgga agatgtttgt ggaaacctgc    600
cagcgccttc gtctgatgaa aggttcagag gccgttaact tagcaccaag agccgcccga    660
tga                                                                 663

<210> SEQ ID NO 67
<211> LENGTH: 258
<212> TYPE: PRT
<213> ORGANISM: Sorghum bicolor

<400> SEQUENCE: 67

Met Ser Pro Pro Leu Glu Leu Asp Tyr Ile Gly Leu Ser Pro Gln Pro
 1               5                  10                  15

Ala Ala Ala Ala Ala Ala Asp Ala Asp Asp Asp Leu Lys Gly Thr
            20                  25                  30

Glu Leu Arg Leu Gly Leu Pro Gly Ser Gly Pro Asp Arg Arg Val
    35                  40                  45

Ala Ala Ala Thr Ala Thr Leu Glu Leu Leu Pro Ala Lys Gly Ala
 50                  55                  60

Lys Arg Gly Phe Ser Asp Glu Ala Pro Pro Ser Pro Ala Ala Ala
65                   70                  75                  80

Ala Gly Lys Gly Lys Lys Val Ala Glu Glu Asp Asp Lys Lys
                85                  90                  95

Val Ala Ala Thr Pro Gln Pro Ala Ala Lys Ala His Val Val Gly Trp
                100                 105                 110

Pro Pro Ile Arg Ser Tyr Arg Lys Asn Thr Met Ala Thr Thr Gln Leu
            115                 120                 125

Lys Gly Ser Lys Glu Asp Thr Glu Ala Lys Gln Gly Gln Gly Phe Leu
        130                 135                 140

Tyr Val Lys Val Ser Met Asp Gly Ala Pro Tyr Leu Arg Lys Ile Asp
145                 150                 155                 160

Leu Lys Thr Tyr Lys Asn Tyr Lys Lys Pro Leu Lys Ala Ser Tyr Leu
                165                 170                 175

Ile Pro Arg Ile Ser Asn Ser Phe Asn Leu Pro Leu Val Trp Val Ser
            180                 185                 190

Gly Lys Asp Gly Leu Ser Glu Tyr Arg Lys Asp Gly Glu Tyr Val Leu
        195                 200                 205

Thr Tyr Glu Asp Lys Asp Gly Asp Trp Met Leu Val Gly Asp Val Pro
    210                 215                 220

Trp Glu Met Phe Ala Asp Ser Cys Arg Arg Leu Arg Ile Met Lys Gly
225                 230                 235                 240

Ser Asp Ala Ile Gly Leu Ala Pro Arg Ala Ala Asp Lys Ser Lys Asn
                245                 250                 255

Arg Asn

<210> SEQ ID NO 68
<211> LENGTH: 657
<212> TYPE: DNA
<213> ORGANISM: Sorghum bicolor

<400> SEQUENCE: 68

```
atgtcgcccc cactcgagct cgactacata ggcctctcgc cgcagccggc cgccgccgcc      60
gccgccgccg atgccgacga cgacctgaag ggtaccgagc tccgcctcgg tctgccaggg     120
tccgggtcgc cggaccgccg tgtcgcggct gccaccgcta ccaccctgga gctgctcccg     180
gccaagggcg ccaagcgcgg gttttctgac gaggcgcccc cgccatctcc cgctgccgct     240
gccgggaagg gaaagaaggt ggcggaagag gaggacgacg acaagaaggt tgcagcgacg     300
ccgcagccgg ccgcaaaagc tcacgtggtg ggatggccac caatccgcag ctaccgcaag     360
aacacgatgg ctaccaccca gctgaagggt agcaaggagg atactgaggc caagcagggc     420
cagggattcc tgtacgtcaa ggtcagcatg gatggcgcgc cgtacctgag gaagattgac     480
ctcaagactt acaagaacta caagaaacct ttaaaagcat catacttgat tcctaggata     540
agcaatagct tcaacttacc gttattttg agtaattgta agattacaaa caatctggca     600 taccttttt tttctttggt gaactttta tttcttgcta aacaaatacc ctggtga        657
```

<210> SEQ ID NO 69
<211> LENGTH: 279
<212> TYPE: PRT

<213> ORGANISM: Sorghum bicolor
<220> FEATURE:
<221> NAME/KEY: misc_feature
<222> LOCATION: (110)..(110)
<223> OTHER INFORMATION: Xaa can be any naturally occurring amino acid

<400> SEQUENCE: 69

Met Pro Pro Pro Leu Glu Ala Arg Asp Phe Leu Gly Ala Gly Ala Thr
1               5                   10                  15

Ser Ser Cys Cys Ser Ser Cys Ser Ser Gly Gly Asp Gly Thr Val
            20                  25                  30

Pro His Leu Ala Leu Arg Leu Gly Leu Pro Gly Ser Asp Ser Pro Gly
                35                  40                  45

Arg Gly Ala Gln Ala Glu His Ala His Val Asp Ala Ala Leu Thr Leu
    50                  55                  60

Gly Pro Ala Pro Ala Pro Ala Pro Arg Gly Ala Lys Arg Gly
65                  70                  75                  80

Phe Ala Asp Ser Leu Asp Arg Ser Ala Lys Arg Asp Gly Ala Ala Ala
                85                  90                  95

Asp Asp Asp Ala Ala Gly Gly Val Thr Gly Glu Asp Lys Xaa Val Ala
            100                 105                 110

Ala Ala Ala Gly Ala Pro Pro Ala Ala Lys Ala Gln Val Val Gly
        115                 120                 125

Trp Pro Pro Val Arg Ser Tyr Arg Lys Asn Thr Leu Ala Ala Ser Ala
130                 135                 140

Thr Lys Thr Lys Val Glu Asp Glu Gly Arg Ser Glu Ala Gly Cys Cys
145                 150                 155                 160

Tyr Val Lys Val Ser Met Asp Gly Ala Pro Tyr Leu Arg Lys Val Asp
                165                 170                 175

Leu Lys Thr Tyr Ser Ser Tyr Glu Asn Leu Ser Leu Gly Leu Glu Lys
            180                 185                 190

Met Phe Ser Cys Phe Ile Thr Gly Gln Asn Ser Ser Cys Lys Thr Ser
        195                 200                 205

Arg Arg Asp Arg Phe Thr Asp Gly Ser Arg Ala Asp Ala Leu Gln Asp
    210                 215                 220

Gln Glu Tyr Val Leu Thr Tyr Glu Asp Lys Asp Ala Asp Trp Met Leu
225                 230                 235                 240

Val Gly Asp Leu Pro Trp Asp Leu Phe Thr Thr Ile Cys Arg Lys Leu
                245                 250                 255

Arg Ile Met Arg Gly Ser Asp Ala Ala Gly Met Ala Pro Arg Ser Leu
            260                 265                 270

Glu Gln Ile Ala Arg Asn Lys
        275

<210> SEQ ID NO 70
<211> LENGTH: 840
<212> TYPE: DNA
<213> ORGANISM: Sorghum bicolor
<220> FEATURE:
<221> NAME/KEY: misc_feature
<222> LOCATION: (329)..(329)
<223> OTHER INFORMATION: n is a, c, g, or t

<400> SEQUENCE: 70
atgccgccgc cgctcgaggc gcgcgacttc ctcggcgccg gcgccacctc gtcgtgctgc        60
tcgtcgtcct gctcctccgg cggcgatggg acggtgccgc acctcgcgct gcggctcggg       120
ctcccggggt ccgactcccc cggccgaggc gcgcaggcgg agcacgccca cgtggacgcc       180

```
gcgctcaccc tcggccccgc ccccgccccc gcgccgccca ggggaggcgc caagcgcggg      240
ttcgccgact ccctcgaccg gtccgcgaag cgggacggtg ctgcggcgga tgacgacgct      300
gctgggggcg taactgggga ggataaggng gtagctgcgg ccgctgccgg agctccgccg      360
gctgccaagg cacaagttgt tggatggcca cctgttagga gctaccgaaa gaatacacta      420
gctgcaagtg ccacaaagac aaaggtggaa gatgaaggta ggagtgaggc gggatgctgt      480
tatgttaagg tcagcatgga tggagcccca tacctaagga aggtagacct caagacctat      540
tcaagctatg agaatctctc gcttggtctg gagaaaatgt tcagctgctt catcactggt      600
caaaacagtt cttgcaagac atcaagaagg gataggttta ctgatggttc tagggctgat      660
gcccttcagg accaagaata tgtccttact tacgaagata agatgctga ctggatgctt       720 gttggtgatc tgccctggga cttgttcacc acaatttgtc ggaaactaag aatcatgaga      780
ggctctgatg ctgctggcat ggctccaaga tcactggaac agatagctcg gaacaaataa      840
```

<210> SEQ ID NO 71
<211> LENGTH: 199
<212> TYPE: PRT
<213> ORGANISM: Sorghum bicolor

<400> SEQUENCE: 71

```
Met Glu Ile Val Asp Ala Asp Asn Leu Ser Ala Thr Glu Leu Arg Leu
1               5                   10                  15

Gly Leu Pro Gly Thr Ser Ser Asp Asp Trp Gln Lys Lys Pro Ser
            20                  25                  30

Pro Ser Val Gly Ala Lys Arg Ala Leu Asp Asp Thr Arg Ser Glu Ala
        35                  40                  45

Ser Gly Thr Ser Ser Pro Ala Thr Ala Ala Asp Leu Asp Leu Asp His
    50                  55                  60

Asp His Asp Ala Ala Pro Pro Lys Ala Gln Val Val Gly Trp Pro
65                  70                  75                  80

Pro Val Arg Ala Tyr Arg Lys Asn Thr Phe Gln Ala Ala Ala Ala
                85                  90                  95

Ala Lys Lys Ala Asp Gln Gln Gln Gln Gln Gly Gly Gly Leu Tyr
            100                 105                 110

Val Lys Val Ser Met Asp Gly Ala Pro Tyr Leu Arg Lys Val Asp Leu
        115                 120                 125

Arg Met Tyr Lys Gly Tyr Arg Glu Leu Arg Glu Ala Leu Asp Ala Leu
    130                 135                 140

Phe Thr Lys Ser Phe Ser Ala Ala Ala Ala Glu Gly Gly Asp His Gln
145                 150                 155                 160

His Ala Ile Ala Tyr Glu Asp Lys Asp Gly Asp Leu Met Leu Val Gly
                165                 170                 175

Asp Val Pro Trp Asp Met Phe Ile Ser Ser Cys Lys Lys Leu Arg Ile
            180                 185                 190

Met Lys Gly Ser Glu Ala Arg
        195
```

<210> SEQ ID NO 72
<211> LENGTH: 600
<212> TYPE: DNA
<213> ORGANISM: Sorghum bicolor

<400> SEQUENCE: 72

```
atggagatcg tcgacgccga caacctgagc gccaccgagc tccgcctcgg cctgccggga      60
```

```
accagcagca gcgacgactg gcagaagaag ccgtcgccct ccgtcggggc caagcgcgct      120
ctggacgaca ccaggagcga ggcctcgggg accagctcgc cggccaccgc cgcagacctc      180
gacctcgacc acgaccacga cgccgcaccg cctcccaagg cgcaagtcgt cgggtggccg      240
ccggtgaggg cgtacaggaa gaacaccttc caggcggcgg cggcggcggc caagaaggcc      300
gaccagcagc agcagcagca gggaggaggg ctgtatgtga aggtgagcat ggacggggcg      360
ccgtacctca ggaaggtgga cctcagaatg tacaaggggt acaggagct cagggaggcg       420 ctggacgccc tcttcaccaa gtccttctcg gccgccgcgg cggagggcgg cgaccaccag      480
cacgccatcg cgtacgagga caaggacggc gatctcatgc tcgtcggaga cgtgccctgg      540
gatatgttca tctcctcatg caagaagctc aggataatga agggctctga ggccaggtga      600

<210> SEQ ID NO 73
<211> LENGTH: 106
<212> TYPE: PRT
<213> ORGANISM: Sorghum bicolor

<400> SEQUENCE: 73

Lys Val Asp Ile Lys Met Tyr Ser Ser Tyr Glu Asp Leu Ser Met Ala
1               5                   10                  15

Leu Glu Lys Met Phe Ser Cys Phe Ile Thr Gly Gln Ser Gly Leu His
            20                  25                  30

Lys Ser Ser Lys Asp Arg Leu Thr Asn Gly Ser Lys Val Asp Ala
        35                  40                  45

Leu Lys Asp Gln Glu Tyr Val Leu Thr Tyr Asp Lys Asp Ala Asp
    50                  55                  60

Trp Met Leu Val Gly Asp Leu Pro Trp Asp Tyr Phe Thr Ser Ile Cys
65                  70                  75                  80

Arg Lys Leu Lys Ile Met Arg Gly Ser Asp Ala Val Gly Ile Ala Pro
                85                  90                  95

Arg Thr Ile Glu Gln Thr Gly Gln Asn Lys
            100                 105

<210> SEQ ID NO 74
<211> LENGTH: 321
<212> TYPE: DNA
<213> ORGANISM: Sorghum bicolor

<400> SEQUENCE: 74
aaggtggaca tcaagatgta ctccagctac gaggacctct ccatggcgct tgagaagatg       60
ttcagctgct tcatcactgg tcaaagtggt ctgcataaat catcgagcaa agacaggctg      120
actaatggct caaggtgga tgccctcaaa gaccaggagt atgtccttac atatgaggat      180
aaggatgcag actggatgct tgttggtgat cttccctggg attattttac ctctatctgt      240
cggaagctca aaatcatgag gggctctgat gctgttggaa tagctccaag aaccatagag      300
cagacaggtc agaacaaata a                                                 321

<210> SEQ ID NO 75
<211> LENGTH: 112
<212> TYPE: PRT
<213> ORGANISM: Sorghum bicolor

<400> SEQUENCE: 75

Ser Cys Thr Ala Pro Ser Val Ala Ala Ala Asn Thr Thr Ala Ser Val
1               5                   10                  15
```

```
Gly Gly Gly Ser Phe Val Lys Val Ser Met Asp Gly Ala Pro Tyr Leu
            20                  25                  30

Arg Lys Val Asp Leu Arg Met Tyr Lys Gly Tyr Arg Glu Leu Arg Glu
        35                  40                  45

Ala Leu Glu Ala Met Phe Val Ser Ser Asn Ser Gly Ser Ala Asn Leu
50                  55                  60

Ser Glu Phe Ala Val Thr Tyr Glu Asp Lys Asp Gly Asp Leu Met Leu
65                  70                  75                  80

Val Gly Asp Val Pro Phe Glu Met Phe Thr Ser Cys Lys Lys Leu
                    85                  90                  95

Arg Ile Met Lys Arg Ser Glu Ala Thr Gly Leu Gly Ser Ala Arg Gln
            100                 105                 110
```

<210> SEQ ID NO 76
<211> LENGTH: 339
<212> TYPE: DNA
<213> ORGANISM: Sorghum bicolor

<400> SEQUENCE: 76

```
agctgcacgg cgccatcggt agccgccgcg aacaccaccg ccagcgtcgg cggcggctcg     60
ttcgtcaaag tgagcatgga cggcgccccg tacctgagga aggtggacct gaggatgtac    120
aagggctaca gggagctccg ggaggccctg gaggccatgt tcgtctcctc caacagcggc    180
agcgccaacc tgtccgagtt cgccgtcacc tacgaggaca aggacggcga cctcatgctc    240
gtcggagacg tgccgttcga gatgttcact agcacttgca agaagctgag gatcatgaag    300
agatctgaag ccacaggcct gggatcagcg aggcaatga                           339
```

<210> SEQ ID NO 77
<211> LENGTH: 190
<212> TYPE: PRT
<213> ORGANISM: Sorghum bicolor

<400> SEQUENCE: 77

```
Thr Arg Pro Lys Arg Thr Thr Ser Pro Gly Thr Ala Val Pro Gly His
1               5                   10                  15

Pro Gln Ser Tyr Gly Val Val Gly Trp Pro Pro Ile Arg Thr Phe Arg
            20                  25                  30

Met Asn Ser Leu Phe Asn Gln Ala Lys Glu Asn Ala Ser Glu Ala Gly
        35                  40                  45

Thr Lys Lys Pro Thr Val Glu Ser Asp Met Gln Glu Asp Lys Glu Glu
50                  55                  60

Ser Lys Lys Gly Arg Val Val Gly Trp Val Lys Val Asn Met Glu Gly
65                  70                  75                  80

Asp Ile Ile Gly Arg Lys Val Asp Leu Asn Ala His Arg Ser Tyr Lys
            85                  90                  95

Thr Leu Ala Ser Ala Leu Glu Leu Met Phe Met Lys Pro Ser Ile Ser
            100                 105                 110

Leu Cys Thr Ser Ser Ser Ser Lys Ser Leu Lys Leu Leu Asp Asn Ser
            115                 120                 125

Ser Glu Tyr Gln Leu Thr Tyr Glu Asp Arg Asp Gly Asp Trp Met Leu
            130                 135                 140

Val Gly Asp Val Pro Trp Glu Met Phe Val Gly Ser Val Lys Arg Leu
145                 150                 155                 160

Lys Ile Met Arg Thr Ser Asp Ala Asn Gly Leu Gly Pro Arg Phe Gln
            165                 170                 175
```

```
Gly Pro His Lys Pro Thr Ala Ala Cys Thr Arg Gly Arg Ile
            180                 185                 190
```

```
<210> SEQ ID NO 78
<211> LENGTH: 978
<212> TYPE: DNA
<213> ORGANISM: Sorghum bicolor

<400> SEQUENCE: 78
gcacgaggcc aaaacgcacc acctcgccgg ggacggccgt tcctggccat ccacagagct    60
atggagtagt gggatggcca cccataagaa ctttcaggat gaacagccta tttaaccagg   120
ccaaagaaaa tgcctctgag gctggcacca agaagcccac cgttgaatct gacatgcagg   180
aagacaagga ggagagcaag aaaggacggg tcgtcggttg ggtgaaggtg aacatggaag   240
gagatatcat tggaaggaag gtggatctca acgcccatcg atcttacaag acccttgcct   300
cagcacttga gctcatgttc atgaagccgt ccatcagtct ttgcacttct agtagttcta   360
agtctctaaa gctattggac aactcatcgg agtatcagct cacctatgag acagggatg    420
gggactggat gctagttgga gatgtaccct gggagatgtt tgtaggttca gtgaagaggc   480
tcaagatcat gaggacctca gatgccaacg gtctcggtcc gcgattccaa gggcctcaca   540
aacctacagc agcttgcaca agaggcagga tatgaaaacc accgatgggc gttaatttgg   600
tgctagagag ctataccgct ggtgaagctt gaactgtgtt tgataccacg taacagcagc   660
ccatatcttt ggcatagttg tgagattact tgtgtctagt ggaaatagta aagttttttt   720
ttccttcttc ttcttcttct tcttcttctt cccttggtg cactcgttga gctttttctc     780
atgggctatg actaggagca tagccccat ctcttctgtc cacactgttt ttacctgtga    840
ggcattgtcg cccaaagtat ctgttctgct gtttcatatt tgtgttcata tctgaattcc   900
cagttgccgc acagtgtctg tgctaattgc tgcggtctgc aatgcaacgc caaccacccg   960
agtgtttggg ggggacag                                                 978
```

```
<210> SEQ ID NO 79
<211> LENGTH: 271
<212> TYPE: PRT
<213> ORGANISM: Zea mays

<400> SEQUENCE: 79

Met Ala Thr Thr Thr Asp Leu Gly Phe Glu Ala Thr Glu Leu Arg Leu
1               5                   10                  15
Gly Leu Pro Gly Gly Gly Gly Gly Glu Pro Ala Leu Gly Gly Glu
            20                  25                  30
Gly Arg Ser Ser Ser Ala Ser Gly Lys Arg Gly Phe Ala Glu Thr
        35                  40                  45
Ile Asp Leu Lys Leu Lys Leu Glu Pro Ala Ala Val Val Glu Ala Glu
    50                  55                  60
Glu Glu Glu Glu Asp His Gly Val Ala Val Ala Leu Glu Lys Glu Glu
65                  70                  75                  80
Glu Ala Gly Lys Met Lys Arg Ser Pro Ser Gln Ser Ser Val Ala Ala
                85                  90                  95
Ala Ala Ala Ala Val Leu Ala Asp Pro Ala Glu Lys Pro Arg Ala Ala
            100                 105                 110
Lys Ala Gln Val Val Gly Trp Pro Pro Val Arg Ser Phe Arg Lys Asn
        115                 120                 125
Ile Met Ser Val Gln Ser Asp Lys Gly Ala Ala Ala Asn Gly Asp
    130                 135                 140
```

```
Lys Ser Ser Pro Ala Ala Gly Gly Ala Ala Phe Val Lys Val Ser
145                 150                 155                 160

Leu Asp Gly Ala Pro Tyr Leu Arg Lys Val Asp Leu Lys Met Tyr Arg
                165                 170                 175

Ser Tyr Gln Gln Leu Ser Lys Ala Leu Glu Asn Met Phe Ser Ser Phe
            180                 185                 190

Thr Ile Gly Ser Cys Gly Ser Gln Gly Met Asn Gly Met Asn Glu Ser
            195                 200                 205

Lys Leu Val Asp Leu Leu Asn Gly Ser Glu Tyr Val Pro Thr Tyr Glu
        210                 215                 220

Asp Lys Asp Gly Asp Trp Met Leu Val Gly Asp Val Pro Trp Glu Met
225                 230                 235                 240

Phe Val Glu Ser Cys Lys Arg Leu Arg Ile Met Lys Gly Ser Glu Ala
                245                 250                 255

Ile Gly Leu Ala Pro Arg Ala Met Glu Lys Cys Lys Asn Arg Ser
            260                 265                 270
```

<210> SEQ ID NO 80
<211> LENGTH: 816
<212> TYPE: DNA
<213> ORGANISM: Zea mays

<400> SEQUENCE: 80

```
atggcgacga cgacggacct gggggttcgag gcgacggagc tccgcctggg cctgccggc      60
gggggaggtg aggggagcc ggcgctgggc ggcgagggga ggagctcttc ctccgcctcc     120
ggcaagaggg gcttcgccga gaccatcgac ctgaagctga agctggagcc agcggccgtc     180
gtggaggcgg aggaggagga ggaggaccac ggcgttgctg ttgcccttga aaggaggag      240
gaggccggga agatgaagcg gtccccgagc cagagcagcg tcgccgccgc cgccgccgcc     300
gtgctggctg accccgccga gaagccgcgc gccgccaagg ctcaggtggt gggatggcca     360
ccggtccggt cgttccggaa gaacatcatg tccgtgcagt ccgacaaggg cgccgccgcc     420
gccaacggcg acaagtcctc gccggcggca ggcggcggtg ccgcgttcgt gaaggtgagc     480
ttggacggcg cgccctacct gcgcaaagtg gacctcaaga tgtacaggag ctaccagcag     540
ctgtccaagg cgctcgagaa catgttcagc tccttcacca tcggaagctg tgggtctcaa     600
gggatgaacg gcatgaacga gagcaagctg gtggatctgc tcaacggctc cgagtacgtg     660
ccgacctacg aggacaagga cggggactgg atgctcgtcg gcgatgtgcc gtgggagatg     720
ttcgtcgaat catgcaagcg ccttcggatc atgaaaggat cagaagccat tggcctggcg     780
ccaagggcca tggagaaatg caagaacaga agctga                               816
```

<210> SEQ ID NO 81
<211> LENGTH: 244
<212> TYPE: PRT
<213> ORGANISM: Zea mays

<400> SEQUENCE: 81

```
Met Ser Pro Pro Leu Asp Leu Asp Tyr Ile Gly Leu Ser Pro Ala Ala
1               5                   10                  15

Ala Ala Ala Ala Ala His Asp Asp Leu Lys Gly Thr Glu Leu Arg Leu
                20                  25                  30

Gly Leu Pro Gly Ser Gly Ser Pro Asp Arg Arg Val Val Ala Ala Thr
            35                  40                  45

Ala Thr Thr Leu Asp Leu Leu Pro Ala Lys Gly Ala Lys Arg Gly Phe
```

```
Ser Asp Glu Ala Pro Thr Pro Ser Pro Gly Ala Ala Ser Gly Lys Gly
 65                  70                  75                  80

Lys Lys Val Ala Glu Glu Asp Asp Lys Lys Val Ala Ala Thr Pro
             85                  90                  95

Gln Pro Val Ala Lys Ala Gln Val Val Gly Trp Pro Pro Ile Arg Ser
            100                 105                 110

Tyr Arg Lys Asn Thr Met Ser Thr Thr Gln Leu Lys Gly Ser Lys Glu
            115                 120                 125

Asp Ala Glu Ala Lys Gln Asp Gln Gly Phe Leu Tyr Val Lys Val Ser
        130                 135                 140

Met Asp Gly Ala Pro Tyr Leu Arg Lys Ile Asp Leu Lys Thr Tyr Lys
145                 150                 155                 160

Asn Tyr Lys Asp Leu Ser Thr Ala Leu Glu Lys Met Phe Ser Gly Phe
                165                 170                 175

Ser Thr Gly Lys Asp Gly Leu Ser Glu Tyr Arg Lys Asp Gly Glu Tyr
            180                 185                 190

Val Leu Thr Tyr Glu Asp Lys Asp Gly Asp Trp Met Leu Val Gly Asp
        195                 200                 205

Val Pro Trp Glu Met Phe Ala Asp Ser Cys Arg Arg Leu Arg Ile Met
210                 215                 220

Lys Gly Ser Asp Ala Ile Gly Leu Ala Pro Arg Ala Ala Asp Lys Ser
225                 230                 235                 240

Lys Asn Arg Asn
```

<210> SEQ ID NO 82
<211> LENGTH: 639
<212> TYPE: DNA
<213> ORGANISM: Zea mays

<400> SEQUENCE: 82

```
atgtcgcccc cactcgacct cgactacata ggcctctcgc cggcggcggc tgccgccgct      60
gcccacgacg acctgaaggg taccgagctc cgccttggtc tgccggggtc cggttcgccg     120
gaccgccgtg ttgtggctgc caccgcaacc accctgacct gctcccggc taagggcgcc     180
aagcgcgggt tttctgacga ggcgccgacg ccatcgcccg gtgcagcttc cgggaaggga     240
aagaaggtag cggaagagga ggacgacaag aaggttgcag cgacgccgca gccggtcgca     300
aaagctcagg tggtgggatg gccaccaatc cgaagctacc gcaagaacac gatgtctacc     360
acccagctga agggcagcaa ggaggatgct gaggccaagc aggaccaggg gttcctgtac     420
gtcaaggtca gcatggatgg cgcgccgtac ctcaggaaga ttgacctcaa gacttacaag     480
aactacaagg acctgtcgac tgcgcttgag aagatgttca gtggcttcag tactggcaag     540
gatggcttat ctgagtaccg caaggatggt gaatatgttc tgacttacga ggacaaggat     600
ggagattgga tgcttgttgg cgatgtacca tgggagtaa                            639
```

<210> SEQ ID NO 83
<211> LENGTH: 239
<212> TYPE: PRT
<213> ORGANISM: Zea mays

<400> SEQUENCE: 83

```
Met Ala Thr Thr Thr Asp Leu Gly Phe Glu Ala Thr Glu Leu Arg Leu
  1               5                  10                  15

Gly Leu Pro Gly Gly Gly Gly Gly Gly Glu Pro Ala Leu Gly Gly Glu
```

```
                    20                  25                  30
Gly Arg Ser Ser Ser Ala Ser Gly Lys Arg Gly Phe Ala Glu Thr
                35                  40                  45
Ile Asp Leu Lys Leu Lys Leu Glu Pro Ala Ala Val Val Glu Ala Glu
 50                  55                  60
Glu Glu Glu Glu Asp His Gly Val Ala Val Ala Leu Glu Lys Glu Glu
 65                  70                  75                  80
Glu Ala Gly Lys Met Lys Arg Ser Pro Ser Gln Ser Ser Val Ala Ala
                 85                  90                  95
Ala Ala Ala Ala Val Leu Ala Asp Pro Ala Glu Lys Pro Arg Ala Ala
                100                 105                 110
Lys Ala Gln Val Val Gly Trp Pro Pro Val Arg Ser Phe Arg Lys Asn
                115                 120                 125
Ile Met Ser Val Gln Ser Asp Lys Gly Ala Ala Ala Asn Gly Asp
                130                 135                 140
Lys Ser Ser Pro Ala Ala Gly Gly Ala Ala Phe Val Lys Val Ser
145                 150                 155                 160
Leu Asp Gly Ala Pro Tyr Leu Arg Lys Val Asp Leu Lys Met Tyr Arg
                165                 170                 175
Ser Tyr Gln Gln Leu Ser Lys Ala Leu Glu Asn Met Phe Ser Ser Phe
                180                 185                 190
Thr Ile Gly Ser Cys Gly Ser Gln Gly Met Asn Gly Met Asn Glu Ser
                195                 200                 205
Lys Leu Val Asp Leu Leu Asn Gly Ser Glu Tyr Val Pro Thr Tyr Glu
                210                 215                 220
Asp Lys Asp Gly Asp Trp Met Leu Val Gly Asp Val Pro Trp Glu
225                 230                 235

<210> SEQ ID NO 84
<211> LENGTH: 720
<212> TYPE: DNA
<213> ORGANISM: Zea mays

<400> SEQUENCE: 84
atggcgacga cgacggacct ggggttcgag gcgacggagc tccgcctggg cctgcccggc      60
gggggaggtg gaggggagcc ggcgctgggc ggcgagggga ggagctcttc ctccgcctcc     120
ggcaagaggg gcttcgccga gaccatcgac ctgaagctga gctggagcc agcggccgtc     180 gtggaggcgg aggaggagga ggaggaccac ggcgttgctg ttgcccttga aggaggag      240 gaggccggga agatgaagcg gtccccgagc cagagcagcg tcgccgccgc cgccgccgcc     300
gtgctggctg accccgccga aagccgcgc ccgccaagg ctcaggtggt gggatggcca     360
ccggtccggt cgttccggaa gaacatcatg tccgtgcagt ccgacaaggg cgccgccgcc     420
gccaacggcg acaagtcctc gccggcggca ggcggcggtg ccgcgttcgt gaaggtgagc     480
ttggacggcg cgccctacct gcgcaaagtg gacctcaaga tgtacaggag ctaccagcag     540
ctgtccaagg cgctcgagaa catgttcagc tccttcacca tcggaagctg tgggtctcaa     600
gggatgaacg gcatgaacga gagcaagctg gtggatctgc tcaacggctc cgagtacgtg     660
ccgacctacg aggacaagga cggggactgg atgctcgtcg gcgatgtgcc gtgggagtga     720

<210> SEQ ID NO 85
<211> LENGTH: 228
<212> TYPE: PRT
<213> ORGANISM: Zea mays
```

<400> SEQUENCE: 85

```
Met Ala Gly Ala Asp Val Asp Val Gly Thr Glu Leu Arg Leu Gly Leu
1               5                   10                  15
Pro Gly Gly Gly Ala Ala Ala Lys Lys Asp Thr Ile Asp Leu Lys
            20                  25                  30
Leu Lys Leu Pro Thr Ala Gly Met Glu Glu Ala Ala Ala Ala Ala Arg
            35                  40                  45
Pro Glu Pro Ala Ala Glu Lys Ala Lys Arg Pro Ala Glu Ala Pro Ala
        50                  55                  60
Ala Asp Ala Glu Lys Pro Pro Ala Pro Lys Ala Gln Ala Val Gly Trp
65                  70                  75                  80
Pro Pro Val Arg Ser Tyr Arg Arg Asn Ala Met Thr Val Val Gln Ala
                85                  90                  95
Val Arg Ser Lys Lys Glu Glu Pro Glu Lys Gln Gln Gln Pro Ala
            100                 105                 110
Ala Ala Asn Ala Phe Val Lys Val Ser Met Asp Gly Ala Pro Tyr Leu
        115                 120                 125
Arg Lys Val Asp Leu Lys Thr Tyr Gly Ser Tyr Lys Asp Leu Ser Ala
    130                 135                 140
Ala Leu Lys Lys Met Phe Gly Thr Phe Val Thr Ala Thr Gly Asn Ser
145                 150                 155                 160
Met Asn Glu Gly Arg Leu Val Asp Pro Ala Gly Asp Ala Asp Asp Val
                165                 170                 175
Val Thr Thr Tyr Glu Asp Lys Asp Gly Asp Trp Met Leu Val Gly Asp
            180                 185                 190
Val Pro Trp Glu Met Phe Val Asp Ser Cys Lys Arg Leu Arg Ile Met
        195                 200                 205
Lys Ser Ser Glu Ala Ile Gly Leu Ala Pro Arg Thr Lys Asp Lys Cys
    210                 215                 220
Lys Asn Lys Ser
225
```

<210> SEQ ID NO 86
<211> LENGTH: 687
<212> TYPE: DNA
<213> ORGANISM: Zea mays

<400> SEQUENCE: 86

```
atggctggcg ccgacgtcga cgtcgggacg gagctccggc tcggcctgcc gggaggaggc      60
gccgcggcgg ccaagaagga caccatcgac ctcaagctga agctgcccac cgccggcatg     120
gaggaggcgg ctgccgccgc caggccggag ccggcagccg agaaggccaa gaggcccgcc     180
gaggcgccgg ccgccgatgc cgagaagcca cctgcaccca aggcacaggc cgtgggctgg     240
ccaccagtcc ggtcgtaccg caggaacgcc atgaccgtcg tccaggccgt gaggagcaag     300
aaggaagagg aacctgagaa gcagcaacag cccgctgccg ccaacgcctt cgtgaaggtc     360
agcatggacg gcgcgcccta cctgcgcaag gtggacctga agacgtacgg cagctacaag     420
gacctctccg ctgcactcaa gaagatgttc ggcaccttcg tcaccgcaac tgggaacagc     480
atgaacgagg ggagattggt tgatccggcc ggcgatgctg atgatgtggt cactacttac     540
gaagacaagg atggtgactg gatgctggtc ggcgacgtcc cgtgggagat gtttgtcgac     600
tcatgcaagc gtctgaggat catgaagagt tctgaagcca taggtcttgc accaagaacg     660
aaggataagt gcaagaacaa gagctga                                         687
```

<210> SEQ ID NO 87
<211> LENGTH: 228
<212> TYPE: PRT
<213> ORGANISM: Zea mays

<400> SEQUENCE: 87

```
Met Ala Gly Ala Asp Val Asp Val Gly Thr Glu Leu Arg Leu Gly Leu
1               5                   10                  15

Pro Gly Gly Gly Ala Ala Ala Lys Lys Asp Thr Ile Asp Leu Lys
            20                  25                  30

Leu Lys Leu Pro Thr Ala Gly Met Glu Glu Ala Ala Ala Ala Arg
        35                  40                  45

Pro Glu Pro Ala Ala Glu Lys Ala Lys Arg Pro Ala Glu Pro Ala
    50                  55                  60

Ala Asp Ala Glu Lys Pro Pro Ala Pro Lys Ala Gln Ala Val Gly Trp
65                  70                  75                  80

Pro Pro Val Arg Ser Tyr Arg Arg Asn Ala Met Thr Val Val Gln Ala
                85                  90                  95

Val Arg Ser Lys Lys Glu Glu Pro Glu Lys Gln Gln Gln Pro Ala
            100                 105                 110

Ala Ala Asn Ala Phe Val Lys Val Ser Met Asp Gly Ala Pro Tyr Leu
        115                 120                 125

Arg Lys Val Asp Leu Lys Thr Tyr Gly Ser Tyr Lys Asp Leu Ser Ala
130                 135                 140

Ala Leu Lys Lys Met Phe Gly Thr Phe Val Thr Ala Thr Gly Asn Ser
145                 150                 155                 160

Met Asn Glu Gly Arg Leu Val Asp Pro Ala Gly Asp Ala Asp Asp Val
                165                 170                 175

Val Thr Thr Tyr Glu Asp Lys Asp Gly Asp Trp Met Leu Val Gly Asp
            180                 185                 190

Val Pro Trp Glu Met Phe Val Asp Ser Cys Lys Arg Leu Arg Ile Met
        195                 200                 205

Lys Ser Ser Glu Ala Ile Gly Leu Ala Pro Arg Thr Lys Asp Lys Cys
    210                 215                 220

Lys Asn Lys Ser
225
```

<210> SEQ ID NO 88
<211> LENGTH: 687
<212> TYPE: DNA
<213> ORGANISM: Zea mays

<400> SEQUENCE: 88

```
atggctggcg ccgacgtcga cgtcgggacg gagctccggc tcggcctgcc gggaggaggc      60
gccgcggcgg ccaagaagga caccatcgac ctcaagctga agctgcccac cgccggcatg     120
gaggaggcgg ctgccgccgc caggccggag ccggcagccg agaaggccaa gaggcccgcc     180
gaggcgccgg ccgccgatgc cgagaagcca cctgcaccca aggcacaggc cgtgggctgg     240
ccaccagtcc ggtcgtaccg caggaacgcc atgaccgtcg tccaggccgt gaggagcaag     300
aaggaagagg aacctgagaa gcagcaacag cccgctgccg ccaacgcctt cgtgaaggtc     360
agcatggacg gcgcgcccta cctgcgcaag gtggacctga agacgtacgg cagctacaag     420
gacctctccg ctgcactcaa gaagatgttc ggcaccttcg tcaccgcaac tgggaacagc     480
atgaacgagg ggagattggt tgatccggcc ggcgatgctg atgatgtggt cactacttac     540
```

```
gaagacaagg atggtgactg gatgctggtc ggcgacgtcc cgtgggagat gtttgtcgac    600
tcatgcaagc gtctgaggat catgaagagt tctgaagcca taggtcttgc accaagaacg    660
aaggataagt gcaagaacaa gagctga                                        687
```

<210> SEQ ID NO 89
<211> LENGTH: 246
<212> TYPE: PRT
<213> ORGANISM: Zea mays

<400> SEQUENCE: 89

```
Met Ser Pro Pro Leu Glu Leu Asp Tyr Ile Gly Leu Ser Pro Pro Ala
1               5                   10                  15

Ala Ala Ala Ala Ala Glu Asn Asp Glu Leu Lys Gly Thr Glu Leu Arg
            20                  25                  30

Leu Gly Leu Pro Gly Ser Gly Ser Pro Asp Arg Arg Val Val Ala Ala
        35                  40                  45

Thr Ala Thr Thr Leu Asp Leu Leu Pro Ala Lys Gly Ala Lys Arg Gly
    50                  55                  60

Phe Ser Asp Glu Ala Pro Pro Ser Pro Val Ala Thr Ala Gly Lys
65                  70                  75                  80

Gly Lys Lys Val Ala Glu Glu Tyr Asp Glu Lys Lys Val Ala Ala
                85                  90                  95

Thr Pro Gln Pro Ala Ala Lys Ala Gln Val Val Gly Trp Pro Pro Val
            100                 105                 110

Cys Asn Tyr Arg Lys Asn Thr Met Thr Thr Thr Gln Leu Glu Gly Ser
        115                 120                 125

Lys Glu Asp Gly Asp Ala Lys Gln Gly Gln Gly Phe Leu Tyr Val Lys
    130                 135                 140

Val Ser Met Asp Gly Ala Pro Tyr Leu Arg Lys Ile Asp Leu Lys Thr
145                 150                 155                 160

Tyr Lys Asn Tyr Lys Asp Leu Ser Thr Ala Leu Glu Lys Met Phe Ser
                165                 170                 175

Gly Phe Ser Thr Gly Lys Asp Gly Ser Ser Glu Tyr Arg Lys Asp Gly
            180                 185                 190

Glu Tyr Val Leu Thr Tyr Glu Asp Lys Asp Gly Asp Trp Met Leu Val
        195                 200                 205

Gly Asp Val Pro Trp Glu Met Phe Ala Gly Ser Cys Arg Arg Leu Arg
    210                 215                 220

Ile Met Lys Gly Ser Asp Ala Ile Gly Leu Ala Pro Arg Ala Ala Asp
225                 230                 235                 240

Lys Ser Lys Asn Arg Asn
                245
```

<210> SEQ ID NO 90
<211> LENGTH: 741
<212> TYPE: DNA
<213> ORGANISM: Zea mays

<400> SEQUENCE: 90

```
atgtcgcctc cactcgagct cgactacata ggcctctcgc cgccggcggc agccgccgcc    60
gctgaaaacg acgaactgaa gggtactgag ctccgcctcg gctgccagg gtccgggtcg    120 ccggaccgcc gtgtcgtggc tgccaccgcg accaccctgg acctgctccc ggccaagggc    180
gccaagcgcg gttttctga cgaggcgccc ccgccatccc ctgttgccac tgccggaaag    240
ggaaagaagg tggcagaaga ggagtacgac gagaagaagg tggcagcgac cccgcagccg    300
```

```
gccgccaaag cacaggtggt gggatggcca ccagtctgca actaccgcaa gaacacgatg    360
actaccaccc agctggaggg cagcaaggag gatggtgatg ccaagcaggg tcaggggttc    420
ctgtacgtca aggtcagcat ggatggcgcg ccgtacctca ggaagatcga cctcaagact    480
tacaagaact acaaggacct gtcgaccgcg cttgagaaga tgttcagtgg cttcagtact    540
ggcaaggacg gctcatctga gtaccgcaag gatggtgaat atgttctgac ttacgaggac    600
aaggatggag attggatgct tgtcggcgac gtaccatggg agatgttcgc cggctcctgc    660
cgcaggctca ggatcatgaa aggctcagat gcgattggac tcgctccaag ggcagccgat    720
aagtccaaga accgcaacta g                                              741
```

```
<210> SEQ ID NO 91
<211> LENGTH: 256
<212> TYPE: PRT
<213> ORGANISM: Zea mays

<400> SEQUENCE: 91
```

```
Met Ser Pro Pro Leu Glu Leu Asp Tyr Ile Gly Leu Ser Pro Pro Ala
1               5                   10                  15

Ala Ala Ala Ala Glu Asn Asp Glu Leu Lys Gly Thr Glu Leu Arg
            20                  25                  30

Leu Gly Leu Pro Gly Ser Gly Ser Pro Asp Arg Arg Val Val Ala Ala
        35                  40                  45

Thr Ala Thr Leu Asp Leu Leu Pro Ala Lys Gly Ala Lys Arg Gly
    50                  55                  60

Phe Ser Asp Glu Ala Pro Pro Ser Pro Val Ala Thr Ala Gly Lys
65                  70                  75                  80

Gly Lys Lys Val Ala Glu Glu Tyr Asp Glu Lys Lys Val Ala Ala
            85                  90                  95

Thr Pro Gln Pro Ala Ala Lys Ala Gln Val Val Gly Trp Pro Pro Val
        100                 105                 110

Cys Asn Tyr Arg Lys Asn Thr Met Thr Thr Thr Gln Leu Glu Gly Ser
        115                 120                 125

Lys Glu Asp Gly Asp Ala Lys Gln Gly Gln Gly Phe Leu Tyr Val Lys
    130                 135                 140

Val Ser Met Asp Gly Ala Pro Tyr Leu Arg Lys Ile Asp Leu Lys Thr
145                 150                 155                 160

Tyr Lys Asn Tyr Lys Asp Leu Ser Thr Ala Leu Glu Lys Met Phe Ser
                165                 170                 175

Gly Phe Ser Thr Gly Lys Asp Gly Ser Ser Glu Tyr Arg Lys Asp Gly
            180                 185                 190

Glu Tyr Val Leu Thr Tyr Glu Asp Lys Asp Gly Asp Trp Met Leu Val
        195                 200                 205

Gly Asp Val Pro Trp Asp Cys His Ile Val Phe Arg Ser Asn Cys Arg
    210                 215                 220

Met Phe Ala Gly Ser Cys Arg Arg Leu Arg Ile Met Lys Gly Ser Asp
225                 230                 235                 240

Ala Ile Gly Leu Ala Pro Arg Ala Ala Asp Lys Ser Lys Asn Arg Asn
                245                 250                 255
```

```
<210> SEQ ID NO 92
<211> LENGTH: 771
<212> TYPE: DNA
<213> ORGANISM: Zea mays
```

<400> SEQUENCE: 92

```
atgtcgcctc cactcgagct cgactacata ggcctctcgc cgccggcggc agccgccgcc    60
gctgaaaacg acgaactgaa gggtactgag ctccgcctcg ggctgccagg gtccgggtcg   120
ccggaccgcc gtgtcgtggc tgccaccgcg accaccctgg acctgctccc ggccaagggc   180
gccaagcgcg ggttttctga cgaggcgccc ccgccatcgc ctgttgccac tgccggaaag   240
ggaaagaagg tggcagaaga ggagtacgac gagaagaagg tggcagcgac cccgcagccg   300
gccgccaaag cacaggtggt gggatggcca ccagtctgca actaccgcaa gaacacgatg   360
actaccaccc agctggaggg cagcaaggag gatggtgatg ccaagcaggg tcagggggttc   420
ctgtacgtca aggtcagcat ggatggcgcg ccgtacctca ggaagatcga cctcaagact   480
tacaagaact acaaggacct gtcgaccgcg cttgagaaga tgttcagtgg cttcagtact   540
ggcaaggacg gctcatctga gtaccgcaag gatggtgaat atgttctgac ttacgaggac   600
aaggatggag attggatgct tgtcggcgac gtaccatggg actgccacat cgtctttcgc   660
tccaattgta ggatgttcgc cggctcctgc cgcaggctca ggatcatgaa aggctcagat   720
gcgattggac tcgctccaag ggcagccgat aagtccaaga accgcaacta g            771
```

<210> SEQ ID NO 93
<211> LENGTH: 223
<212> TYPE: PRT
<213> ORGANISM: Zea mays

<400> SEQUENCE: 93

```
Met Ala Gly Ala Asp Val Asp Val Gly Thr Glu Leu Arg Leu Gly Leu
1               5                   10                  15
Pro Gly Gly Gly Ala Ala Ala Lys Lys Asp Thr Ile Asp Leu Lys
            20                  25                  30
Leu Lys Leu Pro Thr Ala Gly Met Glu Glu Ala Ala Ala Ala Arg
        35                  40                  45
Pro Glu Pro Ala Ala Glu Lys Ala Lys Arg Pro Ala Glu Ala Pro Ala
    50                  55                  60
Ala Asp Ala Glu Lys Pro Pro Ala Pro Lys Ala Gln Ala Val Gly Trp
65                  70                  75                  80
Pro Pro Val Arg Ser Tyr Arg Arg Asn Ala Met Thr Val Val Gln Ala
                85                  90                  95
Val Arg Ser Lys Lys Glu Glu Glu Pro Glu Lys Gln Gln Gln Pro Ala
            100                 105                 110
Ala Ala Asn Ala Phe Val Lys Val Ser Met Asp Gly Ala Pro Tyr Leu
        115                 120                 125
Arg Lys Val Asp Leu Lys Thr Tyr Gly Ser Tyr Lys Asp Leu Ser Ala
    130                 135                 140
Ala Leu Lys Lys Met Phe Gly Thr Phe Val Thr Ala Thr Gly Asn Ser
145                 150                 155                 160
Met Asn Glu Gly Arg Leu Val Asp Pro Ala Gly Asp Ala Asp Asp Val
                165                 170                 175
Val Thr Thr Tyr Glu Asp Lys Asp Gly Asp Trp Met Leu Val Gly Asp
            180                 185                 190
Val Pro Trp Glu Met Phe Val Asp Ser Cys Lys Arg Leu Arg Ile Met
        195                 200                 205
Lys Ser Ser Glu Ala Ile Gly Leu Gly Tyr Thr Lys Asn Glu Gly
    210                 215                 220
```

<210> SEQ ID NO 94
<211> LENGTH: 672
<212> TYPE: DNA
<213> ORGANISM: Zea mays

<400> SEQUENCE: 94

```
atggctggcg ccgacgtcga cgtcgggacg gagctccggc tcggcctgcc gggaggaggc      60
gccgcggcgg ccaagaagga caccatcgac ctcaagctga agctgcccac cgccggcatg     120
gaggaggcgc tgccgccgcc caggccggag ccggcagccg agaaggccaa gaggcccgcc     180
gaggcgccgg ccgccgatgc cgagaagcca cctgcaccca aggcacaggc cgtgggctgg     240
ccaccagtcc ggtcgtaccg caggaacgcc atgaccgtcg tccaggccgt gaggagcaag     300
aaggaagagg aacctgagaa gcagcaacag cccgctgccg ccaacgcctt cgtgaaggtc     360
agcatggacg gcgcgcccta cctgcgcaag gtggacctga agacgtacgg cagctacaag     420
gacctctccg ctgcactcaa gaagatgttc ggcaccttcg tcaccgcaac tgggaacagc     480
atgaacgagg ggagattggt tgatccggcc ggcgatgctg atgatgtggt cactacttac     540
gaagacaagg atggtgactg gatgctggtc ggcgacgtcc cgtgggagat gtttgtcgac     600
tcatgcaagc gtctgaggat catgaagagt tctgaagcca taggtcttgg ttacaccaag     660
aacgaaggat aa                                                         672
```

<210> SEQ ID NO 95
<211> LENGTH: 217
<212> TYPE: PRT
<213> ORGANISM: Zea mays

<400> SEQUENCE: 95

```
Met Ala Gly Ala Asp Val Asp Val Gly Thr Glu Leu Arg Leu Gly Leu
1               5                   10                  15

Pro Gly Gly Gly Ala Ala Ala Ala Lys Lys Asp Thr Ile Asp Leu Lys
            20                  25                  30

Leu Lys Leu Pro Thr Ala Gly Met Glu Glu Ala Leu Pro Pro Pro Arg
        35                  40                  45

Pro Glu Pro Ala Ala Glu Lys Ala Lys Arg Pro Ala Glu Ala Pro Ala
    50                  55                  60

Ala Asp Ala Glu Lys Pro Pro Ala Pro Lys Ala Gln Ala Val Gly Trp
65                  70                  75                  80

Pro Pro Val Arg Ser Tyr Arg Arg Asn Ala Met Thr Val Val Gln Ala
                85                  90                  95

Val Arg Ser Lys Lys Glu Glu Glu Pro Glu Lys Gln Gln Gln Pro Ala
            100                 105                 110

Ala Ala Asn Ala Phe Val Lys Val Ser Met Asp Gly Ala Pro Tyr Leu
        115                 120                 125

Arg Lys Val Asp Leu Lys Thr Tyr Gly Ser Tyr Lys Asp Leu Ser Ala
    130                 135                 140

Ala Leu Lys Lys Met Phe Gly Thr Phe Val Thr Ala Thr Gly Asn Ser
145                 150                 155                 160

Met Asn Glu Gly Arg Leu Val Asp Pro Ala Gly Asp Ala Asp Asp Val
                165                 170                 175

Val Thr Thr Tyr Glu Asp Lys Asp Gly Asp Trp Met Leu Val Gly Asp
            180                 185                 190

Val Pro Trp Glu Met Phe Val Asp Ser Cys Lys Arg Leu Arg Ile Met
        195                 200                 205

Lys Ser Ser Glu Ala Ile Gly Leu Gly
    210                 215
```

<210> SEQ ID NO 96
<211> LENGTH: 654
<212> TYPE: DNA
<213> ORGANISM: Zea mays

<400> SEQUENCE: 96

```
atggctggcg ccgacgtcga cgtcgggacg gagctccggc tcggcctgcc gggaggaggc      60
gccgcggcgg ccaagaagga caccatcgac ctcaagctga agctgcccac cgccggcatg     120
gaggaggcgg ctgccgccgc caggccggag ccggcagccg agaaggccaa gaggcccgcc     180
gaggcgccgg ccgccgatgc cgagaagcca cctgcaccca aggcacaggc cgtgggctgg     240
ccaccagtcc ggtcgtaccg caggaacgcc atgaccgtcg tccaggccgt gaggagcaag     300
aaggaagagg aacctgagaa gcagcaacag cccgctgccg ccaacgcctt cgtgaaggtc     360
agcatggacg gcgcgcccta cctgcgcaag gtggacctga agacgtacgg cagctacaag     420
gacctctccg ctgcactcaa gaagatgttc ggcaccttcg tcaccgcaac tgggaacagc     480
atgaacgagg ggagattggt tgatccggcc ggcgatgctg atgatgtggt cactacttac     540
gaagacaagg atggtgactg gatgctggtc ggcgacgtcc cgtgggagat gtttgtcgac     600
tcatgcaagc gtctgaggat catgaagagt tctgaagcca taggtcttgg ttag           654
```

<210> SEQ ID NO 97
<211> LENGTH: 235
<212> TYPE: PRT
<213> ORGANISM: Vitis vinifera

<400> SEQUENCE: 97

```
Met His Gly Glu Glu Arg Glu Lys Pro Asp Leu Asn Leu Glu Ala Thr
1               5                   10                  15

Glu Leu Arg Leu Gly Leu Pro Gly Gly Ser Glu Gly Ser Glu Val Val
            20                  25                  30

Arg Lys Arg Gly Phe Ser Glu Thr Val Asp Leu Lys Leu Asn Leu Ser
        35                  40                  45

Gly Lys Glu Ala Gly Val Asp Asn Lys Val Lys Ser Leu Gln Lys
    50                  55                  60

Glu Lys Ser Lys Ser Leu Leu Pro Cys Gly Asn Asp Pro Ala Arg Pro
65                  70                  75                  80

Pro Ala Lys Ala Gln Val Val Gly Trp Pro Pro Val Arg Ser Phe Arg
                85                  90                  95

Lys Asn Met Leu Ala Gly Gln Lys Gly Ser Glu Glu Gly Glu Lys
            100                 105                 110

Val Ser Cys Asn Ala Ala Phe Val Lys Val Ser Met Asp Gly Ala Pro
        115                 120                 125

Tyr Leu Arg Lys Val Asp Leu Lys Met Tyr Thr Ser Tyr Gln Glu Leu
    130                 135                 140

Ser Asn Ala Leu Gly Asn Met Phe Ser Ser Phe Thr Ile Gly Asn Tyr
145                 150                 155                 160

Gly Ser Gln Gly Met Lys Asp Phe Met Asn Glu Ser Lys Leu Met Asp
                165                 170                 175

Leu Leu Asn Gly Phe Asp His Val Pro Thr Tyr Glu Asp Lys Asp Gly
            180                 185                 190

Asp Trp Met Leu Val Gly Asp Val Pro Trp Glu Met Phe Val Asp Ser
        195                 200                 205
```

Cys Lys Arg Leu Arg Ile Met Lys Gly Lys Glu Ala Ile Gly Leu Ala
    210                 215                 220

Pro Arg Ala Met Glu Lys Cys Lys Asn Arg Ser
225                 230                 235

<210> SEQ ID NO 98
<211> LENGTH: 708
<212> TYPE: DNA
<213> ORGANISM: Vitis vinifera

<400> SEQUENCE: 98

```
atgcacggcg aggagcggga aaagcccgac ctgaacttgg aggcgacgga gctccggctg      60
gggctgccgg aggaagtgaa aggaagtgag gtggtgagga agagagggtt ttcggaaact     120
gtggatttga agctcaatct gtccgggaaa aagcgggtg ttgatgacaa caaagtgaag     180
agtctgcaga aggagaagag caagagcctt cttccttgtg gtaatgatcc agccagacct     240
ccggccaagg cacaggttgt ggggtggcca ccggttcggt ccttccggaa gaacatgttg     300
gccgggcaga agggcggcag cgaggaaggg gagaaggtga gctgcaacgc agcctttgtg     360
aaggttagca tggacggagc gccgtatctg cgtaaggttg acttgaagat gtacactagt     420
tatcaggagc tgtccaatgc cttgggcaac atgttcagct ccttcactat tgggaattat     480
ggatcacaag gaatgaagga tttcatgaat gagagcaagt tgatggatct tttgaatggt     540
tttgatcatg ttccaacata cgaagacaaa gatgggggatt ggatgctcgt tggagatgtc     600
ccatgggaga tgtttgtgga ttcatgcaaa cgcttgcgca taatgaaagg aaaagaggcg     660
atagggctcg cacctagagc catggagaaa tgcaagaata ggagctaa                   708
```

<210> SEQ ID NO 99
<211> LENGTH: 238
<212> TYPE: PRT
<213> ORGANISM: Vitis vinifera

<400> SEQUENCE: 99

Met Ala Ser Ile Val Cys Ala Glu Arg Asp Lys Phe Asn Leu Asn Tyr
1               5                   10                  15

Glu Glu Thr Glu Leu Arg Leu Gly Leu Gly Leu Pro Gly Gly Gly Gly
            20                  25                  30

Asn Asp Gly Asp Val Ser Lys Thr Ser Gly Lys Arg Gly Phe Ser Glu
        35                  40                  45

Thr Val Asp Leu Lys Leu Asn Leu Leu Ser Lys Asp Ser Val Ala Asp
    50                  55                  60

Gln Ala Glu Lys Met Lys Glu Lys Ser Ala Leu Pro Pro Ser Asn Asp
65                  70                  75                  80

Pro Ala Lys Pro Pro Ala Lys Ala Gln Val Val Gly Trp Pro Pro Val
                85                  90                  95

Arg Ser Phe Arg Lys Asn Ile Leu Thr Val Gln Lys Asn Ser Ser Glu
            100                 105                 110

Glu Glu Lys Ala Ser Ser Ser Ala Ala Phe Val Lys Val Ser Met Asp
        115                 120                 125

Gly Ala Pro Tyr Leu Arg Lys Val Asp Leu Lys Met Tyr Lys Ser Tyr
    130                 135                 140

Gln Glu Leu Ser Asp Ala Leu Gly Lys Met Phe Ser Ser Phe Thr Ile
145                 150                 155                 160

Gly Asn Cys Gly Ser Gln Gly Met Lys Asp Phe Met Asn Glu Ser Lys
                165                 170                 175

```
Leu Ile Asp Leu Leu Asn Gly Ser Asp Tyr Val Pro Thr Tyr Glu Asp
            180                 185                 190

Lys Asp Gly Asp Trp Met Leu Val Gly Asp Val Pro Trp Glu Met Phe
        195                 200                 205

Val Glu Ser Cys Lys Arg Leu Arg Ile Met Lys Gly Ser Glu Ala Ile
        210                 215                 220

Gly Leu Ala Pro Arg Ala Val Glu Lys Cys Lys Asn Arg Ser
225                 230                 235
```

<210> SEQ ID NO 100
<211> LENGTH: 717
<212> TYPE: DNA
<213> ORGANISM: Vitis vinifera

<400> SEQUENCE: 100

```
atggctagca ttgtgtgtgc tgagcgcgat aaatttaacc tcaattatga agagactgag    60
ctgcgtttag cttaggcttg cctggcgga ggtggaaacg atggcgatgt ctccaagact    120
agcgggaaga gagggttctc agaaactgtt gatttgaagc ttaatctttt gtctaaagat    180
tctgtggcag atcaagccga gaagatgaag gagaagagtg ctcttcctcc atccaacgac    240
ccggcaaaac caccagccaa ggcacaagtg gtgggttggc ctccggtgag atcgttccga    300
aagaacatct tgacagtgca aaagaacagc agtgaggagg agaaggctag cagcagtgca    360
gcatttgtga aggttagcat ggatggtgca ccatacctac gtaaggtgga cttaaagatg    420
tacaagagct atcaagaact ctctgatgcc ctaggcaaaa tgttcagctc ctttactatt    480
ggcaactgtg gatcacaagg aatgaaggat ttcatgaatg agagcaaatt gatcgatctt    540
ttgaacggtt ccgattacgt gcctacttat gaagacaaag atggagactg gatgcttgtt    600
ggagacgtgc catgggagat gttcgtcgaa tcttgcaagc gcttgcgcat aatgaaagga    660
tccgaggcca tcggacttgc cccaagagca gtggagaagt gcaagaacag aagctag     717
```

<210> SEQ ID NO 101
<211> LENGTH: 234
<212> TYPE: PRT
<213> ORGANISM: Vitis vinifera

<400> SEQUENCE: 101

```
Met Leu Gly Ala Glu Arg Gly Phe Asp Phe Lys Glu Thr Glu Leu Cys
1               5                   10                  15

Leu Gly Leu Pro Gly Gly Gly Gly Glu Ala Glu Thr Leu Lys Ala
            20                  25                  30

Ser Gly Lys Arg Gly Phe Ser Glu Thr Val Asp Leu Lys Leu Asn Leu
        35                  40                  45

Gln Ser Lys Glu Ser Val Val Asp Leu Asn Glu Asn Val Lys Cys Pro
    50                  55                  60

Pro Lys Glu Lys Asn Leu Leu Pro Cys Thr Lys Asp Pro Ala Lys Pro
65                  70                  75                  80

Pro Ala Lys Ala Gln Val Val Gly Trp Pro Pro Val Arg Ser Phe Arg
                85                  90                  95

Lys Asn Ile Met Ala Gln Lys Asn Ser Ser Glu Glu Glu Lys Gly
            100                 105                 110

Ser Ser Gly Ala Ala Phe Val Lys Val Cys Met Asp Gly Ala Pro Tyr
        115                 120                 125

Leu Arg Lys Val Asp Leu Lys Met Tyr Lys Ser Tyr Gln Glu Leu Ser
    130                 135                 140
```

Asp Ala Leu Gly Lys Met Phe Ser Ser Phe Thr Gly Asn Tyr Gly
145                 150                 155                 160

Ala Gln Gly Met Ile Asp Phe Met Asn Glu Ser Lys Leu Met Asp Leu
                165                 170                 175

Leu Asn Ser Ser Glu Tyr Val Pro Thr Tyr Glu Asp Lys Asp Gly Asp
            180                 185                 190

Trp Met Leu Val Gly Asp Val Pro Trp Glu Met Phe Val Asp Ser Cys
        195                 200                 205

Lys Arg Leu Arg Ile Met Lys Gly Ser Glu Ala Ile Gly Leu Ala Pro
    210                 215                 220

Arg Ala Met Glu Lys Cys Lys Asn Arg Cys
225                 230

<210> SEQ ID NO 102
<211> LENGTH: 705
<212> TYPE: DNA
<213> ORGANISM: Vitis vinifera

<400> SEQUENCE: 102
atgctcgggg ctgagcgtgg ttttgatttc aaagagactg aactctgtct ggggctgcct      60
ggtggaggtg gaggtgaagc cgagacgctt aaggcttctg gcaagagggg gttctccgag     120
actgttgatc tcaaactcaa ccttcagtcc aaggaatcag tagtggatct gaacgagaat     180
gtcaagtgtc cacccaagga gaagaacctc cttccttgca ccaaggatcc ggccaaacca     240
cctgccaagg cacaggtggt gggttggcca ccagttcgat catttaggaa gaacataatg     300
gctcagaaga cagcagcga ggagggtgag aagggaagca gcggtgctgc attcgtgaag     360
gtttgcatgg atggcgcgcc atatcttcgc aaggtggact aaagatgta caagagctac     420
caagaactct ctgatgcatt aggcaagatg ttcagttcct tcaccatggg caactatggg     480
gcccagggaa tgatagattt tatgaatgag agcaagttga tggatctttt gaacagctct     540
gaatatgttc caacctatga agataaggat ggagactgga tgctcgtggg tgatgttcca     600
tgggagatgt ttgttgattc atgcaagcgc ttgcgtataa tgaaaggatc agaagcaatt     660
ggtcttgcac caagagcaat ggagaagtgt aagaatagat gctga                     705

<210> SEQ ID NO 103
<211> LENGTH: 320
<212> TYPE: PRT
<213> ORGANISM: Vitis vinifera

<400> SEQUENCE: 103

Met Ser Lys Gln Leu Glu His Asp Tyr Ile Gly Leu Ser Glu Val Ser
1               5                   10                  15

Ser Met Glu Ser Ser Lys Leu Thr Thr Asp Ser Glu Gly Ser Asn
            20                  25                  30

Gly Leu Asn Leu Lys Ala Thr Glu Leu Arg Leu Gly Leu Pro Gly Ser
        35                  40                  45

Glu Ser Pro Glu Arg Ile Asp Ser Val Gly Gly Leu Asp Lys Asn Gly
    50                  55                  60

Tyr Pro Leu Gly Val Leu Lys Asn Leu Val Ser Gly Ala Lys Arg Gly
65                  70                  75                  80

Phe Ser Asp Ala Ile Asp Gly Gly Ser Gly Lys Trp Val Phe Ser Gly
                85                  90                  95

Ser Gly Gly Ser Glu Thr Asp Leu Thr Lys Gly Gly Leu Phe Ser
            100                 105                 110

```
Pro Arg Gly Gly Asn Gly Gly Lys His Leu Gly Gly Ser Glu Ser
            115                 120                 125

Asn Asn Gln His Ser Ser Leu Gly Thr Pro Val Lys Asn Asp Val Val
130                 135                 140

Pro Gln Ser Pro Lys Pro Met His Glu Lys Lys Pro Gln Ile Ser Ala
145                 150                 155                 160

Pro Ala Ala Lys Ala Gln Val Val Gly Trp Pro Pro Ile Arg Ser Phe
            165                 170                 175

Arg Lys Asn Ser Met Ala Ser Asn Leu Pro Lys Asn Asp Glu Asp Ala
            180                 185                 190

Glu Gly Lys Leu Gly Ser Gly Cys Leu Tyr Val Lys Val Ser Met Asp
        195                 200                 205

Gly Ala Pro Tyr Leu Arg Lys Val Asp Leu Lys Leu Tyr Ser Thr Tyr
        210                 215                 220

Met Glu Leu Ser Ser Ala Leu Glu Lys Met Phe Ser Cys Phe Thr Ile
225                 230                 235                 240

Gly Gln Cys Gly Ser Asn Gly Val Pro Ile Arg Asp Gly Leu Ser Glu
            245                 250                 255

Ser Arg Leu Met Asp Leu Leu His Gly Ser Glu Tyr Val Leu Thr Tyr
            260                 265                 270

Glu Asp Lys Asp Gly Asp Trp Met Leu Val Gly Asp Val Pro Trp Glu
        275                 280                 285

Met Phe Thr Asp Ser Cys Lys Arg Met Arg Ile Met Lys Ser Ser Glu
            290                 295                 300

Ala Ile Gly Leu Ala Pro Arg Ala Met Glu Lys Cys Lys Ser Arg Asn
305                 310                 315                 320

<210> SEQ ID NO 104
<211> LENGTH: 963
<212> TYPE: DNA
<213> ORGANISM: Vitis vinifera

<400> SEQUENCE: 104
atgtctaagc aactggagca tgattacata ggcttgtcag aggtttcttc aatggaaagc      60
tctgagaagc tcaccactga ttcggagggc agcaatggtc tcaacttgaa ggccacagag     120
ctgaggctgg gtttgcctgg ttctgagtcg cctgagagga ttgactcagt tgggggtttg     180
gataagaatg ataccccact tggtgtgctg aagaacttgg tctctggtgc aagagaggc     240 ttctctgacg ccattgatgg tggttccggc aagtgggtct ctccgggag tggtggatcc     300 gagactgatt tgaccaaagg tggtggcttg ttctctccca gaggtggaaa tggtggtggg     360
aagcatcttg gtgggtcgga gagcaacaat cagcactcga gtttgggtac tccagttaag     420
aacgacgtcg ttccgcagtc gccaaagcct atgcatgaga aaaagcctca gatttctgct     480
cctgccgcaa agcacaggt agtagggtgg ccaccaattc ggtctttccg gaagaattca     540
atggcatcta atcttccaaa gaatgatgag gatgcggaag gcaagttagg atccgggtgt     600
ctttacgtca aggtcagtat ggatggtgct ccatacctta ggaaagttga tctcaaatta     660
tactccacct atatggaact ctcttcagct ttagaaaaga tgttcagctg ctttacaatt     720
gggcaatgcg gttctaatgg agttcctatt cgagatggtc tgagtgagag tcgactaatg     780
gatcttctcc atggctctga gtacgtactc acttatgaag acaaggacgg tgactggatg     840
ctagttggtg atgttccttg ggaaatgttt acagactctt gcaagagaat gaggataatg     900
aagagttcag aagccattgg attagcccca agggcaatgg agaaatgcaa gagtcgcaac     960
``` tag                                                                963

<210> SEQ ID NO 105
<211> LENGTH: 193
<212> TYPE: PRT
<213> ORGANISM: Vitis vinifera

<400> SEQUENCE: 105

Met Pro Gly Pro Ala Met Lys Asp Val Ala Pro Ser Ser Pro Lys
1               5                   10                  15

Pro Val Gln Glu Lys Lys Pro Gln Ala Ser Ala Ala Asn Glu His Ala
            20                  25                  30

Ser Ala Pro Ala Lys Ala Gln Val Val Gly Trp Pro Pro Ile Arg
        35                  40                  45

Ser Phe Arg Lys Asn Thr Met Ala Ser Ala Lys Asn Asn Glu Asp
    50                  55                  60

Ala Glu Gly Lys Ser Gly Leu Gly Cys Leu Tyr Val Lys Val Ser Met
65              70                  75                  80

Asp Gly Ala Pro Tyr Leu Arg Lys Val Asp Leu Lys Ile Tyr Cys Asn
                85                  90                  95

Tyr Met Glu Leu Ser Ser Ala Leu Glu Lys Met Phe Ser Cys Phe Thr
            100                 105                 110

Ile Gly Gln Cys Gly Ser His Gly Leu Pro Gly Arg Asp Gly Leu Thr
        115                 120                 125

Glu Ser His Leu Met Asp Leu Leu His Gly Ser Glu Tyr Val Leu Thr
    130                 135                 140

Tyr Glu Asp Lys Asp Gly Asp Trp Met Leu Val Gly Asp Val Pro Trp
145             150                 155                 160

Glu Met Phe Thr Glu Ser Cys Lys Arg Leu Arg Ile Met Lys Gly Ser
                165                 170                 175

Glu Ala Ile Gly Leu Ala Pro Arg Ala Met Glu Lys Cys Lys Asn Arg
            180                 185                 190

Asn

<210> SEQ ID NO 106
<211> LENGTH: 582
<212> TYPE: DNA
<213> ORGANISM: Vitis vinifera

<400> SEQUENCE: 106
atgcctggac ctgccatgaa agatgttgct gctccttcat caccaaagcc tgttcaggaa      60
aagaagcctc aggcctctgc tgcaaacgag catgcaagtg cccctgctgc aaaggcacag     120
gtggtaggat ggccaccaat tcggtctttc gaaagaaca ccatggccag ctcggcgaag      180
aataatgaag atgctgaagg caaatcagga ttgggttgcc tctatgttaa agttagcatg     240
gatggtgctc catacctgag gaaggttgac ctcaaaatct actgcaacta tatggaactc     300
tcatcggctc tggagaagat gttcagctgc tttacaattg gcagtgtgg ttctcatgga      360
cttccagggc gagatgggct gactgagagt cacttaatgg atcttcttca tggttctgaa     420
tatgtgctga catacgagga taaggatgga gattggatgc ttgttggaga tgtcccctgg     480
gagatgttca ctgagtcttg caagagattg aggatcatga agggttcaga ggcaattggg     540
ctagctccaa gggccatgga aaatgcaag aacagaaact ag                         582

<210> SEQ ID NO 107
<211> LENGTH: 359

```
<212> TYPE: PRT
<213> ORGANISM: Vitis vinifera

<400> SEQUENCE: 107

Met Ser Pro Leu Leu Gly Val Gly Glu Glu Gly Gln Ser Asn
1               5                   10                  15

Val Thr Ile Leu Ala Ser Ser Ala Ser Met Glu Ser Val Cys Gln Ile
                20                  25                  30

Ser Ser Gly Leu Lys Glu Arg Asn Tyr Met Gly Leu Ser Glu Cys Ser
            35                  40                  45

Ser Val Asp Ser Ser Ala Ile Ser Thr Asp Ser Asp Gly Asn Lys Ser
        50                  55                  60

Ser Leu Asn Leu Lys Ala Thr Glu Leu Arg Leu Gly Leu Pro Gly Ser
65                  70                  75                  80

Leu Ser Pro Gly Arg Glu Pro Glu Leu Cys Leu Leu Ser Thr Lys
                85                  90                  95

Leu Asp Glu Lys Pro Leu Phe Pro Leu His Pro Ser Lys Asp Leu Thr
                100                 105                 110

Tyr Thr Ser Ser Gln Lys Thr Val Val Ser Gly Asn Lys Arg Gly Phe
            115                 120                 125

Ala Asp Ala Met Asn Gly Phe Ser Glu Gly Lys Phe Leu Ala Asn Ser
        130                 135                 140

Glu Val Asn Val Met Leu Ser Pro Arg Pro Ser Pro Asn Lys Glu Asn
145                 150                 155                 160

Leu Gly Ser Gln Pro Ala Lys Met Lys Glu Met Ala Ser Pro Lys Ile
                165                 170                 175

Val Gln Glu Arg Pro Arg Ala Thr Asn Glu Thr Pro Pro Asn His Thr
            180                 185                 190

Gly Thr Gly Asn Asn Asn Ser Ser Ala Pro Ala Thr Lys Ala Gln Val
        195                 200                 205

Val Gly Trp Pro Pro Ile Arg Ser Phe Arg Lys Asn Thr Leu Ala Thr
210                 215                 220

Thr Ser Lys Asn Thr Glu Val Asp Gly Lys Ala Gly Pro Gly Ala Leu
225                 230                 235                 240

Phe Val Lys Val Ser Met Asp Gly Ala Pro Tyr Leu Arg Lys Val Asp
                245                 250                 255

Leu Arg Asn Tyr Ser Ala Tyr Gln Glu Leu Ser Ser Ala Leu Glu Lys
            260                 265                 270

Met Phe Ser Cys Phe Thr Ile Gly Gln Tyr Gly Ser His Gly Ala Pro
        275                 280                 285

Gly Arg Glu Met Leu Ser Glu Ser Lys Leu Lys Asp Leu Leu His Gly
    290                 295                 300

Ser Glu Tyr Val Leu Thr Tyr Glu Asp Lys Asp Gly Asp Trp Met Leu
305                 310                 315                 320

Val Gly Asp Val Pro Trp Gln Met Phe Ile Glu Thr Cys Lys Arg Leu
                325                 330                 335

Arg Ile Met Lys Ser Cys Asp Ala Ile Gly Leu Ala Pro Arg Ala Val
            340                 345                 350

Glu Lys Cys Lys Asn Arg Asn
        355

<210> SEQ ID NO 108
<211> LENGTH: 1080
<212> TYPE: DNA
<213> ORGANISM: Vitis vinifera
```

<400> SEQUENCE: 108

```
atgtctccac cactgcttgg tgttggggag gaggaaggcc agagtaatgt cacaatattg      60
gcttcttcag cctccatgga aagtgtatgc cagatcagct caggattgaa agagcggaat     120
tacatgggat tgtctgaatg ttcttctgtg gatagctctg caatctccac tgattcagat     180
ggcaataaga gcagtctgaa tctaaaagct acagagctga ggcttgggct tcctggatcc     240
ctgtctcctg gaagagaacc agagctttgc ctgctgagct ccactaagct tgatgagaaa     300
ccccttttcc ctctgcatcc ttcaaaggat cttacttaca cttcatcaca gaagactgtt     360
gtttcaggaa acaaaagagg gtttgctgat gcaatgaatg gtttctcaga ggggaaattt     420
cttgcaaact cagaggtgaa tgtgatgcta tcacctaggc cttccccaaa caaggagaac     480
ctagggtctc agccagccaa gatgaaagag atggcatcac caaagatcgt gcaggagaga     540
cctcgtgcca ccaatgagac ccctcctaac catactggta ctggaaacaa taacagcagt     600
gcacctgcta ccaaggcaca ggttgtgggt tggccaccta aagatctttt aggaagaac      660
acgctggcca ccacttcaaa gaacactgaa gtagacggaa aagcagggcc tggtgctcta     720
tttgtcaaag tcagtatgga tggtgctcct tatttgagga agtagactt gagaaattac      780
tctgcatatc aggaactgtc ttctgctctc gagaagatgt tcagctgttt taccataggt     840
caatatggat cacatggagc tcccggcagg gagatgctga gtgagagcaa attgaaggat     900
ctactacatg gatcagaata tgttctcact tatgaggata aggatggtga ctggatgctt     960
gtgggtgatg tgccctggca gatgtttatt gagacatgca agcggctgag gatcatgaag    1020
agctgtgatg ccattggtct agctcccagg gctgtggaga aatgcaagaa caggaactag    1080
```

<210> SEQ ID NO 109
<211> LENGTH: 180
<212> TYPE: PRT
<213> ORGANISM: Vitis vinifera
<220> FEATURE:
<221> NAME/KEY: misc_feature
<222> LOCATION: (23)..(26)
<223> OTHER INFORMATION: Xaa can be any naturally occurring amino acid

<400> SEQUENCE: 109

```
Met Pro Gln Phe Phe Phe Phe Phe Phe Phe Phe Pro Leu Pro Phe Cys
1               5                   10                  15

Asp Phe Phe Leu Ala Leu Xaa Xaa Xaa Xaa Gln Val Val Gly Trp Pro
            20                  25                  30

Pro Ile Arg Ser Phe Arg Lys Asn Thr Leu Ala Thr Thr Ser Lys Asn
        35                  40                  45

Asn Asp Glu Leu Asp Gly Lys Pro Gly Pro Gly Ala Leu Phe Ile Lys
    50                  55                  60

Val Ser Met Asp Gly Ala Pro Tyr Leu Arg Lys Val Asp Leu Arg Thr
65                  70                  75                  80

Tyr Ser Thr Tyr Gln Glu Leu Ser Ala Leu Glu Lys Met Phe Ser
                85                  90                  95

Cys Phe Thr Ile Gly Gln Cys Gly Ser His Gly Thr Pro Gly Arg Glu
            100                 105                 110

Met Leu Ser Glu Ser Lys Leu Arg Asp Leu His Gly Ser Glu Tyr
            115                 120                 125

Val Leu Thr Tyr Glu Asp Lys Asp Gly Asp Trp Met Leu Val Gly Asp
        130                 135                 140

Val Pro Trp Glu Leu Phe Ile Asn Ser Cys Lys Arg Leu Lys Ile Met
```

```
                145                 150                 155                 160
Lys Ser Ser Asp Ala Ile Gly Leu Ala Pro Arg Val Met Glu Lys Ser
                165                 170                 175

Lys Asn Arg Asn
            180

<210> SEQ ID NO 110
<211> LENGTH: 596
<212> TYPE: DNA
<213> ORGANISM: Vitis vinifera
<220> FEATURE:
<221> NAME/KEY: misc_feature
<222> LOCATION: (69)..(71)
<223> OTHER INFORMATION: n is a, c, g, or t

<400> SEQUENCE: 110
atgcctcagt tttctttttt cttttttttt tttcccctcc cttttttgtga tttttttctt        60 gcactattnn nggaagtaat cataaccaga tcacgactaa taacagtagc agtgcacctg       120
ctgccaaggc acaggttgtt ggttggcccc caataagatc atttaggaag aatacactgg       180
cgaccacttc aaagaataat gatgaacttg atgggaaacc gggtcctggt gctcttttta       240
tcaaagtcag catggatggt gctccttacc tcaggaaggt agacctgaga acatactcaa       300
catatcaaga gctctcttct gcacttgaga agatgttcag ctgttttaca ataggccaat       360
gtggatccca tggaactcca ggaagagaaa tgctaagtga gagcaaattg agggatcttc       420
tacatggatc agagtatgtg cttacttatg aggataagga tggtgattgg atgcttgtgg       480
gagatgttcc atgggagttg tttatcaatt catgcaagag acttaagatt atgaagagtt       540
ctgatgccat tggcttagct cccagggtga tggagaaatc caaaaatcga aactag          596

<210> SEQ ID NO 111
<211> LENGTH: 215
<212> TYPE: PRT
<213> ORGANISM: Vitis vinifera

<400> SEQUENCE: 111

Met Pro Ser Asn Thr Ala Asp Gln Ser Pro Asp Ser Gly Thr Thr Gly
1               5                   10                  15

Met Ser Leu Lys Asp Thr Glu Leu Thr Leu Gly Leu Pro Gly Glu Ala
                20                  25                  30

Gln Val Val Ile Val Gly Gly Lys Ser Cys Ser Lys Arg Gly Tyr Ser
            35                  40                  45

Asp Thr Val Asp Phe Arg Phe Arg Cys Cys Ser Gly Glu Ser Ser Ala
        50                  55                  60

Lys Ala Glu Lys Val Asp Trp Pro Gly Lys Glu Ile Ser Gly Pro Gly
65                  70                  75                  80

Lys Ala Pro Asp Ser Lys Ala Gln Val Val Gly Trp Pro Pro Val Arg
                85                  90                  95

Ser Val Arg Lys Lys Ala Leu Lys Ser Cys Lys Tyr Val Lys Val Ala
                100                 105                 110

Val Asp Gly Ala Pro Tyr Leu Arg Lys Val Asp Leu Glu Val His Arg
            115                 120                 125

Ser Tyr Gln Gln Leu Leu Met Ala Leu Glu Thr Met Phe Asp Cys Phe
        130                 135                 140

Thr Ile Ser Asn Asp Leu Glu Glu Ser Lys Ile Met Asn Pro Val Asn
145                 150                 155                 160

Gly Ala Glu Tyr Val Pro Thr Tyr Glu Asp Lys Asp Gly Asp Trp Met
```

Leu Val Gly Asp Val Pro Trp Asn Met Phe Val Glu Ser Cys Lys Arg
            180                 185                 190

Val Arg Leu Met Lys Ser Ser Glu Ala Ile Gly Leu Gly Asn Asn Val
        195                 200                 205

Phe Phe Asn Trp Asp Leu Asp
    210                 215

<210> SEQ ID NO 112
<211> LENGTH: 648
<212> TYPE: DNA
<213> ORGANISM: Vitis vinifera

<400> SEQUENCE: 112
atgccgtcca acaccgcgga ccaatcgccg gactctggca ccaccggcat gagtttgaag    60
gatactgagt tgaccttggg cttgcctgga gaggctcagg tggtcatcgt cggagggaag   120
agctgctcca acgtggata ctccgacacc gttgatttca ggttccgttg ctgcagcggc    180
gagtcgagcg caaaggctga aaggttgat tggccgggaa aggagatctc cggccccggg    240
aaagctccgg actcaaaggc acaagtggta gggtggccac cagtgagatc ggtaaggaag   300
aaggcgttga agagttgcaa gtacgtgaag gtggcggtgg atggagcacc gtacctgcgg   360
aaagtggatt tggaggtgca ccgtagctac cagcagctgt tgatggcctt ggagacgatg   420
ttcgattgct tcaccatcag caacgatttg aagaaagca agatcatgaa tcctgtaaat    480
ggagcagaat acgtgccaac atacgaagac aaagacgggg actggatgtt agttggagac   540
gttccttgga atatgtttgt ggaatcatgc aagcgggtac ggttgatgaa aagctcagag   600
gctattgggt taggtaataa tgtctttttt aattgggatt tagattaa                648

<210> SEQ ID NO 113
<211> LENGTH: 244
<212> TYPE: PRT
<213> ORGANISM: Vitis vinifera

<400> SEQUENCE: 113

Met Ser Pro Gln Leu Pro Lys Pro Ser Pro Glu Ser Ser Ser Ala Gly
1               5                   10                  15

Leu Tyr Phe Asn Asp Thr Glu Leu Thr Leu Gly Leu Pro Gly Ala Thr
            20                  25                  30

Lys Ser Gly Thr Lys Arg Gly Phe Ser Asp Thr Val Gly Leu Asn Leu
        35                  40                  45

Arg Gly Pro Cys Asn Thr Asp His Ala Ser Asn Pro Ser Glu Asn Asp
    50                  55                  60

Val Ser Gly Asp Ser Lys Pro Pro Ala Lys Thr Gln Ile Val Gly
65                  70                  75                  80

Trp Pro Pro Val Lys Ala Ser Arg Lys Asn Val Ala Lys Ile Ser Lys
                85                  90                  95

Tyr Val Lys Val Ala Val Asp Gly Ala Pro Tyr Leu Arg Lys Val Asp
            100                 105                 110

Leu Glu Met Tyr Gly Ser Tyr Gln Gln Leu Leu Gly Ser Leu Glu Asp
        115                 120                 125

Met Phe Ser Cys Phe Pro Ile Arg Asn Tyr Leu Asn Glu Arg Lys Leu
    130                 135                 140

Met Asp Pro Val Lys Gly Ser Asp Tyr Met Pro Thr Tyr Glu Asp Arg
145                 150                 155                 160

```
Asp Gly Asp Trp Met Leu Val Gly Asp Val Pro Trp Lys Met Phe Val
                165                 170                 175

Glu Ser Cys Lys Arg Leu Arg Leu Met Lys Ser Ile Glu Ala Ile Gly
        180                 185                 190

Leu Gly Lys Glu Val Phe Phe Phe Phe Ser Ser Phe Phe Phe Asn
    195                 200                 205

Ile Lys Leu Tyr Phe Thr Asp Phe Phe Phe Phe Leu Leu Lys Phe
        210                 215                 220

Cys Gly Ala Ala Pro Arg Glu Ser Gln Lys Cys Thr Ser Thr Ser Gly
225                 230                 235                 240

Ser Lys Ser Leu

<210> SEQ ID NO 114
<211> LENGTH: 735
<212> TYPE: DNA
<213> ORGANISM: Vitis vinifera

<400> SEQUENCE: 114
atgtcaccgc agctccccaa accctcgccg gaatcttcct ccgccggcct ctatttcaat      60
gataccgagc tcaccttagg cctccccggc gctaccaagt ccggcaccaa gcgcgggttc     120
tccgacaccg tcggcttgaa cctccgtggc ccctgcaata cggatcacgc tagcaatcca     180
tctgaaaacg atgtttccgg cgactccaag cctccgccgg caaagacaca aattgtgggg     240
tggccgccgg tgaaagcgag tcggaagaat gttgcgaaga tcagcaaata tgtgaaggtg     300
gcggtggacg gagctccgta tttaagaaaa gttgatctgg agatgtacgg cagctatcag     360
cagctgttgg gatctctcga ggacatgttc tcctgcttcc ctattcgtaa ttatcttaat     420
gagaggaagc ttatggatcc tgtgaaggga tccgactaca tgcctaccta tgaggacagg     480
gatggagatt ggatgctggt cggcgacgta ccatggaaaa tgtttgtgga atcatgcaag     540
cgactacggc tgatgaaaag cattgaagca attggactag gtaaagaggt tttttttttt     600 ttttttttcct cttttttctt taatattaaa ttatatttta ctgattttttt tttcttttttc     660 cttttgaaat tttgtggtgc agctccaagg gaatctcaaa aatgcacaag cacaagtgga     720
tcaaaaagcc tatag                                                     735

<210> SEQ ID NO 115
<211> LENGTH: 186
<212> TYPE: PRT
<213> ORGANISM: Vitis vinifera

<400> SEQUENCE: 115

Met Glu Lys Pro Val Val Tyr Asp Asn Gly Leu Asn Leu Glu Ala Thr
1               5                   10                  15

Glu Leu Arg Leu Gly Leu Pro Gly Thr Asn Glu Pro Glu Lys Gln Ser
            20                  25                  30

Ser Thr Ser Val Arg Ser Lys Lys Arg Ala Ser Pro Glu Met Ala Glu
        35                  40                  45

Glu Thr Arg Ser Lys Ser Ser Ser Cys Ile Ser Asp Ala Asp Asp
    50                  55                  60

Ala Pro Pro Lys Ala Gln Val Val Gly Trp Pro Val Arg Ser
65                  70                  75                  80

Tyr Arg Lys Asn Ser Phe Gln Gln Arg Lys Gly Glu Ala Glu Gly Ala
                85                  90                  95

Gly Met Tyr Val Lys Val Ser Met Asp Gly Ala Pro Tyr Leu Arg Lys
            100                 105                 110
```

```
Ile Asp Leu Lys Val Tyr Lys Ser Tyr Pro Glu Leu Leu Asn Ala Leu
        115                 120                 125

Glu Asn Met Phe Lys Phe Arg Ile Gly Glu Tyr Ser Glu Arg Glu Gly
    130                 135                 140

Tyr Asn Gly Ser Asp Tyr Thr Pro Ala Tyr Glu Asp Lys Asp Gly Asp
145                 150                 155                 160

Trp Met Leu Val Gly Asp Val Pro Trp Glu Met Phe Ile Ser Ser Cys
                165                 170                 175

Lys Arg Leu Arg Ile Met Lys Gly Ser Glu
            180                 185

<210> SEQ ID NO 116
<211> LENGTH: 561
<212> TYPE: DNA
<213> ORGANISM: Vitis vinifera

<400> SEQUENCE: 116
atggagaagc cagtggttta cgataacgga cttaatcttg aggcgaccga gctaagacta      60
gggttaccgg ggaccaatga gcctgagaaa caatcatcta ctagtgttag gagcaaaaag     120
agagcatcgc cggagatggc cgaggagact aggtctaaga gcagctcttg tatatccgat     180
gccgacgacg acgcccctcc accaaaagca caagtggtgg ggtggccgcc ggtccgatca     240
taccggaaaa acagcttcca acagaggaaa ggggaagccg aggggccgg aatgtacgtg      300 aaagtgagca tggatggagc tccttacctc agaaagatcg atctcaaggt ttacaagagc     360
tacccggagc tcctcaacgc cttggagaat atgttcaagt tcagaatagg tgagtactca     420
gagagggaag gctacaatgg atctgactat accctgctt atgaagataa agatggtgac      480
tggatgctgg ttggagatgt tccatgggag atgttcatct catcctgtaa gaggctaaga     540
atcatgaagg gatcggaatg a                                               561

<210> SEQ ID NO 117
<211> LENGTH: 256
<212> TYPE: PRT
<213> ORGANISM: Cucumis melo

<400> SEQUENCE: 117

Met Glu Ala Val Gly Leu Asn Met Pro Asn Asn Gln Phe Val Ser Leu
1               5                   10                  15

Lys Glu Thr Glu Leu Cys Leu Gly Leu Pro Gly Gly Gly Gly Gly Gly
            20                  25                  30

Gly Asp Gln Thr Ser Leu Lys Ser Gly Lys Arg Gly Phe Ser Glu
        35                  40                  45

Thr Val Asp Leu Lys Leu Asn Leu Gln Ser Lys Asp Gly Gly Gly Gly
    50                  55                  60

Gly Gly Val Gly Val Gly Val Asp Leu Asn Glu Asn Val Lys Asn Val
65                  70                  75                  80

Ser Thr Asn Val Asp Gly Glu Lys Ser Leu Cys Ser Lys Asp Pro Ala
                85                  90                  95

Lys Pro Pro Ala Lys Ala Gln Val Val Gly Trp Pro Val Arg Ser
            100                 105                 110

Tyr Arg Lys Asn Val Met Ala Gln Lys Asn Thr Ser Gly Gly Glu Gly
        115                 120                 125

Ala Glu Lys Gly Ser Ser Gly Ser Ser Ala Ala Phe Val Lys Val Cys
    130                 135                 140
```

```
Met Asp Gly Ala Pro Tyr Leu Arg Lys Val Asp Leu Lys Met Tyr Gln
145                 150                 155                 160

Ser Tyr Gln Glu Leu Ser Asp Ala Leu Ala Lys Met Phe Ser Ser Phe
                165                 170                 175

Thr Met Gly Glu Tyr Gly Thr Gln Gly Met Ile Asp Phe Met Asn Glu
            180                 185                 190

Arg Lys Leu Met Asp Leu Leu Asn Ser Ser Glu Phe Val Pro Thr Tyr
        195                 200                 205

Glu Asp Lys Asp Gly Asp Trp Met Leu Val Gly Asp Val Pro Trp Glu
    210                 215                 220

Met Phe Val Asp Ser Cys Lys Arg Leu Arg Ile Met Lys Gly Ser Glu
225                 230                 235                 240

Ala Ile Gly Leu Ala Pro Arg Ala Met Glu Lys Cys Lys Ser Arg Ser
                245                 250                 255

<210> SEQ ID NO 118
<211> LENGTH: 771
<212> TYPE: DNA
<213> ORGANISM: Cucumis melo

<400> SEQUENCE: 118
atggaagcag ttggcctgaa tatgcccaac aatcagttcg ttagcttgaa ggagactgag    60
ctctgcctcg gtttgcccgg tggcggtggc ggtggtggag atcagacctc tctcaaatct   120
tctggcaaga gggggttctc tgaaactgtt gatctcaaac ttaaccttca gagcaaggac   180
ggtggaggag gtgcggtgt cggtgtcggg gtggatctca atgagaatgt taagaatgtt   240
tcgacgaacg tggatggtga agagcctc tgctccaagg atcctgccaa gccacccgcc     300
aaagcacaag ttgtgggatg ccaccagtt cgatcgtaca ggaagaacgt gatggcacag    360
aagaacacaa gtggcggcga aggagcggag aagggaagca gtggcagctc agctgccttt   420
gtgaaggttt gcatggatgg tgctccatat ctccgcaagg ttgacctgaa atgtatcag    480 agctaccaag aactttctga tgccttggcc aagatgttca gctccttcac tatgggtgaa   540
tatggtacac aaggaatgat agacttcatg aatgaaagga agttgatgga tcttctcaat   600
agctctgagt ttgttcctac ttatgaagat aaagatggcg attggatgct cgtcggtgat   660
gtcccatggg aaatgtttgt ggattcatgc aagcgtttga gaatcatgaa aggatcagaa   720
gccattggcc ttgccccaag agctatggag aaatgcaaaa gcagaagcta g            771

<210> SEQ ID NO 119
<211> LENGTH: 236
<212> TYPE: PRT
<213> ORGANISM: Cucumis melo

<400> SEQUENCE: 119

Met Glu Ser Gly Lys Asn Asp Glu Tyr Ser Ala Ile Leu Ile Asn Phe
1               5                   10                  15

Glu Gln Thr Glu Leu Arg Leu Gly Leu Pro Gly Gly Asp Gly Gly Gly
                20                  25                  30

Gly Gly Lys Ser Ser Ser Ala Gly Lys Arg Gly Phe Met Glu Thr Val
            35                  40                  45

Asp Leu Lys Leu Asn Leu Ala Ser Ser Met Ala Ser Ala Lys Glu Glu
        50                  55                  60

Gly Thr Asn Leu Glu Glu Ile Lys Ser Cys Ser Gln Gln Pro Asn Asp
65                  70                  75                  80

Phe Ala Lys Pro Pro Ser Lys Thr Gln Val Val Gly Trp Pro Pro Val
```

```
            85                 90                 95
Arg Ser Ser Arg Lys Asn Leu Gly Val Ser Ser Arg Lys Gly Gly
            100                105                110

Asp Glu Gly Gly Gly Ser Phe Val Lys Val Ser Met Asp Gly Ala Pro
            115                120                125

Tyr Leu Arg Lys Val Asp Leu Lys Leu Tyr Gly Ser Tyr Lys Asp Leu
            130                135                140

Ser His Ala Leu Ala Lys Met Phe Ser Ser Phe Thr Ile Gly Lys Cys
145                 150                155                160

Glu Ser Glu Gly Met Lys Asp Phe Met Asn Glu Ser Lys Ser Val Asp
            165                170                175

Leu Leu Asn Gly Ser Glu Tyr Val Pro Thr Tyr Glu Lys Asp Gly
            180                185                190

Asp Trp Met Leu Val Gly Asp Val Pro Trp Glu Met Phe Val Asp Ser
            195                200                205

Cys Lys Arg Leu Arg Ile Met Lys Glu Ser Asp Ala Ile Gly Leu Ala
            210                215                220

Pro Arg Ser Met Glu Lys Gln Lys Asn Asn Arg Ser
225                 230                235

<210> SEQ ID NO 120
<211> LENGTH: 711
<212> TYPE: DNA
<213> ORGANISM: Cucumis melo

<400> SEQUENCE: 120
atggaatcag gaagaacga tgagtacagt gcgatcttga tcaatttcga gcagacggag    60
ctccgcctcg gcttgcccgg cggcgacgga ggcggcggtg ggaagagtag ttcggccggg   120
aagagagggt ttatggaaac tgtggatttg aagcttaatt tagcttcttc aatggcgtcg   180
gcgaaggaag agggaacgaa tttggaagag attaaaagtt gttcgcaaca acctaacgat   240
tttgctaaac ctccgtccaa aacacaagta gtgggttggc caccagtacg atcatctcga   300
aagaacttag gagtgtcgtc gtcaaggaag ggcggagatg agggtggagg gtcgttcgta   360
aaagtaagta tggacggtgc tccttattta cggaaggtgg acttgaagtt atacggcagc   420
tataaagacc tctctcatgc tcttgccaaa atgtttagct ccttcactat tggaaagtgc   480
gaatcagaag gaatgaagga tttcatgaat gaaagcaaat cagtagacct tttgaatggg   540
tcagaatatg tacccaccta cgaagacaaa gatggagatt ggatgcttgt tggggatgtc   600
ccatgggaga tgtttgttga ttcatgcaaa cgtttgagga tcatgaaaga gtctgatgcc   660
attggattag caccaagatc aatggagaaa caaagaaca acagaagctg a            711

<210> SEQ ID NO 121
<211> LENGTH: 220
<212> TYPE: PRT
<213> ORGANISM: Cucumis melo

<400> SEQUENCE: 121

Met Glu Lys Lys Lys Met Gly Phe Glu Glu Thr Glu Leu Arg Leu Gly
1               5                  10                 15

Leu Pro Gly Asn Asn Val Gly Ser Val Glu Ser Gly Glu Val Ala
            20                 25                 30

Ala Arg Lys Arg Gly Phe Ala Glu Thr Val Ser Ser Glu Thr Ile Ser
            35                 40                 45

Lys Val Asp Leu Lys Leu Asn Leu Ser Ser Lys Glu Thr Val Gly Val
```

```
        50                  55                  60
Gly Gly Asp Asp Val Val Ala Asn Ser Asn Pro Ser Asn Lys Asp Lys
 65                  70                  75                  80

Ala Val Leu Thr Ala Asp Pro Ala Lys Pro Pro Ala Lys Ala Gln Val
                 85                  90                  95

Val Gly Trp Pro Pro Val Arg Ser Phe Arg Lys Asn Asn Met Leu Ala
            100                 105                 110

Phe Val Lys Val Ser Met Asp Gly Ala Pro Tyr Leu Arg Lys Val Asp
        115                 120                 125

Leu Lys Met Tyr Lys Ser Tyr Lys Gln Leu Ser Asp Ala Leu Ala Ala
    130                 135                 140

Met Phe Gly Ser Phe Thr Thr Ile Gly Asn Cys Gly Ser Gln Glu Met
145                 150                 155                 160

Lys Asp Phe Met Asn Glu Ser Lys Leu Met Asp Leu Leu Ser Gly Ser
                165                 170                 175

Asp Tyr Val Pro Thr Tyr Glu Asp Lys Asp Gly Asp Trp Met Leu Val
            180                 185                 190

Gly Asp Val Pro Trp Glu Met Phe Val Glu Ser Cys Lys Arg Val Arg
        195                 200                 205

Ile Met Lys Gly Lys Glu Ala Ile Gly Leu Gly Met
    210                 215                 220
```

```
<210> SEQ ID NO 122
<211> LENGTH: 663
<212> TYPE: DNA
<213> ORGANISM: Cucumis melo

<400> SEQUENCE: 122
atggagaaga agaagatggg atttgaagag acggagctcc ggctaggtct acccggaaac    60
aacaacgtcg gcagtgttga atcgggagag gttgctgcta ggaaacgagg ctttgctgaa   120
actgtcagca gtgagaccat ttccaaggtt gatctcaagc tcaatctttc ttccaaagaa   180
accgttggtg tcggtggcga tgacgttgtc gccaattcca accctagcaa caaagacaaa   240
gctgtcctca ccgctgatcc agccaaaccc ccggctaagg cacaagttgt gggatggcca   300
cccgttcgat cgttccgaaa gaacaacatg ttggcgttcg taaaagtgag catggatggc   360
gccccatatc tgcgtaaggt ggacttgaag atgtacaaga gctataaaca actctctgat   420
gctcttgctg ccatgtttgg ttccttcacc accattggca actgtggatc tcaagaaatg   480
aaggatttca tgaatgaaag taagttgatg gatcttttaa gtggctctga ttatgttcca   540
acttatgaag acaaagatgg tgattggatg cttgttggag atgttccatg ggagatgttt   600
gttgaatctt gcaaacgtgt acgtatcatg aaaggaaaag aggccattgg acttggtatg   660
taa                                                                663
```

```
<210> SEQ ID NO 123
<211> LENGTH: 291
<212> TYPE: PRT
<213> ORGANISM: Cucumis melo

<400> SEQUENCE: 123

Met Ser Ile Pro Leu Glu His Asp Tyr Ile Gly Leu Thr Glu Ser Val
  1               5                  10                  15

Pro Ser Leu Glu Ser Ser Glu Lys Ser Ser Asp Lys Arg Asn Asn Ala
             20                  25                  30

Gly Leu Asn Leu Lys Ala Thr Glu Leu Arg Leu Gly Leu Pro Gly Ser
```

```
                35                  40                  45
Glu Ser Pro Gly Arg Asp Asp Gly Phe Glu Asp Asn Asn Gly Phe Leu
 50                  55                  60

His Lys Ser Pro Val Ser Gly Ala Lys Arg Gly Phe Ser Ile Ala Ile
 65                  70                  75                  80

Asp Arg Ala Ser Ala Lys Trp Val Leu Pro Ala Ser Ala Gly Ser Glu
                 85                  90                  95

Ala Asp Ser Ser Thr Asn Gly Gly Leu Phe Ser Pro Arg Gly Val Asn
            100                 105                 110

Glu Asn Lys Thr Gln Pro Pro Ala Ser Ala Val Pro Gly Val Lys Asp
        115                 120                 125

Gly Ile Ser Pro Ser Ala Lys Ala Gln Val Val Gly Trp Pro Pro Ile
130                 135                 140

Arg Ser Phe Arg Lys Asn Ser Met Ala Thr Gln Pro Pro Lys Asn Thr
145                 150                 155                 160

Asp Asp Ala Asp Gly Lys Leu Gly Ser Gly Cys Leu Tyr Val Lys Val
                165                 170                 175

Ser Met Asp Gly Ala Pro Tyr Leu Arg Lys Val Asp Leu Lys Thr Tyr
            180                 185                 190

Val Ser Tyr Val Asp Leu Ser Ser Ala Leu Glu Lys Met Phe Ser Ser
        195                 200                 205

Phe Thr Ile Gly His Cys Gly Ser Asn Gly Val Pro Asn Arg Asp Ala
210                 215                 220

Leu Asn Glu Ser Arg Leu Met Asp Leu Leu His Gly Ser Glu Tyr Val
225                 230                 235                 240

Leu Thr Tyr Glu Asp Lys Asp Gly Asp Trp Met Leu Val Gly Asp Val
                245                 250                 255

Pro Trp Glu Met Phe Thr Glu Ser Cys Thr Arg Met Arg Ile Met Lys
            260                 265                 270

Ser Ser Glu Ala Ile Gly Leu Ala Pro Arg Ala Met Glu Lys Cys Lys
        275                 280                 285

Asn Arg Asn
    290

<210> SEQ ID NO 124
<211> LENGTH: 876
<212> TYPE: DNA
<213> ORGANISM: Cucumis melo

<400> SEQUENCE: 124
atgtctatac cgttagaaca tgattacata ggcttaacag agtctgttcc ttctctggaa     60
agctctgaaa agtcttctga taaacgcaac aatgctggtt tgaaccttaa ggctactgaa    120
ctgaggttgg gtctgccggg atcggagtca ccgggaaggg atgatgggtt tgaggacaat    180
aatgggttcc ttcacaagag ccctgttttct ggggctaaga ggggtttctc catagccatt    240
gatagagctt ctgccaagtg ggttctacca gcttctgccg gatctgaggc tgattcctcc    300
acaaatgggg gtttgttttc tcctagaggt gttaatgaga ataagactca accacctgct    360
tccgctgtcc ctggtgtcaa agatggtatt tctccgtcag ccaaggcaca agttgtagga    420
tggccaccca ttcgttcttt tcgtaagaat tcaatggcaa cacagccccc taaaaataca    480
gatgatgcag atggcaagtt gggatcaggc tgcctttatg tcaaggtaag tatggatggc    540
gcaccgtacc tcaggaaggt tgatctgaaa acctatgtaa gctatgtgga cctctcatca    600
gccctggaga aaatgttcag cagtttcaca attggtcact gtggctctaa tggagttcca    660
```

```
aaccgggatg cactgaacga gagtaggttg atggatctgc tccatggctc tgaatatgta    720
ctcacctacg aagataagga tggtgactgg atgctcgttg gtgatgttcc ttgggagatg    780
ttcactgaat cttgcacaag gatgaggatc atgaagagtt cggaggctat tgggttagct    840
ccaagggcca tgagaagtg caaaaaccgt aattag                               876
```

```
<210> SEQ ID NO 125
<211> LENGTH: 205
<212> TYPE: PRT
<213> ORGANISM: Cucumis melo

<400> SEQUENCE: 125
```

```
Met Glu Val Ser Arg Lys Met Val Asn Met Leu Glu Thr Asp Leu Cys
1               5                   10                  15

Leu Gly Leu Pro Gly Gly Gly Ala Glu Pro Glu Thr Pro Lys Ala Asn
            20                  25                  30

Gly Lys Arg Gly Phe Ser Glu Thr Val Asp Leu Lys Leu Asn Ile Gln
        35                  40                  45

Ser Lys Thr Gly Val Thr Val Asp Leu Thr Pro Lys Asn Ser Asp Thr
    50                  55                  60

Ser Thr Asp Glu Glu Asn Leu Ile Thr Ser Lys Asp Pro Ala Lys Pro
65                  70                  75                  80

Pro Ala Lys Ala Gln Val Val Gly Trp Pro Pro Val Arg Ser Tyr Arg
                85                  90                  95

Lys Asn Ala Met Ser Gln Lys Ser Pro Asp Ser Gly Glu Lys Gly Gly
            100                 105                 110

Ser Ser Gly Gly Ser Ala Met Phe Val Lys Val Cys Met Asp Gly Ala
        115                 120                 125

Pro Tyr Leu Arg Lys Val Asp Leu Lys Met Tyr Lys Ser Tyr Gln Glu
    130                 135                 140

Leu Ser Asn Ala Leu Ala Lys Met Phe Ser Ser Phe Thr Met Ala Gly
145                 150                 155                 160

Asp Tyr Gly Ala Gln Gly Met Ile Asp Phe Met Asn Glu Ser Lys Leu
                165                 170                 175

Met Asp Leu Leu Asn Ser Ser Glu Tyr Val Pro Thr Tyr Glu Asp Lys
            180                 185                 190

Asp Gly Asp Trp Met Leu Val Gly Asp Val Pro Trp Glu
        195                 200                 205
```

```
<210> SEQ ID NO 126
<211> LENGTH: 618
<212> TYPE: DNA
<213> ORGANISM: Cucumis melo

<400> SEQUENCE: 126
```

```
atggaggtta gccgcaaaat ggtcaacatg ctggaaactg atctctgtct cggccttccc    60
ggcggtggcg ccgagcccga gactcccaaa gcaaatggaa aaagagggtt ctctgaaacc   120
gttgatctga aactcaatat ccaatctaag actggagtta ccgtcgatct gactccaaag   180
aatagtgata cttcgactga tgaggagaat ctcataacct ctaaagatcc tgcaaagcca   240
cctgccaagg cacaagttgt gggatggcca cccgtgcgat cctaccggaa gaatgcgatg   300
tctcaaaaga gccctgactc cggagaaaaa ggcggaagca gcggcggttc agctatgttt   360
gtcaaagttt gtatggatgg cgcacccttat ctgcgaaagg tcgacctgaa gatgtacaaa   420
agctaccaag agctctcgaa cgccttggcc aagatgttca gctccttcac catggccggt   480
```

```
gactatgggg cccaaggaat gatagacttc atgaatgaaa gcaagttgat ggatcttctg      540
aacagctctg agtatgtgcc aacttatgaa gataaggatg gtgattggat gctggttgga      600
gatgtacctt gggagtaa                                                    618
```

<210> SEQ ID NO 127
<211> LENGTH: 355
<212> TYPE: PRT
<213> ORGANISM: Cucumis melo

<400> SEQUENCE: 127

```
Met Ser Pro Pro Leu Leu Asp Val Gly Glu Val Glu Ser Arg Ser
1               5                   10                  15

Asn Val Thr Leu Leu Ala Ser Ser Asn Ser Met Glu Ser Val Ser Pro
            20                  25                  30

Asn Asn Leu Gly Phe Glu Glu Arg Asn Tyr Met Gly Leu Ser Asp Ser
                35                  40                  45

Ser Ser Glu Asp Ser Cys Met Thr Ala Thr Lys Ser Asp Gly Asn Lys
    50                  55                  60

Pro Ser Leu Asn Leu Lys Ala Thr Glu Leu Arg Leu Gly Leu Pro Gly
65                  70                  75                  80

Ser Glu Ser Pro Glu Arg Asp Pro Asp Asn Cys Leu Arg Ser Ser Ser
                85                  90                  95

Gln Leu Asp Glu Lys Pro Leu Phe Pro Leu His Pro Ser Ser Asp Gly
            100                 105                 110

His Tyr Ser Ser Pro Gln Lys Thr Val Val Ser Gly Asn Lys Arg Gly
        115                 120                 125

Phe Ser Asp Ala Met Asn Glu Phe Ser Glu Glu Lys Tyr His Ala Asn
    130                 135                 140

Val Gly Leu Lys Ala Gly Ser Leu Leu Glu Asn Leu Gly Ser Gln Met
145                 150                 155                 160

Gly Lys Val Lys Glu Pro Thr Thr Gln Lys Ala Val Gln Glu Arg Pro
                165                 170                 175

Gln Glu Asn Ser Glu Ser Arg Pro Ser His Asn Glu Thr Ala Asn Asn
            180                 185                 190

Asn Thr Ser Ala Pro Val Ser Lys Ala Gln Val Val Gly Trp Pro Pro
        195                 200                 205

Ile Arg Ser Phe Arg Lys Asn Thr Leu Ala Thr Thr Ser Lys Asn Asn
    210                 215                 220

Asp Glu Val Asp Gly Lys Ala Met Ala Gly Ala Leu Phe Ile Lys Val
225                 230                 235                 240

Ser Met Asp Gly Ala Pro Tyr Leu Arg Lys Val Asp Leu Arg Asn Tyr
                245                 250                 255

Ser Ala Tyr Gln Glu Leu Ser Ser Ala Leu Glu Lys Met Phe Ser Cys
            260                 265                 270

Phe Thr Ile Gly Gln Tyr Gly Ala His Gly Ala Leu Gly Met Glu Lys
        275                 280                 285

Met Ser Glu Ser Lys Leu Lys Asp Leu Leu His Gly Ser Glu Tyr Val
    290                 295                 300

Leu Thr Tyr Glu Asp Lys Asp Gly Asp Trp Met Leu Val Gly Asp Val
305                 310                 315                 320

Pro Trp Glu Met Phe Ile Asp Ser Cys Lys Arg Leu Arg Ile Met Lys
                325                 330                 335

Ser Ser Asp Ala Ile Gly Leu Ala Pro Arg Ala Val Glu Lys Cys Arg
```

Asn Arg Ser
        355

<210> SEQ ID NO 128
<211> LENGTH: 1068
<212> TYPE: DNA
<213> ORGANISM: Cucumis melo

<400> SEQUENCE: 128

```
atgtctccac cattacttga tgttggggag gtggaggaaa gtcgcagcaa tgtcactctg      60
ttggcttcct caaactcgat ggagagtgtc agtcccaaca atttgggatt tgaagagcgt     120
aattacatgg gattatctga ttcttcttca gaggacagct gtatgactgc cacaaaatcc     180
gatgggaaca aaccctcgct gaatcttaag gctacagaac tgaggcttgg tctccctgga     240
tctgaatccc ccgagaggga tccggataat tgcttgcgta gctcttctca acttgatgaa     300
aaaccactat ttcctttgca cccatcaagt gatggtcatt actcttcccc acaaaagact     360
gttgtctcag gcaacaaaag ggggtttttct gatgctatga acgaattctc agaggaaaaa     420
tatcacgcta acgtaggttt gaaagctggt tctttgctag agaaccttgg aagtcaaatg     480
gggaaagtga agagccaac tacacaaaag gctgtacaag agaggcctca gaaaatagt      540
gaatctagac catctcataa tgaaactgct aataacaaca ccagcgcacc tgtttccaag     600
gcacaggttg tgggttggcc gcccataaga tctttcagga agaacacatt ggctacaact     660
tcaaagaaca acgatgaagt tgatggaaag gcaatggctg gggcactctt tattaaagtc     720
agcatggatg gtgctcctta tcttaggaag gtagatctga ggaattactc tgcctatcag     780
gagctgtctt ctgcccttga aagatgttc agctgtttca ctataggtca atatggagct     840
catggagctc tgggcatgga aaaatgagt gagagcaagc tgaaagatct tcttcatggc     900
tcagaatatg ttctaacata tgaggataaa gatggtgact ggatgctcgt tggtgatgtc     960
ccttgggaga tgttcatcga ctcttgtaag aggctgagga ttatgaagag ctcagatgca    1020
attggactgg ctcctagggc agtggagaag tgccgaaaca ggagctag                1068
```

<210> SEQ ID NO 129
<211> LENGTH: 171
<212> TYPE: PRT
<213> ORGANISM: Cucumis melo

<400> SEQUENCE: 129

Met Met Asn Tyr Gln Leu Glu Asn Ser Met Lys Cys Arg Ala Gln Val
1               5                   10                  15

Val Gly Trp Pro Pro Ile Arg Ser Phe Arg Lys Asn Thr Met Thr Thr
            20                  25                  30

Thr Asn Ser Thr Lys Asn Thr Asp Glu Gly Glu Gly Lys Ser Gly Pro
        35                  40                  45

Ser Gly Cys Leu Tyr Val Lys Val Ser Met Glu Gly Ala Pro Tyr Leu
    50                  55                  60

Arg Lys Val Asp Leu Lys Leu Tyr Ser Asn Tyr Ser Glu Leu Ser Leu
65                  70                  75                  80

Ala Leu Glu Lys Met Phe Ser Cys Phe Thr Ile Gly Gln Cys Gly Thr
                85                  90                  95

Glu Gly His Pro Thr Lys Glu Arg Leu Ser Glu Ser Asn Ser Lys Asp
            100                 105                 110

Phe Leu His Gly Ser Glu Tyr Val Leu Thr Cys Glu Asp Lys Asp Gly

```
              115                 120                 125
Asp Trp Met Leu Val Gly Asp Val Pro Trp Glu Met Phe Thr Glu Ser
    130                 135                 140

Cys Arg Arg Leu Arg Ile Met Lys Gly Ser Glu Ala Ile Gly Leu Ala
145                 150                 155                 160

Pro Arg Ala Thr Glu Lys Cys Lys Asn Arg Asn
                165                 170

<210> SEQ ID NO 130
<211> LENGTH: 516
<212> TYPE: DNA
<213> ORGANISM: Cucumis melo

<400> SEQUENCE: 130
atgatgaatt accaactgga aaattctatg aaatgcaggg cacaggttgt gggatggcca      60
cccattcgat ccttcaggaa gaacaccatg accactacca attcgacaaa gaacactgat     120
gaaggcgagg gcaaatcagg accatctggt tgcctctatg taaaagttag catggaaggg     180
gctccatatc taaggaaggt agatctcaaa ctgtacagca actattctga actatcattg     240
gctttggaga aaatgtttag ctgcttcact attgggcagt gtggtactga aggacatcca     300
actaaagagc gtctgagtga agtaattcg aaggacttcc ttcatggatc tgagtatgtg     360
ctgacatgtg aagataaaga tggagattgg atgcttgttg gtgatgtccc ttgggagatg     420
ttcacggagt catgtagaag actccgaatc atgaaaggtt ctgaagcaat tgggctagca     480
ccgagggcca cagagaagtg caagaaccga aactag                               516

<210> SEQ ID NO 131
<211> LENGTH: 377
<212> TYPE: PRT
<213> ORGANISM: Cucumis melo

<400> SEQUENCE: 131

Met Ser Pro Pro Leu Leu Asn Ser Val Glu Glu Ala Leu Gly Asn Val
1               5                   10                  15

Pro Val Val Ala Ala Ser Pro Ser Met Asp Cys His Ser Gln Asn Gly
            20                  25                  30

Thr Lys Phe Arg Glu Arg Asn Tyr Leu Arg Leu Ser Pro Cys Ser Ser
        35                  40                  45

Val Asp Ser Ser Ala Val Ser Asn Leu Ser Glu Glu Asn Lys Ser Asn
    50                  55                  60

Leu Asn Leu Lys Ala Thr Glu Leu Arg Leu Gly Leu Pro Gly Ser Leu
65                  70                  75                  80

Ser Pro Glu Arg Asp Gln Glu Phe Thr Leu Ile Ser Ser Gly Glu Pro
                85                  90                  95

Asp Glu Lys Thr Leu Leu Gln Leu Leu Pro Ser Thr Asp Gly Tyr Ser
            100                 105                 110

Val Ala Ser Gln Lys Asn Ile Ile Ala Gly Ser Lys Arg Gly Phe Ser
        115                 120                 125

Asp Thr Met Glu Gly Tyr Ser Glu Val Lys Gly Pro Leu Tyr Thr Glu
    130                 135                 140

Arg Asn Trp Met Phe His Ala Ala Ser Ser Asp Pro Glu Ser Pro Tyr
145                 150                 155                 160

Pro Val Ser Gln Gly Lys Phe His Ala Ser Gly Ile Asn Ala Met
                165                 170                 175

Leu Ser Ser Arg Pro Ser Gly Pro His Pro Asn Ala Thr Lys Glu Leu
```

```
                180                 185                 190
Pro Ser Lys Gly Leu Gln Glu Trp Pro Cys Glu Thr Lys Gly Ser Asp
                195                 200                 205

Asn Gly Asn Lys Gly Ala Thr Asn Asp His Asn Asn Ala Pro Ala Ser
    210                 215                 220

Lys Ala Gln Val Val Gly Trp Pro Pro Ile Lys Ser Phe Arg Lys Asn
225                 230                 235                 240

Ser Leu Val Thr Asn Ser Lys Asn Asn Asp Glu Val Asp Gly Lys Pro
                245                 250                 255

Gly Ser Ser Ala Leu Phe Val Lys Val Ser Met Glu Gly Ala Pro Tyr
            260                 265                 270

Leu Arg Lys Val Asp Leu Arg Thr Tyr Ser Thr Tyr Gln Glu Leu Ser
        275                 280                 285

Ser Ala Leu Glu Lys Met Phe Ser Cys Phe Thr Leu Gly Gln Cys Gly
    290                 295                 300

Ser His Gly Val Ser Gly Arg Asp Lys Leu Ser Glu Ser Lys Leu Arg
305                 310                 315                 320

Asp His Leu His Gly Ser Glu Tyr Val Leu Thr Tyr Glu Asp Arg Asp
                325                 330                 335

Gly Asp Trp Met Leu Val Gly Glu Ile Pro Trp Glu Met Phe Ile Asp
            340                 345                 350

Ser Cys Lys Arg Leu Lys Ile Val Lys Gly Ser Asp Ala Ile Gly Leu
        355                 360                 365

Ala Pro Arg Ala Thr Glu Ile Gln Lys
    370                 375

<210> SEQ ID NO 132
<211> LENGTH: 1134
<212> TYPE: DNA
<213> ORGANISM: Cucumis melo

<400> SEQUENCE: 132
atgtcacctc cactgctgaa ttctgtagag gaggctcttg gcaatgtccc tgtagtggct      60
gcttcacctt ctatggactg tcattcccaa aatggtacca aatttagaga gcggaactac     120
ctccggctat caccctgttc ttcggtggac agctctgcgg tgtctaactt gtcagaggag     180
aacaaaagca acctcaattt gaaagctacc gagttgagac ttggtctacc tggatctctg     240
tcacctgaaa gagatcagga atttaccttg ataagctctg agaacctga tgagaaaact      300 ttacttcaat tgcttccttc aacggatggg tatagtgtgg catcacagaa gaatattatt     360
gctggcagca aaagaggttt ttctgatacc atggaggggt actcagaggt gaaaggcccc     420
ctttacaccg aaagaaattg gatgtttcat gcagccagtt cggatcctga gtctccatat     480
cctgtgagcc aagggaagtt tcatgccagt tcaggtataa atgcaatgct atcgtccagg     540
ccgtctggtc cccatccaaa tgcaaccaaa gaattgccct caagggatt gcaggaatgg      600 ccctgtgaga ctaaaggatc tgacaatggc aataaaggtg ctacgaatga ccacaacaat     660
gctccggctt caaaggcgca ggttgttggt tggccaccta ttaaatcatt ccggaaaaat     720
tcattggtca ctaactctaa aaacaatgat gaagttgacg gaaagccagg ttcaagtgct     780 cttttttgtga aagtgagcat ggagggagct ccatatttga ggaaggtaga tctgagaact     840
tactctacat atcaggaact ctcttctgcc ctcgagaaga tgtttagctg ttttactcta     900
ggtcaatgtg gatcccatgg agtttctggg agggataaac tgagtgagag caagttaagg     960
gatcatctgc atggatccga atatgtgctt acatatgaag atagagatgg tgactggatg    1020
```

-continued

```
cttgttgggg aaatcccctg ggagatgttc attgattcct gcaagaggct gaaaatcgta    1080
aagggctctg acgcaattgg tttagcccca agagcaacgg agatccaaaa atag          1134
```

<210> SEQ ID NO 133
<211> LENGTH: 197
<212> TYPE: PRT
<213> ORGANISM: Cucumis melo

<400> SEQUENCE: 133

```
Met Ala Lys Leu Ala Ala Ser Ser Asp His Pro Asp Leu Asn Phe Gln
1               5                   10                  15

Ala Thr Glu Leu Arg Leu Gly Leu Pro Gly Ser Asp Glu Pro Asp Arg
            20                  25                  30

Arg Thr Glu Ser Lys Ser Asn Lys Arg Pro Phe Ser Glu Ile Asp Lys
        35                  40                  45

Glu Ser Asn Ser Ser Ile Ser Asn Asn Gly Asn Cys Leu Asp Gln Thr
    50                  55                  60

Ser Gln Pro Pro Pro Ser Lys Ala Gln Val Val Gly Trp Pro Pro Val
65                  70                  75                  80

Arg Ser Tyr Arg Lys Asn Tyr Leu Ala Gly Lys Lys Ser Glu Thr Glu
                85                  90                  95

Ser Ser Ser Gly Gly Tyr Val Lys Val Ser Met Asp Gly Ala Pro Tyr
            100                 105                 110

Leu Arg Lys Ile Asp Leu Thr Ile Tyr Lys Ser Tyr Thr Glu Leu Val
        115                 120                 125

Lys Ala Leu Glu Asn Met Phe Lys Phe Asn Leu Gly Gly Tyr Ser Glu
    130                 135                 140

Lys Glu Gly Phe Asn Asn Gly Ser Asp Tyr Ala Pro Thr Tyr Glu Asp
145                 150                 155                 160

Lys Asp Gly Asp Trp Met Leu Val Gly Asp Val Pro Trp Glu Met Phe
                165                 170                 175

Ile Ser Ser Cys Lys Arg Leu Arg Ile Met Lys Gly Ser Glu Ala Arg
            180                 185                 190

Gly Leu Gly Cys Leu
        195
```

<210> SEQ ID NO 134
<211> LENGTH: 594
<212> TYPE: DNA
<213> ORGANISM: Cucumis melo

<400> SEQUENCE: 134

```
atggccaaac tggcagcttc ttctgatcac ccagatctca acttccaagc cacggagctc     60
cgccttggcc tccccggctc cgacgagccc gatcgccgca ccgagtcaaa gtcgaacaag    120 agacccttt  cagagatcga taaggaaagt aacagcagca tttccaacaa tggaaattgc    180
ctcgatcaaa cctcccaacc tcctccctcc aaagcacaag ttgttggatg gccaccggtt    240
cgatcgtacc gaaaaaatta tttagctgga agaaaagtg agacagaaag ttcgagcgga    300
gggtatgtga agtgagcat  ggatggagct ccatacctca ggaagatcga tttaaccatt    360
tacaaaagtt acacggagct cgtaaaggcc ttggagaaca tgttcaaatt caatctaggt    420
ggttactccg aaaaagaagg tttcaataat ggatctgatt atgctccaac ttatgaagac    480
aaagatggcg attggatgct ggtcggcgac gtcccatggg aaatgttcat ctcttcttgc    540
aaaagattga gaattatgaa aggatcagaa gcaagagggt tggatgtttt ataa          594
```

<210> SEQ ID NO 135
<211> LENGTH: 170
<212> TYPE: PRT
<213> ORGANISM: Cucumis melo

<400> SEQUENCE: 135

```
Met Ser Phe Glu Glu Thr Glu Leu Arg Glu Val Val Gly Trp Pro
1               5                   10                  15

Pro Ile Ser Cys Cys Arg Lys Lys Arg Leu Gly Leu Gln Lys Gly Ser
                20                  25                  30

Lys Glu Glu Glu Ser Asp Glu Asp Gln Glu Lys Asn Val Met Lys Lys
            35                  40                  45

Lys Ile Arg Phe Val Lys Val Ser Leu Asp Gly Ala Pro Tyr Leu Arg
        50                  55                  60

Lys Val Asp Leu Ser Met Tyr Asn Ser Tyr Asn Gln Leu Ser His Ala
65                  70                  75                  80

Leu Ala Lys Phe Phe Gly Ala Phe Thr Ile Gly Lys Cys Gly Ser Glu
                85                  90                  95

Ala Gly Gly Met Lys Glu Leu Met Asn Glu Leu Lys Val Asn Val Asp
            100                 105                 110

Cys Ser Asp Tyr Val Pro Thr Tyr Gln Asp Lys Asp Gly Asp Trp Met
        115                 120                 125

Leu Leu Gly Asp Val Pro Trp Gln Met Phe Val Glu Ser Cys Lys Arg
    130                 135                 140

Val Arg Ile Met Lys Gly Lys Glu Ala Ile Glu Ile Ala Pro Arg Ala
145                 150                 155                 160

Ala Glu Lys Cys Lys Asn Asn Asn Lys Ser
                165                 170
```

<210> SEQ ID NO 136
<211> LENGTH: 513
<212> TYPE: DNA
<213> ORGANISM: Cucumis melo

<400> SEQUENCE: 136

```
atgtcgtttg aggagacaga gctaagggaa gaagtggtgg gttggccacc aataagttgc      60
tgtagaaaga agagattggg gcttcaaaag ggaagtaaag aggaagaaag tgatgaagac     120
caagagaaga atgtgatgaa gaagaagatt aggtttgtga aggttagcct tgatggtgca     180
ccttatcttc gtaaggttga cttgagcatg tacaacagct acaatcaact ttctcatgcc     240
ttagccaaat tctttggagc cttcaccatt ggtaagtgtg gatcagaagc aggtgggatg     300
aaagagttga tgaatgaatt gaaagtaaat gtagattgtt ctgattatgt tccaacctat     360
caagacaaag atggtgattg gatgcttctt ggtgatgttc cttggcagat gtttgttgaa     420
tcttgcaagc gtgttcgtat aatgaaagga aagaagcca ttgagattgc accaagagct     480
gcagagaagt gcaagaacaa caataagagc taa                                  513
```

<210> SEQ ID NO 137
<211> LENGTH: 249
<212> TYPE: PRT
<213> ORGANISM: Solanum tuberosum

<400> SEQUENCE: 137

```
Met Thr Ser Val Leu Gly Ala Glu Cys Asp Lys Ile Arg Leu Asp Tyr
1               5                   10                  15
```

Glu Ala Glu Thr Glu Leu Arg Leu Gly Leu Pro Gly Ala Asn Gly Asn
           20                  25                  30

Glu Val Glu Ser Thr Asn Lys Asn Asn Gly Lys Arg Val Phe Ser Glu
       35                  40                  45

Thr Val Asp Leu Lys Leu Asn Leu Ser Asn Ser Lys Asp Ser Thr Leu
   50                  55                  60

Met Asp Asn Ile Asn Gln Val Asp Asn Met Lys Glu Lys Lys Asn Asn
65                  70                  75                  80

Ile Val Val Pro Ser Ser Asn Asp Pro Ala Lys Ser Pro Ala Lys Ala
               85                  90                  95

Gln Val Val Gly Trp Pro Pro Val Arg Ser Phe Arg Lys Asn Val Met
              100                 105                 110

Thr Val Gln Lys Asn Thr Thr Gly Ala Gly Glu Ser Ser Gly Thr Gly
          115                 120                 125

Thr Gly Ala Ala Phe Val Lys Val Ser Val Asp Gly Ala Pro Tyr Leu
   130                 135                 140

Arg Lys Val Asp Leu Lys Met Tyr Lys Ser Tyr Gln Gln Leu Ser Asp
145                 150                 155                 160

Ala Leu Gly Lys Met Phe Ser Ser Phe Thr Ile Gly Asn Cys Gly Thr
              165                 170                 175

Gln Gly Phe Lys Asp Phe Met Asn Glu Ser Lys Leu Ile Asp Leu Leu
          180                 185                 190

Asn Gly Ser Asp Tyr Val Pro Thr Tyr Glu Asp Lys Asp Gly Asp Trp
      195                 200                 205

Met Leu Val Gly Asp Val Pro Trp Glu Met Phe Val Asp Ser Cys Lys
210                 215                 220

Arg Leu Arg Ile Met Lys Gly Ser Glu Ala Ile Gly Leu Ala Pro Arg
225                 230                 235                 240

Ala Val Glu Lys Cys Lys Asn Arg Ser
              245

<210> SEQ ID NO 138
<211> LENGTH: 750
<212> TYPE: DNA
<213> ORGANISM: Solanum tuberosum

<400> SEQUENCE: 138

```
atgacgagcg tgttgggtgc agagtgtgac aaaatccgat ggattatga agcggagacg     60 gagctgaggc tcgggttgcc tggagccaat ggaaatgaag ttgaatcaac taataagaac    120
aatggcaaaa gggtcttttc agaaactgtt gatttgaaat aaacctttc taattcaaag    180 gattctacat taatggataa tattaatcaa gttgataaca tgaaggagaa gaagaataat    240
attgttgtgc caagctctaa tgatcctgct aagtcaccag ccaaggcaca gttgtgggt    300 tggccaccag tgagatcatt caggaagaat gtaatgactg ttcagaaaaa caccaccggc    360
gccggcgaaa gctccggcac cggcaccggc gcagcctttg tgaaagttag tgttgacggt    420
gcaccatact tacgtaaagt ggacttgaag atgtacaaaa gttaccaaca actctctgat    480
gcacttggca aatgttcag ttcttttact attggaaatt gtgggactca aggatttaag    540
gatttcatga atgagagcaa attgatagac ctcttaaatg gttcagacta tgtaccaact    600
tatgaagaca aggatggtga ttggatgctt gttggtgatg taccttggga gatgtttgtt    660
gattcatgca aacgtttaag gataatgaaa ggatcagagg ctattggact agcaccaaga    720
gcagtggaga aatgcaaaaa caggagctga                                     750
```

<210> SEQ ID NO 139
<211> LENGTH: 250
<212> TYPE: PRT
<213> ORGANISM: Solanum tuberosum

<400> SEQUENCE: 139

Met Thr Ser Val Leu Gly Ala Glu Cys Asp Lys Ile Arg Leu Asp Tyr
1               5                   10                  15

Glu Ala Glu Thr Glu Leu Arg Leu Gly Leu Pro Gly Ala Gly Asn Glu
            20                  25                  30

Leu Glu Ser Ser Asn Lys Asn Asn Gly Lys Arg Val Phe Ser Glu Thr
        35                  40                  45

Val Asp Leu Lys Leu Asn Leu Ser Asn Ser Lys Asp Ser Thr Leu Met
    50                  55                  60

Asp Asn Ile Asn Ile Asn Gln Val Asp Asn Met Lys Glu Lys Lys Asn
65                  70                  75                  80

Asn Ile Val Val Pro Ser Ser Asn Asp Pro Ala Lys Pro Ala Lys
                85                  90                  95

Ala Gln Val Val Gly Trp Pro Pro Val Arg Ser Phe Arg Lys Asn Val
            100                 105                 110

Met Thr Val Gln Lys Asn Thr Thr Gly Ala Gly Glu Ile Ser Gly Thr
        115                 120                 125

Gly Thr Gly Ala Ala Phe Val Lys Val Ser Val Asp Gly Ala Pro Tyr
    130                 135                 140

Leu Arg Lys Val Asp Leu Lys Met Tyr Lys Ser Tyr Gln Gln Leu Ser
145                 150                 155                 160

Asp Ala Leu Gly Lys Met Phe Ser Ser Phe Thr Ile Gly Asn Cys Gly
                165                 170                 175

Thr Gln Gly Phe Lys Asp Phe Met Asn Glu Ser Lys Leu Ile Asp Leu
            180                 185                 190

Leu Asn Gly Ser Asp Tyr Val Pro Thr Tyr Glu Asp Lys Asp Gly Asp
        195                 200                 205

Trp Met Leu Val Gly Asp Val Pro Trp Glu Met Phe Val Asp Ser Cys
    210                 215                 220

Lys Arg Leu Arg Ile Met Lys Gly Ser Glu Ala Ile Gly Leu Ala Pro
225                 230                 235                 240

Arg Ala Val Glu Lys Cys Lys Asn Arg Ser
                245                 250

<210> SEQ ID NO 140
<211> LENGTH: 756
<212> TYPE: DNA
<213> ORGANISM: Solanum tuberosum

<400> SEQUENCE: 140
atgacaagcg tgttgggtgc ggagtgtgac aaaatccgat tggattatga agcggagacg      60
gagctgaggc tcggattgcc cggagctaat gggaatgaac tggaatcgag taataagaac     120
aatggcaaaa gggtcttttc agaaactgtt gatttgaaat taaacctttc taattcaaag     180
gattccacat taatggataa tattaatatt aatcaagttg ataacatgaa ggagaagaag     240
aataatattg ttgtgccaag ctctaatgat cctgctaagc caccagccaa ggcacaagtt     300
gtgggttggc caccagtgag atcattcagg aagaatgtaa tgactgttca gaaaacacc      360 accggcgccg gcgaaatctc cggcaccggc accggcgcag cctttgtgaa agttagtgtt     420
gacggtgcac catacttacg taaagtggac ttgaagatgt acaaaagtta ccaacaactc     480

```
tctgatgcac ttggcaaaat gtttagctct tttactattg gaaattgtgg gactcaagga    540
tttaaggatt tcatgaatga gagcaaattg atagacctct tgaatggttc agactatgta    600
ccaacttatg aagacaaaga tggtgattgg atgcttgttg gtgatgtacc ttgggagatg    660
tttgttgatt catgcaaacg tttacggata atgaaaggat cagaagctat tgggctagca    720
ccaagagcag tggagaaatg caagaacagg agttaa                              756
```

```
<210> SEQ ID NO 141
<211> LENGTH: 236
<212> TYPE: PRT
<213> ORGANISM: Solanum tuberosum

<400> SEQUENCE: 141
```

Met Asp Leu Lys Glu Thr Glu Leu Cys Leu Gly Leu Pro Gly Gly Gly
1               5                   10                  15

Gly Gly Gly Gly Glu Leu Ile Arg Asp Asn Asn Asn Asn Asn Asn Lys
            20                  25                  30

Val Asn Gly Lys Arg Gly Phe Ser Glu Thr Val Asp Leu Lys Leu Asn
        35                  40                  45

Phe His Gln Ala Ser Asp Asp Ile Ser Cys Ala Met Glu Asn Asn Lys
    50                  55                  60

Met Lys Ser Ser Val Thr Thr Thr Lys Glu Val Val Cys Asn Lys Asp
65                  70                  75                  80

Pro Ile Lys Pro Pro Ala Lys Ala Gln Val Val Gly Trp Pro Pro Val
                85                  90                  95

Arg Ser Phe Arg Lys Asn Val Met Ala Gln Lys Ser Asn Thr Glu Glu
            100                 105                 110

Ser Glu Lys Thr Thr Ala Ala Phe Val Lys Val Cys Met Asp Gly Ala
        115                 120                 125

Pro Tyr Leu Arg Lys Val Asp Leu Lys Met Tyr Lys Ser Tyr Gln Glu
    130                 135                 140

Leu Ser Asp Ala Leu Ala Lys Met Phe Ser Ser Phe Thr Asn Gly Asn
145                 150                 155                 160

Tyr Gly Ser Gln Gly Met Ile Asp Phe Met Asn Glu Ser Lys Leu Met
                165                 170                 175

Asp Leu Leu Asn Ser Ser Glu Tyr Val Pro Thr Tyr Glu Asp Lys Asp
            180                 185                 190

Gly Asp Trp Met Leu Val Gly Asp Val Pro Trp Glu Met Phe Val Asp
        195                 200                 205

Ser Cys Lys Arg Leu Arg Ile Met Lys Gly Ser Glu Ala Ile Gly Leu
    210                 215                 220

Ala Pro Arg Ala Met Glu Lys Cys Lys Ser Arg Ile
225                 230                 235

```
<210> SEQ ID NO 142
<211> LENGTH: 711
<212> TYPE: DNA
<213> ORGANISM: Solanum tuberosum

<400> SEQUENCE: 142
atggatttga agaaactga gttgtgtttg gactacctg gtggtggtgg tggcggaggt    60
gaattaattc gcgataataa taataataat aacaaggtta atgggaaaag agggttttct   120
gagactgtta atttgaagct caattttcat caagctagtg atgatatttc ttgtgctatg   180
gagaataata agatgaagag cagtgttact actactaaag aagttgtttg taacaaagat   240
```

```
ccaatcaagc cacctgccaa ggcacaagtt gtgggttggc caccagtgag atcatttagg    300
aagaatgtaa tggctcaaaa gagcaacact gaagaaagtg agaagactac tgctgcattt    360
gtcaaagttt gcatggatgg tgcaccttac ctacgtaagg ttgatttgaa aatgtacaaa    420
agttaccaag aactttctga tgctttggct aagatgttta gctcctttac taatggaaat    480
tatgggtccc aaggaatgat agattttatg aatgagagca aattgatgga tctccttaac    540
agttctgaat atgtaccaac ctatgaagat aaagatggag attggatgct tgttggagat    600
gtaccttggg agatgtttgt tgattcatgc aagcgtttac gcataatgaa aggatcagaa    660
gctattggac ttgcaccaag agctatggag aaatgcaaga gcaggatcta a            711
```

<210> SEQ ID NO 143
<211> LENGTH: 218
<212> TYPE: PRT
<213> ORGANISM: Solanum tuberosum

<400> SEQUENCE: 143

```
Met Asp Leu Lys Thr Glu Leu Cys Leu Gly Leu Pro Gly Gly Gly Gly
 1               5                  10                  15

Asp His Asn Ile Lys Lys Arg Gly Phe Ser Gln Thr Val Asp Leu Lys
            20                  25                  30

Leu Asn Leu His His Asn Asp Asn Ile Pro Ser Met Asn Ile Asn Asn
        35                  40                  45

Pro Pro Lys Asp Asn Ser Ser Asn Lys Pro Pro Thr Lys Ala Gln Val
    50                  55                  60

Val Gly Trp Pro Pro Val Arg Ser Phe Arg Lys Asn Met Leu Ser Gln
65                  70                  75                  80

Lys Gly Asn Asn Asn Asn Asn Asn Glu Glu Ile Ser Glu Lys Asp
                85                  90                  95

Glu Lys Thr Ile Ala Phe Val Lys Val Ser Met Asp Gly Ala Pro Tyr
            100                 105                 110

Leu Arg Lys Val Asp Leu Lys Met Tyr Lys Ser Tyr Gln Gln Leu Ser
        115                 120                 125

His Ser Leu Thr Asn Met Phe Ser Ser Phe Thr Met Gly Asn Tyr Gly
    130                 135                 140

Ser Gln Gly Met Ile Asp Phe Met Asn Glu Arg Lys Leu Met Asp Val
145                 150                 155                 160

Leu Asn Ser Ser Asp Tyr Val Pro Thr Tyr Glu Asp Lys Asp Gly Asp
                165                 170                 175

Trp Met Leu Val Gly Asp Val Pro Trp Gln Met Phe Val Asp Ser Cys
            180                 185                 190

Lys Arg Leu Arg Ile Met Lys Gly Ser Glu Ala Ile Gly Leu Ala Pro
        195                 200                 205

Arg Ala Met Glu Lys Cys Lys Asn Arg Ser
    210                 215
```

<210> SEQ ID NO 144
<211> LENGTH: 657
<212> TYPE: DNA
<213> ORGANISM: Solanum tuberosum

<400> SEQUENCE: 144

```
atggacttga aaactgagtt atgtttgggg ctgcctggtg gtggaggaga tcacaatatt     60
aagaaaagag gattttctca aactgttgat ctcaaactca acctccatca taatgataat    120
```

| attccttcta tgaacatcaa caatcctcca aaggataatt cctccaacaa gccaccaact | 180 |
| aaggctcaag tggtggggtg gccaccagta agatctttca gaaagaacat gttgtctcaa | 240 |
| aaagggaata ataataataa taataatgaa gaaattagtg agaaggatga aaaaacaata | 300 |
| gcatttgtga aggtttccat ggatggtgca ccttaccttc gtaaggtaga tttaaagatg | 360 |
| tacaagagtt accaacaact ctctcattct ttgaccaaca tgtttagctc cttcactatg | 420 |
| ggtaattatg ggtcccaagg aatgatagat tttatgaatg agaggaaact gatggatgtc | 480 |
| ctcaatagtt ctgactatgt accaacctat gaagataagg atggggattg gatgcttgtt | 540 |
| ggagatgtac cttggcaaat gtttgttgat tcatgcaagc gtttacgcat aatgaaagga | 600 |
| tcagaagcta ttggactagc accaagagcc atggagaaat gcaagaacag gagctga | 657 |

<210> SEQ ID NO 145
<211> LENGTH: 208
<212> TYPE: PRT
<213> ORGANISM: Solanum tuberosum

<400> SEQUENCE: 145

Met Ser Ser Asn Lys Leu Asp Phe Glu Glu Thr Glu Leu Arg Leu Gly
1               5                   10                  15

Leu Pro Gly Gly Ala Arg Lys Asn Val Tyr Gly Asp Asn Asp Thr Cys
            20                  25                  30

Asn Val Asn Gly Lys Arg Gly Phe Val Asp Leu Lys Leu Asn Leu Ser
        35                  40                  45

Ser Asp Ile Asn Asn Ile Lys Asn Ser Thr His Lys Thr Pro Ala Ala
    50                  55                  60

Lys Ala Gln Val Val Gly Trp Pro Pro Val Arg Ser Phe Arg Lys Asn
65                  70                  75                  80

Ile Leu Thr Ser Gln Lys Leu Asp Arg Glu Asn Asp Asn Ile Leu Val
                85                  90                  95

Lys Val Ser Met Asp Gly Ala Pro Tyr Leu Arg Lys Val Asp Leu Asn
            100                 105                 110

Met Tyr Lys Ser Tyr Gln Glu Leu Phe Asp Ala Leu Thr Lys Met Phe
        115                 120                 125

Asn Ser Phe Thr Ile Val Gln Gly Met Lys Asp Phe Met His Glu Gly
    130                 135                 140

Lys Leu Met Asp Leu Leu Asn Ser Ser Asp Tyr Val Pro Thr Tyr Glu
145                 150                 155                 160

Asp Lys Asp Gly Asp Trp Met Leu Val Gly Asp Val Pro Trp Gly Met
                165                 170                 175

Phe Val Asp Ser Cys Lys Arg Leu Arg Ile Met Lys Gly Thr Glu Ala
            180                 185                 190

Ile Gly Leu Ala Pro Arg Ala Met Glu Lys Cys Lys Asn Arg Asn Gly
        195                 200                 205

<210> SEQ ID NO 146
<211> LENGTH: 627
<212> TYPE: DNA
<213> ORGANISM: Solanum tuberosum

<400> SEQUENCE: 146

| atgagtagta ataagttgga ttttgaggag acagaattaa ggctagggtt gcctggtgga | 60 |
| gcaagaaaaa atgtttatgg tgataatgat acttgtaatg ttaatggtaa agaggctttt | 120 |
| gtagatttga agcttaatct ttcttctgat attaacaaca tcaagaattc aacacacaaa | 180 |

```
acccagctg ccaaggcaca agttgtgggt tggccgcccg taaggtcctt tcgaaagaat    240
attttgactt ctcaaaagct tgatcgagag aatgataata ttttggtgaa ggtgagcatg    300
gatggtgcac cttaccttag gaaagtggac ttaaacatgt acaagagtta tcaagaatta    360
tttgatgcct taaccaagat gttcaattcc ttcactattg tccaaggaat gaaagatttc    420
atgcatgagg ggaaactgat ggaccttttg aatagttctg attatgttcc tacctatgaa    480
gacaaagatg gtgattggat gcttgttgga gatgtcccat ggggatgtt tgttgattct    540 tgcaaacgct tgcgcatcat gaaaggaact gaagcaatag gactagcacc aagggctatg    600
gagaagtgca agaacagaaa tggatga                                        627
```

<210> SEQ ID NO 147
<211> LENGTH: 278
<212> TYPE: PRT
<213> ORGANISM: Solanum tuberosum

<400> SEQUENCE: 147

```
Met Ser Val Pro Leu Glu His Asp Tyr Ile Gly Leu Ser Glu Pro Ser
1               5                   10                  15

Leu Met Glu Arg Ser Ser Asp Lys Ile Ser Ser Ser Ser Ser Ser Ser
            20                  25                  30

Val Leu Asn Leu Lys Glu Thr Glu Leu Arg Leu Gly Leu Pro Gly Ser
        35                  40                  45

Glu Ser His Gly Val Ser Leu Phe Gly Lys Asp Leu Asp Pro Leu Ser
    50                  55                  60

Asn Phe Thr Ser Arg Thr Lys Arg Gly Phe Ser Asp Ala Ile Asp Ala
65                  70                  75                  80

Ser Gly Lys Ser Asp Leu Ser Ile Asn Cys Arg Ser Glu Ala Asp Arg
                85                  90                  95

Glu Asn Gly Asn Leu Leu Phe Ser Pro Lys Arg Gly Asn Gly Gly Ser
            100                 105                 110

Asn Pro Val Glu Glu Lys Lys Pro Ile Pro His Thr Ser Lys Ala Gln
        115                 120                 125

Val Val Gly Trp Pro Pro Ile Arg Ser Phe Arg Lys Asn Thr Leu Ala
    130                 135                 140

Thr Lys Lys Asn Asp Asp Glu Gly Arg Thr Gly Ser Ser Cys Leu Tyr
145                 150                 155                 160

Val Lys Val Ser Met Asp Gly Ala Pro Tyr Leu Arg Lys Val Asp Ile
                165                 170                 175

Lys Thr Tyr Ser Asn Tyr Ala Ala Leu Ser Ser Ala Leu Glu Lys Met
            180                 185                 190

Phe Ser Cys Phe Ser Ile Gly Gln Cys Ala Ser Asp Lys Ile Pro Gly
        195                 200                 205

Gln Glu Lys Leu Ser Glu Ser His Leu Met Asp Leu Leu Asn Gly Ser
    210                 215                 220

Glu Tyr Val Leu Thr Tyr Glu Asp Lys Asp Gly Asp Trp Met Leu Val
225                 230                 235                 240

Gly Asp Val Pro Trp Glu Met Phe Ile Asp Ser Cys Lys Arg Leu Arg
                245                 250                 255

Ile Met Lys Ser Ser Glu Ala Ile Gly Leu Ala Pro Arg Ala Ile Asn
            260                 265                 270

Lys Cys Lys Asn Gln Asn
        275
```

<210> SEQ ID NO 148
<211> LENGTH: 837
<212> TYPE: DNA
<213> ORGANISM: Solanum tuberosum

<400> SEQUENCE: 148

```
atgtctgtac cattagaaca tgattatata ggtttatcag aaccttcttt aatggaaaga      60
agttctgata agatttcttc ttcttcttct tcctctgttc taaaccttaa ggagactgag     120
ctgagacttg ggttgcctgg ttctgagtct catggggttt ctcttttttgg caaagatttg    180
gacccttttaa gcaattttac atcaagaaca aaaagggggtt tttctgatgc aattgatgca   240
tctgaaaaat cggatttgtc tattaattgc agatctgaag ctgataggga aaacgggaac    300
ttgttgtttt ccccaaaaag agggaatgga ggttcaaacc ctgttgaaga aaaaaagcct    360
atccctcata cttcaaaggc acaagtggta ggatggccac caattagatc attcaggaaa    420
aatacactgg ctactaagaa aaatgatgat gaagggagaa caggttcaag ttgcctttat    480
gttaaggtta gcatggatgg tgctccatat ctgaggaaag ttgatatcaa aacttacagt    540
aactatgcag cgctctcatc agcacttgaa aagatgttca gctgctttag tattggtcag    600
tgtgccagtg ataagattcc agggcaagag aagctcagtg aaagtcactt gatggatctt    660
ctcaatggtt ctgagtatgt gctgacttat gaggacaagg atggtgattg gatgctagtt    720
ggcgatgttc cttgggagat gttcatagac tcatgcaaga gattgcggat catgaagagc    780
tcagaggcaa ttgggctagc tccaagggcc ataataagt gcaagaacca aaattag       837
```

<210> SEQ ID NO 149
<211> LENGTH: 349
<212> TYPE: PRT
<213> ORGANISM: Solanum tuberosum

<400> SEQUENCE: 149

```
Met Ser Pro Pro Leu Leu Gly Val Gly Glu Glu Glu Gly Gln Ser Asn
1               5                   10                  15

Val Thr Leu Leu Ala Ser Ser Thr Ser Leu Gly Ser Ile Cys Ile Lys
                20                  25                  30

Gly Ser Ala Leu Lys Glu Arg Asn Tyr Met Gly Leu Ser Asp Cys Ser
            35                  40                  45

Ser Val Asp Ser Cys Asn Ile Ser Thr Ser Ser Glu Asp Asn Asn Gly
        50                  55                  60

Cys Gly Leu Asn Leu Lys Ala Thr Glu Leu Arg Leu Gly Leu Pro Gly
65                  70                  75                  80

Ser Gln Ser Pro Glu Arg Gly Glu Glu Thr Cys Pro Val Ser Ser Thr
                85                  90                  95

Lys Val Asp Glu Lys Leu Leu Phe Pro Leu His Pro Ser Lys Asp Thr
            100                 105                 110

Ala Phe Ser Val Ser Gln Lys Thr Val Val Ser Gly Asn Lys Arg Gly
        115                 120                 125

Phe Ser Asp Ala Met Asp Gly Phe Ser Glu Gly Lys Phe Leu Ser Asn
    130                 135                 140

Ser Gly Val Lys Ala Gly Asp Thr Lys Glu Thr Ser Arg Val Gln Pro
145                 150                 155                 160

Pro Lys Met Lys Asp Ala Asn Thr Gln Ser Thr Val Pro Glu Arg Pro
                165                 170                 175

Ser Ala Val Asn Asp Ala Ser Asn Arg Ala Gly Ser Gly Ala Pro Ala
            180                 185                 190
```

```
Thr Lys Ala Gln Val Val Gly Trp Pro Pro Ile Arg Ser Phe Arg Lys
            195                 200                 205
Asn Thr Leu Ala Ser Ala Ser Lys Asn Asn Glu Glu Val Asp Gly Lys
            210                 215                 220
Ala Gly Ser Pro Ala Leu Phe Ile Lys Val Ser Met Asp Gly Ala Pro
225                 230                 235                 240
Tyr Leu Arg Lys Val Asp Leu Arg Thr Cys Ser Ala Tyr Gln Glu Leu
            245                 250                 255
Ser Ser Ala Leu Glu Lys Met Phe Ser Cys Phe Thr Ile Gly Gln Tyr
            260                 265                 270
Gly Ser His Gly Ala Pro Gly Lys Asp Met Leu Ser Glu Ser Lys Leu
            275                 280                 285
Lys Asp Leu Leu His Gly Ser Glu Tyr Val Leu Thr Tyr Glu Asp Lys
            290                 295                 300
Asp Gly Asp Trp Met Leu Val Gly Asp Val Pro Trp Glu Met Phe Ile
305                 310                 315                 320
Asp Thr Cys Lys Arg Leu Arg Ile Met Lys Gly Ser Asp Ala Ile Gly
            325                 330                 335
Leu Ala Pro Arg Ala Met Glu Lys Cys Arg Ser Arg Asn
            340                 345

<210> SEQ ID NO 150
<211> LENGTH: 1050
<212> TYPE: DNA
<213> ORGANISM: Solanum tuberosum

<400> SEQUENCE: 150
atgtctccgc cgctccttgg tgttggggag gaggagggcc agagtaatgt aactctactg      60
gcttcttcaa cttccttagg aagcatatgc ataaaaggat cagctcttaa agagcgaaac     120
tatatgggtc tatctgattg ttcgtcggtg acagctgta  atatttccac ctcatcagag     180
gacaataatg ggtgtggatt aaatctcaag gcaacggagc tcaggctcgg tctacctgga     240
tctcagtctc ccgaaagagg tgaggagact tgccctgtga gctcgacaaa ggttgatgag     300
aagctgctct ccccttgca  cccttccaaa gatactgctt tctcggtatc gcagaaaaca     360
gtagttagtg caacaaacg  aggattttca gacgctatgg atggattctc agaggggaag     420
tttctgtcga attccggtgt gaaagcaggt gatacaaagg agacctcacg tgtgcaacca     480
cctaaaatga agatgctaa  tactcagagt acagttccag agaggccttc tgctgtgaat     540
gatgcctcaa accgtgcggg cagtggtgcc cctgctacaa aggcacaggt tgttggttgg     600
ccacccattc gatcttttag aaagaacact ctagcctctg cctcgaagaa taacgaagag     660
gttgacggaa aagctggctc accagctctt tttattaagg tcagcatgga tggtgctccc     720
tatttgagga aagtggacct cagaacctgt tctgcatacc aggagctatc ttctgctctt     780
gaaaaaatgt tcagctgttt tacaataggt caatatggat ctcatggagc tcctgggaag     840
gatatgttaa gtgagagcaa attgaaggat ttgcttcatg gatctgagta tgtcctcact     900
tacgaagata aggatgggga ctggatgctt gtcggtgatg tcccctggga gatgtttatc     960
gatacttgca aaaggttgag gatcatgaaa ggttcagatg ccattggcct ggccccaagg    1020
gctatggaaa agtgtcggag cagaaattag                                     1050

<210> SEQ ID NO 151
<211> LENGTH: 252
<212> TYPE: PRT
<213> ORGANISM: Solanum tuberosum
```

<400> SEQUENCE: 151

```
Met Ala Asn Met Lys Ala Ser Val His Leu Pro Glu Ser Ile Tyr Ser
1               5                   10                  15
Gly Leu Thr Ala Phe Phe Gln Ser Thr Lys Arg Tyr Phe Ile Ser Pro
            20                  25                  30
Asn Tyr Leu Lys Arg Gly Lys Met Ser Ser Glu Thr Ala Lys Ser Ala
        35                  40                  45
Asn Gly Leu Thr Glu Thr Asn Asn Ser Gly Leu Asn Phe Asn Glu Thr
    50                  55                  60
Glu Leu Thr Leu Gly Leu Pro Gly Glu Ser Arg Lys Gln Ile Ser Gly
65                  70                  75                  80
Ala Lys Arg Gly Asn Ser Asp Gly Met Glu Leu Ser Leu Gly Ser Ser
                85                  90                  95
Thr Ser Gly Glu Arg Arg Arg Asp Ile Cys Glu Val Asn His Ser Lys
            100                 105                 110
Asn Glu Ile Ser Thr Gly Asn Lys Pro Pro Ala Lys Ala Gln Val Ile
        115                 120                 125
Gly Trp Pro Pro Val Arg Ser Tyr Arg Lys Asn Val Ile Glu Lys Cys
    130                 135                 140
Lys Tyr Val Lys Val Ala Val Asp Gly Ala Pro Tyr Leu Arg Lys Val
145                 150                 155                 160
Asp Leu Glu Met Tyr Asp Ser Tyr Gln Lys Leu Leu Asn Ala Leu Glu
                165                 170                 175
Asn Met Phe Thr Cys Leu Thr Ile Cys Asn Ser Gln Ser Glu Ser Lys
            180                 185                 190
Leu Met Asp Leu Thr Asn Gly Val Glu Tyr Val Pro Thr Tyr Glu Asp
        195                 200                 205
Lys Asp Gly Asp Trp Met Leu Val Gly Asp Val Pro Trp Lys Met Phe
    210                 215                 220
Val Asp Thr Cys Lys Arg Ile Arg Leu Met Lys Ser Thr Glu Ala Ile
225                 230                 235                 240
Gly Leu Ala Pro Arg Thr Pro Gly Arg Ser Ser Ser
                245                 250
```

<210> SEQ ID NO 152
<211> LENGTH: 759
<212> TYPE: DNA
<213> ORGANISM: Solanum tuberosum

<400> SEQUENCE: 152

| | | |
|---|---|---|
| atggctaaca tgaaagcctc cgtccaccta cccgagagca tatatagtgg cctaaccgca | 60 |
| tttttcaaa gcaccaaaag atatttcatt tcaccaaact atctaaaaag ggggaaaatg | 120 |
| tcatcggaga cagccaaatc agcgaacggt ttgacggaaa caataattc cggccttaat | 180 |
| ttcaatgaaa ctgagctaac tctcggctta cccggcgaat cgcggaagca aatctccggt | 240 |
| gcaaaacgtg gaaattccga cggtatggaa ttaagcctag gaagctcaac ttccggtgaa | 300 |
| cgccgccgtg atatctgcga agttaatcac tcgaaaaacg aaatctctac cggaaacaaa | 360 |
| cctccagcaa aggcacaagt aattggatgg ccgccggtga gatcatacag aaaaaacgtg | 420 |
| atagaaaagt gcaaatacgt gaaggtagca gttgacggag ctccttactt gagaaaagta | 480 |
| gatctggaga tgtacgacag ttaccagaag ttgttgaatg cttagaaaa catgttact | 540 |
| tgcctaacaa tctgtaattc tcaaagtgaa agcaagctta tggaccttac aaatggtgta | 600 |

```
gaatatgtac ctacttatga agataaagat ggagactgga tgcttgtagg agatgttcca      660
tggaaaatgt tgttgatac gtgtaagaga attagattga tgaagagcac ggaggctata       720
ggattagctc caagaacacc tgggagatcg tcgagttga                              759
```

<210> SEQ ID NO 153
<211> LENGTH: 196
<212> TYPE: PRT
<213> ORGANISM: Solanum tuberosum

<400> SEQUENCE: 153

```
Met Thr Ser Ile Val Gly Asn Gln Lys Asp Leu Asn Phe Lys Ala Thr
1               5                   10                  15

Glu Leu Arg Leu Gly Leu Pro Gly Thr Glu Asp Gln Glu Ser Asp Gln
            20                  25                  30

Glu Ile Ser Asn Ser Lys Asn Asn Lys Arg Ala Leu Pro Glu Ser
        35                  40                  45

Thr His Asp Glu Glu Asp Cys Glu Ser Lys Ser Ser Asp His Val
    50                  55                  60

Lys Thr Pro Pro Val Ala Lys Ala Gln Ile Val Gly Trp Pro Pro
65                  70                  75                  80

Val Arg Ser Asn Arg Lys Asn Ile Ile Gln Pro Lys Lys Thr Glu Ser
                85                  90                  95

Glu Ser Gly Met Tyr Val Lys Val Ser Met Asp Gly Ala Pro Tyr Leu
            100                 105                 110

Arg Lys Ile Asp Leu Lys Met Tyr Lys Cys Tyr Gln Glu Leu Leu Lys
        115                 120                 125

Ala Leu Glu Asn Met Phe Lys Leu Thr Ile Gly Glu Tyr Ser Glu Arg
    130                 135                 140

Glu Gly Tyr Lys Gly Ser Glu Phe Ala Pro Ala Tyr Glu Asp Lys Asp
145                 150                 155                 160

Gly Asp Leu Met Leu Val Gly Asp Val Pro Trp Glu Met Phe Met Ser
                165                 170                 175

Ser Cys Lys Arg Leu Arg Ile Met Lys Gly Ser Glu Ala Arg Gly Leu
            180                 185                 190

Gly Cys Gly Val
        195
```

<210> SEQ ID NO 154
<211> LENGTH: 591
<212> TYPE: DNA
<213> ORGANISM: Solanum tuberosum

<400> SEQUENCE: 154

```
atgacaagta tagtgggcaa tcagaaagat ctgaatttca agccactga gctgagatta        60 ggtttgcctg gtacagaaga tcaagaatct gaccaagaaa tatcaaattc caagaataac      120
aacaaagggg cttacctga tcaactcat gatgaagaag attgtgaatc taagtcaagt        180
tctgatcatg tcaaaacccc accacctgtt gccaaggcac aaattgtggg ttggccacca      240
gtgagatcta acaggaaaaa catcatccaa ccaaagaaaa cagaatctga atctggaatg      300
tatgtcaaag ttagcatgga tggtgcccct tatctaagaa aaattgatct gaaaatgtat      360
aaatgttatc aagaactact aaaagcctta gaaaacatgt tcaaactcac cataggtgaa      420
tactcagaaa gagaaggcta taaaggctct gaatttgccc ctgcttatga agacaaagat      480
ggtgatttga tgcttgttgg tgatgttcct tgggaaatgt ttatgtcttc ttgtaagagg      540
```
ctgagaataa tgaaaggatc agaagcaaga ggcttgggat gtggagttta a 591

<210> SEQ ID NO 155
<211> LENGTH: 176
<212> TYPE: PRT
<213> ORGANISM: Solanum tuberosum

<400> SEQUENCE: 155

```
Met Thr Ser Val Leu Gly Ala Glu Cys Asp Lys Ile Arg Leu Asp Tyr
1               5                   10                  15

Glu Ala Glu Thr Glu Leu Arg Leu Gly Leu Pro Gly Ala Asn Gly Asn
            20                  25                  30

Glu Leu Glu Ser Ser Asn Lys Asn Asn Gly Lys Arg Val Phe Ser Glu
        35                  40                  45

Thr Val Asp Leu Lys Leu Asn Leu Ser Asn Ser Lys Asp Ser Thr Leu
    50                  55                  60

Met Asp Asn Ile Asn Ile Asn Gln Val Asp Asn Met Lys Glu Lys Lys
65                  70                  75                  80

Asn Asn Ile Val Val Pro Ser Ser Asn Asp Pro Ala Lys Pro Pro Ala
                85                  90                  95

Lys Ala Gln Val Val Gly Trp Pro Pro Val Arg Ser Phe Arg Lys Asn
            100                 105                 110

Val Met Thr Val Gln Lys Asn Thr Thr Gly Ala Gly Glu Ile Ser Gly
        115                 120                 125

Thr Gly Thr Gly Ala Ala Phe Val Lys Val Ser Val Asp Gly Ala Pro
    130                 135                 140

Tyr Leu Arg Lys Val Asp Leu Lys Met Tyr Lys Ser Tyr Gln Gln Leu
145                 150                 155                 160

Ser Asp Ala Leu Gly Lys Met Phe Ser Ser Phe Thr Ile Gly Lys Tyr
                165                 170                 175
```

<210> SEQ ID NO 156
<211> LENGTH: 531
<212> TYPE: DNA
<213> ORGANISM: Solanum tuberosum

<400> SEQUENCE: 156
atgacaagcg tgttgggtgc ggagtgtgac aaaatccgat tggattatga agcggagacg     60
gagctgaggc tcggattgcc cggagctaat gggaatgaac tggaatcgag taataagaac    120
aatggcaaaa gggtcttttc agaaactgtt gatttgaaat taaaccttc taattcaaag     180 gattccacat taatggataa tattaatatt aatcaagttg ataacatgaa ggagaagaag    240
aataatattg ttgtgccaag ctctaatgat cctgctaagc caccagccaa ggcacaagtt    300
gtgggttggc caccagtgag atcattcagg aagaatgtaa tgactgttca gaaaaacacc    360
accggcgccg gcgaaatctc cggcaccggc accggcgcag cctttgtgaa agttagtgtt    420
gacggtgcac catacttacg taaagtggac ttgaagatga caaaagtta ccaacaactc    480 tctgatgcac ttggcaaaat gtttagctct tttactattg gtaaatattg a            531

<210> SEQ ID NO 157
<211> LENGTH: 185
<212> TYPE: PRT
<213> ORGANISM: Solanum tuberosum

<400> SEQUENCE: 157

```
Met Arg Ile Tyr Glu Lys Asp Ile Asn Asp Leu Glu Ala Thr Glu Leu
1               5                   10                  15
```

```
Arg Leu Gly Leu Pro Gly Ile Ile Asn Asp Glu Ser Ser Thr Ser Thr
            20                  25                  30

Ser Thr Ser Lys Asn Ser Arg Lys Arg Pro Ser Ser Ser Val Asn
        35                  40                  45

Glu Asn Glu Gln Gln Asp Ser Ala Pro Ala Pro Lys Ala Gln Val Val
 50                  55                  60

Gly Trp Pro Pro Val Arg Ser Tyr Arg Lys Asn His Val Ser Lys Leu
 65                  70                  75                  80

Ser Glu Ser Asp Asn Asn Ser Ser Gly Met Tyr Leu Lys Val Ser Met
                85                  90                  95

Asp Gly Ala Pro Tyr Leu Arg Lys Ile Asp Leu Gln Val Tyr Lys Ser
            100                 105                 110

Tyr Gln Glu Leu Leu Lys Ala Leu Gln Ser Met Phe Lys Cys Thr Ile
        115                 120                 125

Gly Val Tyr Ser Glu Arg Glu Gly Tyr Asn Gly Ser Asp Tyr Ala Pro
130                 135                 140

Thr Tyr Glu Asp Lys Asp Gly Asp Trp Met Leu Val Gly Asp Val Pro
145                 150                 155                 160

Trp Glu Met Phe Ile Ser Ser Cys Lys Arg Leu Arg Ile Ile Lys Gly
                165                 170                 175

Ser Glu Ala Lys Gly Leu Ala Cys Leu
            180                 185

<210> SEQ ID NO 158
<211> LENGTH: 558
<212> TYPE: DNA
<213> ORGANISM: Solanum tuberosum

<400> SEQUENCE: 158
atgagaattt acgagaagga tatcaatgat cttgaggcaa ctgagctaag attaggtttg       60
cctgggataa taacgatga atcttcaaca tcaactagta cttctaaaaa tagcagaaaa      120
agaccttcat ctagtagtgt aaatgaaaat gaacaacaag actcagctcc tgcaccaaaa      180
gcacaagttg ttggttggcc accagttcga tcatacagga aaaatcatgt gtctaaatta      240
tcagaatctg ataataattc ctcaggaatg tatttaaaag ttagcatgga tggagcacct      300
tatttgagga aaattgatct tcaggtttac aaaagttatc aagagctact caaggcttta      360
caaagcatgt tcaagtgcac tattggagtg tattcagaaa gagaaggata taatggatct      420
gattatgcac caacatatga agacaaggat ggtgattgga tgcttgttgg tgatgtacca      480
tgggagatgt ttataagttc ttgcaaaagg cttagaatta tcaaaggatc tgaagctaaa      540
ggtctagcat gtctataa                                                   558

<210> SEQ ID NO 159
<211> LENGTH: 320
<212> TYPE: PRT
<213> ORGANISM: Lactuca sativa

<400> SEQUENCE: 159

Met Ser Pro Gln Leu Leu Gly Val Gln Glu His Ile Gln Gly Asn Thr
 1               5                  10                  15

Ser Phe Pro Thr Ser Thr Cys Ser Met Glu Ser Asn Tyr Gln Lys Ile
            20                  25                  30

Pro Gly Leu Thr Glu Arg Asn Tyr Leu Gly Phe Ser Asp Cys Ser Ser
        35                  40                  45
```

Val Asp Ser Ser Asn Val Ser Thr Ile Ser Glu Val Asn Lys Asn Ser
 50                  55                  60

Leu Asn Leu Lys Ala Thr Glu Leu Arg Leu Gly Leu Pro Gly Ser Gln
 65                  70                  75                  80

Ser Pro Glu Arg Asp Gln Glu Asn Ser Leu Thr Ser Ser Glu Lys Leu
                 85                  90                  95

Asp Glu Lys Pro Leu Phe Pro Leu Leu Pro Ser Ser Ser Ser Ser Gln
            100                 105                 110

Lys Ile Ile Ser Ser Gly His Lys Arg Val Phe Thr Asp Thr Met Asp
        115                 120                 125

Ser Ser Ser Glu Thr Lys Gly Val Ile Ser Ser Asn Ser Glu Leu Pro
130                 135                 140

Ser Ile Lys Cys Ser Thr Pro Ile Ser Lys Val Asn Asn Ser Asn
145                 150                 155                 160

Pro Pro Ser Ser Lys Ala Gln Val Val Gly Trp Pro Val Arg Ser
                165                 170                 175

Phe Arg Lys Asn Met Leu Ala Val Asn Ser Lys Asn Asn Asp Glu Val
            180                 185                 190

Asp Gly Lys Pro Gly Leu Ser Ala Leu Phe Val Lys Val Ser Met Asp
        195                 200                 205

Gly Ala Pro Tyr Leu Arg Lys Val Asp Leu Arg Gly Tyr Ser Thr Tyr
210                 215                 220

Gln Glu Leu Ser Ser Ala Leu Glu Lys Met Phe Ser Cys Phe Thr Ile
225                 230                 235                 240

Gly Gln Cys Gly Ser Gln Gly Gly Pro Leu Arg Gly Ser Leu Ser Glu
                245                 250                 255

Ser Lys Leu Arg Asp Leu Leu His Gly Ser Glu Tyr Val Val Thr Tyr
            260                 265                 270

Glu Asp Lys Asp Gly Asp Trp Met Leu Val Gly Asp Val Pro Trp Asp
        275                 280                 285

Met Phe Ile Gly Ser Cys Lys Arg Leu Lys Ile Met Lys Gly Ser Asp
290                 295                 300

Ala Ile Gly Leu Ala Pro Arg Ala Ser Val Lys Ser Asn Asn Arg Asn
305                 310                 315                 320

<210> SEQ ID NO 160
<211> LENGTH: 963
<212> TYPE: DNA
<213> ORGANISM: Lactuca sativa

<400> SEQUENCE: 160
atgtctccac aactcttagg tgttcaagaa cacatacaag ggaacacctc cttccccact    60
tccacatgct ccatggaatc aaattaccag aaaatccctg gattaactga agaaattac    120 ctcggattct ctgattgttc ctctgtcgac agctcaaacg tctccaccat atcagaagtc    180
aacaaaaaca gtctcaacct taaagcaacc gaattaagac taggccttcc aggatcccaa    240
tcaccagaaa gagatcaaga aaacagctta acaagctctg aaaaactcga tgaaaaaccc    300
ttgtttccat tactcccttc ttcttcttct tcacaaaaga ttatctcatc tggacacaaa    360
agggtattca ctgataccat ggatagttct tctgaaacaa aggagtcat atcatcaaat    420 tctgagcttc catcaattaa atgttcaact cctattagca agtaaacaa caactccaat    480 cctccttctt ccaaagctca gtggtgggg tggcctccag ttagatcatt tcgcaagaac    540
atgttagctg taaattcaaa gaacaatgat gaagtagatg gaaagcctgg acttagtgct    600

```
ttatttgtaa aagttagtat ggatggagct cctatttaa ggaaagttga tctcagaggc    660
tactctactt atcaagaact ttcttcagct cttgagaaga tgtttagttg tttcaccatt    720
ggtcaatgtg atcacaagg aggtccatta aggggagtc taagtgagag caagttgagg     780
gatcttttac atggatcaga gtatgttgtt acatatgaag ataaagatgg tgattggatg    840
cttgtgggag atgttccatg ggatatgttt attggttcat gcaagaggtt gaagatcatg    900
aaaggctcgg atgctattgg tttagctcct agggcaagtg taaaatcgaa caatagaaac    960
tag                                                                  963
```

<210> SEQ ID NO 161
<211> LENGTH: 340
<212> TYPE: PRT
<213> ORGANISM: Lactuca sativa

<400> SEQUENCE: 161

```
Met Thr Pro Pro Leu Leu Gly Val Glu Asp Gly Gln Gly Asn Val Ser
1               5                   10                  15

Ala Ser Thr Met Glu Ser Ile Phe Gln Lys Thr Ser Gly Leu Thr Glu
            20                  25                  30

Arg Asn Tyr Leu Gly Leu Ser Asp Cys Ser Ser Val Asp Ser Ser Ala
        35                  40                  45

Val Ser Asn Ile Ser Glu Val Asn Arg Asn Asn Leu Asn Leu Lys Ala
    50                  55                  60

Thr Glu Leu Arg Leu Gly Leu Pro Gly Ser Gln Ser Pro Glu Arg Asp
65                  70                  75                  80

Pro Gln Thr Asn Ser Glu Asn Leu Asp Glu Lys Pro Leu Phe Pro Leu
                85                  90                  95

Leu Pro Ser Lys Asp Gly Ile Cys Ser Ser Ala Ser Gln Lys Ile Ile
            100                 105                 110

Val Ser Gly Asn Lys Arg Gly Phe Ser Asp Thr Ile Glu Gly Asn Trp
        115                 120                 125

Met Phe Ala Ser Ser Ala Thr Asp Ser Asp Ala Ser Lys Thr Gln Gly
    130                 135                 140

Lys Ala Asn Asn Ser Asn Thr Gln Ser Pro Met Ile Lys Asp Ser Thr
145                 150                 155                 160

Thr Ser Ser Lys Ala Pro Leu Pro Ile Thr Leu Asn Lys Val Asn Ser
                165                 170                 175

Ser Ser Ser Asn Pro Pro Ala Ala Lys Ala Gln Val Val Gly Trp Pro
            180                 185                 190

Pro Val Arg Ser Phe Arg Lys Asn Ile Leu Ala Thr Asn Ser Lys Asn
        195                 200                 205

Asn Asp Glu Val Asp Gly Lys Pro Gly Pro Gly Ala Leu Phe Val Lys
    210                 215                 220

Val Ser Met Asp Gly Ala Pro Tyr Leu Arg Lys Val Asp Leu Arg Ser
225                 230                 235                 240

Tyr Thr Thr Tyr Gln Glu Leu Ser Ser Ala Leu Glu Lys Met Phe Ser
                245                 250                 255

Cys Phe Thr Ile Gly Gln Cys Gly Ser Gln Gly Ala Pro Gly Arg Glu
            260                 265                 270

Ser Leu Ser Glu Ser Lys Leu Arg Asp Leu Leu His Gly Ser Glu Tyr
        275                 280                 285

Val Leu Thr Tyr Glu Asp Lys Asp Gly Asp Trp Met Leu Val Gly Asp
    290                 295                 300
```

Val Pro Trp Asp Met Phe Ile Gly Ser Cys Lys Arg Leu Lys Ile Met
305                 310                 315                 320

Lys Gly Ser Asp Ala Ile Gly Leu Ala Pro Arg Ser Met Glu Lys Ser
            325                 330                 335

Lys Asn Arg Asn
            340

<210> SEQ ID NO 162
<211> LENGTH: 1023
<212> TYPE: DNA
<213> ORGANISM: Lactuca sativa

<400> SEQUENCE: 162

```
atgactccac cactcttagg cgttgaagat ggacagggaa acgtctcggc ttccaccatg      60
gaatcgattt tccaaaaaac ctctggatta actgaacgaa actaccttgg attatcagat     120
tgttcatcag tcgatagctc tgctgtttct aacatctcag aagtgaacag aaacaatcta     180
aaccttaaag ctactgaact acgacttggt cttccaggat ctcaatcccc tgaacgtgat     240
ccacaaacaa actccgagaa tctcgatgaa aaaccttgt tcccattact tccttcaaaa      300
gatggaatct gttcttccgc ttcacaaaag atcatcgttt ctggaaataa agaggattc      360
tccgacacca ttgaagggaa ctggatgttt gcttcatctg caactgattc tgatgcttca     420
aagactcaag aaaagcgaa taatagtaac actcaatctc ccatgattaa agattcaaca     480
acatcatcaa aggctccatt accaattact cttaacaaag tcaacagttc tagttctaat     540
cctcctgctg ctaaggcaca gtggtgggt tggcctccag ttagatcatt tcggaagaac      600
attttggcta caaattcaaa gaacaatgat gaggtggatg gaaaacctgg acctggtgct     660
ttatttgtga agttagtat ggatggagct ccatatctga ggaaggttga tttaaggagt      720
tacactactt atcaagaact ctcatctgca cttgaaaaaa tgtttagttg tttcactatt     780
ggtcaatgtg atcacaagg agctccagga agggaaagtt taagtgagag taaattgagg     840
gatcttttac atggttcaga gtatgtgctt acatatgaag ataaagatgg tgattggatg     900
cttgtgggag atgttccttg ggatatgttt attggttctt gcaagaggtt gaagatcatg     960
aaggggtctg atgctattgg tttagctccg aggtcaatgg aaaagtcaaa gaacagaaat    1020
taa                                                                  1023
```

<210> SEQ ID NO 163
<211> LENGTH: 298
<212> TYPE: PRT
<213> ORGANISM: Lactuca sativa

<400> SEQUENCE: 163

Met Ser Met Ser Ile Glu Glu His Asp Tyr Ile Gly Leu Ser Glu Ala
1               5                   10                  15

Asn Met Glu Lys Lys Ala Cys Asp Ile Thr Glu Asn Lys Asp Leu Asn
            20                  25                  30

Leu Lys Ala Thr Glu Leu Arg Leu Gly Leu Pro Gly Ser Glu Ser Pro
        35                  40                  45

Glu Arg Glu Ala Val Asn Gly Gly Pro Ile Lys Asn Leu Val Ala Gly
    50                  55                  60

Ala Lys Arg Gly Phe Ser Asp Thr Ile Asn Gly Ser Gly Lys Trp
65                  70                  75                  80

Val Phe Ala Gly Lys Gly Gly Ser Glu Val Asp Leu Val Lys Asn Gly
                85                  90                  95

Gly Leu Phe Ser Cys Met Lys Ala Glu Asn Lys Asn Ser Gly Cys Val
            100                 105                 110

Lys Glu Thr Ala Val Leu Ala Ser Pro Lys Pro Val Leu Leu Glu Asn
        115                 120                 125

Lys Ser Gln Val Ser Val Asn Ala Asn Val Pro Ala Pro Lys Gln Gln
    130                 135                 140

Val Val Gly Trp Pro Pro Ile Arg Ser Phe Arg Lys Asn Thr Met Ala
145                 150                 155                 160

Val Ser Gln Thr Lys Asn Gln Glu Asp Lys Asp Pro Lys Met Gly Ser
                165                 170                 175

Gly Cys Leu Tyr Val Lys Val Ser Met Asp Gly Ala Pro Tyr Leu Arg
            180                 185                 190

Lys Val Asp Leu Gln Met Tyr Ser Ser Tyr Leu Asp Leu Ser Ser Ala
        195                 200                 205

Leu Glu Lys Met Phe Ser Cys Phe Thr Ile Gly Gln Tyr Gly Ser His
    210                 215                 220

Gly Ala His Thr Arg Asp Gly Leu Ser Glu Ser Arg Leu Met Asp Leu
225                 230                 235                 240

Leu His Gly Ser Glu Tyr Val Leu Thr Tyr Glu Asp Lys Asp Gly Asp
                245                 250                 255

Trp Met Leu Val Gly Asp Val Pro Trp Asp Met Phe Ile Gly Ser Cys
            260                 265                 270

Lys Arg Met Arg Ile Met Lys Ser Ser Asp Ala Ile Gly Leu Ala Pro
        275                 280                 285

Arg Ala Met Glu Lys Cys Arg Asn Arg Thr
    290                 295

<210> SEQ ID NO 164
<211> LENGTH: 897
<212> TYPE: DNA
<213> ORGANISM: Lactuca sativa

<400> SEQUENCE: 164
atgtctatgt ccattgaaga acatgattac atagggttgt cagaggcaaa tatggagaaa      60
aaagcctgtg atataaccga aaataaagat ttgaatttaa aagccactga attgaggctt     120
gggttgcctg gttcggagtc gccggaaaga gaggctgtta acggtggtcc aatcaagaat     180
ttggtcgccg gagctaaaag gggtttctct gataccatta tggtggttc tgggaaatgg      240 gttttcgctg gtaagggtgg atctgaagtt gatttggtta aaaatggcgg attgtttttct    300 tgtatgaaag ctgaaaacaa gaactccggt tgtgtaaaag agacagctgt tttggcttct     360
ccgaagcctg ttttacttga aaacaagtct caagtttctg taaatgcaaa tgttcctgct     420
ccaaagcaac aagttgtagg atggcctcca attcgatcct ttcgtaagaa caccatggct     480
gttagccaaa caaagaatca agaagataag gatccaaaaa tgggttcggg ttgtctttat     540
gtgaaggtga gcatggatgg agctccatat ttgaggaaag tggatctcca gatgtactct     600
agctacttgg atctttcttc ggctcttgaa aaaatgtta gctgctttac aattggtcaa      660
tatggtagcc atggagctca cacaagagac ggattaagtg agagtcgact aatggactta     720
cttcatggtt ctgagtatgt attgacctat gaagataaag atggcgattg gatgctcgta     780
ggtgatgttc catgggatat gttcattggc tcttgtaaga ggatgaggat catgaaaagt     840
tcagatgcaa ttggcttagc ccctcgagcc atggagaagt gccgaaaccg aacttag       897

<210> SEQ ID NO 165

<211> LENGTH: 310
<212> TYPE: PRT
<213> ORGANISM: Lactuca sativa

<400> SEQUENCE: 165

```
Met Ser Val Pro Leu Glu His Asp Tyr Ile Gly Leu Ser Asp Ala Ser
1               5                   10                  15
Ser Leu Glu Arg Ser Ser Glu Ser Ser Asn Ile Ser Ser Asp Ser Glu
            20                  25                  30
Thr Asn Asn Val Leu Asn Leu Lys Ala Thr Glu Leu Arg Leu Gly Leu
        35                  40                  45
Pro Gly Phe Ala Lys Asn Ser Glu Glu Ser Ala Thr Lys Phe Ala His
    50                  55                  60
Val Lys Asn Phe Met Ser Gly Ala Lys Arg Gly Phe Ser Asp Val Asn
65                  70                  75                  80
Ile Glu Gly Pro Gly Lys Trp Val Met Asn Gly Ser Glu Ala Asp
                85                  90                  95
Leu Gly Lys Thr Ser Ser Val Leu Phe Ser Pro Arg Gly Gly Ile Asn
            100                 105                 110
Gly Gly Leu Glu Lys Asn Gln Val Gln Gln Ser Ile Ser Pro Ser Asn
        115                 120                 125
Val Gln Pro Ile Glu Glu Lys Lys Glu His Val Ser Arg Asn Val
    130                 135                 140
Ala Pro Pro Ser Ala Lys Ala Gln Val Val Gly Trp Pro Pro Ile Arg
145                 150                 155                 160
Ser Phe Arg Lys Asn Thr Met Val Thr Asn Leu Ser Lys Asn Ala Gly
                165                 170                 175
Asp Val Ala Thr Ala Glu Gly Asn Ser Gly Gly Gly Cys Leu Tyr
            180                 185                 190
Val Lys Val Ser Met Asp Gly Ala Pro Tyr Leu Arg Lys Ile Asp Leu
        195                 200                 205
Lys Ile Tyr His Asn Tyr Ala Glu Leu Ser Gln Ala Leu Glu Lys Met
    210                 215                 220
Phe Ser Cys Phe Thr Leu Gly Gln Cys Thr Ser Ser Gly Leu Arg Arg
225                 230                 235                 240
Arg Glu Gly Leu Ser Glu Ser Asn Leu Lys Asp Leu Leu His Gly Ser
                245                 250                 255
Glu Cys Val Leu Thr Tyr Glu Asp Lys Asp Gly Asp Trp Met Leu Val
            260                 265                 270
Gly Asp Val Pro Trp Glu Met Phe Ile Asp Ser Cys Lys Arg Leu Arg
        275                 280                 285
Ile Met Lys Gly Ser Glu Ala Ile Gly Leu Ala Pro Arg Ser Met Asp
    290                 295                 300
Lys Cys Lys Asn Lys Asn
305                 310
```

<210> SEQ ID NO 166
<211> LENGTH: 933
<212> TYPE: DNA
<213> ORGANISM: Lactuca sativa

<400> SEQUENCE: 166

```
atgtctgtgc cactggaaca tgattacata ggcttatcag atgcttcttc gttggaaaga      60
agctctgaat cctccaatat ctcttccgat tcggaaacca acaatgttct taatcttaaa     120
gccactgaac tccgacttgg gttgcctggt tttgccaaaa attccgaaga aagcgccacc     180
```

```
aaatttgctc atgttaagaa cttcatgtca ggagctaaaa gaggattttc tgatgttaat    240
attgagggtc ccggcaaatg ggttatgaac ggtggttctg aagctgattt gggtaaaact    300
tcttctgttt tgttttctcc tagaggcggg attaatggtg gtttagagaa aaatcaagta    360
caacaatcga tttcaccttc taatgttcaa cctattgaag aaaagaagaa agaacatgtc    420
agtcgaaatg ttgctcctcc ttctgctaag gcacaggtgg taggatggcc acccataaga    480
tctttccgga agaacaccat ggtcaccaat ttgtcgaaaa acgccggtga tgtagcgacg    540
gcggaaggga attccggtgg cggagggtgt ctttatgtga aggtgagcat ggatggcgct    600
ccatatctga ggaagattga tctcaagatt taccataact atgcagaact tcacaagct     660 cttgagaaaa tgtttagttg cttcactctt gggcaatgta cctctagtgg acttcgaagg    720
agagaagggc ttagtgaaag taacctaaaa gatcttcttc atggatctga atgtgtgttg    780
acatatgaag ataaggatgg tgattggatg cttgttggtg atgttccttg ggagatgttc    840
atagattcat gcaaaagatt aaggatcatg aaaggctcag aagcaatcgg attagctcca    900
aggtcgatgg ataagtgcaa gaataaaaac tag                                 933
```

```
<210> SEQ ID NO 167
<211> LENGTH: 309
<212> TYPE: PRT
<213> ORGANISM: Lactuca sativa

<400> SEQUENCE: 167

Met Ser Val Pro Leu Glu His Asp Tyr Ile Gly Leu Ser Glu Pro Ser
1               5                   10                  15

Ser Met Glu Lys Ala Ser Glu Ser Ser Asn His Ser Ser Glu Ser Asp
            20                  25                  30

Lys Asn Asn Ala Leu Asn Leu Lys Ala Thr Glu Leu Arg Leu Gly Leu
        35                  40                  45

Pro Gly Leu Gly Gln Asp Leu Glu Glu Asn Ala Cys Lys Asn Ser Pro
    50                  55                  60

Val Lys Asn Phe Val Ser Gly Ala Lys Arg Gly Phe Ser Asp Val Asn
65                  70                  75                  80

Phe Asp Gly Ser Cys Lys Trp Gly Phe Asn Gly Gly Tyr Glu Gly Asp
                85                  90                  95

Ser Val Lys Gly Ser Cys Ser Thr Thr Ser Val Leu Phe Gly Ile Asn
            100                 105                 110

Ser Gly Lys Glu Ser Lys Gln Thr Gln Gln Pro Ser Pro Leu Pro Leu
        115                 120                 125

Glu Glu Lys Lys Lys Ala Ser Val Thr Thr Glu Asn Gly Arg Ser Arg
    130                 135                 140

Thr Pro Pro Ser Ser Lys Ala Gln Val Val Gly Trp Pro Pro Ile Arg
145                 150                 155                 160

Ser Phe Arg Lys Asn Thr Met Thr Ala Asn Leu Ser Lys Asn Asp Asp
                165                 170                 175

Ala Asn Ala Ala Glu Glu Asn Leu Gly Cys Leu Tyr Val Lys Val Ser
            180                 185                 190

Met Asp Gly Ala Pro Tyr Leu Arg Lys Val Asp Leu Lys Thr Cys Lys
        195                 200                 205

Asn Tyr Ser Gln Leu Ser Lys Ala Leu Glu Lys Met Phe Asp Arg Phe
    210                 215                 220

Thr Leu Gly Gln Cys Thr Ser Asn Gly Leu Arg Gly Gln Glu Gly Leu
225                 230                 235                 240
```

```
Cys Glu Ser Asn Leu Lys Asp Leu Leu His His Asn Glu Ser Val Leu
            245                 250                 255

Thr Tyr Glu Asp Lys Asp Gly Asp Trp Met Leu Val Gly Asp Val Pro
        260                 265                 270

Trp Glu Met Phe Ile Asp Ser Cys Lys Arg Leu Arg Ile Met Lys Gly
    275                 280                 285

Ser Glu Ala Ile Gly Leu Ala Pro Arg Ser Met Glu Lys Ser Lys Asn
    290                 295                 300

Gln Ile Arg Gly Val
305
```

<210> SEQ ID NO 168
<211> LENGTH: 930
<212> TYPE: DNA
<213> ORGANISM: Lactuca sativa

<400> SEQUENCE: 168

```
atgtctgtgc cactcgaaca tgattacata gggttatcag aaccttcttc aatggaaaaa    60
gcatccgaat cttccaatca ttcatccgaa agtgacaaga acaatgctct taacctcaaa   120
gccactgaat tgcgactagg attacctggt ttaggtcaag atttggagga aaacgcctgc   180
aaaaatagcc ctgtgaagaa cttcgtgtca ggagctaaaa gagggttttc tgatgttaat   240
tttgatggtt cttgcaaatg gggtttcaac ggcggatatg aaggtgattc tgtgaagggt   300
tcttgttcta ctacttctgt tcttttttggg attaattccg gtaaagagag taaacaaaca   360
cagcaaccaa gtcctcttcc tcttgaagaa aagaagaaag cttctgttac tactgaaaat   420
ggcagaagca gaactccccc ttcttccaag gctcaggtgg taggatggcc accaattcga   480
tcttttagga gaacaccat gacagcgaac ctctccaaga tgacgatgc taatgctgca   540
gaagagaatt tgggatgcct ttatgtgaag gttagcatgg atggtgctcc atatttaagg   600
aaggtcgacc tcaagacttg caaaaattac tcccaactt caaaggctct tgagaaaatg   660
tttgaccgtt ttacccttgg tcaatgtact tctaatggac tacgagggca agaaggtctt   720
tgtgaaagta acctcaagga tcttttacat cacaatgaaa gtgtattgac ttatgaagac   780
aaagatggtg attggatgct tgttggtgat gtcccttggg agatgtttat agactcatgc   840
aagcgattaa ggatcatgaa agggtcagaa gcaattgggc tagctccaag gtcaatggag   900
aagagcaaga accaaataag gggggtatga                                    930
```

<210> SEQ ID NO 169
<211> LENGTH: 287
<212> TYPE: PRT
<213> ORGANISM: Lactuca sativa

<400> SEQUENCE: 169

```
Met Ser Met Ser Leu Lys Glu Leu Asp Tyr Ile Ser Ser Glu Ala
1               5                   10                  15

Glu Met Glu Lys Ile Thr His Lys Gln Asp Leu Asn Leu Lys Ala Thr
            20                  25                  30

Glu Leu Arg Leu Gly Leu Pro Gly Ser Glu Ser Pro Glu Arg Asn Thr
        35                  40                  45

Ile Asn Gly Gly Gly Thr Ala Ala Leu Lys Ile Leu Val Ser Gly Ala
    50                  55                  60

Lys Arg Val Phe Ser Asp Thr Ile Lys Thr Ser Ser Gly Thr Trp Gly
65                  70                  75                  80
```

Phe Ser Asp Asn Gly Gly Ser Glu Val Asp Phe Val Arg Asn Ser Ala
                 85                  90                  95

Phe Phe Ser Ser Ser Ser Ser Pro Arg Gly Glu Asn Lys Asn Pro
            100                 105                 110

Ser Ser Val Lys Asp Ala Val Val Ser Ser Ser Lys Asn Tyr Leu
            115                 120                 125

His Asp Lys His Ser Gln Ile Ser Ala Ser Asn Gly Gln Asp Ser Val
    130                 135                 140

Ala Ala Ser Lys Gly Gln Val Val Gly Trp Pro Ile Arg Ser Phe
145             150                 155                 160

Arg Lys Asn Cys Met Val Val Lys Asn Thr Lys Asn Glu Glu Asp Thr
                165                 170                 175

Gly Ser Gln Cys Val Tyr Val Lys Val Ser Met Asp Gly Ala Pro Tyr
            180                 185                 190

Leu Arg Lys Val Asp Leu Lys Ile Tyr Lys Ser Tyr Leu Asp Leu Ser
        195                 200                 205

Ser Ala Leu Glu Lys Met Phe Cys Ser Phe Thr Leu Gly Leu Arg Glu
    210                 215                 220

Ser Pro Met Asp Leu Leu Asn Gly Pro Glu Tyr Val Leu Thr Tyr Glu
225             230                 235                 240

Asp Lys Asp Gly Asp Leu Met Leu Val Gly Asp Val Pro Trp Asp Met
                245                 250                 255

Phe Thr Gly Ser Cys Lys Arg Met Arg Ile Met Lys Ser Ser Asp Ala
            260                 265                 270

Thr Gly Leu Ala Pro Arg Ala Met Glu Lys Gly Lys Val Arg Asn
        275                 280                 285

<210> SEQ ID NO 170
<211> LENGTH: 864
<212> TYPE: DNA
<213> ORGANISM: Lactuca sativa

<400> SEQUENCE: 170
atgtccatgt ccttaaaaga actcgattac atttcctcat cagaagcaga aatggagaaa      60
ataacccaca agcaagattt gaatttgaaa gccactgagt taagactcgg tctgcctggt     120
tccgagtcgc ctgagagaaa caccatcaat gggggtggta cagctgccct gaagattctg     180
gtgtcaggag ccaaaagggt tttctcagac accattaaaa cttcttctgg aacatggggt     240
ttctctgata tggtggatc tgaggttgat tttgttagaa atagtgcctt tttttcatct     300
tcttcgtctt ctccaagagg tgaaaataag aaccctagtc tgtaaaaga cgctgttgtt     360
tcatcgtcat ctaagaacta tttacatgac aaacactctc aaatttctgc atcaaatggt     420
caagattcag ttgctgcttc aaagggacag gtggttggag gcctccaat cgatcttttt     480
cgaaagaatt gtatggttgt gaagaacacg aaaaatgagg aagacacagg atcacaatgt     540
gtttatgtca agttagtat ggatggagct ccatatttga aaaagtgga tctcaaaatc     600
tacaaaagct acttggatct ttcatcggct ttagaaaaaa tgttttgtag cttcactctt     660
gggttgcgtg aaagcccaat ggatcttctt aatgggcctg aatatgtact aacgtatgaa     720
gacaaagatg gtgatttgat gcttgttggt gatgttccct gggatgtt tactggttct     780
tgcaagagga tgcggatcat gaagagttca gatgcaaccg gtttagcccc tcgagccatg     840
gagaagggta agttcgtaa ttag                                              864

<210> SEQ ID NO 171

<211> LENGTH: 306
<212> TYPE: PRT
<213> ORGANISM: Lactuca sativa

<400> SEQUENCE: 171

Met Ser Glu Pro Leu Glu His Asp Tyr Ile Gly Leu Ser Asp Ser Ser
1               5                   10                  15

Ser Met Glu Arg Ser Ser Glu Ser Ser Asn Phe Ser Thr Glu Thr Glu
            20                  25                  30

Lys Asn Asn Ala Phe Asn Leu Lys Ala Thr Glu Leu Arg Leu Gly Leu
        35                  40                  45

Pro Gly Phe Thr Lys Asp Ile Glu Glu Asp Ser Lys Ile Gly Phe
    50                  55                  60

Val Ser Thr Lys Asn Phe Phe Pro Gly Asp Lys Arg Gly Phe Ser Asp
65                  70                  75                  80

Val Asp Ala Asp Asp Cys Arg Asn Trp Arg Phe Asn Gly Gly Cys Asp
                85                  90                  95

Ala Asp Ser Asn Lys Val Ser Ser Ser Ala Leu Phe Ser Ser Lys
            100                 105                 110

Asn Val Lys Tyr Thr Asp Leu Glu Ile Asn Gln Leu Ala Ile Leu Ser
        115                 120                 125

Ser Val Met Asn Gln Ile Glu Glu Lys Lys Ala Pro Phe Thr Thr
    130                 135                 140

Glu Asn Gly Ser Ala Pro Ile Ala Lys Ala Gln Val Val Gly Trp
145                 150                 155                 160

Pro Pro Ile Arg Ser Phe Arg Lys Asn Thr Met Ala Thr Asn Leu Pro
                165                 170                 175

Lys Asn Asp Gly Val Ala Glu Asn Leu Gly Thr Gly Gly Cys Leu Tyr
            180                 185                 190

Val Lys Val Ser Met Asp Gly Ala Pro Tyr Leu Arg Lys Val Asp Leu
        195                 200                 205

Lys Thr His Cys Asn Tyr Ala Asp Leu Ser Lys Ala Leu Glu Arg Leu
    210                 215                 220

Phe Thr Cys Phe Thr Leu Gly Lys Cys Pro Ser Asn Gly Arg Arg Glu
225                 230                 235                 240

Gly Leu Ser Glu Ser Asn Leu Lys Glu Leu Leu His Gly Ser Glu Cys
                245                 250                 255

Val Leu Thr Tyr Glu Asp Lys Asp Gly Asp Trp Met Leu Val Gly Asp
            260                 265                 270

Val Pro Trp Glu Met Phe Ile Asp Ser Cys Lys Arg Leu Arg Ile Met
        275                 280                 285

Lys Gly Ser Glu Ala Thr Gly Leu Ala Pro Arg Pro Met Ser Ser Gly
    290                 295                 300

Arg Thr
305

<210> SEQ ID NO 172
<211> LENGTH: 921
<212> TYPE: DNA
<213> ORGANISM: Lactuca sativa

<400> SEQUENCE: 172
atgtctgagc cattagaaca cgattacata ggcttatcag actcatcttc catggaaaga      60
agctctgaat cctccaattt ctcaacggaa actgaaaaga acaatgcttt taacctcaaa     120
gccaccgagc tccgacttgg cttgcctggt ttcaccaaag atatcgagga agacgacagc     180

```
aaaattggat tgtatctac taagaacttt tttccaggtg ataagcgagg gttttctgat    240
gttgatgccg acgattgtag aaattggagg tttaatggcg gatgtgacgc tgattcgaac    300
aaggtttcat cttcttctgc tttgttctcc tctaaaaatg taaagtacac cgatttggag    360
ataaatcagc ttgcaatttt atcttctgtc atgaatcaaa tcgaagagaa gaagaaagct    420
ccatttacta ctgaaaatgg aagtgctcct cccattgcta aggcacaagt ggttggatgg    480
ccacctattc gatcatttcg gaagaacacc atggccacca acttaccaaa aaacgacggc    540
gttgctgaga atttaggcac cggaggctgc ctttatgtga aggttagcat ggatggagct    600
ccatacttac gaaaagttga tctcaaaacc cattgcaact atgcagatct ttccaaggct    660
ctcgagagat tgttcacctg cttcactctt ggcaaatgtc cttctaatgg gcgtcgagaa    720
ggtttaagtg aaagtaattt aaaggaactc tacatggct ctgaatgtgt gctaacatac    780
gaagacaaag atggtgattg gatgcttgtt ggtgatgttc cttgggagat gttcatagac    840
tcttgcaaga gattaaggat catgaaaggt tccgaagcaa ctggattagc cccaagaccc    900
atgagcagtg gaaggacata a                                             921

<210> SEQ ID NO 173
<211> LENGTH: 234
<212> TYPE: PRT
<213> ORGANISM: Lactuca sativa

<400> SEQUENCE: 173

Met Met Asn Leu Met Glu Thr Glu Leu Cys Leu Gly Leu Pro Gly Gly
1               5                   10                  15

Gly Gly Ser Gly Cys Glu Ala Glu Thr Leu Lys Val Thr Gly Lys Arg
            20                  25                  30

Gly Tyr Ala Glu Thr Val Asp Leu Met Leu Asn Leu Gln Pro Asn Asp
        35                  40                  45

Gln Ser Ser Ser Thr Asn Leu Asn Asp Met Lys Leu Gln Asn Ser
    50                  55                  60

Lys Asn Asn Lys Asp Leu Ile Lys Pro Pro Ala Lys Ala Gln Val Val
65                  70                  75                  80

Gly Trp Pro Pro Val Arg Asn Tyr Arg Lys Asn Val Met Ala Gln Lys
                85                  90                  95

Ser Asn Asn Glu Glu Thr Glu Lys Val Val Ala Ala Thr Thr Gly Ser
            100                 105                 110

Asn Asn His Ala Ala Phe Val Lys Val Ser Met Asp Gly Ala Pro Tyr
        115                 120                 125

Leu Arg Lys Val Asp Leu Lys Leu Tyr Glu Ser Tyr Gln Gln Leu Ser
130                 135                 140

Asp Ala Leu Ala Lys Met Phe Ser Ser Phe Thr Met Gly Glu Tyr Gly
145                 150                 155                 160

Ser Gln Gly Met Ile Asp Phe Met Asn Glu Ser Lys Leu Met Asp Leu
                165                 170                 175

Leu Asn Ser Ser Glu Tyr Val Pro Ser Tyr Glu Asp Lys Asp Gly Asp
            180                 185                 190

Trp Met Leu Val Gly Asp Val Pro Trp Ala Met Phe Val Asp Ser Cys
        195                 200                 205

Lys Arg Leu Arg Ile Met Lys Gly Ser Asp Ala Ile Gly Leu Ala Pro
    210                 215                 220

Arg Ala Met Glu Lys Cys Lys Asn Arg Cys
225                 230
```

<210> SEQ ID NO 174
<211> LENGTH: 705
<212> TYPE: DNA
<213> ORGANISM: Lactuca sativa

<400> SEQUENCE: 174

```
atgatgaacc tcatggaaac ggagctatgc cttggcctgc cgggtggagg aggcagtggc      60
tgtgaggcgg agaccttaaa ggtcaccgga aaacgtggct acgcagagac tgttgatctt     120
atgctcaatc tacaaccaaa tgaccagtcc tcatcttcaa ctaatctaaa tgatatgaag     180
ttacagaact ctaagaacaa caaagatttg atcaagccac cagccaaggc acaggtggta     240
ggatggccac cagtgcgaaa ctatcgcaaa aacgtgatgg ctcagaagag caataatgag     300
gaaactgaga aggtggtggc agccaccacc ggtagtaaca accatgcggc ctttgtgaag     360
gtttcaatgg atggagcacc gtatcttcgc aaggtggacc ttaaattgta tgagagttat     420
caacaattat cagatgcttt agccaagatg tttagctcct tcaccatggg agagtatgga     480
tcccaaggaa tgattgattt catgaatgag agcaagttga tggatctcct taacagttct     540
gaatatgttc caagctatga agataaagat ggtgattgga tgcttgttgg tgacgtccca     600
tgggcaatgt tgttgattc ttgtaagcga cttcgaatca tgaagggatc agatgcaatt     660
ggacttgccc aagagcaat ggaaaaatgc aagaacaggt gttaa                     705
```

<210> SEQ ID NO 175
<211> LENGTH: 222
<212> TYPE: PRT
<213> ORGANISM: Lactuca sativa

<400> SEQUENCE: 175

```
Met Met Asn Leu Lys Glu Thr Glu Leu Cys Leu Gly Leu Pro Gly Gly
1               5                   10                  15

Gly Gly Gly Gly Ser Gly Gly Asn Glu Ala Glu Met Leu Lys Thr Thr
            20                  25                  30

Gly Lys Arg Gly Phe Ser Glu Thr Ile Asp Leu Lys Leu Asn Leu Gln
        35                  40                  45

Pro Asn Glu Ser Leu Ser Ser Asn Asp Asn Thr Ser Thr Thr Thr His
    50                  55                  60

Val Lys Pro Pro Thr Lys Ala Gln Val Val Gly Trp Pro Pro Val Arg
65                  70                  75                  80

Asn Tyr Arg Lys Asn Ile Met Ala Gln Lys Ser Asn Thr Asp Glu Pro
                85                  90                  95

Glu Lys Val Ala Ala Thr Thr Ala Thr Phe Val Lys Val Ser Met Asp
            100                 105                 110

Gly Ala Pro Tyr Leu Arg Lys Val Asp Leu Lys Met Tyr Thr Ser Tyr
        115                 120                 125

Gln Glu Leu Ala Asp Ala Leu Ala Lys Met Phe Ser Ser Phe Thr Met
    130                 135                 140

Gly Asn Tyr Gly Arg Gln Gly Met Ile Asp Phe Met Asn Glu Ser Lys
145                 150                 155                 160

Leu Met Asp Leu Leu Asn Ser Ser Glu Tyr Val Pro Ser Tyr Glu Asp
                165                 170                 175

Lys Asp Gly Asp Trp Met Leu Val Gly Asp Val Pro Trp Gln Met Phe
            180                 185                 190

Val Ala Ser Cys Lys Arg Leu Arg Ile Met Lys Gly Ser Asp Ala Ile
        195                 200                 205
```

```
Gly Leu Ala Pro Arg Ala Met Glu Lys Cys Lys Ser Arg Cys
        210                 215                 220
```

<210> SEQ ID NO 176
<211> LENGTH: 669
<212> TYPE: DNA
<213> ORGANISM: Lactuca sativa

<400> SEQUENCE: 176

```
atgatgaacc taaaggagac tgagctctgc cttggcttac ctggtggcgg cggtggaggc    60
agtggtggca acgaggcgga gatgttgaaa accactggaa aacgaggctt ctctgaaacc   120
attgatctta agcttaatct tcaaccaaat gagtcattgt catctaacga caacacctcc   180
actacaactc atgtcaaacc accaaccaaa gcacaagtgg taggctggcc accagtgagg   240
aactaccgga aaatataat ggctcaaaag agcaacacag atgaaccgga aaggtggct    300
gccaccactg caactttcgt gaaagtttca atggatggtg caccatatct tcgaaaggtt   360
gacctaaaga tgtacacaag ctaccaagaa ctagccgatg ctttggccaa aatgtttagt   420
tccttcacca tgggaaaatta tgggagacaa ggaatgatag acttcatgaa cgaaagcaag   480
ttgatggatc tgctgaacag ttcagaatat gttcccagtt acgaagataa ggatggtgat   540
tggatgcttg tcggcgatgt tccatggcag atgtttgtgg cttcatgcaa aaggctccga   600
ataatgaaag atcggatgc gattgggctt gcaccaagag caatggagaa atgcaagagc   660
aggtgctaa                                                           669
```

<210> SEQ ID NO 177
<211> LENGTH: 380
<212> TYPE: PRT
<213> ORGANISM: Cucumis sativus

<400> SEQUENCE: 177

```
Met Ser Pro Pro Leu Leu Asn Ser Val Glu Glu Ala Leu Gly Asn Val
1               5                   10                  15

Pro Val Val Ala Ala Ser Pro Ser Met Asp Cys His Ser Gln Asn Gly
            20                  25                  30

Thr Lys Phe Arg Glu Arg Asn Tyr Leu Arg Leu Ser Pro Cys Ser Ser
        35                  40                  45

Val Asp Ser Ser Ala Val Ser Asn Leu Ser Glu Glu Asn Lys Ser Asn
    50                  55                  60

Leu Asn Leu Lys Ala Thr Glu Leu Arg Leu Gly Leu Pro Gly Ser Leu
65                  70                  75                  80

Ser Pro Glu Arg Asp Gln Glu Phe Thr Leu Ile Ser Ser Val Glu Pro
                85                  90                  95

Asp Glu Lys Thr Leu Leu Gln Leu Leu Pro Ser Thr Asp Gly Tyr Ser
            100                 105                 110

Val Ser Leu Gln Lys Asn Ile Val Ser Gly Ser Lys Arg Val Phe Ser
        115                 120                 125

Asp Thr Met Glu Gly Tyr Ser Glu Val Lys Gly Pro Leu Tyr Thr Glu
    130                 135                 140

Arg Asn Trp Met Phe His Ala Ala Ser Ser Asp Pro Glu Ser Pro Tyr
145                 150                 155                 160

Pro Val Ser Gln Gly Lys Phe His Ala Asn Ser Gly Ile Asn Ala Met
                165                 170                 175

Leu Ser Ser Arg Ala Ser Gly Pro His Pro Asn Ile Thr Lys Glu Leu
            180                 185                 190
```

```
Pro Ser Lys Gly Leu Gln Glu Trp Pro Cys Glu Thr Lys Gly Ser Asp
        195                 200                 205

Asn Gly Asn Lys Gly Ala Ser Asn Asp His Asn Asn Ala Pro Ala Ala
    210                 215                 220

Lys Ala Gln Val Val Gly Trp Pro Pro Ile Lys Ser Phe Arg Lys Asn
225                 230                 235                 240

Ser Phe Val Thr Asn Ser Lys Asn Asn Asp Glu Val Asp Gly Lys Pro
            245                 250                 255

Gly Ser Ser Ala Leu Phe Val Lys Val Ser Met Glu Gly Ala Pro Tyr
                260                 265                 270

Leu Arg Lys Val Asp Leu Arg Thr Tyr Ser Thr Tyr Gln Glu Leu Ser
        275                 280                 285

Ser Ala Leu Glu Lys Met Phe Ser Cys Phe Thr Leu Gly Gln Cys Gly
    290                 295                 300

Ser His Gly Ala Ser Gly Arg Asp Lys Leu Ser Glu Ser Lys Leu Arg
305                 310                 315                 320

Asp His Leu His Gly Ser Glu Tyr Val Leu Thr Tyr Glu Asp Arg Asp
            325                 330                 335

Gly Asp Trp Met Leu Val Gly Glu Ile Pro Trp Glu Met Phe Ile Asp
                340                 345                 350

Ser Cys Lys Arg Leu Lys Ile Val Lys Gly Ser Asp Ala Ile Gly Leu
        355                 360                 365

Ala Pro Arg Ala Thr Glu Arg Thr Lys Asn Arg Ile
    370                 375                 380

<210> SEQ ID NO 178
<211> LENGTH: 1143
<212> TYPE: DNA
<213> ORGANISM: Cucumis sativus

<400> SEQUENCE: 178
atgtcacctc cactgctgaa ttctgtagag gaggctcttg caatgtccc tgtagtggct      60 gcttcacctt ctatggactg tcattcccaa aatggtacca aatttagaga gcggaactac     120
ctccggctat caccctgttc ttcagtggac agctctgcgg tgtctaactt gtcagaggag     180
aacaaaagca atctcaattt gaaagctacc gagttgagac ttggtctacc tggatctctg     240
tcacctgaaa gagatcagga atttaccttg ataagctctg tagaacctga tgagaaaact     300
ctacttcaat gcttccttc aacggatggg tatagtgtgt cattacagaa gaatattgtt     360
tctggcagca aaagagtttt ctctgatacc atggaggggg actcagaggt gaaaggcccc     420
ctttacaccg aaagaaattg gatgtttcat gcagccagtt cggatcctga gtctccatat     480
cctgtgagcc aagggaagtt tcatgctaat tcagggataa atgcaatgct atcatcgagg     540
gcttctggtc acatcccaaa tataaccaaa gaattgccat caagggatt gcaggaatgg     600 ccctgtgaga ctaaaggatc tgacaatggc aataaaggtg cttcaaatga ccacaacaat     660
gctcctgctg caaaggcgca ggttgttggt tggccaccta ttaaatcatt ccggaaaaat     720
tcatttgtca ctaactctaa aaacaatgat gaagttgacg gaaagccagg ttcaagtgct     780 cttttttgtga aagtgagcat ggagggagct ccatatttga ggaaggtaga tctgagaact     840
tactctacat atcaggaact ctcttctgcc ctcgagaaga tgtttagctg ttttactcta     900
ggtcaatgtg gatcccatgg agcttccggg agggataaac tgagtgagag caagttaagg     960
gatcatctgc atggatccga atatgtgctt acatatgaag atagggatgg tgactggatg    1020
```

```
cttgttgggg aaatcccctg ggagatgttc attgattcct gcaagaggct gaaaattgtg  1080
aagggctctg acgcaattgg tttagcccca agagcaacgg agagaaccaa aataggatt   1140 tag                                                                 1143
```

<210> SEQ ID NO 179
<211> LENGTH: 355
<212> TYPE: PRT
<213> ORGANISM: Cucumis sativus

<400> SEQUENCE: 179

```
Met Ser Pro Pro Leu Leu Asp Val Gly Glu Val Glu Ser Arg Ser
1               5                   10                  15

Asn Val Thr Leu Leu Ala Ser Ser Asn Ser Met Glu Ser Val Ser Pro
            20                  25                  30

Asn Asn Leu Glu Phe Glu Glu Arg Asn Tyr Met Gly Leu Ser Asp Ser
        35                  40                  45

Ser Ser Glu Asp Ser Cys Met Thr Ala Thr Lys Ser Asp Gly Asn Lys
    50                  55                  60

Pro Ser Leu Asn Leu Lys Ala Thr Glu Leu Arg Leu Gly Leu Pro Gly
65                  70                  75                  80

Ser Glu Ser Pro Glu Arg Asp Pro Asp Asn Cys Leu Arg Ser Ser Ser
                85                  90                  95

Gln Leu Asp Glu Lys Pro Leu Phe Pro Leu His Pro Ser Ser Asp Gly
            100                 105                 110

Leu Tyr Ser Ser Pro Gln Lys Thr Val Val Ser Gly Asn Lys Arg Gly
        115                 120                 125

Phe Ser Asp Ala Met Asn Glu Phe Ser Glu Glu Lys Tyr His Ala Asn
    130                 135                 140

Ile Gly Leu Lys Ala Gly Ser Leu Leu Glu Asn Leu Gly Ser Gln Met
145                 150                 155                 160

Gly Lys Val Lys Glu Pro Thr Thr Gln Lys Ala Val Gln Glu Arg Pro
                165                 170                 175

Gln Glu Asn Ser Glu Ser Arg Pro Ser His Asn Glu Thr Ala Asn Asn
            180                 185                 190

Asn Thr Ser Thr Pro Val Ser Lys Ala Gln Val Val Gly Trp Pro Pro
        195                 200                 205

Ile Arg Ser Phe Arg Lys Asn Thr Leu Ala Thr Thr Ser Lys Asn Asn
    210                 215                 220

Asp Glu Val Asp Gly Lys Ala Met Ala Gly Ala Leu Phe Ile Lys Val
225                 230                 235                 240

Ser Met Asp Gly Ala Pro Tyr Leu Arg Lys Val Asp Leu Arg Asn Tyr
                245                 250                 255

Ser Ala Tyr Gln Glu Leu Ser Ser Ala Leu Glu Lys Met Phe Ser Cys
            260                 265                 270

Phe Thr Ile Gly Gln Tyr Gly Ala His Gly Ala Leu Gly Met Glu Lys
        275                 280                 285

Met Ser Glu Ser Lys Leu Lys Asp Leu Leu His Gly Ser Glu Tyr Val
    290                 295                 300

Leu Thr Tyr Glu Asp Lys Asp Gly Asp Trp Met Leu Val Gly Asp Val
305                 310                 315                 320

Pro Trp Glu Met Phe Ile Asp Ser Cys Lys Arg Leu Arg Ile Met Lys
                325                 330                 335

Ser Ser Asp Ala Ile Gly Leu Ala Pro Arg Ala Val Glu Lys Cys Arg
            340                 345                 350
```

-continued

Asn Arg Ser
        355

<210> SEQ ID NO 180
<211> LENGTH: 1068
<212> TYPE: DNA
<213> ORGANISM: Cucumis sativus

<400> SEQUENCE: 180

| atgtctccac cattacttga tgttggggag gtggaggaaa gtcgcagcaa tgtcactctg | 60 |
| ttggcttcct caaactcgat ggagagtgtc agtccgaaca atttggaatt gaagagcgt | 120 |
| aattacatgg gattatctga ttcttcttca gaggacagct gtatgactgc cacaaaatct | 180 |
| gatgaaaca aaccctcgct gaatcttaag gctacagaac tgaggcttgg tctccctgga | 240 |
| tctgaatccc ccgagagaga tccagataat tgcctgcgta gctcttctca acttgatgaa | 300 |
| aaaccactat ttcctttgca cccatcaagt gatggtctct actcttcccc acaaaagact | 360 |
| gtcgtctcag gcaacaaaag ggggttttct gatgctatga cgaattctc agaggaaaaa | 420 |
| tatcacgcta acataggttt gaaagctggt tctttgctag aaccttgg aagtcaaatg | 480 |
| gggaaagtga aagagccaac tacacaaaag gctgtacaag agaggcctca agaaaatagt | 540 |
| gaatctagac catctcacaa tgaaactgca ataacaaca ccagcacacc tgtttccaag | 600 |
| gcacaggttg tgggttggcc gcccataaga tctttcagga agaacacatt ggctacaact | 660 |
| tcaaagaaca atgatgaagt tgatggaaag gcaatggctg gggcactctt tatcaaagtc | 720 |
| agcatggatg gtgctcctta tcttaggaag gtagatctga ggaattactc tgcctatcag | 780 |
| gagctgtctt ctgcccttga aagatgttc agctgtttca ctataggtca atatggagct | 840 |
| catggagctc tgggcatgga gaaaatgagt gagagcaagc tgaaagatct tcttcatggc | 900 |
| tccgaatatg tattaacata tgaggataaa gatggtgact ggatgctcgt tggtgatgtc | 960 |
| ccttgggaga tgttcatcga ctcttgtaag aggctgagga ttatgaagag ctccgatgca | 1020 |
| attggactgg ctcctagggc ggtggagaag tgccgaaaca ggagctag | 1068 |

<210> SEQ ID NO 181
<211> LENGTH: 302
<212> TYPE: PRT
<213> ORGANISM: Cucumis sativus

<400> SEQUENCE: 181

Met Ser Ile Pro Leu Glu His Asp Tyr Ile Gly Leu Thr Glu Ser Val
1               5                   10                  15

Pro Ser Leu Glu Asn Ser Glu Lys Ser Ser Asp Lys Arg Asn Ser Ala
            20                  25                  30

Gly Leu Asn Leu Lys Ala Thr Glu Leu Arg Leu Gly Leu Pro Gly Ser
        35                  40                  45

Glu Ser Pro Gly Arg Asp Asp Gly Phe Glu Asp Lys Asn Gly Phe Leu
    50                  55                  60

His Lys Ser Ser Val Ser Gly Ala Lys Arg Gly Phe Ser Ile Ala Ile
65                  70                  75                  80

Asp Arg Ala Ser Ala Lys Trp Val Leu Pro Ser Ala Gly Ser Glu
                85                  90                  95

Ala Asp Ser Ser Thr Asn Gly Gly Leu Phe Ser Pro Arg Gly Val Asn
            100                 105                 110

Glu Asn Lys Thr Gln Pro Pro Ala Ser Ala Val Ser Gly Val Lys Asp
        115                 120                 125

```
Gly Ile Ser Pro Ser Ala Lys Pro Leu His Glu Glu Lys Pro Gln Leu
        130                 135                 140

Ser Pro Pro Ala Ala Lys Ala Gln Val Val Gly Trp Pro Pro Ile Arg
145                 150                 155                 160

Ser Phe Arg Lys Asn Ser Met Ala Thr Gln Pro Pro Lys Asn Thr Asp
                165                 170                 175

Asp Ala Asp Gly Lys Leu Gly Ser Gly Cys Leu Tyr Val Lys Val Ser
            180                 185                 190

Met Asp Gly Ala Pro Tyr Leu Arg Lys Val Asp Leu Lys Thr Tyr Val
        195                 200                 205

Ser Tyr Val Asp Leu Ser Ser Ala Leu Glu Lys Met Phe Ser Ser Phe
    210                 215                 220

Thr Ile Gly His Tyr Gly Ser Asn Gly Val Pro Asn Arg Asp Ala Leu
225                 230                 235                 240

Asn Glu Ser Arg Leu Met Asp Leu Leu His Gly Ser Glu Tyr Val Leu
                245                 250                 255

Thr Tyr Glu Asp Lys Asp Gly Asp Trp Met Leu Val Gly Asp Val Pro
            260                 265                 270

Trp Glu Met Phe Thr Glu Ser Cys Thr Arg Met Arg Ile Met Lys Ser
        275                 280                 285

Ser Glu Ala Ile Gly Leu Gly Met Leu Cys Tyr Gly Leu Gln
    290                 295                 300

<210> SEQ ID NO 182
<211> LENGTH: 909
<212> TYPE: DNA
<213> ORGANISM: Cucumis sativus

<400> SEQUENCE: 182
atgtctatac cgttagaaca tgattacata ggcttaacag agtctgttcc ttctctggaa      60
aactctgaaa gtcttctga taaacgcaac agtgctggtt tgaaccttaa ggctactgaa     120
ctgaggttgg gtctgccggg atcggagtca ccgggaaggg atgatgggtt tgaggataag     180
aatgggttcc ttcacaagag ctctgttttct ggggctaaga ggggtttctc catagccatt     240
gatagagctt ctgccaagtg ggttctacca gcttctgccg gatctgaggc agactcctcc     300
acaaatgggg gtttgttttc tcctagaggt gttaatgaga ataagactca accacctgct     360
tccgctgtct ccggtgtcaa agacggtatt tctccgtcag ccaagccact tcatgaggaa     420
aagcctcagc tttctccccc tgcagctaag gcacaagttg taggatggcc accattcgt     480 tctttccgta agaattcaat ggcaacacag ccccctaaaa atacagatga tgcggatggt     540
aagttgggat caggctgcct ttatgtcaag gtaagtatgg atggcgcacc gtacctcagg     600
aaggttgatc tgaaaaccta tgtaagctat gtggacctct catcagccct ggagaaaatg     660
ttcagcagct tcacaattgg tcactatggc tctaatggag ttccaaaccg ggatgcatta     720
aacgagagta ggttgatgga tctgctccat ggctctgaat atgtactcac ctacgaagat     780
aaggatggtg actggatgct cgttggtgat gttccatggg agatgttcac tgaatcttgc     840
acaaggatga ggatcatgaa gagttcagag gctattgggt taggtatgct atgctatgga     900
cttcaataa                                                            909

<210> SEQ ID NO 183
<211> LENGTH: 349
<212> TYPE: PRT
<213> ORGANISM: Cucumis sativus
```

<400> SEQUENCE: 183

| | | | | | | | | | | | | | | | |
|---|---|---|---|---|---|---|---|---|---|---|---|---|---|---|---|
| Met | Ser | Lys | Pro | Leu | Glu | His | Asn | Tyr | Ile | Gly | Leu | Thr | Glu | Ala | Ser |
| 1 | | | | 5 | | | | | 10 | | | | | 15 | |
| Ser | Met | Glu | Arg | Ser | Pro | Glu | Lys | Asn | Pro | Ser | Ser | Ser | Ser | Ser | Ser |
| | | | 20 | | | | | 25 | | | | | 30 | | |
| Asp | Ser | Ser | Asp | Ser | Cys | Ser | His | Val | Thr | Asn | Glu | Glu | Lys | Lys | Cys |
| | | 35 | | | | | 40 | | | | | 45 | | | |
| Ala | Thr | Val | Ser | Phe | Lys | Asp | Thr | Glu | Leu | Arg | Leu | Gly | Leu | Pro | Gly |
| | 50 | | | | | 55 | | | | | 60 | | | | |
| Ser | Gln | Ser | Pro | Glu | Arg | Lys | Ser | Gly | Ser | Glu | Ile | Ser | Phe | Phe | Gly |
| 65 | | | | | 70 | | | | | 75 | | | | | 80 |
| Asn | Asp | Phe | Glu | Asp | Lys | Gln | Ser | Asn | Gly | Phe | Ser | Ser | Pro | Cys | Pro |
| | | | | 85 | | | | | 90 | | | | | 95 | |
| Leu | Asn | Leu | Lys | Asn | Leu | Val | Ser | Gly | Ser | Lys | Arg | Gly | Phe | Ser | Asp |
| | | | 100 | | | | | 105 | | | | | 110 | | |
| Ala | Ile | Asp | Gly | Ser | Ser | Ala | Lys | Trp | Val | Phe | Ser | Gly | Ser | Asn | Gly |
| | | 115 | | | | | 120 | | | | | 125 | | | |
| Ser | Glu | Val | Lys | Leu | Gly | Glu | Gly | Ala | Val | Leu | Phe | Ser | Pro | Lys | Ser |
| | 130 | | | | | 135 | | | | | 140 | | | | |
| Gly | Lys | Pro | Thr | Ile | Gly | Gly | Leu | Gly | Ser | Asn | Val | Asn | Thr | Pro | Gln |
| 145 | | | | | 150 | | | | | 155 | | | | | 160 |
| Ser | Cys | Val | Thr | Leu | Lys | Ala | Val | Lys | Glu | Val | Leu | Pro | Val | Pro | Gln |
| | | | | 165 | | | | | 170 | | | | | 175 | |
| Ser | Ser | Asn | Ser | Val | Gln | Glu | Lys | Lys | Pro | Gln | Val | Ser | Glu | Asn | Gly |
| | | | 180 | | | | | 185 | | | | | 190 | | |
| Gly | Ala | Pro | Leu | Ala | Lys | Ala | Gln | Val | Val | Gly | Trp | Pro | Pro | Ile | Arg |
| | | 195 | | | | | 200 | | | | | 205 | | | |
| Ser | Phe | Arg | Lys | Asn | Thr | Met | Thr | Thr | Thr | Asn | Ser | Thr | Lys | Asn | Thr |
| | 210 | | | | | 215 | | | | | 220 | | | | |
| Asp | Glu | Gly | Glu | Gly | Lys | Ser | Gly | Ser | Ser | Gly | Cys | Leu | Tyr | Val | Lys |
| 225 | | | | | 230 | | | | | 235 | | | | | 240 |
| Val | Ser | Met | Glu | Gly | Ala | Pro | Tyr | Leu | Arg | Lys | Val | Asp | Leu | Lys | Leu |
| | | | | 245 | | | | | 250 | | | | | 255 | |
| Tyr | Ser | Asn | Tyr | Ser | Glu | Leu | Ser | Leu | Ala | Leu | Glu | Lys | Met | Phe | Ser |
| | | | 260 | | | | | 265 | | | | | 270 | | |
| Cys | Phe | Thr | Ile | Gly | Gln | Cys | Gly | Thr | Glu | Gly | Leu | Pro | Thr | Lys | Glu |
| | | 275 | | | | | 280 | | | | | 285 | | | |
| Arg | Leu | Ser | Glu | Ser | Asn | Ser | Lys | Asp | Phe | Leu | His | Gly | Ser | Glu | Tyr |
| | 290 | | | | | 295 | | | | | 300 | | | | |
| Val | Leu | Thr | Cys | Glu | Asp | Lys | Asp | Gly | Asp | Trp | Met | Leu | Val | Gly | Asp |
| 305 | | | | | 310 | | | | | 315 | | | | | 320 |
| Val | Pro | Trp | Glu | Met | Phe | Thr | Glu | Ser | Cys | Arg | Arg | Leu | Arg | Ile | Met |
| | | | | 325 | | | | | 330 | | | | | 335 | |
| Lys | Gly | Ser | Glu | Ala | Ile | Gly | Leu | Asp | Lys | Glu | Phe | His | | | |
| | | | 340 | | | | | 345 | | | | | | | |

<210> SEQ ID NO 184
<211> LENGTH: 1050
<212> TYPE: DNA
<213> ORGANISM: Cucumis sativus

<400> SEQUENCE: 184
atgtctaaac ccttggaaca taattacata ggattaacag aggcttcttc gatggaaaga    60

```
agccctgaga agaatccttc atcgtcgtct tcctctgatt cttccgactc ttgttctcat    120
gttactaacg aggagaagaa atgtgccact gtgagtttca aggatactga attgaggctc    180
ggtttacctg gttctcagtc gcctgagagg aaatcgggaa gtgagatttc cttctttggg    240
aatgattttg aggataaaca gagtaatggg ttctcttctc cttgtccttt gaatttgaag    300
aatcttgttt ctgggtctaa gaggggtttc tcagacgcca ttgatgggtc ttctgcaaaa    360
tgggttttct ctgggagtaa tggatctgag gttaagttgg gtgaaggggc tgtgctgttc    420
tcgcccaaaa gtgggaagcc gacgattggt ggcttaggga gcaatgttaa tacaccacag    480
tcttgtgtta ctttgaaagc tgtgaaggaa gtgcttcctg ttcctcaatc ttcaaattct    540
gttcaggaga gaagccgca ggtttcagaa atggcggtg ctcctttggc taaggcacag     600
gttgtgggat ggccacccat tcgatccttc aggaagaaca ccatgaccac taccaattcg    660
acaaagaaca ctgatgaagg cgagggcaaa tcaggatcgt ctggttgcct ctatgtaaaa    720
gttagcatgg aagggctcc ttatctaagg aaggtagatc tcaaactgta cagcaactat     780
tctgaactat cgttggcttt ggagaaaatg tttagctgct tcactattgg gcagtgtggt    840
actgaaggac ttccaactaa agagcgtctg agtgaaagta attcgaagga tttccttcat    900
ggatctgagt atgtgctgac atgtgaagat aaagatggag attggatgct tgttggtgat    960
gtcccttggg agatgttcac ggagtcatgt agaagactcc gaatcatgaa aggttctgaa   1020
gcaattgggc tagataaaga atttcactga                                    1050
```

<210> SEQ ID NO 185
<211> LENGTH: 237
<212> TYPE: PRT
<213> ORGANISM: Cucumis sativus

<400> SEQUENCE: 185

```
Met Glu Val Ser Arg Lys Met Val Asn Met Leu Glu Thr Asp Leu Cys
1               5                   10                  15

Leu Gly Leu Pro Gly Gly Gly Ala Glu Pro Glu Thr Pro Lys Ala Asn
            20                  25                  30

Gly Lys Arg Gly Phe Ser Glu Thr Val Asp Leu Lys Leu Asn Ile Gln
        35                  40                  45

Ser Lys Pro Gly Val Thr Val Asp Leu Thr Pro Gln Asn Asn Asp Thr
    50                  55                  60

Ser Thr Asp Glu Glu Ser Leu Ile Ala Ser Lys Asp Pro Ala Lys Pro
65                  70                  75                  80

Pro Ala Lys Ala Gln Val Val Gly Trp Pro Pro Val Arg Ser Tyr Arg
                85                  90                  95

Lys Asn Ala Met Ser Gln Lys Ser Ser Glu Ala Gly Glu Lys Gly Gly
            100                 105                 110

Ser Ser Gly Gly Ser Ala Met Phe Val Lys Val Cys Met Asp Gly Ala
        115                 120                 125

Pro Tyr Leu Arg Lys Val Asp Leu Lys Met Tyr Lys Ser Tyr Gln Glu
    130                 135                 140

Leu Ser Asn Ala Leu Ala Lys Met Phe Ser Ser Phe Thr Met Ala Gly
145                 150                 155                 160

Asp Tyr Gly Ala Gln Gly Met Ile Asp Phe Met Asn Glu Ser Lys Leu
                165                 170                 175

Met Asp Leu Leu Asn Ser Ser Glu Tyr Val Pro Thr Tyr Glu Asp Lys
            180                 185                 190

Asp Gly Asp Trp Met Leu Val Gly Asp Val Pro Trp Glu Met Phe Val
```

```
                195                 200                 205
Asp Ser Cys Lys Arg Leu Arg Ile Met Lys Gly Ser Glu Ala Ile Gly
    210                 215                 220

Leu Ala Pro Arg Ala Met Glu Lys Cys Lys Ser Arg Ser
225                 230                 235
```

<210> SEQ ID NO 186
<211> LENGTH: 714
<212> TYPE: DNA
<213> ORGANISM: Cucumis sativus

<400> SEQUENCE: 186

```
atggaggtta gccgcaaaat ggtcaacatg ctggaaactg atctctgcct cggccttccc     60
ggcggtggcg ctgagccgga gactcccaaa gctaatggaa aagagggtt ctctgaaact     120
gttgatttga aactcaatat ccaatctaag ccaggagtta ccgtcgatct cactccacag    180
aataatgata cttcaactga tgaggagagt ctcatagcct ctaaagatcc tgcaaagcca    240
cctgccaagg cacaagttgt gggatggcca cccgtgcgat cctaccggaa gaatgcgatg    300
tcccaaaaga gctctgaagc cggagaaaaa ggcggaagca gcggcggttc agctatgttt    360
gtcaaagttt gtatggatgg cgcgccttat ctgcgaaagg tcgacctgaa gatgtacaaa    420
agctaccaag agctctcgaa cgccttggcc aagatgttca gctccttcac catggccggt    480
gactatgggg cccaaggaat gatagacttc atgaatgaaa gcaagttgat ggatcttctg    540
aacagctctg agtatgtgcc aacttatgaa gataaggatg tgattggat gctggttgga    600
gatgtacctt gggagatgtt tgttgattca tgcaagcgct taaggataat gaaaggatca    660
gaagctattg gacttgcccc aagagcaatg gaaaaatgca aagcagaag ctaa           714
```

<210> SEQ ID NO 187
<211> LENGTH: 230
<212> TYPE: PRT
<213> ORGANISM: Cucumis sativus

<400> SEQUENCE: 187

```
Met Glu Lys Lys Met Gly Phe Glu Glu Thr Glu Leu Arg Leu Gly
1               5                   10                  15

Leu Pro Gly Asn Asn Asn Ile Gly Ser Ser Glu Leu Gly Glu Val Ala
                20                  25                  30

Ala Arg Lys Arg Gly Phe Ala Glu Thr Val Ser Ser Glu Thr Ile Ser
            35                  40                  45

Lys Val Asp Leu Lys Leu Asn Leu Ser Ser Lys Glu Thr Val Gly Val
    50                  55                  60

Gly Asp Asp Asp Leu Val Ala Asp Ser Asn Pro Ser Asn Lys Asp Lys
65                  70                  75                  80

Ala Val Leu Thr Ala Asp Pro Ala Lys Pro Ala Lys Ala Gln Val
                85                  90                  95

Val Gly Trp Pro Pro Val Arg Ser Phe Arg Lys Asn Asn Met Leu Ala
            100                 105                 110

Phe Val Lys Val Ser Met Asp Gly Ala Pro Tyr Leu Arg Lys Val Asp
        115                 120                 125

Leu Lys Met Tyr Lys Ser Tyr Lys Gln Leu Ser Asp Ala Leu Ala Ala
    130                 135                 140

Met Phe Gly Ser Phe Thr Thr Ile Gly Asn Cys Gly Ser Gln Glu Met
145                 150                 155                 160

Lys Asp Phe Met Asn Glu Ser Lys Leu Met Asp Leu Leu Ser Gly Ser
```

```
                    165                 170                 175
Asp Tyr Val Pro Thr Tyr Glu Asp Lys Asp Gly Asp Trp Met Leu Val
                180                 185                 190

Gly Asp Val Pro Trp Glu Met Phe Val Glu Ser Cys Lys Arg Leu Arg
            195                 200                 205

Ile Met Lys Gly Lys Glu Ala Ile Gly Leu Ala Pro Arg Ala Met Glu
    210                 215                 220

Lys Cys Lys Asn Arg Ser
225                 230

<210> SEQ ID NO 188
<211> LENGTH: 693
<212> TYPE: DNA
<213> ORGANISM: Cucumis sativus

<400> SEQUENCE: 188
atggagaaga agaagatggg atttgaagag acggagctcc ggcttggtct tcccggaaac     60
aacaacatcg aagcagtga attgggtgag gttgctgctc ggaaacgagg ttttgctgaa    120
actgtcagca gtgagaccat ttccaaggtt gatctcaagc tcaatctttc ttccaaagaa    180
accgttggtg tcggtgacga tgaccttgtc gccgattcca accctagcaa caaagacaaa    240
gctgtcctca ccgctgatcc agccaaaccc ccggctaagg cacaagttgt gggatggcca    300
cccgttcgtt ccttccgaaa gaacaacatg ttggcgtttg tgaaagtaag catggatggc    360
gcaccatatc tgcgtaaggt ggacttgaag atgtacaaga gctacaaaca actctctgat    420
gctcttgctg ccatgtttgg ttccttcacc accattggta actgtggatc tcaagaaatg    480
aaggatttca tgaatgaaag taagttgatg gatctttaa gtggctctga ttatgttcca    540
acttatgaag acaagatgg tgattggatg cttgttggag atgttccgtg ggagatgttt    600
gttgaatctt gcaaacgtct acgtatcatg aaaggaaaag aggccattgg acttgcacca    660
agggctatgg agaaatgcaa gaatagaagc tga                                693

<210> SEQ ID NO 189
<211> LENGTH: 197
<212> TYPE: PRT
<213> ORGANISM: Cucumis sativus

<400> SEQUENCE: 189

Met Ala Phe Glu Lys Asp Leu Asn Leu Glu Ala Thr Glu Leu Arg Leu
1               5                   10                  15

Gly Leu Pro Gly Thr Ser Pro Asp Asp Gln Ser Asn Ser Pro Ile Asn
            20                  25                  30

Arg Thr Asn Ser Asn Lys Arg Ala Leu Pro Ser Asp Asp Gln Asn Ser
        35                  40                  45

Ser Glu Ser Arg Arg Glu Ile Asn Ser Asp Thr Ser Lys Cys Ser Gln
    50                  55                  60

Glu Asn Thr Pro Pro Thr Lys Ala Gln Val Val Gly Trp Pro Pro Val
65                  70                  75                  80

Arg Ser Phe Arg Lys Asn Ser Leu Gln Ala Lys Lys Glu Glu Thr
                85                  90                  95

Ala Ala Gly Met Phe Ile Lys Val Ser Met Asp Gly Ala Pro Phe Leu
            100                 105                 110

Arg Lys Val Asp Leu Lys Ile Tyr Gln Gly Tyr Pro Asp Leu Leu Gln
        115                 120                 125

Ala Leu Glu Asn Met Phe Lys Phe Ser Leu Gly Lys Phe Cys Glu Arg
```

130                 135                 140
Glu Gly Tyr Asn Gly Ser Glu Phe Val Pro Thr Tyr Glu Asp Lys Asp
145                 150                 155                 160

Gly Asp Trp Met Leu Val Gly Asp Val Pro Trp Glu Met Phe Met Ser
                165                 170                 175

Ser Cys Lys Lys Leu Arg Ile Met Lys Gly Ser Glu Ala Lys Gly Leu
            180                 185                 190

Gly Cys Gly Ser Val
        195

<210> SEQ ID NO 190
<211> LENGTH: 594
<212> TYPE: DNA
<213> ORGANISM: Cucumis sativus

<400> SEQUENCE: 190
atggcctttg agaaagatct caacttggaa gccaccgagc tccgattggg tctcccggga      60
acttcacccg acgatcaatc taattctccc atcaaccgaa ccaactccaa caaaagagct     120
ttgccctccg acgaccaaaa ctcctccgaa tctcgccgag aaattaactc tgataccctcc   180 aaatgcagcc aagaaaatac ccctcctacc aaggcacaag ttgtggggtg gccaccggtg     240
agatcatttc gaaagaattc tttacaagca agaaaaaag aagagacggc ggccggaatg      300
ttcataaaag tgagcatgga tggagctcca tttcttagga agttgatct taagatctat      360 caaggatatc ctgaccttct tcaagctttg gagaacatgt tcaaattttc tcttggcaag     420
ttttgtgaga gagaaggata taatgggtcg gaatttgttc aacgtatga agataaagat      480 ggtgactgga tgctcgtcgg cgatgttcca tgggaaatgt tcatgagctc atgcaagaag     540
ctaaggatca tgaaaggatc agaagcaaaa ggtttaggct gtggatcagt gtga           594

<210> SEQ ID NO 191
<211> LENGTH: 186
<212> TYPE: PRT
<213> ORGANISM: Cucumis sativus

<400> SEQUENCE: 191

Met Glu Ser Asn Val Thr Phe His Asn Asp Leu Asn Leu Glu Ala Thr
1               5                   10                  15

Glu Leu Arg Leu Gly Leu Pro Gly Ile Val Ser Glu Arg Asp Asp Ser
            20                  25                  30

Ser Ala Thr Ser Ser Ala Val Lys Pro Asn Asn Lys Arg Asn Phe Gln
        35                  40                  45

Asn Asp Ser Ala Pro Pro Lys Ala Gln Val Val Gly Trp Pro Pro
    50                  55                  60

Ile Arg Ser Phe Arg Lys Asn Thr Leu Gln Val Lys Lys Thr Glu Ala
65                  70                  75                  80

Thr Thr Thr Ala Val Asp Gly Gly Ile Tyr Val Lys Val Ser Met
                85                  90                  95

Asp Gly Ala Pro Tyr Leu Arg Lys Ile Asp Leu Ser Val Tyr Lys Gly
            100                 105                 110

Tyr Pro Glu Leu Leu Lys Ala Leu Glu Asp Met Phe Lys Phe Thr Ile
        115                 120                 125

Gly Gln Tyr Ser Glu Arg Glu Gly Tyr Lys Gly Ser Asp Phe Ala Pro
    130                 135                 140

Thr Tyr Glu Asp Lys Asp Gly Asp Trp Met Leu Val Gly Asp Val Pro
145                 150                 155                 160

Trp Gln Met Phe Ile Ser Ser Cys Lys Arg Met Arg Ile Met Lys Gly
                165                 170                 175

Ser Glu Val Gly Gly Leu Ser Cys Gly Val
            180                 185

<210> SEQ ID NO 192
<211> LENGTH: 561
<212> TYPE: DNA
<213> ORGANISM: Cucumis sativus

<400> SEQUENCE: 192

| | | | | | |
|---|---|---|---|---|---|
| atggaatcca | atgttacgtt | tcacaacgat | ctcaatcttg | aagccaccga | gcttcgtctt | 60 |
| ggacttcccg | gaatcgtttc | tgaaagagat | gattcgtcgg | cgacttcatc | tgcagtcaaa | 120 |
| cctaataaca | agaggaattt | ccagaatgat | tctgcacctc | ccccaaaggc | tcaggttgtg | 180 |
| gggtggccac | cgattagatc | ttttaggaaa | aatacacttc | aggtgaagaa | aacagaggcc | 240 |
| acgacgacgg | cggtggacgg | cggagggatt | tatgtgaaag | tcagtatgga | tggtgctcct | 300 |
| tatttgagga | agatcgatct | aagtgtttat | aaaggctatc | ctgagcttct | taaggctttg | 360 |
| gaggatatgt | tcaagttcac | tatcggtcaa | tactctgaga | gagaaggtta | taaaggatct | 420 |
| gattttgccc | aacatatga | agataaagat | ggtgattgga | tgcttgtggg | tgatgttcca | 480 |
| tggcaaatgt | ttatttcatc | ttgtaagagg | atgagaatca | tgaaaggatc | tgaagttgga | 540 |
| ggattaagct | gtggcgtatg | a | | | | 561 |

<210> SEQ ID NO 193
<211> LENGTH: 204
<212> TYPE: PRT
<213> ORGANISM: Cucumis sativus

<400> SEQUENCE: 193

Met Ala Phe Gln Asn Gly Leu Asn Leu Asp Ala Thr Glu Leu Arg Leu
1               5                   10                  15

Gly Pro Pro Gly Leu Asp Glu Asn Lys Leu Gln Asp Gln Gln Leu Pro
            20                  25                  30

Gln Ser Ile Arg Ile Asn Lys Arg Pro Leu Leu Pro Glu Ser Asn
        35                  40                  45

Gln Ser Ser Ser Gly Ser Asn Ile Ser Val Ser Ser Asp Ala Thr Leu
    50                  55                  60

Asp Thr Pro Pro Pro Ser Lys Ala Gln Ile Val Gly Trp Pro Pro Val
65                  70                  75                  80

Gln Ser Phe Arg Arg Asn Ser Leu Gln Gly Lys Lys Thr Thr Thr Val
                85                  90                  95

Ala Ala Thr Thr Ala Ala Gln Glu Ser Ser Gly Asn Phe Val Lys Val
            100                 105                 110

Ser Met Asp Gly Ala Pro Tyr Leu Arg Lys Ile Asp Leu Ser Leu Tyr
        115                 120                 125

Lys Gly Tyr Pro Val Leu Leu Gln Thr Leu Glu Asp Met Phe Lys Phe
    130                 135                 140

Thr Val Gly Glu Tyr Ser Glu Arg Glu Gly Tyr Lys Gly Ser Glu Tyr
145                 150                 155                 160

Val Pro Thr Tyr Glu Asp Lys Asp Gly Asp Trp Met Leu Val Gly Asp
                165                 170                 175

Val Pro Trp Glu Met Phe Thr Ser Ser Cys Lys Arg Leu Arg Ile Met
            180                 185                 190

```
Lys Gly Ser Glu Ala Lys Gly Leu Gly Cys Val Ala
        195                 200
```

<210> SEQ ID NO 194
<211> LENGTH: 615
<212> TYPE: DNA
<213> ORGANISM: Cucumis sativus

<400> SEQUENCE: 194

| | |
|---|---|
| atggcatttc aaaatgggtt aaacctcgac gcgacggagc tccgccttgg accaccgggc | 60 |
| ctcgatgaaa ataaattaca agatcaacaa ctacctcaat ccatcagaat caacaaaaga | 120 |
| ccattactat taccagaatc caaccaaagt tcttctggat caaatatatc cgtttcttct | 180 |
| gatgccacac ttgacactcc acctccctcc aaggctcaga ttgtgggatg ccaccggtt | 240 |
| caatcattta agaagaaatag ccttcaaggg aagaagacga cgacggtggc cgcgacaacg | 300 |
| gcggcacagg agagtagtgg aaattttgtg aaagtaagca tggatggagc tccttatttg | 360 |
| agaaaaattg atcttagttt atacaaagga taccctgtac tcctccaaac tttagaagac | 420 |
| atgttcaaat tcaccgtagg tgaatactct gagagagaag gctataaagg atctgaatat | 480 |
| gtaccaactt atgaagataa agatggtgat tggatgttgg ttggagatgt cccatgggaa | 540 |
| atgtttacgt catcgtgcaa acgattgaga atcatgaaag gatcagaagc aaagggatta | 600 |
| ggatgtgttg cataa | 615 |

<210> SEQ ID NO 195
<211> LENGTH: 107
<212> TYPE: PRT
<213> ORGANISM: Cucumis sativus

<400> SEQUENCE: 195

```
Met Asp Gly Ala Pro Tyr Leu Arg Lys Val Asp Leu Lys Leu Tyr Ala
1               5                   10                  15
Ser Tyr Lys Glu Leu Ser His Ala Leu Ala Gln Met Phe Ser Ser Phe
            20                  25                  30
Thr Ile Gly Lys Cys Glu Ser Glu Gly Met Lys Asp Phe Met Asn Glu
        35                  40                  45
Ser Lys Ser Val Asp Leu Leu Asn Gly Ser Glu Tyr Val Pro Thr Tyr
    50                  55                  60
Glu Asp Lys Asp Gly Asp Trp Met Leu Val Gly Asp Val Pro Trp Glu
65                  70                  75                  80
Met Phe Val Asp Ser Cys Lys Arg Leu Arg Ile Met Lys Glu Ser Asp
                85                  90                  95
Ala Ile Gly Leu Gly Lys Ser Ser Ser Ser Thr
            100                 105
```

<210> SEQ ID NO 196
<211> LENGTH: 321
<212> TYPE: DNA
<213> ORGANISM: Cucumis sativus

<400> SEQUENCE: 196

| | |
|---|---|
| atggacggtg ctccttattt acggaaggtg gacttgaagt tatacgccag ctataaggaa | 60 |
| ctctctcatg ctcttgctca aatgtttagc tccttcacca ttggaaagtg tgaatcagaa | 120 |
| gggatgaagg atttcatgaa tgaaagcaaa tcagtagacc ttttgaatgg gtcagaatat | 180 |
| gtacctactt atgaagacaa agatggagat tggatgctcg ttggggatgt cccatgggag | 240 |
| atgtttgttg attcatgcaa acgtttgagg atcatgaaag agtctgatgc cattggatta | 300 |

```
ggtaagtcat catcttctac t                                             321
```

<210> SEQ ID NO 197
<211> LENGTH: 253
<212> TYPE: PRT
<213> ORGANISM: Medicago truncatula

<400> SEQUENCE: 197

```
Met Thr Asn Val Gly Asp Ala Glu Arg Asp Lys Tyr Ser Leu Ile Asn
1               5                   10                  15

Phe Glu Glu Thr Glu Leu Arg Leu Gly Leu Pro Gly Ala Gly Asp His
            20                  25                  30

Gly Glu Ser Pro Val Lys Asn Ser Cys Gly Lys Arg Gly Phe Ser Glu
        35                  40                  45

Thr Ala Asn Val Asp Leu Lys Leu Asn Leu Ser Pro Ile Asn Asp Ser
    50                  55                  60

Ala Ser Ser Ser Thr Ile Ala Ser Val Ala Glu Asn Lys Gly Lys
65                  70                  75                  80

Asp Thr Thr Thr Ser Ala Thr Val Ser Pro Pro Arg Ala Lys Ala
                85                  90                  95

Gln Val Val Gly Trp Pro Val Arg Ser Phe Arg Lys Asn Ile Val
            100                 105                 110

Asn Val His Gln Lys Ser Asn Ser Glu Thr Glu Val Asp Lys Ser Ile
        115                 120                 125

Ser Gly Gly Gly Gly Asn Gly Ala Phe Val Lys Val Ser Met Asp Gly
    130                 135                 140

Ala Pro Tyr Leu Arg Lys Val Asp Leu Lys Leu Tyr Lys Ser Tyr Gln
145                 150                 155                 160

Glu Leu Ser Asp Ala Leu Ala Lys Met Phe Ser Phe Thr Ile Asp
                165                 170                 175

Asn Cys Gly Ser Gln Val Thr Lys Asp Phe Met Asn Glu Ser Lys Leu
            180                 185                 190

Ile Asp Leu Leu Asn Gly Ser Asp Tyr Val Pro Thr Tyr Glu Asp Lys
        195                 200                 205

Asp Gly Asp Trp Met Leu Val Gly Asp Val Pro Trp Glu Met Phe Val
    210                 215                 220

Gln Ser Cys Lys Arg Leu Arg Ile Met Lys Gly Ser Glu Ala Ile Gly
225                 230                 235                 240

Leu Ala Pro Arg Ala Val Glu Lys Cys Lys Asn Arg Ser
                245                 250
```

<210> SEQ ID NO 198
<211> LENGTH: 762
<212> TYPE: DNA
<213> ORGANISM: Medicago truncatula

<400> SEQUENCE: 198

```
atgactaacg ttggggatgc agagagagac aagtacagct tgataaattt tgaggagacc      60
gagttacgac tcggtcttcc aggtgcaggt gatcacggag aatcacctgt taaaaatagt     120
tgtggaaaga gaggtttctc agaaactgct aatgttgatt tgaagcttaa tctttctcct     180
ataaatgatt ctgcttcatc ttcttcaact atagcttctg tagctgaaaa caaaggcaaa     240
gacacaacaa cttctgctac tgtttctcct cctcctcgtg ctaaggcaca agttgtggga     300
tggccaccag ttagatcctt tagaaagaac atagtaaatg ttcatcaaaa gagcaatagt     360
```

```
gaaacagaag tagataagag cataagtggt ggtggtggga atggagcatt tgttaaggtg    420
agtatggatg gtgcaccata tctacgtaag gtggacctta aattgtacaa gagttaccaa    480
gagctgtcag atgcgctggc taaaatgttt agttccttca caattgacaa ttgtgggtcc    540
caagttacca aagacttcat gaatgaaagc aaattgattg acctttttgaa cggttctgat    600 tatgtaccaa catatgaaga caaagatggt gattggatgc ttgttggtga tgttccttgg    660
gaaatgttcg ttcaatcgtg caagcgtctt cgcataatga aaggttctga ggcaattggg    720
ctagcgccaa gggcagtgga aaaatgcaag aacagaagct ga                       762
```

<210> SEQ ID NO 199
<211> LENGTH: 229
<212> TYPE: PRT
<213> ORGANISM: Medicago truncatula
<220> FEATURE:
<221> NAME/KEY: misc_feature
<222> LOCATION: (41)..(41)
<223> OTHER INFORMATION: Xaa can be any naturally occurring amino acid

<400> SEQUENCE: 199

```
Met Ala Thr Met Gly His Gly Leu Asn Leu Lys Glu Thr Glu Leu Cys
1               5                   10                  15

Leu Gly Leu Pro Gly Gly Gly Ser Glu Val Glu Thr Ser Arg Ala Ser
            20                  25                  30

Gly Lys Lys Gly Phe Ser Asp Thr Xaa Asp Leu Lys Leu Asn Leu Gln
        35                  40                  45

Thr Lys Glu Asp Leu Asn Glu Lys Ser Ala Ser Lys Glu Lys Thr Leu
50                  55                  60

Leu Lys Asp Pro Ala Lys Pro Pro Ala Lys Ala Gln Val Val Gly Trp
65                  70                  75                  80

Pro Pro Val Arg Ser Tyr Arg Lys Asn Met Met Ala Gln Lys Val Asn
                85                  90                  95

Asn Thr Glu Asp Thr Glu Lys Thr Thr Ser Asn Thr Thr Ala Ala Ala
            100                 105                 110

Phe Val Lys Val Ser Met Asp Gly Ala Pro Tyr Leu Arg Lys Val Asp
        115                 120                 125

Leu Thr Met Tyr Lys Thr Tyr Lys Asp Leu Ser Asp Ala Leu Ala Lys
130                 135                 140

Met Phe Ser Ser Phe Thr Thr Gly Asn Tyr Gly Ala Gln Gly Met Ile
145                 150                 155                 160

Asp Phe Met Asn Glu Ser Lys Leu Met Asp Leu Leu Asn Ser Ser Glu
                165                 170                 175

Tyr Val Pro Thr Tyr Glu Asp Lys Asp Gly Asp Trp Met Leu Val Gly
            180                 185                 190

Asp Val Pro Trp Glu Met Phe Val Gly Ser Cys Lys Arg Leu Arg Ile
        195                 200                 205

Met Lys Gly Ser Glu Ala Ile Gly Leu Ala Pro Arg Ala Met Glu Lys
    210                 215                 220

Cys Lys Asn Arg Ser
225
```

<210> SEQ ID NO 200
<211> LENGTH: 690
<212> TYPE: DNA
<213> ORGANISM: Medicago truncatula
<220> FEATURE:
<221> NAME/KEY: misc_feature
<222> LOCATION: (65)..(65)

<223> OTHER INFORMATION: n is a, c, g, or t

<400> SEQUENCE: 200

```
atggctacta tggggcatgg tttgaacctg aaggagactg agctttgtct gggtctgcct      60
ggtgnggctc tgaggtggaa acttcaaggg cttctggaaa gaaaggtttt tctgatactc     120
ttcgatctta agcttaatct tcaaaccaag gaagatctga atgagaagag tgcttcaaag     180
gagaagaccc tccttaagga ccctgctaag ccaccagcta aggctcaagt agttggttgg     240
ccaccagtga ggtcatacag gaagaacatg atggcacaaa aggttaacaa tactgaggac     300
actgagaaga caacaagtaa cactactgct gctgcttttg ttaaggtttc catggatgga     360
gcaccttacc ttcgtaaggt tgacttgaca atgtacaaaa cctacaaaga tttatctgat     420
gccttagcca aaatgttcag ctccttcacc actggtaact atggggccca aggaatgata     480
gacttcatga atgagagcaa gttgatggat cttcttaaca gctctgagta tgtgccaacc     540
tatgaagata aggatggcga ctggatgctc gtgggagatg tcccatggga gatgtttgtt     600
ggatcatgca agcgtcttcg cataatgaaa ggatcagaag ctattggact tgcaccaaga     660
gcaatggaga aatgcaaaaa ccgaagctga                                       690
```

<210> SEQ ID NO 201
<211> LENGTH: 245
<212> TYPE: PRT
<213> ORGANISM: Medicago truncatula

<400> SEQUENCE: 201

```
Met Glu Val Val Ala Gly Met Lys Lys Glu Glu Lys Met Val Phe Asp
1               5                   10                  15

Glu Thr Glu Leu Arg Leu Gly Leu Gly Leu Pro Gly Lys Thr Thr Glu
            20                  25                  30

Val Val Arg Lys Arg Gly Phe Ser Glu Thr Glu Ser Glu Ser Glu Thr
        35                  40                  45

Asn Thr Val Asp Leu Lys Leu Asn Leu Ser Thr Lys Glu Gly Ala Thr
    50                  55                  60

Asp Pro Gln Phe Lys Pro Lys Glu Lys Ala Leu Leu Leu Ser Asp Ser
65                  70                  75                  80

Gly Ala Lys Pro Pro Ala Lys Ala Gln Val Val Gly Trp Pro Pro Val
                85                  90                  95

Arg Ser Phe Arg Lys Asn Met Phe Ala Ala Gln Lys Ser Asn Glu Gly
            100                 105                 110

Ser Glu Glu Ser Glu Lys Lys Asn Ser Asn Asn Pro Ile Ser Phe
            115                 120                 125

Val Lys Val Ser Met Asp Gly Ala Pro Tyr Leu Arg Lys Val Asp Leu
    130                 135                 140

Lys Met Tyr Lys Ser Tyr Pro Glu Leu Ser Asp Ala Leu Ala Lys Met
145                 150                 155                 160

Phe Asn Ser Phe Thr Thr Gly Asn Cys Glu Ser Gln Gly Ile Lys Asp
                165                 170                 175

Phe Met Asn Glu Ser Asn Lys Leu Met Asp Leu Leu Asn Ser Ser Asp
            180                 185                 190

Tyr Val Pro Thr Tyr Glu Asp Lys Asp Gly Asp Trp Met Leu Val Gly
        195                 200                 205

Asp Val Pro Trp Glu Met Phe Ile Asp Ser Cys Lys Arg Leu Arg Ile
    210                 215                 220

Met Lys Gly Lys Glu Ala Ile Gly Leu Ala Pro Arg Ala Met Glu Lys
```

```
                 225                 230                 235                 240

Cys Lys Asn Arg Ser
                245

<210> SEQ ID NO 202
<211> LENGTH: 738
<212> TYPE: DNA
<213> ORGANISM: Medicago truncatula

<400> SEQUENCE: 202
atggaagttg ttgcagggat gaaaaaggag gaaagatgg tgtttgatga aactgaactg      60
aggttaggac ttggattgcc agggaaaaca acagaagtag taaggaagag aggtttttct    120
gaaactgaga gtgaaagtga acaaacact gtggatttga agcttaatct ttctactaag     180
gaaggagcaa cagatccaca atttaagcca aggagaagg ctcttctgct ctctgattct     240
ggtgccaagc ctcctgctaa ggcacaagtg gtagggtggc caccagtgcg gtcattccgt    300
aagaacatgt ttgctgccca aaagagcaat gaaggatcag aagaaagtga aaagaagaat    360
agcaataata atccaataag ctttgtgaaa gttagcatgg atggagcacc ttacctccgt    420
aaagtagacc tcaagatgta caagagttac ccagagctct ctgatgcctt ggccaaaatg    480
tttaactcct ttaccacagg aaattgtgaa tcccaaggca ttaaggattt catgaatgag    540
agtaataagt tgatggatct attgaacagc tccgactatg tcccaactta tgaagacaaa    600
gatggcgact ggatgcttgt cggtgatgta ccatgggaga tgtttattga ttcatgcaag    660
cgtctacgta tcatgaaagg aaaggaagcc attggactcg caccaagagc catggaaaaa    720
tgcaagaaca ggagctag                                                  738

<210> SEQ ID NO 203
<211> LENGTH: 250
<212> TYPE: PRT
<213> ORGANISM: Medicago truncatula
<220> FEATURE:
<221> NAME/KEY: misc_feature
<222> LOCATION: (238)..(238)
<223> OTHER INFORMATION: Xaa can be any naturally occurring amino acid

<400> SEQUENCE: 203

Met Glu Val Val Gly Met Lys Lys Glu Asn Met Gly Phe Glu Glu Thr
1               5                   10                  15

Glu Leu Arg Leu Gly Ile Gly Phe Leu Gly Asn Asn Gly Ser Ala Thr
            20                  25                  30

Ala Thr Glu Gly Val Val Arg Lys Arg Gly Phe Ser Glu Thr Glu Thr
        35                  40                  45

Asp Asp Asp Thr Thr Thr Met Asp Leu Met Leu Asn Leu Ser Ser Lys
    50                  55                  60

Glu Ala Thr Ala Glu Val Asp Pro Ser Asp Ile Thr Thr Lys Thr Leu
65                  70                  75                  80

Gln Lys Glu Lys Thr Leu Leu Pro Ala Asp Pro Ala Lys Pro Pro Ala
                85                  90                  95

Lys Ala Gln Val Val Gly Trp Pro Pro Val Arg Ser Tyr Arg Lys Asn
            100                 105                 110

Met Leu Ala Met Gln Lys Ser Glu Ser Glu Lys Asn Ser Ser Ser Asn
        115                 120                 125

Phe Asn Ala Ile Thr Phe Val Lys Val Ser Met Asp Gly Ala Pro Tyr
    130                 135                 140

Leu Arg Lys Val Asp Leu Lys Met Tyr Thr Ser Tyr Ser Gln Leu Ser
```

145                 150                 155                 160
Asp Ser Leu Gly Lys Met Phe Ser Phe Thr Ile Gly Asn Cys Glu
                    165                 170                 175

Ser Gln Gly Met Lys Asp Phe Met Asn Glu Ser Lys Leu Met Asp Leu
                180                 185                 190

Leu Asn Asn Ser Asp Tyr Val Pro Thr Tyr Glu Asp Lys Asp Gly Asp
            195                 200                 205

Trp Met Leu Val Gly Asp Val Pro Trp Glu Met Phe Val Glu Ser Cys
        210                 215                 220

Lys Arg Leu Arg Ile Met Lys Gly Lys Glu Ala Ile Gly Xaa Ala Pro
225                 230                 235                 240

Arg Ala Met Glu Lys Cys Lys Asn Arg Ser
                245                 250

<210> SEQ ID NO 204
<211> LENGTH: 900
<212> TYPE: DNA
<213> ORGANISM: Medicago truncatula

<400> SEQUENCE: 204
atggaagttg ttggtatgaa gaaggagaat atgggatttg aggaaactga gttgagactt        60
ggaattggat ttcttggaaa taatggatca gccacagcta ctgaaggagt tgtaaggaag       120
agaggatttt ctgagactga aactgatgat gatacaacta ctatggattt gatgcttaat       180
ctttcctcta aggaagctac tgctgaggta gatccaagtg atataaccac aagactttg        240 caaaaggaga gaccctttt gcctgcagat cctgccaagc tcctgcaaa ggctcaagtg         300 gtgggttggc cacctgtccg gtcgtaccgg aagaacatgt tagcaatgca aaagagtgaa       360
agtgagaaga cagcagttc caatttcaat gcaattacat ttgtgaaagt tagtatggat        420
ggagctcctt accttcgtaa ggttgacttg aagatgtaca caagttactc acagctttct      480
gattccttag gcaaaatgtt cagctccttc accattggca actgtgaatc tcaaggaatg      540
aaggatttca tgaatgagag taagttgatg gatcttttaa acaattctga ttatgttcca      600
acctatgaag acaaggatgg tgactggatg cttgtcggtg acgtcccatg ggagatgttt      660
gttgaatcat gcaaacgttt gcgtatcatg aaaggaaagg aggctattgg gtatagcacc      720
aagagctatg gaaaaatgca agaacaggag ctagacttgc tggtcgcact tgttcgccac      780
ctgctccatc ttttgtcata ttttggtacc tgcaggatgt tcagtatagt taatttgtgt      840
aatgttatat ggttttatt ttttgataaa attgttatat ggtttgttat acatatataa       900

<210> SEQ ID NO 205
<211> LENGTH: 337
<212> TYPE: PRT
<213> ORGANISM: Medicago truncatula
<220> FEATURE:
<221> NAME/KEY: misc_feature
<222> LOCATION: (208)..(208)
<223> OTHER INFORMATION: Xaa can be any naturally occurring amino acid

<400> SEQUENCE: 205

Met Ser Pro Thr Ala Val Val Thr Glu Asp Glu Gly Arg Arg Lys Leu
1               5                   10                  15

Ser Ser Thr Met Glu Arg Asn Tyr Leu Gly Leu Ser Asp Cys Ser Ser
                20                  25                  30

Val Asp Ser Cys Asp Ser Thr Leu Pro Ser Leu Cys Asp Glu Lys Lys
            35                  40                  45

| | | | | | | | | | | | |
|---|---|---|---|---|---|---|---|---|---|---|---|
|Val|Asn|Leu|Asn|Leu|Lys|Ala|Thr|Glu|Leu|Arg|Leu|Gly|Leu|Pro|Gly|
| |50| | | |55| | | |60| | | | | | |

Ser Gln Ser Pro Glu Arg Glu Met Asp Ser Asp Phe Tyr Leu Thr Lys
65                  70                  75                  80

Leu Asp Glu Lys Pro Leu Phe Pro Leu Leu Pro Ala Lys Asp Gly Leu
                85                  90                  95

Gln Lys Asn Val Val Ser Gly Asn Lys Arg Gly Phe Ala Asp Thr Val
            100                 105                 110

Asp Gly Phe Ser Gln Gly Lys Phe Asn Gly Asn Thr Gly Ile Asn Val
            115                 120                 125

Met Leu Ser Pro Arg Pro Ala Gly Ala Gln Ala Ser Thr Val Lys Glu
    130                 135                 140

Met Pro Ser Lys Val Leu Gln Glu Arg Pro Cys Ala Ala Arg Gly Thr
145                 150                 155                 160

Ala Gly His Asn His Ala Gly Ala Ala Ser Val Ala Gly Cys Ala Pro
                165                 170                 175

Ala Ser Lys Ala Gln Val Val Gly Trp Pro Pro Ile Arg Ser Phe Arg
            180                 185                 190

Lys Asn Ser Met Ala Pro Ala Ser Lys Asn Thr Asn Asp Glu Val Xaa
            195                 200                 205

Gly Leu Glu Lys Pro Gly Pro Ala Ala Leu Phe Val Lys Val Ser Met
    210                 215                 220

Asp Gly Ala Pro Tyr Leu Arg Lys Val Asp Leu Arg Thr Tyr Ala Thr
225                 230                 235                 240

Tyr Gln Gln Leu Ser Ser Ala Leu Glu Lys Met Phe Ser Cys Phe Thr
                245                 250                 255

Leu Gly Gln Cys Gly Ser His Gly Ala Pro Gly Lys Glu Met Met Ser
            260                 265                 270

Glu Ser Lys Leu Arg Asp Leu His Gly Ser Glu Tyr Val Leu Thr
            275                 280                 285

Tyr Glu Asp Lys Asp Gly Asp Trp Met Leu Val Gly Asp Val Pro Trp
    290                 295                 300

Glu Met Phe Ile Asp Thr Cys Arg Arg Leu Lys Ile Met Lys Gly Ser
305                 310                 315                 320

Asp Ala Ile Gly Leu Ala Pro Arg Ala Met Glu Lys Ser Lys Ser Arg
            325                 330                 335

Ser

<210> SEQ ID NO 206
<211> LENGTH: 660
<212> TYPE: DNA
<213> ORGANISM: Medicago truncatula

<400> SEQUENCE: 206

```
atgtctccga cggctgtggt tacggaggac gaagggcggc gcaaactgtc gtcgacgatg      60
gaacggaatt acttgggatt gtctgattgt tcatcggtgg acagttgtga ttcaactctc     120
ccaagtttgt gtgatgagaa aaaagtgaac ttgaatttga aggctactga gttgaggttg     180
ggtcttcctg gatctcaatc acccgagagg gaaatggatt cggattttta cttaacaaag     240
cttgatgaga aaccattgtt ccctttactt cctgcaaaag atggtttgca gaagaatgtg     300
gtttcgggga taagagaggg atttgctgat accgttgatg gttttctca gggtaagttt     360
aatggtaata cggggattaa cgtgatgcta tcgcctagac ctgctggagc tcaggcgagc     420
acagtgaaag aaatgccgag taaggttttg caggaaaggc cttgtgcagc tagaggaact     480
```

```
gctggtcata atcatgcagg tgctgcttct gtcgctggtt gtgcaccggc atcaaaggca    540
caagttgttg gttggcctcc tataagatca tttagaaaaa actcaatggc ccccgcttcc    600
aagaacacca atgatgaagt tgggattgg aaaaaccagg tcccgctgca ctctttgtga     660
```

<210> SEQ ID NO 207
<211> LENGTH: 293
<212> TYPE: PRT
<213> ORGANISM: Medicago truncatula
<220> FEATURE:
<221> NAME/KEY: misc_feature
<222> LOCATION: (221)..(221)
<223> OTHER INFORMATION: Xaa can be any naturally occurring amino acid

<400> SEQUENCE: 207

```
Met Ser Val Pro Val Glu Gln Gly Tyr Gly Glu Val Pro Ser Met Glu
 1               5                  10                  15

Thr Lys Glu Arg Ser Ile Gly Leu Asn Leu Lys Ala Thr Glu Leu Arg
             20                  25                  30

Leu Gly Leu Pro Gly Ser Glu Ser Pro Glu Arg Glu Asn Gly Gly Val
         35                  40                  45

Leu Lys Ser Leu Val Ser Gly Ala Lys Arg Gly Phe Ser Asp Ala Ile
     50                  55                  60

Thr Asp Gly Gly Ser Gly Lys Trp Val Leu Ser Gly Asn Gly Gly Ser
 65                  70                  75                  80

Glu Val Gly Leu Cys Lys Asp Gly Asn Leu Phe Ser Pro Lys Ala Lys
                 85                  90                  95

Gly Val Gly Glu Cys Asn Asn Gln Gln Asn Pro Phe Ser Ala Ser Val
            100                 105                 110

Val Val Lys Glu Thr Val Thr His Ser Pro Lys Pro Leu His Asp Asn
        115                 120                 125

Lys Pro Gln Val Ser Pro Pro Ser Ser Lys Ala Gln Val Val Gly Trp
    130                 135                 140

Pro Pro Ile Arg Ser Phe Arg Lys Asn Ser Met Val Ser Gln Pro Gln
145                 150                 155                 160

Lys Asn Asp Ala Asp Ala Glu Ala Lys Ser Glu Cys Leu Tyr Val Lys
                165                 170                 175

Val Ser Met Glu Gly Ala Pro Tyr Leu Arg Lys Val Asp Leu Asn Gly
            180                 185                 190

Phe Ser Ser Tyr Arg Glu Leu Ser Ser Ala Leu Glu Lys Met Phe Ser
        195                 200                 205

Cys Phe Thr Ile Ser Gln Cys Gly Ser Tyr Gly Val Xaa Leu Ser Arg
    210                 215                 220

Lys Asn Leu Ser Glu Ser Arg Leu Val Asp Leu Leu His Gly Ser Glu
225                 230                 235                 240

Tyr Val Leu Thr Tyr Glu Asp Lys Asp Gly Asp Trp Met Leu Val Gly
                245                 250                 255

Asp Val Pro Trp Glu Met Phe Thr Glu Ser Cys Lys Arg Leu Arg Ile
            260                 265                 270

Met Lys Ser Ser Glu Ala Ile Gly Leu Ala Pro Arg Ala Met Glu Lys
        275                 280                 285

Cys Lys Ser Arg Asn
    290
```

<210> SEQ ID NO 208
<211> LENGTH: 681

```
<212> TYPE: DNA
<213> ORGANISM: Medicago truncatula

<400> SEQUENCE: 208
atgtctgtgc cagtggaaca aggttatgga gaggttcctt caatggaaac caaagagaga      60
agcattggtt tgaacctcaa agctactgaa ctaaggttag ggttaccagg ctctgagtca     120
ccagagagag aaaatggtgg tgtgcttaag agtttggtat ctggtgctaa aggggtttc     180
tctgatgcta ttactgatgg tggttctggg aagtgggttt gtctggaaa tggtggatct     240
gaagtggggt tgtgtaaaga tggaaacttg ttctctccta aagctaaagg tgttggtgaa     300
tgtaataacc aacaaaaccc tttctctgct tcagttgttg ttaaagaaac tgttacacac     360
tctccaaagc ctttgcatga taacaaaacca caggtttctc ctccttcttc aaaggcgcaa     420
gttgtgggat ggcctccaat ccgatctttc aggaagaact caatggtttc acagcctcaa     480
aagaatgatg ctgatgcaga agccaagtct gaatgcctat atgtaaaagt cagcatggaa     540
ggtgctccat acttgaggaa agtggatctg aatggtttta gctcttatag ggagctttct     600
tcagcactcg aaaagatgtt cagttgtttt acaatcagtc aatgtggctc atatggagtt     660
tcttgtcgag aaaaaatcta a                                               681

<210> SEQ ID NO 209
<211> LENGTH: 348
<212> TYPE: PRT
<213> ORGANISM: Medicago truncatula

<400> SEQUENCE: 209

Met Ser Pro Pro Leu Leu Pro Glu Glu Gly Gln Ser Asn Pro
1               5                   10                  15

Ser Thr Val Ala Ser Ala Ser Pro Gln Ser Leu Asp Arg Phe Ser Gln
            20                  25                  30

Thr Ala Ala Gly Leu Lys Glu Arg Asn Tyr Leu Gly Leu Ser Asp Cys
        35                  40                  45

Ser Ser Val Asp Ser Ser Thr Val Pro Ser Leu Ser Asp Glu Lys Lys
    50                  55                  60

Glu Asn Leu Asn Leu Lys Ala Thr Glu Leu Arg Leu Gly Leu Pro Gly
65                  70                  75                  80

Ser Gln Ser Pro Glu Arg Asp Leu Asp Leu Phe Pro Leu Asn Ser Thr
                85                  90                  95

Lys Leu Asp Glu Lys Pro Leu Phe Pro Leu Leu Pro Thr Lys Asp Gly
            100                 105                 110

Ile Cys Ser Leu Ser Gln Lys Thr Val Val Ser Gly Asn Lys Arg Gly
        115                 120                 125

Phe Ala Asp Thr Leu Glu Val Phe Pro Glu Ala Lys Tyr Thr Ala Asn
    130                 135                 140

Thr Arg Val Asn Ile Leu Leu Ser Pro Arg Pro Ser Gly Ala Gln Pro
145                 150                 155                 160

Thr Thr Ile Lys Glu Met Pro Lys Lys Val Gln Glu Ser Pro Cys
                165                 170                 175

Thr Ala Asn Gly Thr Gly Ala Pro Ile Ser Gly Ser Ala Pro Ala Ala
            180                 185                 190

Lys Ala Gln Val Val Gly Trp Pro Pro Ile Arg Ser Phe Arg Lys Asn
        195                 200                 205

Ser Leu Ala Thr Thr Ser Lys Asn Asn Asp Glu Val Asp Gly Lys Pro
    210                 215                 220
```

```
Gly Ala Ala Ala Leu Phe Val Lys Val Ser Met Asp Gly Ala Pro Tyr
225                 230                 235                 240

Leu Arg Lys Val Asp Leu Arg Asn Tyr Thr Thr Tyr Gln Glu Leu Ser
            245                 250                 255

Ser Asp Leu Glu Lys Met Phe Ser Cys Phe Thr Leu Gly Gln Cys Gly
        260                 265                 270

Ser His Gly Arg Pro Gly Lys Glu Met Leu Ser Glu Ser Lys Leu Lys
        275                 280                 285

Asp Phe Leu His Gly Ser Glu Tyr Val Val Thr Tyr Glu Asp Lys Asp
    290                 295                 300

Gly Asp Trp Met Leu Val Gly Asp Val Pro Trp Asp Met Phe Ile Asp
305                 310                 315                 320

Thr Cys Lys Arg Leu Lys Ile Met Lys Gly Ser Asp Ala Ile Gly Leu
                325                 330                 335

Ala Pro Arg Ala Met Glu Lys Ser Lys Ser Arg Ser
                340                 345
```

<210> SEQ ID NO 210
<211> LENGTH: 1047
<212> TYPE: DNA
<213> ORGANISM: Medicago truncatula

<400> SEQUENCE: 210

```
atgtctccgc cactgctgct tcctgaagag aagggcaga gcaaccctc aacggtagca        60
tctgcatctc cacaatcctt ggaccgtttt tctcaaactg cagctgggtt gaaggaacgc       120
aattacctcg gattgtctga ttgctcatcg gttgacagtt ctactgtccc aagcttgtct       180
gatgagaaaa aagagaacct aaatttgaaa gcgacggagt taaggctcgg acttcctgga       240
tctcagtcgc ctgaaaggga tcttgatctt tttccgttga actcaacaaa acttgacgag       300
aaaccacttt tccctttgct tcccaccaaa gatggaatct gctcgttgtc ccaaaagacc       360
gttgtttcag caacaaaag aggtttcgcc gacacactgg aagtgtttcc tgaggcaaaa       420
tatactgcta atactcgcgt aaacatactg cttcgccga ccttctgg agctcagcct        480
actacaatta agaaatgcc aaagaaggtg gtacaagaga gcccttgtac agcgaatgga       540
actggagctc ccatcagtgg cagtgcaccg gctgctaaag cacaagttgt tggttggcct       600
cctattagat catttaggaa aaactcactg gccaccactt caaagaacaa tgacgaagtg       660
gatggaaagc ctggtgcagc tgcactattt gtgaaggtta gcatggatgg cgctccttat       720
cttaggaagg tagatctaag aaactataca acataccagg aactgtcgtc tgaccttgag       780
aagatgttca gctgttttac cttaggtcaa tgtggttcgc atggacgtcc agggaaagaa       840
atgttgagtg agagtaaatt gaaggacttc ctgcatggtt ctgaatatgt ggtcacttat       900
gaagataaag atggtgactg gatgcttgta ggagatgtac catgggacat gttcattgac       960
acatgcaaaa gactgaaaat catgaagggt tctgatgcaa ttggcttagc tccaagggcc      1020
atggaaaaat ccaagagcag gagctag                                           1047
```

<210> SEQ ID NO 211
<211> LENGTH: 347
<212> TYPE: PRT
<213> ORGANISM: Medicago truncatula

<400> SEQUENCE: 211

```
Met Ser Leu Pro Arg Leu Gly Ile Gly Asp Glu Glu Ser Lys Ser Asn
1               5                   10                  15
```

```
Val Thr Leu Leu Glu Lys Ser Leu His Leu Asn Gly Ser Lys Pro Lys
         20                  25                  30

Glu Phe Asn Tyr Met Gly Leu Pro Ser Ser Asn Cys Ser Ser Val Asp
             35                  40                  45

Ser Ser Val Pro Lys Ile Gln Ser Phe Lys Asp Glu Thr Lys Ser Asn
 50                  55                  60

Leu Asn Leu Lys Ala Thr Glu Leu Arg Leu Gly Leu Pro Gly Ser Leu
 65                  70                  75                  80

Ser Pro Glu Arg Asp Ser Ser Asp Phe Cys Leu Arg Ser Ser Lys Gln
                 85                  90                  95

Phe Asp Glu Lys Pro Leu Phe Pro Leu His Pro Gln Lys Asp Asp His
            100                 105                 110

Leu Phe Glu Ser Lys Pro Ala Val Leu Gly Asn Lys Arg Gly Phe Ser
        115                 120                 125

Asp Ala Met Asn Val Phe Ser Glu Gly Lys Leu Lys Pro Ser Ser Lys
    130                 135                 140

Met Leu Glu Asn Val Ala Gly Gln Lys Val Lys Ala Asp Glu Ile Ala
145                 150                 155                 160

Thr Val Lys Ile Gly Leu Glu Arg Pro Asn Gly Val Gly Glu Ser Lys
                165                 170                 175

Pro Gly Leu Asn Gly Ser Ala Asn Asn Gly Asn Ser Thr Ala Pro Ala
            180                 185                 190

Ser Lys Ala Gln Val Val Gly Trp Pro Pro Ile Arg Ser Phe Arg Lys
        195                 200                 205

Asn Ser Leu Thr Thr Ala Ser Lys Asn Thr Glu Glu Val Asp Gly Lys
210                 215                 220

Leu Gly Ser Gly Gly Ala Val Phe Val Lys Val Ser Met Asp Gly Ala
225                 230                 235                 240

Pro Tyr Leu Arg Lys Val Asp Leu Lys Asn Tyr Thr Ala Tyr Ser Glu
                245                 250                 255

Leu Ser Ser Ser Leu Glu Lys Met Phe Ser Cys Phe Thr Ile Gly Gln
            260                 265                 270

Cys Glu Ser His Gly Asn Gln Met Leu Asn Glu Thr Lys Leu Arg Asp
        275                 280                 285

Leu Leu His Gly Ser Glu Tyr Val Ile Thr Tyr Glu Asp Lys Asp Gly
    290                 295                 300

Asp Trp Met Leu Val Gly Asp Val Pro Trp Glu Met Phe Ile Asp Thr
305                 310                 315                 320

Cys Arg Arg Leu Arg Ile Met Lys Ser Ser Asp Ala Ile Gly Leu Ala
                325                 330                 335

Pro Arg Ala Val Glu Lys Ser Lys Ser Arg Asn
            340                 345

<210> SEQ ID NO 212
<211> LENGTH: 1044
<212> TYPE: DNA
<213> ORGANISM: Medicago truncatula

<400> SEQUENCE: 212
atgtctctac caaggctagg gataggtgat gaggaaagta aaagcaatgt tactttgttg      60
gaaaaaagtt tgcatttgaa tggttcaaaa ccaaaagagt tcaactacat gggattacca    120
tcctctaatt gttcatcagt ggatagttca gttccaaaaa ttcaatcttt taaagatgag    180
accaaaagta atttgaatct taaagctact gagcttagat tgggacttcc aggatcactt    240
```

```
tctcctgaaa gagattcatc agattttgt ttgagaagtt caaagcagtt tgatgaaaag    300
cctctttttc ctttgcaccc tcaaaaagat gatcatcttt ttgaatcaaa gcctgctgtt    360
ttaggtaaca aaagagggtt ttctgatgcc atgaatgttt tttcagaggg gaaattgaag    420
cctagctcca aaatgcttga gaatgttgcc gggcagaaag tgaaagccga tgaaatagca    480
acagttaaga ttggtcttga gacctaatg gtgttggtg aaagcaaacc aggtcttaat     540
ggttctgcaa ataatggaaa tagcactgct cctgctagca aggcacaggt tgttggttgg    600
cctccaataa gatcatttag gaaaaattca ttaacaactg cttcaaagaa cactgaagag    660
gttgatggaa aattgggatc aggaggtgca gtgtttgtga aggttagcat ggatggtgct    720
ccttatttaa gaaaagtaga cttgaagaat tacactgcat attcagaact atcttcttct    780
cttgagaaga tgttcagctg tttcaccata ggtcaatgtg aatctcatgg aaaccagatg    840
ctgaatgaaa ccaagctgag ggatctgctt catgggtcag aatatgttat tacttatgag    900
gataaagatg gtgattggat gcttgtcggt gatgttccct gggagatgtt tattgataca    960
tgcaggagac taagaatcat gaagagctct gatgccattg gtttagcccc cagagcagtt    1020
gaaaaaagta aaagcaggaa ctaa                                           1044
```

<210> SEQ ID NO 213
<211> LENGTH: 326
<212> TYPE: PRT
<213> ORGANISM: Medicago truncatula
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid

<400> SEQUENCE: 213

```
Pro Arg Ala Asp Asp Tyr Ile Gly Leu Ala Asn Asn Pro Ser Met Asp
1               5                   10                  15

Lys Thr Ser Ser Ser Leu Asn Phe Lys Glu Thr Glu Leu Arg Leu Gly
                20                  25                  30

Xaa Pro Gly Cys Glu Ser Pro Asp Arg Lys Ser Val Ser Ala Ala Gly
            35                  40                  45

Ala Gly Gly Gly Val Ser Phe Phe Ala Asn Lys Asp Leu Lys Ser Ile
        50                  55                  60

Asn Val Cys Ser Pro Leu Lys Asn Leu Val Ala Ser Val Gly Ala Lys
65                  70                  75                  80

Arg Gly Phe Ser Asp Ala Ile Asp Glu Ser Ser Lys Lys Trp Ser Phe
                85                  90                  95

Ser Met Asn Asp Gly Ser Glu Gly Gly Ser Leu Phe Ser Pro Arg Gly
            100                 105                 110

Gly Asn Val Gly Lys Pro Leu Ala Gly Leu Glu Thr Gln Thr Asn Ile
        115                 120                 125

Gln Lys Ile Asn Thr Asn Ala Thr Lys Asn Ile Lys Glu Val Leu His
    130                 135                 140

Gln Ser Val His Glu Lys Asn Lys Gln Val Ser Gly Thr Asn Glu His
145                 150                 155                 160

Ala Asn Ala Pro Ala Ala Lys Ala Gln Val Val Gly Trp Pro Pro Ile
                165                 170                 175

Arg Ser Phe Arg Lys Asn Thr Met Ala Ser Asn Leu Thr Lys Asn Asn
            180                 185                 190
```

```
Asp Glu Ala Glu Gly Lys Pro Glu Phe Asp Cys Leu Tyr Val Lys Val
            195                 200                 205

Ser Met Asp Gly Ala Pro Tyr Leu Arg Lys Val Asp Leu Lys Thr Tyr
    210                 215                 220

Asn Asn Tyr Met Glu Leu Ser Ser Ala Leu Glu Lys Met Phe Thr Cys
225                 230                 235                 240

Phe Thr Ile Gly Gln Cys Asn Ser Pro Gly Leu Pro Gly Lys Asp Gly
                245                 250                 255

Leu Ser Glu Ser Ser Leu Arg Asp Leu Leu His Gly Ser Glu Tyr Val
            260                 265                 270

Leu Thr Tyr Glu Asp Lys Asp Gly Asp Trp Met Leu Val Gly Asp Val
        275                 280                 285

Pro Trp Gly Met Phe Ala Asp Ser Cys Arg Arg Leu Arg Ile Met Lys
    290                 295                 300

Gly Ser Asp Ala Ile Gly Leu Gly Met Lys Xaa Pro Arg Ala Met Glu
305                 310                 315                 320

Lys Ser Arg Ser Gln Asn
            325

<210> SEQ ID NO 214
<211> LENGTH: 1020
<212> TYPE: DNA
<213> ORGANISM: Medicago truncatula
<220> FEATURE:
<221> NAME/KEY: misc_feature
<222> LOCATION: (98)..(98)
<223> OTHER INFORMATION: n is a, c, g, or t

<400> SEQUENCE: 214
cctcgtgccg atgattacat aggtttagca aataatcctt caatggacaa acatcttca      60
tctctcaact tcaaggaaac tgagctcaga ctaggctnac ctggttgtga atctcctgat    120
agaaaatcag tttctgctgc tggtgctggt ggtggagtct ctttctttgc caacaaagat    180
ttgaagagca ttaatgtttg ttctcctttg aagaaccttg tagctagtgt tggagctaaa    240
agaggtttct ctgatgctat tgatgagtct tctaagaaat ggagtttctc tatgaatgat    300
ggatctgaag gaggtagttt gttctcgcca agaggaggga atgttggaaa acctcttgct    360
ggtttagaga ctcaaactaa tattcaaaag attaatacaa atgcaacaaa aacatcaaa    420
gaggttcttc atcaatctgt acatgaaaag aataaacagg tttctggaac aaatgagcat    480
gctaatgctc ctgctgcaaa ggcacaggtt gtgggatggc caccaattcg atcgtttcga    540
aagaacacga tggcgtcaaa tttgacaaag aacaatgatg aagctgaggg aaaaccagaa    600
tttgactgtc tctatgtaaa agtgagtatg gatggtgctc cttatctcag aaaggttgat    660
ctcaagacct acaacaacta tatggaactt tcttcagctc ttgagaagat gttcacctgc    720
tttaccattg gtcaatgcaa ttcgcctgga cttcctggga agatggact aagtgagagc    780
tctttgaggg atcttcttca tggatctgag tatgttctta catatgaaga taaagatgga    840
gattggatgc ttgtaggcga cgttccttgg gggatgttcg ctgactcgtg taggagacta    900
cggatcatga aagctctga tgcaattggg ctaggtatga actccaaga gcaatggaaa    960
aatctaggag ccaaaactag tccagaaaaa ctcgttggac aaagaggag aattcactga    1020

<210> SEQ ID NO 215
<211> LENGTH: 238
<212> TYPE: PRT
<213> ORGANISM: Helianthus annuus
```

<400> SEQUENCE: 215

```
Met Asp Pro Ile Pro Lys Thr His Asn Gln Asp Leu Asn Leu Lys Ala
1               5                   10                  15

Thr Glu Leu Arg Leu Gly Leu Pro Gly Ser Glu Ser Pro Glu Arg Thr
            20                  25                  30

Thr Ile Gly Gly Ala Lys Asn Pro Asn Leu Val Ser Gly Ala Lys Arg
        35                  40                  45

Gly Phe Ser Asp Thr Ile Asn Phe Val Lys Asn Gly Ala Phe Leu Ala
    50                  55                  60

Glu Asn Lys Asn Thr Ser Gly Lys Asp Thr Ala Val Ser Ser
65                  70                  75                  80

Pro Lys Val Pro Val Ala Ala Ser Lys Ala Gln Val Val Gly Trp Pro
                85                  90                  95

Pro Ile Arg Ser Phe Arg Lys Asn Ser Met Ala Ala Lys Asn Thr Lys
            100                 105                 110

Asn Glu Asp Asp Pro Asn Ala Glu Ile Gly Ser Cys Val Tyr Val Lys
        115                 120                 125

Val Ser Met Asp Gly Ala Pro Tyr Leu Arg Lys Val Asp Leu Lys Ile
    130                 135                 140

Tyr Ser Ser Tyr Gln Asp Leu Ser Leu Ala Leu Glu Lys Met Phe Ser
145                 150                 155                 160

Ser Phe Thr Leu Gly Gln Tyr Gly Thr His Gly Ser Ser Glu Asn Pro
                165                 170                 175

Leu Met Asn Leu Leu Asn Gly Ser Glu Tyr Val Leu Thr Tyr Glu Asp
            180                 185                 190

Lys Asp Gly Asp Leu Met Leu Val Gly Asp Val Pro Trp Asp Met Phe
        195                 200                 205

Thr Gly Thr Cys Lys Arg Met Arg Ile Met Lys Ser Ser Asp Ala Ile
    210                 215                 220

Gly Leu Ala Pro Arg Val Ala Asp Lys Cys Lys Ser Gly Asn
225                 230                 235
```

<210> SEQ ID NO 216
<211> LENGTH: 717
<212> TYPE: DNA
<213> ORGANISM: Helianthus annuus

<400> SEQUENCE: 216

```
atggacccaa tacccaaaac ccacaaccaa gatttgaact tgaaagccac cgagttaaga      60
ctcggtctgc ctggttctga gtcacctgaa agaaccacta ttggtggtgc caagaaccct     120
aatttggtct caggagccaa aggggtttc tcagatacca ttaattttgt taaaaatggt     180 gccttttgg ctgaaaacaa gaataatact tctgggaaag atactgctgt tcatcttca      240 cctaaagttc ctgttgctgc ttcaaaggca caagttgtgg gatggcctcc aattcggtct     300
tttcgaaaga attcaatggc tgctaaaaac acgaagaacg aagatgaccc gaatgccgaa     360
atcggatcat gtgtttatgt gaaagttagt atggatggag ctccatattt gaggaaagtg     420
gatcttaaga tctattcaag ttatcaggat ctttctttgg ctttagagaa aatgtttagt     480
agcttcaccc ttggtcaata cggtactcac gggtcgagtg aaaacccatt gatgaatctt     540
ctgaacggtt ctgaatatgt actaacttac gaagacaaag atggtgactt gatgctcgtt     600
ggagatgttc cctgggatat gtttactgga acttgtaaga gatgcggat catgaagagt      660 tcagatgcaa tcggcttagc ccctcgagtc gcagacaaat gcaaaagcgg taactag        717
```

<210> SEQ ID NO 217
<211> LENGTH: 280
<212> TYPE: PRT
<213> ORGANISM: Kochia scoparia

<400> SEQUENCE: 217

```
Met Leu Ser Asn Glu Arg Asp Lys Tyr Thr Ile Asp Phe Glu Glu Thr
1               5                   10                  15
Glu Leu Arg Leu Gly Leu Gly Leu Gly Ile Gly Leu Ala Gly Ala Ala
            20                  25                  30
Asp Gly Asp Gln Leu Ala Lys Asn Asn Asn Gly Lys Arg Gly Phe Ser
        35                  40                  45
Glu Thr Glu Gly Asp Ser Ser Val Asp Leu Lys Leu Asn Leu Ser Ser
    50                  55                  60
Ser Thr Thr Thr Thr Ala Ser Thr Thr Thr Asn Thr Thr Ala Thr
65                  70                  75                  80
Lys Thr Thr Ala Glu Asn Val Lys Glu Ser Lys Leu Asp Lys Ser Val
                85                  90                  95
Asn Ser Gly Val Asp Gln Lys Leu Lys Glu Lys Val Ala Ser Thr Thr
            100                 105                 110
Ala Asp Pro Ala Lys Pro Thr Pro Ala Lys Thr Gln Val Val Gly Trp
        115                 120                 125
Pro Pro Val Arg Ala Phe Arg Lys Asn Ile Val Ala Ala Gln Lys Lys
130                 135                 140
Thr Ser Asp Asp Gln Thr Asp Gln Lys Ala Ser Ser Asn Ala Ile Thr
145                 150                 155                 160
Ser Ala Ala Phe Val Lys Val Ser Met Asp Gly Ala Pro Tyr Leu Arg
                165                 170                 175
Lys Val Asp Leu Lys Leu Tyr Lys Ser Tyr Gln Asp Leu Ser Asp Ala
            180                 185                 190
Leu Gly Lys Met Phe Ser Ser Phe Thr Ile Gly Asn Cys Gly Ser Gln
        195                 200                 205
Gly Met Lys Asp Phe Met Asn Glu Ser Lys Leu Ile Asp Leu Leu Asn
    210                 215                 220
Gly Ser Glu Tyr Val Pro Thr Tyr Glu Asp Lys Asp Gly Asp Trp Met
225                 230                 235                 240
Leu Val Gly Asp Val Pro Trp Glu Met Phe Val Gly Ser Cys Lys Arg
                245                 250                 255
Leu Arg Ile Met Lys Gly Ser Glu Ala Ile Gly Leu Ala Pro Arg Ala
            260                 265                 270
Val Glu Lys Cys Lys Asn Arg Ser
        275                 280
```

<210> SEQ ID NO 218
<211> LENGTH: 843
<212> TYPE: DNA
<213> ORGANISM: Kochia scoparia

<400> SEQUENCE: 218

```
atgttgagta acgagagaga caagtacacg atcgatttcg aggagacgga gctcaggctt    60
gggctcgggc tcgggatcgg gctggcgggg gctgctgacg gggatcagtt ggcgaagaat   120
aataacggga gagggggtt ttctgagacg gaaggcgact ccagtgttga cttgaagctt   180
aatctgtcgt cctcaacaac gacgacagcc agcactacca ccaccaacac caccgcaacc   240
```

-continued

```
aaaactacag cggagaacgt gaaagagtca agttggata  aaagtgtcaa ttccggcgtt   300
gatcagaagt tgaaggagaa agttgcttct accactgctg atcctgctaa gcctacacca   360
gctaagacac aagttgtagg ttggccaccc gttagagcgt tcaggaagaa catcgtcgcg   420
gcccaaaaga gacgtccga  tgatcaaact gatcagaagg cttctagcaa tgccatcaca   480
agcgccgcgt ttgtgaaggt tagcatggat ggtgcgcctt acttgcgtaa agtggacttg   540
aaattgtaca agagttatca agacctttct gatgctttgg gcaagatgtt cagttctttt   600
accataggta attgcgggtc acagggaatg aaggatttca tgaacgagag caaattgatt   660
gatcttctga atggttccga gtacgtgcca acttatgaag ataaagatgg cgattggatg   720
cttgttggcg acgtgccatg ggagatgttc gtcggatcat gcaaacgcct ccgaatcatg   780
aagggatcag aagccattgg actagcacca agggcagttg agaagtgcaa gaacagaagc   840
tga                                                                 843
```

<210> SEQ ID NO 219
<211> LENGTH: 280
<212> TYPE: PRT
<213> ORGANISM: Kochia scoparia

<400> SEQUENCE: 219

```
Met Leu Ser Asn Glu Arg Asp Lys Tyr Thr Ile Asp Phe Glu Glu Thr
1               5                   10                  15
Glu Leu Arg Leu Gly Leu Gly Leu Ile Gly Leu Ala Gly Ala Ala
            20                  25                  30
Asp Gly Asp Gln Leu Ala Lys Asn Asn Asn Gly Lys Arg Gly Phe Ser
        35                  40                  45
Glu Thr Glu Gly Asp Ser Ser Val Asp Leu Lys Leu Asn Leu Ser Ser
    50                  55                  60
Ser Thr Thr Thr Thr Ala Ser Thr Thr Thr Asn Thr Thr Ala Thr
65                  70                  75                  80
Lys Thr Thr Ala Glu Asn Val Lys Glu Ser Lys Leu Asp Lys Ser Val
                85                  90                  95
Asn Ser Gly Val Asp Gln Lys Leu Lys Glu Lys Val Ala Ser Thr Thr
            100                 105                 110
Ala Asp Pro Ala Lys Pro Thr Pro Ala Lys Thr Gln Val Val Asn Trp
        115                 120                 125
Pro Pro Val Arg Ala Phe Arg Lys Asn Ile Val Ala Ala Gln Lys Lys
    130                 135                 140
Thr Ser Asp Asp Gln Thr Asp Gln Lys Ala Ser Ser Asn Ala Ile Thr
145                 150                 155                 160
Ser Ala Ala Phe Val Lys Val Ser Met Asp Gly Ala Pro Tyr Leu Arg
                165                 170                 175
Lys Val Asp Leu Lys Leu Tyr Lys Ser Tyr Gln Asp Leu Ser Asp Ala
            180                 185                 190
Leu Gly Lys Met Phe Ser Ser Phe Thr Ile Gly Asn Cys Gly Ser Gln
        195                 200                 205
Gly Met Lys Asp Phe Met Asn Glu Ser Lys Leu Ile Asp Leu Leu Asn
    210                 215                 220
Gly Ser Glu Tyr Val Pro Thr Tyr Glu Asp Lys Asp Gly Asp Trp Met
225                 230                 235                 240
Leu Val Gly Asp Val Pro Trp Glu Met Phe Val Gly Ser Cys Lys Arg
                245                 250                 255
Leu Arg Ile Met Lys Gly Ser Glu Ala Ile Gly Leu Ala Pro Arg Ala
```

```
                260               265               270
Val Glu Lys Cys Lys Asn Arg Ser
        275               280
```

<210> SEQ ID NO 220
<211> LENGTH: 843
<212> TYPE: DNA
<213> ORGANISM: Kochia scoparia

<400> SEQUENCE: 220

```
atgttgagta acgagagaga caagtacacg atcgatttcg aggagacgga gctcaggctt    60
gggctcgggc tcgggatcgg gctggcgggg gctgctgacg gggatcagtt ggcgaagaat   120
aataacggga gagggggtt ttctgagacg gaaggcgact ccagtgttga cttgaagctt   180
aatctgtcgt cctcaacaac gacgacagcc agcactacca ccaccaacac caccgcaacc   240
aaaactacag cggagaacgt gaaagagtca agttggata aaagtgtcaa ttccggcgtt   300
gatcagaagt tgaaggagaa agttgcttct accactgctg atcctgctaa gcctacacca   360
gctaagacac aagttgtaaa ttggccaccc gttagagcgt tcaggaagaa catcgtcgcg   420
gcccaaaaga gacgtccga tgatcaaact gatcagaagg cttctagcaa tgccatcaca   480
agcgccgcgt ttgtgaaggt tagcatggat ggtgcgcctt acttgcgtaa agtggacttg   540
aaattgtaca agagttatca agaccttct gatgctttgg gcaagatgtt cagttctttt   600
accataggta attgcgggtc acagggaatg aaggattca tgaacgagag caaattgatt   660
gatcttctga tggttccga gtacgtgcca acttatgaag ataaagatgg cgattggatg   720
cttgttggcg acgtgccatg ggagatgttc gtcggatcat gcaaacgcct ccgaatcatg   780
aagggatcag aagccattgg actagcacca agggcagttg agaagtgcaa gaacagaagc   840
tga                                                                 843
```

<210> SEQ ID NO 221
<211> LENGTH: 24
<212> TYPE: DNA
<213> ORGANISM: Artificial sequence
<220> FEATURE:
<223> OTHER INFORMATION: Primer

<400> SEQUENCE: 221

```
gtaagttaat cacgtaacta attc                                           24
```

<210> SEQ ID NO 222
<211> LENGTH: 20
<212> TYPE: DNA
<213> ORGANISM: Artificial sequence
<220> FEATURE:
<223> OTHER INFORMATION: Primer

<400> SEQUENCE: 222

```
gctagaagcc ttctgatcag                                                20
```

<210> SEQ ID NO 223
<211> LENGTH: 31
<212> TYPE: DNA
<213> ORGANISM: Artificial sequence
<220> FEATURE:
<223> OTHER INFORMATION: Primer

<400> SEQUENCE: 223

```
cgtaactaat tcttaattgt tgttcttca g                                    31
```

```
<210> SEQ ID NO 224
<211> LENGTH: 19
<212> TYPE: DNA
<213> ORGANISM: Artificial sequence
<220> FEATURE:
<223> OTHER INFORMATION: Primer

<400> SEQUENCE: 224
tgaacgctct aacgggtgg                                                19

<210> SEQ ID NO 225
<211> LENGTH: 16
<212> TYPE: DNA
<213> ORGANISM: Artificial sequence
<220> FEATURE:
<223> OTHER INFORMATION: Probe

<400> SEQUENCE: 225
cacaagttgt aaattg                                                   16

<210> SEQ ID NO 226
<211> LENGTH: 17
<212> TYPE: DNA
<213> ORGANISM: Artificial sequence
<220> FEATURE:
<223> OTHER INFORMATION: Probe

<400> SEQUENCE: 226
cacaagttgt aggttgg                                                  17

<210> SEQ ID NO 227
<211> LENGTH: 24
<212> TYPE: DNA
<213> ORGANISM: Artificial sequence
<220> FEATURE:
<223> OTHER INFORMATION: Primer

<400> SEQUENCE: 227
atgttgagta acgagagaga caag                                          24

<210> SEQ ID NO 228
<211> LENGTH: 24
<212> TYPE: DNA
<213> ORGANISM: Artificial sequence
<220> FEATURE:
<223> OTHER INFORMATION: Primer

<400> SEQUENCE: 228
tcagcttctg ttcttgcact tctc                                          24

<210> SEQ ID NO 229
<211> LENGTH: 25
<212> TYPE: DNA
<213> ORGANISM: Artificial sequence
<220> FEATURE:
<223> OTHER INFORMATION: Primer

<400> SEQUENCE: 229
caccatggag caacaccaac cccag                                         25

<210> SEQ ID NO 230
<211> LENGTH: 21
<212> TYPE: DNA
<213> ORGANISM: Artificial sequence
<220> FEATURE:
<223> OTHER INFORMATION: Primer
```

<400> SEQUENCE: 230
cttcttagca atcagctcaa g    21

<210> SEQ ID NO 231
<211> LENGTH: 26
<212> TYPE: DNA
<213> ORGANISM: Artificial sequence
<220> FEATURE:
<223> OTHER INFORMATION: Primer

<400> SEQUENCE: 231
caccatgaat tatttcccag aagaag    26

<210> SEQ ID NO 232
<211> LENGTH: 23
<212> TYPE: DNA
<213> ORGANISM: Artificial sequence
<220> FEATURE:
<223> OTHER INFORMATION: Primer

<400> SEQUENCE: 232
ctacaaggtc catacgaatt ctg    23

<210> SEQ ID NO 233
<211> LENGTH: 30
<212> TYPE: DNA
<213> ORGANISM: Artificial sequence
<220> FEATURE:
<223> OTHER INFORMATION: Primer

<400> SEQUENCE: 233
caccatgggt tcaaaaaagt gcaaaaattc    30

<210> SEQ ID NO 234
<211> LENGTH: 23
<212> TYPE: DNA
<213> ORGANISM: Artificial sequence
<220> FEATURE:
<223> OTHER INFORMATION: Primer

<400> SEQUENCE: 234
tcatagcgtc agaacaaaag gag    23

<210> SEQ ID NO 235
<211> LENGTH: 27
<212> TYPE: DNA
<213> ORGANISM: Artificial sequence
<220> FEATURE:
<223> OTHER INFORMATION: Primer

<400> SEQUENCE: 235
caccatgaga gagggcaccg ataacag    27

<210> SEQ ID NO 236
<211> LENGTH: 21
<212> TYPE: DNA
<213> ORGANISM: Artificial sequence
<220> FEATURE:
<223> OTHER INFORMATION: Primer

<400> SEQUENCE: 236
ctacaatatc ctcacatgtt c    21

<210> SEQ ID NO 237

```
<211> LENGTH: 48
<212> TYPE: DNA
<213> ORGANISM: Artificial sequence
<220> FEATURE:
<223> OTHER INFORMATION: Primer

<400> SEQUENCE: 237
tacgacgtac cagattacgc tcatatgttg agtaacgaga gagacaag                    48

<210> SEQ ID NO 238
<211> LENGTH: 45
<212> TYPE: DNA
<213> ORGANISM: Artificial sequence
<220> FEATURE:
<223> OTHER INFORMATION: Primer

<400> SEQUENCE: 238
agctcgagct cgatggatcc cgagaagtgc aagaacagaa gctga                       45

<210> SEQ ID NO 239
<211> LENGTH: 45
<212> TYPE: DNA
<213> ORGANISM: Artificial sequence
<220> FEATURE:
<223> OTHER INFORMATION: Primer

<400> SEQUENCE: 239
ctgatctcag aggaggacct gcatatggag caacaccaac cccag                       45

<210> SEQ ID NO 240
<211> LENGTH: 48
<212> TYPE: DNA
<213> ORGANISM: Artificial sequence
<220> FEATURE:
<223> OTHER INFORMATION: Primer

<400> SEQUENCE: 240
ggccgctgca ggtcgacgga tcccttattc agtgcacaac ggtgatgc                    48

<210> SEQ ID NO 241
<211> LENGTH: 46
<212> TYPE: DNA
<213> ORGANISM: Artificial sequence
<220> FEATURE:
<223> OTHER INFORMATION: Primer

<400> SEQUENCE: 241
ctgatctcag aggaggacct gcatatgaat tatttcccag aagaag                      46

<210> SEQ ID NO 242
<211> LENGTH: 47
<212> TYPE: DNA
<213> ORGANISM: Artificial sequence
<220> FEATURE:
<223> OTHER INFORMATION: Primer

<400> SEQUENCE: 242
ggccgctgca ggtcgacgga tcccctacaa ggtccatacg aattctg                     47

<210> SEQ ID NO 243
<211> LENGTH: 47
<212> TYPE: DNA
<213> ORGANISM: Artificial sequence
<220> FEATURE:
<223> OTHER INFORMATION: Primer

<400> SEQUENCE: 243
```

```
ctgatctcag aggaggacct gcatatgaga gagggcaccg ataacag                           47
```

<210> SEQ ID NO 244
<211> LENGTH: 45
<212> TYPE: DNA
<213> ORGANISM: Artificial sequence
<220> FEATURE:
<223> OTHER INFORMATION: Primer

<400> SEQUENCE: 244

```
ggccgctgca ggtcgacgga tcccctacaa tatcctcaca tgttc                            45
```

<210> SEQ ID NO 245
<211> LENGTH: 50
<212> TYPE: DNA
<213> ORGANISM: Artificial sequence
<220> FEATURE:
<223> OTHER INFORMATION: Primer

<400> SEQUENCE: 245

```
ctgatctcag aggaggacct gcatatgggt tcaaaaaagt gcaaaaattc                       50
```

<210> SEQ ID NO 246
<211> LENGTH: 47
<212> TYPE: DNA
<213> ORGANISM: Artificial sequence
<220> FEATURE:
<223> OTHER INFORMATION: Primer

<400> SEQUENCE: 246

```
ggccgctgca ggtcgacgga tccctcatag cgtcagaaca aaaggag                          47
```

<210> SEQ ID NO 247
<211> LENGTH: 168
<212> TYPE: PRT
<213> ORGANISM: Arabidopsis thaliana

<400> SEQUENCE: 247

```
Met Glu Val Thr Asn Gly Leu Asn Leu Lys Asp Thr Glu Leu Arg Leu
1               5                   10                  15

Gly Leu Pro Gly Ala Gln Glu Gln Gln Leu Glu Leu Ser Cys Val
            20                  25                  30

Arg Ser Asn Asn Lys Arg Lys Asn Asn Asp Ser Thr Glu Glu Ser Ala
        35                  40                  45

Pro Pro Pro Ala Lys Thr Gln Ile Val Gly Trp Pro Pro Val Arg Ser
    50                  55                  60

Asn Arg Lys Asn Asn Asn Lys Asn Val Ser Tyr Val Lys Val Ser
65                  70                  75                  80

Met Asp Gly Ala Pro Tyr Leu Arg Lys Ile Asp Leu Lys Met Tyr Lys
                85                  90                  95

Asn Tyr Pro Glu Leu Leu Lys Ala Leu Glu Asn Met Phe Lys Phe Thr
            100                 105                 110

Val Gly Glu Tyr Ser Glu Arg Glu Gly Tyr Lys Gly Ser Gly Phe Val
        115                 120                 125

Pro Thr Tyr Glu Asp Lys Asp Gly Asp Trp Met Leu Val Gly Asp Val
    130                 135                 140

Pro Trp Asp Met Phe Ser Ser Ser Cys Gln Lys Leu Arg Ile Met Lys
145                 150                 155                 160

Gly Ser Glu Ala Pro Thr Ala Leu
                165
```

<210> SEQ ID NO 248
<211> LENGTH: 174
<212> TYPE: PRT
<213> ORGANISM: Arabidopsis thaliana

<400> SEQUENCE: 248

Met Ala Tyr Glu Lys Val Asn Glu Leu Asn Leu Lys Asp Thr Glu Leu
1               5                   10                  15

Cys Leu Gly Leu Pro Gly Arg Thr Glu Lys Ile Lys Glu Glu Gln Glu
            20                  25                  30

Val Ser Cys Val Lys Ser Asn Asn Lys Arg Leu Phe Glu Glu Thr Arg
        35                  40                  45

Asp Glu Glu Ser Thr Pro Pro Thr Lys Thr Gln Ile Val Gly Trp
    50                  55                  60

Pro Pro Val Arg Ser Ser Arg Lys Asn Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
            100                 105                 110

Lys Val Met Ile Gly Glu Tyr Cys Glu Arg Glu Gly Tyr Lys Gly Ser
        115                 120                 125

Gly Phe Val Pro Thr Tyr Glu Asp Lys Asp Gly Asp Trp Met Leu Val
    130                 135                 140

Gly Asp Val Pro Trp Asp Met Phe Ser Ser Cys Lys Arg Leu Arg
145                 150                 155                 160

Ile Met Lys Gly Ser Asp Ala Pro Ala Leu Asp Ser Ser Leu
                165                 170

<210> SEQ ID NO 249
<211> LENGTH: 189
<212> TYPE: PRT
<213> ORGANISM: Arabidopsis thaliana

<400> SEQUENCE: 249

Met Asp Glu Phe Val Asn Leu Lys Glu Thr Glu Leu Arg Leu Gly Leu
1               5                   10                  15

Pro Gly Thr Asp Asn Val Cys Glu Ala Lys Glu Arg Val Ser Cys Cys
            20                  25                  30

Asn Asn Asn Asn Lys Arg Val Leu Ser Thr Asp Thr Glu Lys Glu Ile
            35                  40                  45

Glu Ser Ser Ser Arg Lys Thr Glu Thr Ser Pro Pro Arg Lys Ala Gln
    50                  55                  60

Ile Val Gly Trp Pro Pro Val Arg Ser Tyr Arg Lys Asn Asn Ile Gln
65                  70                  75                  80

Ser Lys Lys Asn Glu Ser Glu His Glu Gly Gln Gly Ile Tyr Val Lys
                85                  90                  95

Val Ser Met Asp Gly Ala Pro Tyr Leu Arg Lys Ile Asp Leu Ser Cys
            100                 105                 110

Tyr Lys Gly Tyr Ser Glu Leu Leu Lys Ala Leu Glu Val Met Phe Lys
        115                 120                 125

Phe Ser Val Gly Glu Tyr Phe Glu Arg Asp Gly Tyr Lys Gly Ser Asp
    130                 135                 140

Phe Val Pro Thr Tyr Glu Asp Lys Asp Gly Asp Trp Met Leu Ile Gly
145                 150                 155                 160

Asp Val Pro Trp Glu Met Phe Ile Cys Thr Cys Lys Arg Leu Arg Ile
                165                 170                 175

Met Lys Gly Ser Glu Ala Lys Gly Leu Gly Cys Gly Val
            180                 185

<210> SEQ ID NO 250
<211> LENGTH: 186
<212> TYPE: PRT
<213> ORGANISM: Arabidopsis thaliana

<400> SEQUENCE: 250

Met Glu Lys Val Asp Val Tyr Asp Glu Leu Val Asn Leu Lys Ala Thr
1               5                   10                  15

Glu Leu Arg Leu Gly Leu Pro Gly Thr Glu Thr Val Ser Cys Gly
            20                  25                  30

Lys Ser Asn Lys Arg Val Leu Pro Glu Ala Thr Glu Lys Glu Ile Glu
        35                  40                  45

Ser Thr Gly Lys Thr Glu Thr Ala Ser Pro Pro Lys Ala Gln Ile Val
    50                  55                  60

Gly Trp Pro Pro Val Arg Ser Tyr Arg Lys Asn Asn Val Gln Thr Lys
65                  70                  75                  80

Lys Ser Glu Ser Glu Gly Gln Gly Asn Tyr Val Lys Val Ser Met Asp
                85                  90                  95

Gly Ala Pro Tyr Leu Arg Lys Ile Asp Leu Thr Met Tyr Lys Gln Tyr
            100                 105                 110

Pro Glu Leu Met Lys Ser Leu Glu Asn Met Phe Lys Phe Ser Val Gly
        115                 120                 125

Glu Tyr Phe Glu Arg Glu Gly Tyr Lys Gly Ser Asp Phe Val Pro Thr
    130                 135                 140

Tyr Glu Asp Lys Asp Gly Asp Trp Met Leu Val Gly Asp Val Pro Trp
145                 150                 155                 160

Glu Met Phe Val Ser Ser Cys Lys Arg Leu Arg Ile Met Lys Gly Ser
                165                 170                 175

Glu Val Lys Gly Leu Gly Cys Gly Gly Leu
            180                 185

<210> SEQ ID NO 251
<211> LENGTH: 163
<212> TYPE: PRT
<213> ORGANISM: Arabidopsis thaliana

<400> SEQUENCE: 251

Met Ala Asn Glu Ser Asn Asn Leu Gly Leu Glu Ile Thr Glu Leu Arg
1               5                   10                  15

Leu Gly Leu Pro Gly Asp Ile Val Val Ser Gly Glu Ser Ile Ser Gly
            20                  25                  30

Lys Lys Arg Ala Ser Pro Glu Val Glu Ile Asp Leu Lys Cys Glu Pro
        35                  40                  45

Ala Lys Lys Ser Gln Val Val Gly Trp Pro Pro Val Cys Ser Tyr Arg
    50                  55                  60

Arg Lys Asn Ser Leu Glu Arg Thr Lys Ser Ser Tyr Val Lys Val Ser
65                  70                  75                  80

Val Asp Gly Ala Ala Phe Leu Arg Lys Ile Asp Leu Glu Met Tyr Lys
                85                  90                  95

Cys Tyr Gln Asp Leu Ala Ser Ala Leu Gln Ile Leu Phe Gly Cys Tyr
            100                 105                 110

```
Ile Asn Phe Asp Asp Thr Leu Lys Glu Ser Glu Cys Val Pro Ile Tyr
        115                 120                 125

Glu Asp Lys Asp Gly Asp Trp Met Leu Ala Gly Asp Val Pro Trp Glu
130                 135                 140

Met Phe Leu Gly Ser Cys Lys Arg Leu Arg Ile Met Lys Arg Ser Cys
145                 150                 155                 160

Asn Arg Gly

<210> SEQ ID NO 252
<211> LENGTH: 189
<212> TYPE: PRT
<213> ORGANISM: Arabidopsis thaliana

<400> SEQUENCE: 252

Met Ala Lys Glu Gly Leu Ala Leu Glu Ile Thr Glu Leu Arg Leu Gly
1               5                   10                  15

Leu Pro Gly Asp Asn Tyr Ser Glu Ile Ser Val Cys Gly Ser Ser Lys
            20                  25                  30

Lys Lys Lys Arg Val Leu Ser Asp Met Met Thr Ser Ser Ala Leu Asp
        35                  40                  45

Thr Glu Asn Glu Asn Ser Val Val Ser Val Glu Asp Glu Ser Leu
    50                  55                  60

Pro Val Val Lys Ser Gln Ala Val Gly Trp Pro Pro Val Cys Ser Tyr
65                  70                  75                  80

Arg Arg Lys Lys Asn Asn Glu Glu Ala Ser Lys Ala Ile Gly Tyr Val
                85                  90                  95

Lys Val Ser Met Asp Gly Val Pro Tyr Met Arg Lys Ile Asp Leu Gly
            100                 105                 110

Ser Ser Asn Ser Tyr Ile Asn Leu Val Thr Val Leu Glu Asn Leu Phe
        115                 120                 125

Gly Cys Leu Gly Ile Gly Val Ala Lys Glu Gly Lys Lys Cys Glu Tyr
    130                 135                 140

Ile Ile Ile Tyr Glu Asp Lys Asp Arg Asp Trp Met Leu Val Gly Asp
145                 150                 155                 160

Val Pro Trp Gln Met Phe Lys Glu Ser Cys Lys Arg Leu Arg Ile Val
                165                 170                 175

Lys Arg Ser Asp Ala Thr Gly Phe Gly Leu Gln Gln Asp
            180                 185

<210> SEQ ID NO 253
<211> LENGTH: 243
<212> TYPE: PRT
<213> ORGANISM: Arabidopsis thaliana

<400> SEQUENCE: 253

Met Ile Gly Gln Leu Met Asn Leu Lys Ala Thr Glu Leu Cys Leu Gly
1               5                   10                  15

Leu Pro Gly Gly Ala Glu Ala Val Glu Ser Pro Ala Lys Ser Ala Val
            20                  25                  30

Gly Ser Lys Arg Gly Phe Ser Glu Thr Val Asp Leu Met Leu Asn Leu
        35                  40                  45

Gln Ser Asn Lys Glu Gly Ser Val Asp Leu Lys Asn Val Ser Ala Val
    50                  55                  60

Pro Lys Glu Lys Thr Thr Leu Lys Asp Pro Ser Lys Pro Pro Ala Lys
65                  70                  75                  80
```

```
Ala Gln Val Val Gly Trp Pro Pro Val Arg Asn Tyr Arg Lys Asn Met
                85                  90                  95

Met Thr Gln Gln Lys Thr Ser Ser Gly Ala Glu Glu Ala Ser Ser Glu
           100                 105                 110

Lys Ala Gly Asn Phe Gly Gly Gly Ala Ala Gly Ala Gly Leu Val Lys
       115                 120                 125

Val Ser Met Asp Gly Ala Pro Tyr Leu Arg Lys Val Asp Leu Lys Met
130                 135                 140

Tyr Lys Ser Tyr Gln Asp Leu Ser Asp Ala Leu Ala Lys Met Phe Ser
145                 150                 155                 160

Ser Phe Thr Met Gly Asn Tyr Gly Ala Gln Gly Met Ile Asp Phe Met
               165                 170                 175

Asn Glu Ser Lys Leu Met Asn Leu Leu Asn Ser Ser Glu Tyr Val Pro
           180                 185                 190

Ser Tyr Glu Asp Lys Asp Gly Asp Trp Met Leu Val Gly Asp Val Pro
       195                 200                 205

Trp Glu Met Phe Val Glu Ser Cys Lys Arg Leu Arg Ile Met Lys Gly
       210                 215                 220

Ser Glu Ala Val Gly Leu Ala Pro Arg Ala Met Glu Lys Tyr Cys Lys
225                 230                 235                 240

Asn Arg Ser

<210> SEQ ID NO 254
<211> LENGTH: 321
<212> TYPE: PRT
<213> ORGANISM: Arabidopsis thaliana

<400> SEQUENCE: 254

Met Ser Tyr Arg Leu Leu Ser Val Asp Lys Asp Glu Leu Val Thr Ser
1               5                   10                  15

Pro Cys Leu Lys Glu Arg Asn Tyr Leu Gly Leu Ser Asp Cys Ser Ser
           20                  25                  30

Val Asp Ser Ser Thr Ile Pro Asn Val Val Gly Lys Ser Asn Leu Asn
       35                  40                  45

Phe Lys Ala Thr Glu Leu Arg Leu Gly Leu Pro Glu Ser Gln Ser Pro
   50                  55                  60

Glu Arg Glu Thr Asp Phe Gly Leu Leu Ser Pro Arg Thr Pro Asp Glu
65                  70                  75                  80

Lys Leu Leu Phe Pro Leu Leu Pro Ser Lys Asp Asn Gly Ser Ala Thr
               85                  90                  95

Thr Gly His Lys Asn Val Val Ser Gly Asn Lys Arg Gly Phe Ala Asp
           100                 105                 110

Thr Trp Asp Glu Phe Ser Gly Val Lys Gly Ser Val Arg Pro Gly Gly
       115                 120                 125

Gly Ile Asn Met Met Leu Ser Pro Lys Val Lys Asp Val Ser Lys Ser
130                 135                 140

Ile Gln Glu Glu Arg Ser His Ala Lys Gly Gly Leu Asn Asn Ala Pro
145                 150                 155                 160

Ala Ala Lys Ala Gln Val Val Gly Trp Pro Pro Ile Arg Ser Tyr Arg
               165                 170                 175

Lys Asn Thr Met Ala Ser Ser Thr Ser Lys Asn Thr Asp Glu Val Asp
           180                 185                 190

Gly Lys Pro Gly Leu Gly Val Leu Phe Val Lys Val Ser Met Asp Gly
       195                 200                 205
```

```
Ala Pro Tyr Leu Arg Lys Val Asp Leu Arg Thr Tyr Thr Ser Tyr Gln
    210                 215                 220

Gln Leu Ser Ser Ala Leu Glu Lys Met Phe Ser Cys Phe Thr Leu Gly
225                 230                 235                 240

Gln Cys Gly Leu His Gly Ala Gln Gly Arg Glu Arg Met Ser Glu Ile
                245                 250                 255

Lys Leu Lys Asp Leu Leu His Gly Ser Glu Phe Val Leu Thr Tyr Glu
            260                 265                 270

Asp Lys Asp Gly Asp Trp Met Leu Val Gly Asp Val Pro Trp Glu Ile
        275                 280                 285

Phe Thr Glu Thr Cys Gln Lys Leu Lys Ile Met Lys Gly Ser Asp Ser
    290                 295                 300

Ile Gly Leu Ala Pro Gly Ala Val Glu Lys Ser Lys Asn Lys Glu Arg
305                 310                 315                 320

Val

<210> SEQ ID NO 255
<211> LENGTH: 336
<212> TYPE: PRT
<213> ORGANISM: Arabidopsis thaliana

<400> SEQUENCE: 255

Met Ser Pro Glu Glu Glu Leu Gln Ser Asn Val Ser Val Ala Ser Ser
1               5                   10                  15

Ser Pro Thr Ser Asn Cys Ile Ser Arg Asn Thr Leu Gly Gly Leu Lys
            20                  25                  30

Glu His Asn Tyr Leu Gly Leu Ser Asp Cys Ser Ser Val Gly Ser Ser
        35                  40                  45

Thr Leu Ser Pro Leu Ala Glu Asp Asp Lys Ala Thr Ile Ser Leu Lys
    50                  55                  60

Ala Thr Glu Leu Thr Leu Gly Leu Pro Gly Ser Gln Ser Pro Ala Arg
65                  70                  75                  80

Asp Thr Glu Leu Asn Leu Leu Ser Pro Ala Lys Leu Asp Glu Lys Pro
                85                  90                  95

Phe Phe Pro Leu Leu Pro Ser Lys Asp Glu Ile Cys Ser Ser Ser Gln
            100                 105                 110

Lys Asn Asn Ala Ser Gly Asn Lys Arg Gly Phe Ser Asp Thr Met Asp
        115                 120                 125

Gln Phe Ala Glu Ala Lys Ser Ser Val Tyr Thr Glu Lys Asn Trp Met
130                 135                 140

Phe Pro Glu Ala Ala Ala Thr Gln Ser Val Thr Lys Lys Asp Val Pro
145                 150                 155                 160

Gln Asn Ile Pro Lys Gly Gln Ser Ser Thr Thr Asn Asn Ser Ser Ser
                165                 170                 175

Pro Pro Ala Ala Lys Ala Gln Ile Val Gly Trp Pro Pro Val Arg Ser
            180                 185                 190

Tyr Arg Lys Asn Thr Leu Ala Thr Thr Cys Lys Asn Ser Asp Glu Val
        195                 200                 205

Asp Gly Arg Pro Gly Ser Gly Ala Leu Phe Val Lys Val Ser Met Asp
    210                 215                 220

Gly Ala Pro Tyr Leu Arg Lys Val Asp Leu Arg Ser Tyr Thr Asn Tyr
225                 230                 235                 240

Gly Glu Leu Ser Ser Ala Leu Glu Lys Met Phe Thr Thr Phe Thr Leu
                245                 250                 255
```

```
Gly Gln Cys Gly Ser Asn Gly Ala Ala Gly Lys Asp Met Leu Ser Glu
                260                 265                 270

Thr Lys Leu Lys Asp Leu Leu Asn Gly Lys Asp Tyr Val Leu Thr Tyr
            275                 280                 285

Glu Asp Lys Asp Gly Asp Trp Met Leu Val Gly Asp Val Pro Trp Glu
        290                 295                 300

Met Phe Ile Asp Val Cys Lys Leu Lys Ile Met Lys Gly Cys Asp
305                 310                 315                 320

Ala Ile Gly Leu Ala Pro Arg Ala Met Glu Lys Ser Lys Met Arg Ala
                325                 330                 335

<210> SEQ ID NO 256
<211> LENGTH: 261
<212> TYPE: PRT
<213> ORGANISM: Arabidopsis thaliana

<400> SEQUENCE: 256

Met Asn Gly Leu Gln Glu Val Cys Ser Ser Gly Ser Val Met Ile
1               5                   10                  15

Gly Leu Pro Ala Glu Glu Asp Glu Asn Ala Ala His Ser Ser Glu Asp
                20                  25                  30

Ser Ser Cys Pro Asp Glu Ser Val Ser Glu Thr Glu Leu Asp Leu Ala
            35                  40                  45

Leu Gly Leu Ser Ile Gly Arg Arg Lys Val Arg Ser Ser Leu Ser Ser
50                  55                  60

Ser Ser Ser Ser Leu Thr Arg Glu Ser Gly Thr Lys Arg Ser Ala Asp
65                  70                  75                  80

Ser Ser Pro Ala Ala Ala Ser Asn Ala Thr Arg Gln Val Ala Val Gly
                85                  90                  95

Trp Pro Pro Leu Arg Thr Tyr Arg Ile Asn Ser Leu Val Asn Gln Ala
                100                 105                 110

Lys Ser Leu Ala Thr Glu Gly Gly Leu Ser Ser Gly Ile Gln Lys Glu
            115                 120                 125

Thr Thr Lys Ser Val Val Val Ala Ala Lys Asn Asp Asp Ala Cys Phe
130                 135                 140

Ile Lys Ser Ser Arg Thr Ser Met Leu Val Lys Val Thr Met Asp Gly
145                 150                 155                 160

Val Ile Ile Gly Arg Lys Val Asp Leu Asn Ala Leu Asp Ser Tyr Ala
                165                 170                 175

Ala Leu Glu Lys Thr Leu Asp Leu Met Phe Phe Gln Ile Pro Ser Pro
            180                 185                 190

Val Thr Arg Ser Asn Thr Gln Gly Tyr Lys Thr Ile Lys Glu Thr Cys
        195                 200                 205

Thr Ser Lys Leu Leu Asp Gly Ser Ser Glu Tyr Ile Ile Thr Tyr Gln
    210                 215                 220

Asp Lys Asp Gly Asp Trp Met Leu Val Gly Asp Val Pro Trp Gln Met
225                 230                 235                 240

Phe Leu Gly Ser Val Thr Arg Leu Arg Ile Met Lys Thr Ser Ile Gly
                245                 250                 255

Ala Gly Val Gly Lys
            260

<210> SEQ ID NO 257
<211> LENGTH: 246
<212> TYPE: PRT
<213> ORGANISM: Arabidopsis thaliana
```

<400> SEQUENCE: 257

```
Met Glu Gly Gly Ser Ala Ser Gly Ser Ala Ser Ala Leu Ser Asn Asp
1               5                   10                  15

Glu Asn Leu Val Val Ser Cys Glu Asp Ser Ser Pro Ile Gly Asn
            20                  25                  30

Glu Leu Glu Leu Gly Leu Thr Leu Ser Leu Gly Arg Lys Gly Tyr Arg
            35                  40                  45

Asp Cys Arg Val Tyr Ala Asp Asp Ser Ser Ser Ser Ser Ser Ser Ser
    50                  55                  60

Ser Leu Ser Arg Ala Ser Val Ile Ala Gly Ile Lys Arg Thr Ala Asp
65                  70                  75                  80

Ser Met Ala Ala Thr Ser Gly Gln Val Val Gly Trp Pro Pro Ile Arg
                85                  90                  95

Thr Tyr Arg Met Asn Ser Met Val Asn Gln Ala Lys Ala Ser Ala Thr
            100                 105                 110

Glu Asp Pro Asn Leu Glu Ile Ser Gln Ala Val Asn Lys Asn Arg Ser
            115                 120                 125

Asp Ser Thr Lys Met Arg Asn Ser Met Phe Val Lys Val Thr Met Asp
130                 135                 140

Gly Ile Pro Ile Gly Arg Lys Ile Asp Leu Asn Ala His Lys Cys Tyr
145                 150                 155                 160

Glu Ser Leu Ser Asn Thr Leu Glu Glu Met Phe Leu Lys Pro Lys Leu
                165                 170                 175

Gly Ser Arg Thr Leu Glu Thr Asp Gly His Met Glu Thr Pro Val Lys
            180                 185                 190

Ile Leu Pro Asp Gly Ser Ser Gly Leu Val Leu Thr Tyr Glu Asp Lys
            195                 200                 205

Glu Gly Asp Trp Met Leu Val Gly Asp Val Pro Trp Gly Met Phe Ile
210                 215                 220

Gly Ser Val Arg Arg Leu Arg Ile Met Lys Thr Ser Glu Ala Thr Gly
225                 230                 235                 240

Lys Ala Gln Met Ile Leu
                245
```

<210> SEQ ID NO 258
<211> LENGTH: 239
<212> TYPE: PRT
<213> ORGANISM: Arabidopsis thaliana

<400> SEQUENCE: 258

```
Met Arg Gly Val Ser Glu Leu Glu Val Gly Lys Ser Asn Leu Pro Ala
1               5                   10                  15

Glu Ser Glu Leu Glu Leu Gly Leu Gly Leu Ser Leu Gly Gly Gly Ala
            20                  25                  30

Trp Lys Glu Arg Gly Arg Ile Leu Thr Ala Lys Asp Phe Pro Ser Val
            35                  40                  45

Gly Ser Lys Arg Ser Ala Glu Ser Ser Ser His Gln Gly Ala Ser Pro
    50                  55                  60

Pro Arg Ser Ser Gln Val Val Gly Trp Pro Pro Ile Gly Leu His Arg
65                  70                  75                  80

Met Asn Ser Leu Val Asn Asn Gln Ala Met Lys Ala Ala Arg Ala Glu
                85                  90                  95

Glu Gly Asp Gly Glu Lys Lys Val Val Lys Asn Asp Glu Leu Lys Asp
            100                 105                 110
```

```
Val Ser Met Lys Val Asn Pro Lys Val Gln Gly Leu Gly Phe Val Lys
        115                 120                 125

Val Asn Met Asp Gly Val Gly Ile Gly Arg Lys Val Asp Met Arg Ala
130                 135                 140

His Ser Ser Tyr Glu Asn Leu Ala Gln Thr Leu Glu Glu Met Phe Phe
145                 150                 155                 160

Gly Met Thr Gly Thr Thr Cys Arg Glu Lys Val Lys Pro Leu Arg Leu
                165                 170                 175

Leu Asp Gly Ser Ser Asp Phe Val Leu Thr Tyr Glu Asp Lys Glu Gly
            180                 185                 190

Asp Trp Met Leu Val Gly Asp Val Pro Trp Arg Met Phe Ile Asn Ser
        195                 200                 205

Val Lys Arg Leu Arg Ile Met Gly Thr Ser Glu Ala Ser Gly Leu Ala
    210                 215                 220

Pro Arg Arg Gln Glu Gln Lys Asp Arg Gln Arg Asn Asn Pro Val
225                 230                 235

<210> SEQ ID NO 259
<211> LENGTH: 247
<212> TYPE: PRT
<213> ORGANISM: Arabidopsis thaliana

<400> SEQUENCE: 259

Met Ile Thr Glu Leu Glu Met Gly Lys Gly Ser Glu Leu Glu Leu
1               5                   10                  15

Gly Leu Gly Leu Ser Leu Gly Gly Thr Ala Ala Lys Ile Gly Lys
            20                  25                  30

Ser Gly Gly Gly Gly Ala Trp Gly Glu Arg Gly Arg Leu Leu Thr Ala
        35                  40                  45

Lys Asp Phe Pro Ser Val Gly Ser Lys Arg Ala Ala Asp Ser Ala Ser
    50                  55                  60

His Ala Gly Ser Ser Pro Pro Arg Ser Ser Gln Val Val Gly Trp
65                  70                  75                  80

Pro Pro Ile Gly Ser His Arg Met Asn Ser Leu Val Asn Asn Gln Ala
                85                  90                  95

Thr Lys Ser Ala Arg Glu Glu Glu Ala Gly Lys Lys Lys Val Lys
            100                 105                 110

Asp Asp Glu Pro Lys Asp Val Thr Lys Val Asn Gly Lys Val Gln
        115                 120                 125

Val Gly Phe Ile Lys Val Asn Met Asp Gly Val Ala Ile Gly Arg Lys
    130                 135                 140

Val Asp Leu Asn Ala His Ser Ser Tyr Glu Asn Leu Ala Gln Thr Leu
145                 150                 155                 160

Glu Asp Met Phe Phe Arg Thr Asn Pro Gly Thr Val Gly Leu Thr Ser
                165                 170                 175

Gln Phe Thr Lys Pro Leu Arg Leu Leu Asp Gly Ser Ser Glu Phe Val
            180                 185                 190

Leu Thr Tyr Glu Asp Lys Glu Gly Asp Trp Met Leu Val Gly Asp Val
        195                 200                 205

Pro Trp Arg Met Phe Ile Asn Ser Val Lys Arg Leu Arg Val Met Lys
    210                 215                 220

Thr Ser Glu Ala Asn Gly Leu Ala Ala Arg Asn Gln Glu Pro Asn Glu
225                 230                 235                 240

Arg Gln Arg Lys Gln Pro Val
```

<210> SEQ ID NO 260
<211> LENGTH: 228
<212> TYPE: PRT
<213> ORGANISM: Arabidopsis thaliana

<400> SEQUENCE: 260

Met Asn Leu Lys Glu Thr Glu Leu Cys Leu Gly Leu Pro Gly Gly Thr
1               5                   10                  15

Glu Thr Val Glu Ser Pro Ala Lys Ser Gly Val Gly Asn Lys Arg Gly
            20                  25                  30

Phe Ser Glu Thr Val Asp Leu Lys Leu Asn Leu Gln Ser Asn Lys Gln
        35                  40                  45

Gly His Val Asp Leu Asn Thr Asn Gly Ala Pro Lys Glu Lys Thr Phe
    50                  55                  60

Leu Lys Asp Pro Ser Lys Pro Pro Ala Lys Ala Gln Val Val Gly Trp
65                  70                  75                  80

Pro Pro Val Arg Asn Tyr Arg Lys Asn Val Met Ala Asn Gln Lys Ser
                85                  90                  95

Gly Glu Ala Glu Ala Met Ser Ser Gly Gly Thr Val Ala Phe
            100                 105                 110

Val Lys Val Ser Met Asp Gly Ala Pro Tyr Leu Arg Lys Val Asp Leu
        115                 120                 125

Lys Met Tyr Thr Ser Tyr Lys Asp Leu Ser Asp Ala Leu Ala Lys Met
    130                 135                 140

Phe Ser Ser Phe Thr Met Gly Ser Tyr Gly Ala Gln Gly Met Ile Asp
145                 150                 155                 160

Phe Met Asn Glu Ser Lys Val Met Asp Leu Leu Asn Ser Ser Glu Tyr
                165                 170                 175

Val Pro Ser Tyr Glu Asp Lys Asp Gly Asp Trp Met Leu Val Gly Asp
            180                 185                 190

Val Pro Trp Pro Met Phe Val Glu Ser Cys Lys Arg Leu Arg Ile Met
        195                 200                 205

Lys Gly Ser Glu Ala Ile Gly Leu Ala Pro Arg Ala Met Glu Lys Phe
    210                 215                 220

Lys Asn Arg Ser
225

<210> SEQ ID NO 261
<211> LENGTH: 179
<212> TYPE: PRT
<213> ORGANISM: Arabidopsis thaliana

<400> SEQUENCE: 261

Met Ser Pro Glu Glu Tyr Val Arg Val Trp Pro Asp Ser Gly Asp Leu
1               5                   10                  15

Gly Gly Thr Glu Leu Thr Leu Ala Leu Pro Gly Thr Pro Thr Asn Ala
            20                  25                  30

Ser Glu Gly Pro Lys Lys Phe Gly Asn Lys Arg Arg Phe Leu Glu Thr
        35                  40                  45

Val Asp Leu Lys Leu Gly Glu Ala His Glu Asn Asn Tyr Ile Ser Ser
    50                  55                  60

Met Val Thr Asn Asp Gln Leu Val Gly Trp Pro Pro Val Ala Thr Ala
65                  70                  75                  80

Arg Lys Thr Val Arg Arg Lys Tyr Val Lys Val Ala Leu Asp Gly Ala

```
                            85                  90                  95
Ala Tyr Leu Arg Lys Val Asp Leu Gly Met Tyr Asp Cys Tyr Gly Gln
                100                 105                 110

Leu Phe Thr Ala Leu Glu Asn Met Phe Gln Gly Ile Ile Thr Ile Cys
            115                 120                 125

Arg Val Thr Glu Leu Glu Arg Lys Gly Glu Phe Val Ala Thr Tyr Glu
        130                 135                 140

Asp Lys Asp Gly Asp Leu Met Leu Val Gly Asp Val Pro Trp Met Met
145                 150                 155                 160

Phe Val Glu Ser Cys Lys Arg Met Arg Leu Met Lys Thr Gly Asp Ala
                165                 170                 175

Ile Gly Leu

<210> SEQ ID NO 262
<211> LENGTH: 236
<212> TYPE: PRT
<213> ORGANISM: Arabidopsis thaliana

<400> SEQUENCE: 262

Met Ile Asn Phe Glu Ala Thr Glu Leu Arg Leu Gly Leu Pro Gly Gly
1               5                   10                  15

Asn His Gly Gly Glu Met Ala Gly Lys Asn Asn Gly Lys Arg Gly Phe
            20                  25                  30

Ser Glu Thr Val Asp Leu Lys Leu Asn Leu Ser Ser Thr Ala Met Asp
        35                  40                  45

Ser Val Ser Lys Val Asp Leu Glu Asn Met Lys Glu Lys Val Val Lys
    50                  55                  60

Pro Pro Ala Lys Ala Gln Val Val Gly Trp Pro Pro Val Arg Ser Phe
65                  70                  75                  80

Arg Lys Asn Val Met Ser Gly Gln Lys Pro Thr Thr Gly Asp Ala Thr
                85                  90                  95

Glu Gly Asn Asp Lys Thr Ser Gly Ser Ser Gly Ala Thr Ser Ser Ala
            100                 105                 110

Ser Ala Cys Ala Thr Val Ala Tyr Val Lys Val Ser Met Asp Gly Ala
        115                 120                 125

Pro Tyr Leu Arg Lys Ile Asp Leu Lys Leu Tyr Lys Thr Tyr Gln Asp
    130                 135                 140

Leu Ser Asn Ala Leu Ser Lys Met Phe Ser Ser Phe Thr Ile Gly Asn
145                 150                 155                 160

Tyr Gly Pro Gln Gly Met Lys Asp Phe Met Asn Glu Ser Lys Leu Ile
                165                 170                 175

Asp Leu Leu Asn Gly Ser Asp Tyr Val Pro Thr Tyr Glu Asp Lys Asp
            180                 185                 190

Gly Asp Trp Met Leu Val Gly Asp Val Pro Trp Glu Met Phe Val Asp
        195                 200                 205

Ser Cys Lys Arg Ile Arg Ile Met Lys Gly Ser Glu Ala Ile Gly Leu
    210                 215                 220

Ala Pro Arg Ala Leu Glu Lys Cys Lys Asn Arg Ser
225                 230                 235

<210> SEQ ID NO 263
<211> LENGTH: 229
<212> TYPE: PRT
<213> ORGANISM: Arabidopsis thaliana

<400> SEQUENCE: 263
```

Met Met Gly Ser Val Glu Leu Asn Leu Arg Glu Thr Glu Leu Cys Leu
1               5                   10                  15

Gly Leu Pro Gly Gly Asp Thr Val Ala Pro Val Thr Gly Asn Lys Arg
                20                  25                  30

Gly Phe Ser Glu Thr Val Asp Leu Lys Leu Asn Leu Asn Asn Glu Pro
            35                  40                  45

Ala Asn Lys Glu Gly Ser Thr Thr His Asp Val Thr Phe Asp Ser
50                      55                  60

Lys Glu Lys Ser Ala Cys Pro Lys Asp Pro Ala Lys Pro Pro Ala Lys
65                  70                  75                  80

Ala Gln Val Val Gly Trp Pro Pro Val Arg Ser Tyr Arg Lys Asn Val
                85                  90                  95

Met Val Ser Cys Gln Lys Ser Ser Gly Gly Pro Glu Ala Ala Ala Phe
                100                 105                 110

Val Lys Val Ser Met Asp Gly Ala Pro Tyr Leu Arg Lys Ile Asp Leu
            115                 120                 125

Arg Met Tyr Lys Ser Tyr Asp Glu Leu Ser Asn Ala Leu Ser Asn Met
        130                 135                 140

Phe Ser Ser Phe Thr Met Gly Lys His Gly Gly Glu Glu Gly Met Ile
145                 150                 155                 160

Asp Phe Met Asn Glu Arg Lys Leu Met Asp Leu Val Asn Ser Trp Asp
                165                 170                 175

Tyr Val Pro Ser Tyr Glu Asp Lys Asp Gly Asp Trp Met Leu Val Gly
            180                 185                 190

Asp Val Pro Trp Pro Met Phe Val Asp Thr Cys Lys Arg Leu Arg Leu
        195                 200                 205

Met Lys Gly Ser Asp Ala Ile Gly Leu Ala Pro Arg Ala Met Glu Lys
210                 215                 220

Cys Lys Ser Arg Ala
225

<210> SEQ ID NO 264
<211> LENGTH: 267
<212> TYPE: PRT
<213> ORGANISM: Arabidopsis thaliana

<400> SEQUENCE: 264

Met Glu Gly Tyr Ser Arg Asn Gly Glu Ile Ser Pro Lys Leu Leu Asp
1               5                   10                  15

Leu Met Ile Pro Gln Glu Arg Arg Asn Trp Phe His Asp Glu Lys Asn
                20                  25                  30

Ser Val Phe Lys Thr Glu Glu Lys Leu Glu Leu Lys Leu Gly Pro
            35                  40                  45

Pro Gly Glu Glu Asp Asp Glu Ser Met Ile Arg His Met Lys Lys
50                  55                  60

Glu Pro Lys Asp Lys Ser Ile Leu Ser Leu Ala Gly Lys Tyr Phe Ser
65                  70                  75                  80

Pro Ser Ser Thr Lys Thr Thr Ser His Lys Arg Thr Ala Pro Gly Pro
                85                  90                  95

Val Val Gly Trp Pro Pro Val Arg Ser Phe Arg Lys Asn Leu Ala Ser
            100                 105                 110

Gly Ser Ser Ser Lys Leu Gly Asn Asp Ser Thr Thr Ser Asn Gly Val
        115                 120                 125

Thr Leu Lys Asn Gln Lys Cys Asp Ala Ala Ala Lys Thr Thr Glu Pro

```
                    130                 135                 140
Lys Arg Gln Gly Gly Met Phe Val Lys Ile Asn Met Tyr Gly Val Pro
145                 150                 155                 160

Ile Gly Arg Lys Val Asp Leu Ser Ala His Asn Ser Tyr Glu Gln Leu
                165                 170                 175

Ser Phe Thr Val Asp Lys Leu Phe Arg Gly Leu Leu Ala Ala Gln Arg
                180                 185                 190

Asp Phe Pro Ser Ser Ile Glu Asp Lys Pro Ile Thr Gly Leu Leu
                195                 200                 205

Asp Gly Asn Gly Glu Tyr Thr Leu Thr Tyr Glu Asp Asn Glu Gly Asp
            210                 215                 220

Lys Met Leu Val Gly Asp Val Pro Trp Gln Met Phe Val Ser Ser Val
225                 230                 235                 240

Lys Arg Leu Arg Val Ile Lys Thr Ser Glu Ile Ser Ser Ala Leu Thr
                245                 250                 255

Tyr Gly Asn Gly Lys Gln Glu Lys Met Arg Arg
            260                 265

<210> SEQ ID NO 265
<211> LENGTH: 197
<212> TYPE: PRT
<213> ORGANISM: Arabidopsis thaliana

<400> SEQUENCE: 265

Met Glu Lys Glu Gly Leu Gly Leu Glu Ile Thr Glu Leu Arg Leu Gly
1               5                   10                  15

Leu Pro Gly Arg Asp Val Ala Glu Lys Met Met Lys Lys Arg Ala Phe
                20                  25                  30

Thr Glu Met Asn Met Thr Ser Ser Gly Ser Asn Ser Asp Gln Cys Glu
            35                  40                  45

Ser Gly Val Val Ser Ser Gly Gly Asp Ala Glu Lys Val Asn Asp Ser
        50                  55                  60

Pro Ala Ala Lys Ser Gln Val Val Gly Trp Pro Pro Val Cys Ser Tyr
65                  70                  75                  80

Arg Lys Lys Asn Ser Cys Lys Glu Ala Ser Thr Thr Lys Val Gly Leu
                85                  90                  95

Gly Tyr Val Lys Val Ser Met Asp Gly Val Pro Tyr Leu Arg Lys Met
                100                 105                 110

Asp Leu Gly Ser Ser Gln Gly Tyr Asp Asp Leu Ala Phe Ala Leu Asp
            115                 120                 125

Lys Leu Phe Gly Phe Arg Gly Ile Gly Val Ala Leu Lys Asp Gly Asp
        130                 135                 140

Asn Cys Glu Tyr Val Thr Ile Tyr Glu Asp Lys Asp Gly Asp Trp Met
145                 150                 155                 160

Leu Ala Gly Asp Val Pro Trp Gly Met Phe Leu Glu Ser Cys Lys Arg
                165                 170                 175

Leu Arg Ile Met Lys Arg Ser Asp Ala Thr Gly Phe Gly Leu Gln Pro
                180                 185                 190

Arg Gly Val Asp Glu
        195

<210> SEQ ID NO 266
<211> LENGTH: 175
<212> TYPE: PRT
<213> ORGANISM: Arabidopsis thaliana
```

<400> SEQUENCE: 266

| | | | | | | | | | | | | | | |
|---|---|---|---|---|---|---|---|---|---|---|---|---|---|---|
| Met | Gly | Arg | Gly | Arg | Ser | Ser | Ser | Ser | Ile | Glu | Ser | Ser | Ser | |
| 1 | | | | 5 | | | | | 10 | | | | | 15 |
| Lys | Ser | Asn | Pro | Phe | Gly | Ala | Ser | Ser | Thr | Arg | Asn | Leu | Ser | Thr |
| | | | 20 | | | | | 25 | | | | | 30 | |
| Asp | Leu | Arg | Leu | Gly | Leu | Ser | Phe | Gly | Thr | Ser | Ser | Gly | Thr | Gln | Tyr |
| | | 35 | | | | | 40 | | | | | 45 | | |
| Phe | Asn | Gly | Gly | Tyr | Gly | Tyr | Ser | Val | Ala | Ala | Pro | Ala | Val | Glu | Asp |
| | 50 | | | | | 55 | | | | | 60 | | | |
| Ala | Glu | Tyr | Val | Ala | Ala | Val | Glu | Glu | Glu | Glu | Asn | Glu | Cys | Asn |
| 65 | | | | | 70 | | | | | 75 | | | | | 80 |
| Ser | Val | Gly | Ser | Phe | Tyr | Val | Lys | Val | Asn | Met | Glu | Gly | Val | Pro | Ile |
| | | | | 85 | | | | | 90 | | | | | 95 |
| Gly | Arg | Lys | Ile | Asp | Leu | Met | Ser | Leu | Asn | Gly | Tyr | Arg | Asp | Leu | Ile |
| | | | 100 | | | | | 105 | | | | | 110 | |
| Arg | Thr | Leu | Asp | Phe | Met | Phe | Asn | Ala | Ser | Ile | Leu | Trp | Ala | Glu | Glu |
| | | 115 | | | | | 120 | | | | | 125 | | |
| Glu | Asp | Met | Cys | Asn | Glu | Lys | Ser | His | Val | Leu | Thr | Tyr | Ala | Asp | Lys |
| | 130 | | | | | 135 | | | | | 140 | | | |
| Glu | Gly | Asp | Trp | Met | Met | Val | Gly | Asp | Val | Pro | Trp | Glu | Met | Phe | Leu |
| 145 | | | | | 150 | | | | | 155 | | | | | 160 |
| Ser | Thr | Val | Arg | Arg | Leu | Lys | Ile | Ser | Arg | Ala | Asn | Tyr | His | Tyr |
| | | | | 165 | | | | | 170 | | | | | 175 |

<210> SEQ ID NO 267
<211> LENGTH: 269
<212> TYPE: PRT
<213> ORGANISM: Arabidopsis thaliana

<400> SEQUENCE: 267

| | | | | | | | | | | | | | | | |
|---|---|---|---|---|---|---|---|---|---|---|---|---|---|---|---|
| Met | Glu | Gly | Cys | Pro | Arg | Asn | Arg | Glu | Ile | Gly | Pro | Lys | Leu | Leu | Asp |
| 1 | | | | 5 | | | | | 10 | | | | | 15 | |
| Leu | Ile | Pro | Gln | Gly | Arg | Lys | Trp | Tyr | Gln | Glu | Asp | Lys | Asn | Asn | Thr |
| | | | 20 | | | | | 25 | | | | | 30 | | |
| Asp | Gln | Glu | Lys | Lys | Leu | Glu | Leu | Arg | Leu | Gly | Pro | Pro | Gly | Gly | Asp |
| | | 35 | | | | | 40 | | | | | 45 | | | |
| Glu | Glu | Asp | His | Ser | Ala | Ile | Lys | Lys | Asn | Thr | Glu | Ile | Arg | Asn |
| | 50 | | | | | 55 | | | | | 60 | | | |
| Ile | Lys | Lys | Glu | Thr | Glu | Asp | Lys | Ser | Phe | His | Cys | Phe | Asn | Gly | Asn |
| 65 | | | | | 70 | | | | | 75 | | | | | 80 |
| His | Phe | Ser | Pro | Ser | Asn | Lys | Thr | Thr | Ser | Val | Pro | His | Ile | Ser | Gln |
| | | | | 85 | | | | | 90 | | | | | 95 |
| Lys | Arg | Thr | Ala | Pro | Gly | Pro | Val | Val | Gly | Trp | Pro | Val | Arg | Ser |
| | | | 100 | | | | | 105 | | | | | 110 | |
| Phe | Arg | Lys | Asn | Leu | Ala | Ser | Thr | Ser | Ser | Lys | Leu | Gly | Asn | Glu |
| | | 115 | | | | | 120 | | | | | 125 | | |
| Ser | Ser | His | Gly | Gly | Gln | Ile | Asn | Lys | Ser | Asp | Asp | Gly | Glu | Lys | Gln |
| | 130 | | | | | 135 | | | | | 140 | | | |
| Val | Glu | Thr | Lys | Lys | Glu | Gly | Met | Phe | Val | Lys | Ile | Asn | Met | Asp | Gly |
| 145 | | | | | 150 | | | | | 155 | | | | | 160 |
| Val | Pro | Ile | Gly | Arg | Lys | Val | Asp | Leu | Asn | Ala | Tyr | Asn | Ser | Tyr | Glu |
| | | | 165 | | | | | 170 | | | | | 175 |
| Gln | Leu | Ser | Phe | Val | Val | Asp | Lys | Leu | Phe | Arg | Gly | Leu | Leu | Ala | Ala |
| | | | 180 | | | | | 185 | | | | | 190 |

```
Gln Arg Asp Ile Ser Asp Gly Gln Gly Glu Lys Pro Ile Ile Gly
        195                 200                 205

Leu Leu Asp Gly Lys Gly Glu Phe Thr Leu Thr Tyr Glu Asp Asn Glu
    210                 215                 220

Gly Asp Lys Met Leu Val Gly Asp Val Pro Trp Gln Met Phe Val Ser
225                 230                 235                 240

Ser Val Lys Arg Leu Arg Val Ile Lys Ser Ser Glu Ile Ser Ser Ala
                245                 250                 255

Leu Thr Phe Gly Cys Ser Lys Gln Glu Lys Met Met His
        260                 265

<210> SEQ ID NO 268
<211> LENGTH: 305
<212> TYPE: PRT
<213> ORGANISM: Arabidopsis thaliana

<400> SEQUENCE: 268

Met Ser Val Ser Val Ala Ala Glu His Asp Tyr Ile Gly Leu Ser Glu
1               5                   10                  15

Phe Pro Thr Met Glu Ala Thr Thr Met Ser Asp Lys Thr Lys Thr Arg
            20                  25                  30

Asp Asn Asn Asn Gly Leu Asn Phe Lys Ala Thr Glu Leu Arg Leu Gly
        35                  40                  45

Leu Pro Gly Ser Glu Ser Pro Glu Arg Val Asp Ser Arg Phe Leu Ala
    50                  55                  60

Leu Asn Lys Ser Ser Cys Pro Val Ser Gly Ala Lys Arg Val Phe Ser
65                  70                  75                  80

Asp Ala Ile Asn Asp Ser Asn Lys Trp Val Phe Ser Pro Gly Ser Thr
                85                  90                  95

Thr Ala Thr Gly Asp Val Gly Ser Gly Ser Gly Pro Arg Thr Ser Val
            100                 105                 110

Val Lys Asp Gly Lys Ser Thr Thr Phe Thr Lys Pro Ala Val Pro Val
        115                 120                 125

Lys Glu Lys Lys Ser Ser Ala Thr Ala Pro Ala Ser Lys Ala Gln Val
    130                 135                 140

Val Gly Trp Pro Pro Ile Arg Ser Phe Arg Lys Asn Ser Met Ala Ser
145                 150                 155                 160

Ser Gln Ser Gln Lys Pro Gly Asn Asn Ser Glu Thr Glu Glu Ala Glu
                165                 170                 175

Ala Lys Ser Gly Pro Glu Gln Pro Cys Leu Tyr Val Lys Val Ser Met
            180                 185                 190

Glu Gly Ala Pro Tyr Leu Arg Lys Ile Asp Leu Lys Thr Tyr Lys Ser
        195                 200                 205

Tyr Leu Glu Leu Ser Ser Ala Leu Glu Lys Met Phe Ser Cys Phe Thr
    210                 215                 220

Ile Gly Gln Phe Gly Ser His Gly Gly Cys Gly Arg Asp Gly Leu Asn
225                 230                 235                 240

Glu Ser Arg Leu Thr Asp Leu Leu Arg Gly Ser Glu Tyr Val Val Thr
                245                 250                 255

Tyr Glu Asp Lys Asp Ser Asp Trp Met Leu Val Gly Asp Val Pro Trp
            260                 265                 270

Glu Met Phe Ile Cys Ser Cys Lys Lys Leu Arg Ile Met Lys Ser Ser
        275                 280                 285

Glu Ala Ile Gly Leu Ala Pro Arg Val Met Glu Lys Cys Arg Ser Arg
    290                 295                 300
```

Asn
305

<210> SEQ ID NO 269
<211> LENGTH: 175
<212> TYPE: PRT
<213> ORGANISM: Arabidopsis thaliana

<400> SEQUENCE: 269

```
Met Glu Glu Glu Lys Arg Leu Glu Leu Arg Leu Ala Pro Pro Cys His
1               5                   10                  15

Gln Phe Thr Ser Asn Asn Asn Ile Asn Gly Ser Lys Gln Lys Ser Ser
            20                  25                  30

Thr Lys Glu Thr Ser Phe Leu Ser Asn Asn Arg Val Glu Val Ala Pro
        35                  40                  45

Val Val Gly Trp Pro Pro Val Arg Ser Ser Arg Arg Asn Leu Thr Ala
    50                  55                  60

Gln Leu Lys Glu Glu Met Lys Lys Glu Ser Asp Glu Glu Lys Glu
65                  70                  75                  80

Leu Tyr Val Lys Ile Asn Met Glu Gly Val Pro Ile Gly Arg Lys Val
            85                  90                  95

Asn Leu Ser Ala Tyr Asn Asn Tyr Gln Gln Leu Ser His Ala Val Asp
            100                 105                 110

Gln Leu Phe Ser Lys Lys Asp Ser Trp Asp Leu Asn Arg Gln Tyr Thr
        115                 120                 125

Leu Val Tyr Glu Asp Thr Glu Gly Asp Lys Val Leu Val Gly Asp Val
    130                 135                 140

Pro Trp Glu Met Phe Val Ser Thr Val Lys Arg Leu His Val Leu Lys
145                 150                 155                 160

Thr Ser His Ala Phe Ser Leu Ser Pro Arg Lys His Gly Lys Glu
            165                 170                 175
```

<210> SEQ ID NO 270
<211> LENGTH: 251
<212> TYPE: PRT
<213> ORGANISM: Arabidopsis thaliana

<400> SEQUENCE: 270

```
Met Glu Leu Asp Leu Gly Leu Ser Leu Ser Pro His Lys Ser Ser Lys
1               5                   10                  15

Leu Gly Phe Asn Phe Asp Leu Asn Lys His Cys Ala Ile Glu Gly Ala
            20                  25                  30

Ala Ser Cys Leu Gly Thr Glu Lys Leu Arg Phe Glu Ala Thr Phe Gly
        35                  40                  45

Leu Gly Asn Val Glu Glu Asn Cys Tyr Met Pro Lys Gln Arg Leu Phe
    50                  55                  60

Ala Leu Asn Gly Gln Pro Asn Glu Glu Asp Pro Leu Glu Ser
65                  70                  75                  80

Glu Ser Ser Ile Val Tyr Asp Asp Glu Glu Glu Asn Ser Glu Val Val
            85                  90                  95

Gly Trp Pro Pro Val Lys Thr Cys Met Ile Lys Tyr Gly Ser Tyr His
            100                 105                 110

His Arg His Ile Arg Asn His His Cys Pro Tyr His His Arg Gly
        115                 120                 125

Arg Arg Ile Thr Ala Met Asn Asn Asn Ile Ser Asn Pro Thr Thr Ala
    130                 135                 140
```

```
Thr Val Gly Ser Ser Ser Ser Ile Ser Ser Arg Ser Met
145                 150                 155                 160

Tyr Val Lys Val Lys Met Asp Gly Val Ala Ile Ala Arg Lys Val Asp
                165                 170                 175

Ile Lys Leu Phe Asn Ser Tyr Glu Ser Leu Thr Asn Ser Leu Ile Thr
            180                 185                 190

Met Phe Thr Glu Tyr Glu Asp Cys Asp Arg Glu Asp Thr Asn Tyr Thr
        195                 200                 205

Phe Thr Phe Gln Gly Lys Glu Gly Asp Trp Leu Leu Arg Gly Asp Val
    210                 215                 220

Thr Trp Lys Ile Phe Ala Glu Ser Val His Arg Ile Ser Ile Ile Arg
225                 230                 235                 240

Asp Arg Pro Cys Ala Tyr Thr Arg Cys Leu Phe
                245                 250
```

<210> SEQ ID NO 271
<211> LENGTH: 172
<212> TYPE: PRT
<213> ORGANISM: Arabidopsis thaliana

<400> SEQUENCE: 271

```
Met Gly Arg Gly Arg Ser Ser Ser Ser Ile Glu Ser Ser Cys
1               5                   10                  15

Lys Ser Asn Pro Phe Gly Val Ser Ser Asn Thr Arg Asn Leu Ser
            20                  25                  30

Thr Asp Leu Arg Leu Gly Leu Ser Phe Gly Ser Ser Gly Gln Tyr
        35                  40                  45

Tyr Asn Gly Gly Asp Asn His Glu Tyr Asp Gly Val Gly Ala Ala Glu
    50                  55                  60

Glu Met Met Ile Met Glu Glu Glu Gln Asn Glu Cys Asn Ser Val
65                  70                  75                  80

Gly Ser Phe Tyr Val Lys Val Asn Met Glu Gly Val Pro Ile Gly Arg
                85                  90                  95

Lys Ile Asp Leu Leu Ser Leu Asn Gly Tyr His Asp Leu Ile Thr Thr
            100                 105                 110

Leu Asp Tyr Met Phe Asn Ala Ser Ile Leu Trp Ala Glu Glu Glu Asp
        115                 120                 125

Met Cys Ser Glu Lys Ser His Val Leu Thr Tyr Ala Asp Lys Glu Gly
    130                 135                 140

Asp Trp Met Met Val Gly Asp Val Pro Trp Glu Met Phe Leu Ser Ser
145                 150                 155                 160

Val Arg Arg Leu Lys Ile Ser Arg Ala Tyr His Tyr
                165                 170
```

<210> SEQ ID NO 272
<211> LENGTH: 158
<212> TYPE: PRT
<213> ORGANISM: Arabidopsis thaliana

<400> SEQUENCE: 272

```
Met Glu Val Ser Asn Ser Cys Ser Ser Phe Ser Ser Ser Val Asp
1               5                   10                  15

Ser Thr Lys Pro Ser Pro Ser Glu Ser Ser Val Asn Leu Ser Leu Ser
            20                  25                  30

Leu Thr Phe Pro Ser Thr Ser Pro Gln Arg Glu Ala Arg Gln Asp Trp
        35                  40                  45
```

Pro Pro Ile Lys Ser Arg Leu Arg Asp Thr Leu Lys Gly Arg Arg Leu
 50                  55                  60

Leu Arg Arg Gly Asp Asp Thr Ser Leu Phe Val Lys Val Tyr Met Glu
65                  70                  75                  80

Gly Val Pro Ile Gly Arg Lys Leu Asp Leu Cys Val Phe Ser Gly Tyr
                85                  90                  95

Glu Ser Leu Leu Glu Asn Leu Ser His Met Phe Asp Thr Ser Ile Ile
            100                 105                 110

Cys Gly Asn Arg Asp Arg Lys His His Val Leu Thr Tyr Glu Asp Lys
        115                 120                 125

Asp Gly Asp Trp Met Met Val Gly Asp Ile Pro Trp Asp Met Phe Leu
    130                 135                 140

Glu Thr Val Arg Arg Leu Lys Ile Thr Arg Pro Glu Arg Tyr
145                 150                 155

<210> SEQ ID NO 273
<211> LENGTH: 191
<212> TYPE: PRT
<213> ORGANISM: Arabidopsis thaliana

<400> SEQUENCE: 273

Met Asp Pro Asn Thr Pro Ala Asp Phe Phe Lys Gly Ser Ser Lys Phe
1               5                   10                  15

His Thr Tyr Tyr Ser Gln Thr Lys Lys Gly Gly Val Ile Asp Leu
            20                  25                  30

Gly Leu Ser Leu Arg Thr Ile Gln His Glu Thr Tyr Leu Pro Pro Ala
        35                  40                  45

Arg Met Ile Gly Leu Asp Gly Tyr Gly Glu Leu Ile Asp Trp Ser Gln
    50                  55                  60

Pro Ser Tyr Asn Ser Ile Thr Gln Leu Lys Ser Glu Asp Thr Gly His
65                  70                  75                  80

Gln Arg Leu Ala Gln Gly Tyr Tyr Asn Asn Glu Gly Glu Ser Arg Gly
                85                  90                  95

Lys Tyr Ala Tyr Val Lys Val Asn Leu Asp Gly Leu Val Val Gly Arg
            100                 105                 110

Lys Val Cys Leu Val Asp Gln Gly Ala Tyr Ala Thr Leu Ala Leu Gln
        115                 120                 125

Leu Asn Asp Met Phe Gly Met Gln Thr Val Ser Gly Leu Arg Leu Phe
    130                 135                 140

Gln Thr Glu Ser Glu Phe Ser Leu Val Tyr Arg Asp Arg Glu Gly Ile
145                 150                 155                 160

Trp Arg Asn Val Gly Asp Val Pro Trp Lys Glu Phe Val Glu Ser Val
                165                 170                 175

Asp Arg Met Arg Ile Ala Arg Arg Asn Asp Ala Leu Leu Pro Phe
            180                 185                 190

<210> SEQ ID NO 274
<211> LENGTH: 171
<212> TYPE: PRT
<213> ORGANISM: Arabidopsis thaliana

<400> SEQUENCE: 274

Met Asn Ser Phe Glu Pro Gln Ser Gln Asp Ser Leu Gln Arg Arg Phe
1               5                   10                  15

His Gln Asp Asn Ser Thr Thr Gln Gln Pro Arg Asp Thr Thr Thr Pro
            20                  25                  30

Phe Ile Pro Lys Pro Ala Ser Lys Asn His Asn Asn Ser Asn Ser Ser
            35                  40                  45

Ser Gly Ala Ala Gly Arg Ser Phe Gln Gly Phe Gly Leu Asn Val Glu
    50                  55                  60

Asp Asp Leu Val Ser Ser Val Val Pro Val Thr Val Val Leu Glu
65                  70                  75                  80

Gly Arg Ser Ile Cys Gln Arg Ile Ser Leu Asp Lys His Gly Ser Tyr
                    85                  90                  95

Gln Ser Leu Ala Ser Ala Leu Arg Gln Met Phe Val Asp Gly Ala Asp
                100                 105                 110

Ser Thr Asp Asp Leu Asp Leu Ser Asn Ala Ile Pro Gly His Leu Ile
                115                 120                 125

Ala Tyr Glu Asp Met Glu Asn Asp Leu Leu Ala Gly Asp Leu Thr
            130                 135                 140

Trp Lys Asp Phe Val Arg Val Ala Lys Arg Ile Arg Ile Leu Pro Val
145                 150                 155                 160

Lys Gly Asn Thr Arg Gln Val Lys Arg Asn Glu
                165                 170

<210> SEQ ID NO 275
<211> LENGTH: 185
<212> TYPE: PRT
<213> ORGANISM: Arabidopsis thaliana

<400> SEQUENCE: 275

Met Tyr Cys Ser Asp Pro Pro His Pro Leu His Leu Val Ala Ser Asp
1               5                   10                  15

Lys Gln Gln Lys Asp His Lys Leu Ile Leu Ser Trp Lys Lys Pro Thr
            20                  25                  30

Met Asp Ser Asp Pro Leu Gly Val Phe Pro Asn Ser Pro Lys Tyr His
            35                  40                  45

Pro Tyr Tyr Ser Gln Thr Thr Glu Phe Gly Gly Val Ile Asp Leu Gly
    50                  55                  60

Leu Ser Leu Arg Thr Ile Gln His Glu Ile Tyr His Ser Ser Gly Gln
65                  70                  75                  80

Arg Tyr Cys Ser Asn Glu Gly Tyr Arg Arg Lys Trp Gly Tyr Val Lys
                85                  90                  95

Val Thr Met Asp Gly Leu Val Val Gly Arg Lys Val Cys Val Leu Asp
                100                 105                 110

His Gly Ser Tyr Ser Thr Leu Ala His Gln Leu Glu Asp Met Phe Gly
            115                 120                 125

Met Gln Ser Val Ser Gly Leu Arg Leu Phe Gln Met Glu Ser Glu Phe
            130                 135                 140

Cys Leu Val Tyr Arg Asp Glu Glu Gly Leu Trp Arg Asn Ala Gly Asp
145                 150                 155                 160

Val Pro Trp Asn Glu Phe Ile Glu Ser Val Glu Arg Leu Arg Ile Thr
                165                 170                 175

Arg Arg Asn Asp Ala Val Leu Pro Phe
            180                 185

<210> SEQ ID NO 276
<211> LENGTH: 200
<212> TYPE: PRT
<213> ORGANISM: Kochia scoparia

<400> SEQUENCE: 276

Met Ala Ala Arg Ser Glu Thr Tyr Glu Asn Asp Leu His Leu Glu Ala
1               5                   10                  15

Thr Glu Leu Arg Leu Gly Leu Pro Gly Ser Lys Asp Ser Glu Lys Gln
            20                  25                  30

Asp Thr Ser Asn Asn Ala Val Arg Ser Val Asn Lys Arg Ser Ser Pro
        35                  40                  45

Asp Gln Val Pro Glu Asp Ser Ser Ser Thr Asn Asn Ser Ser Ile Ser
    50                  55                  60

Asp Ala Arg Asn Asp Asp Gly Pro Pro Ser Lys Thr Gln Ile Val
65                  70                  75                  80

Gly Trp Pro Pro Ile Arg Ser Tyr Arg Lys Asn Thr Phe Gln Pro Lys
                85                  90                  95

Lys Ser Glu Ala Asp Ala Ser Gly Met Tyr Val Lys Val Ser Met Asp
                100                 105                 110

Gly Ala Pro Tyr Leu Arg Lys Ile Asp Leu Lys Val Tyr Gln Ser Tyr
                115                 120                 125

Pro Glu Leu Leu Lys Ala Met Glu Asn Met Phe Lys Ile Cys Ile Gly
    130                 135                 140

Thr Tyr Ser Glu Arg Asp Gly Tyr Asn Gly Ser Asp Val Ala Pro Thr
145                 150                 155                 160

Tyr Glu Asp Lys Asp Gly Asp Trp Met Leu Val Gly Asp Val Pro Trp
                165                 170                 175

Glu Met Phe Ile Thr Ser Cys Lys Arg Leu Arg Ile Met Lys Ser Ser
                180                 185                 190

Glu Ala Lys Gly Leu Gly Cys Leu
                195                 200

<210> SEQ ID NO 277
<211> LENGTH: 189
<212> TYPE: PRT
<213> ORGANISM: Kochia scoparia

<400> SEQUENCE: 277

Met Glu Ile Ile Lys Lys Gly Ile Glu His Asp Asp Thr Glu Leu Arg
1               5                   10                  15

Leu Gly Leu Pro Gly Thr Glu Phe Lys Thr Pro Thr Pro Gln Thr
            20                  25                  30

Gln Thr Asn Lys Arg Ser Phe Ser Asp Ile Lys Glu Ser Thr Ser
        35                  40                  45

Asn Asp Ala Asp Lys Ser Ala Asn Ile Thr Ser Ala Pro Pro Lys
    50                  55                  60

Ala Gln Val Met Gly Trp Pro Pro Val Arg Asn Tyr Arg Lys Asn Cys
65                  70                  75                  80

Leu Gln Ala Met Lys Lys Glu Ala Glu Asn Ala Gly Val Tyr Val Lys
                85                  90                  95

Val Ser Met Asp Gly Ala Ala Tyr Leu Arg Lys Ile Asp Met Lys Leu
                100                 105                 110

Tyr Lys Gly Tyr Ser Glu Leu Leu Lys Ala Leu Asp Asp Met Phe Lys
            115                 120                 125

Val Lys Leu Gly Glu Tyr Ser Glu Arg Glu Gly Tyr Asn Gly Thr Glu
    130                 135                 140

Phe Val Pro Thr Tyr Glu Asp Lys Asp Gly Asp Trp Met Leu Leu Gly
145                 150                 155                 160

Asp Val Pro Trp Asp Met Phe Ile Asn Ser Cys Lys Arg Leu Arg Ile

```
                    165                 170                 175
Met Lys Gly Ser Asp Ala Arg Gly Leu Gly Cys Leu Ala
            180                 185

<210> SEQ ID NO 278
<211> LENGTH: 188
<212> TYPE: PRT
<213> ORGANISM: Kochia scoparia

<400> SEQUENCE: 278

Met Ser Lys Ala Gly Phe Glu His Glu Ile Thr Glu Leu Arg Leu Gly
1               5                   10                  15

Leu Pro Thr Arg Ser Ser Cys Arg Asp Gln Gly Glu Val Val Asn
            20                  25                  30

Lys Asn Glu Lys Lys Arg Val Tyr Ser Ser Ile Glu Glu Arg Ala Glu
        35                  40                  45

Lys Pro Ala Leu Val Val Gly Ser Asn Lys Ser Pro Ala Val Gly Trp
    50                  55                  60

Pro Pro Val Cys Ser Tyr Arg Arg Ser Ile Gly Ser Glu Lys Glu
65              70                  75                  80

Cys Met Glu Ala Ser Lys Arg Leu Val Lys Ile Ser Met Asp Gly Val
                85                  90                  95

Pro Phe Leu Arg Lys Ile Asp Val Asn Ser Tyr Lys Gln Tyr Ser Asp
            100                 105                 110

Leu Val Ala Ala Val Glu Leu Leu Phe Ala Cys Ser Arg Ile Lys Glu
        115                 120                 125

Ala Leu Glu Asp Ala Asp Asn Ser Glu Tyr Ile Pro Ile Tyr Glu Asp
    130                 135                 140

Lys Asp Gly Asp Trp Leu Leu Val Gly Asp Val Pro Trp Asn Met Phe
145                 150                 155                 160

Val Glu Ser Cys Lys Arg Leu Arg Ile Met Lys Arg Ala Asp Ala Lys
                165                 170                 175

Gly Phe Gly Leu Gln Ser Lys Lys His Cys His Gly
            180                 185

<210> SEQ ID NO 279
<211> LENGTH: 192
<212> TYPE: PRT
<213> ORGANISM: Kochia scoparia

<400> SEQUENCE: 279

Met Gly Thr Gln Glu Val Ser Ser Leu Asp Tyr Lys Glu Thr Glu Leu
1               5                   10                  15

Thr Leu Gly Ile Pro Gly Lys Lys Val Ser Asn Ser Glu Asp Lys Ser
            20                  25                  30

Leu Leu Lys Arg Arg Tyr Ser Asp Thr Leu Asp Leu Asn Leu Gly Arg
        35                  40                  45

His Ala Lys Asn Asp Gln Thr Thr Ser Ser Pro Ala Asn Pro Ser
    50                  55                  60

Lys Asn Gln Leu Val Gly Trp Pro Pro Val Arg Ala Ser Arg Lys Asn
65              70                  75                  80

Val Met Lys Ser Tyr Lys Tyr Val Lys Val Ala Val Asp Gly Ala Pro
                85                  90                  95

Tyr Leu Arg Lys Val Asp Leu Glu Leu Tyr Asn Ser Tyr Gln Glu Leu
            100                 105                 110

Leu Lys Ala Leu Glu Asp Met Phe Ser Ser Phe Thr Ile Arg Asn Phe
```

115                 120                 125
Phe Asn Asp Gly Lys Leu Met Asp Pro Asn Gly Ser Asp Tyr Val Pro
    130                 135                 140

Thr Tyr Glu Asp Lys Asp Gly Asp Trp Met Met Val Gly Asp Thr Pro
145                 150                 155                 160

Trp Lys Met Phe Val Glu Ser Cys Lys Arg Ile Arg Leu Met Lys Ser
                165                 170                 175

Ser Glu Ala Val Gly Leu Glu Pro Arg Thr Ser Ser Ser Thr Val Asp
            180                 185                 190

<210> SEQ ID NO 280
<211> LENGTH: 329
<212> TYPE: PRT
<213> ORGANISM: Kochia scoparia

<400> SEQUENCE: 280

Met Ser Ser Pro Leu Glu His Asp Tyr Ile Gly Leu Ser Glu Val Ser
1               5                   10                  15

Ser Met Glu Asn Ser Ala Val Lys Pro Asn Tyr Lys Ala Lys Ala Ser
                20                  25                  30

Ala Leu Lys Thr Asp Leu Ser Leu Gly Leu Pro Gly Ser Glu Ser Pro
            35                  40                  45

Glu Arg Lys Pro Gly Phe Gly Phe Thr Ile Phe Gly Lys Asp Phe Glu
        50                  55                  60

Gly Lys Thr Gln Asn Gly Tyr Ser Ile Gly Ser Leu Lys Ser Pro Ser
65                  70                  75                  80

Ser Gly Ala Lys Arg Gly Phe Ser Asp Ala Ile Asp Gly Cys Glu Lys
                85                  90                  95

Trp Val Leu Ser Ile Asn Gly Lys Ser Asp Thr Asn Leu Ser Lys Asp
            100                 105                 110

Gly Val Leu Tyr Ser Pro Arg Gly Ala Gln Ser Gly Lys Asn Phe Gly
        115                 120                 125

Gly Phe Glu Gly Asn Asn Ala Gln Lys Leu Ala Leu Leu Lys Glu Val
130                 135                 140

Asn Val Asn Val Pro Ser Ser Pro Lys Pro Ala Gln Glu Asn Gln Lys
145                 150                 155                 160

Thr Gln Val Ser Ala Ala Asn Glu Asn Gly Ser Ala Pro Ala Ala Lys
                165                 170                 175

Ala Gln Val Val Gly Trp Pro Pro Ile Arg Ser Tyr Arg Lys Asn Thr
            180                 185                 190

Leu Ala Ser Thr Ser Ala Lys Asn Asn Glu Gln Thr Glu Glu Lys Ser
        195                 200                 205

Ala Ala Ala Cys Leu Tyr Val Lys Val Ser Met Asp Gly Ala Pro Tyr
210                 215                 220

Leu Arg Lys Val Asp Leu Gln Thr Tyr Arg Asn Tyr Met Asp Leu Ser
225                 230                 235                 240

Thr Ser Leu Glu Lys Met Phe Ser Cys Phe Ile Thr Gly Gln Tyr Ala
                245                 250                 255

Ser Lys Gly His Gly Lys Gln Asp Gly Met Gly Glu Ser Gln Ser Lys
            260                 265                 270

Asp Leu Gln Asn Ala Glu Phe Val Leu Thr Tyr Glu Asp Lys Asp Gly
        275                 280                 285

Asp Trp Met Leu Val Gly Asp Val Pro Trp Lys Met Phe Thr Glu Asn
        290                 295                 300

Cys Arg Lys Leu Arg Ile Met Lys Gly Ser Glu Ala Ile Gly Leu Asp
305                 310                 315                 320

Val Val Glu Lys Ala Lys Asn Glu Val
            325

<210> SEQ ID NO 281
<211> LENGTH: 325
<212> TYPE: PRT
<213> ORGANISM: Kochia scoparia

<400> SEQUENCE: 281

Met Ser Pro Pro Leu Leu Gly Val Gly Gly Gly Gln Ser Asn Glu
1               5                   10                  15

Asn Pro Leu Val Pro Ser Pro Thr Cys Ala Glu Ser Gly Leu Lys Glu
                20                  25                  30

His Asn Tyr Phe Gly Leu Ser Glu Cys Ser Ser Val Asp Ser Ser Asn
            35                  40                  45

Val Ser Ser Leu Ser Glu Asp Asn Lys Asp Ser Leu Asn Phe Lys Ala
        50                  55                  60

Thr Glu Leu Arg Leu Gly Leu Pro Gly Ser Gln Ser Pro Gln Arg Asp
65                  70                  75                  80

Ser Asp Leu Cys Leu Leu Ser Gly Ser Lys Leu Asn Glu Lys Pro Leu
                85                  90                  95

Phe Pro Leu Thr Pro Leu Met Asp Gly Ile Ser Ser Ser Gln Lys
                100                 105                 110

Ala Ala Val Ser Gly Ser Lys Arg Gly Phe Ser Asp Thr Glu His Asn
            115                 120                 125

Trp Ala Phe Lys Ser Ala Gly His Asp Ser Glu Ala Pro Lys Thr Gly
130                 135                 140

Asp Gln Ala Thr Leu Lys Pro Ala Val Pro Gln Ala Pro Ser Lys Asn
145                 150                 155                 160

Gly Ala Pro Gln Thr Thr Gln Lys Ala Ser Gly Glu Leu Pro Arg Pro
                165                 170                 175

Asn Gly Asn Asn Ser Ala Pro Ala Ala Lys Ala Gln Val Val Gly Trp
            180                 185                 190

Pro Pro Ile Arg Ser Phe Arg Lys Asn Thr Leu Ala Thr Thr Ser Lys
        195                 200                 205

Asn Ser Asp Pro Leu Phe Val Lys Val Ser Met Asp Gly Ala Pro Tyr
210                 215                 220

Leu Arg Lys Val Asp Leu Arg Thr Tyr Ala Thr Tyr Gln Glu Leu Ser
225                 230                 235                 240

Ser Gly Leu Glu Lys Met Phe Ser Cys Phe Thr Leu Gly Gln Cys Gly
                245                 250                 255

Ser Asn Met Ser Glu Thr Lys Leu Arg Asp Leu Leu His Gly Ser Glu
            260                 265                 270

Tyr Val Leu Thr Tyr Glu Asp Lys Asp Gly Asp Trp Met Leu Val Gly
        275                 280                 285

Asp Val Pro Trp Glu Met Phe Ile Glu Ser Cys Lys Arg Leu Lys Ile
290                 295                 300

Met Lys Gly Ser Asp Ala Ile Gly Leu Ala Pro Arg Ala Met Glu Lys
305                 310                 315                 320

Ser Lys Ser Arg Thr
            325

<210> SEQ ID NO 282

<211> LENGTH: 441
<212> TYPE: PRT
<213> ORGANISM: Kochia scoparia

<400> SEQUENCE: 282

```
Arg Lys Gln Arg Lys Lys Gly Glu Val Glu Thr Thr His Ser Thr
1               5                   10                  15

Thr Pro Asp Arg Trp Val Pro Thr Phe Ile Thr Ile Ser Thr His Thr
            20                  25                  30

Tyr His Leu Ser Leu Ser Leu Gln Phe Ser Leu Ser Ile Phe Pro His
        35                  40                  45

Phe Tyr Leu Pro Phe Phe Phe Leu Phe Leu Ser Ile Phe Leu Phe
    50                  55                  60

Phe Ile His Leu Val Leu Leu Ser Leu Ser Lys Thr Gly Gln Thr
65                  70                  75                  80

Asn Lys Gln Asn Lys Ser Pro Phe Phe Phe Phe Ala Lys Phe Ile
                85                  90                  95

Arg Ser Phe Gln Phe Phe Ile Phe Leu Ala Asn Cys Asn Gln Thr
                100                 105                 110

Phe Ile Phe Leu Leu His Asn Ser Ile Lys Asp Ser Ile Phe Ser Met
                115                 120                 125

Glu Ala Val Val Gly Gly Ala Ala Ser Gly Gly Ser Ser Glu Ser
130                 135                 140

Thr Val Ile Ser Lys Glu Val Val Val Glu Gln Pro Phe Glu Val
145                 150                 155                 160

Ser Asp Asp Ser Glu Leu Glu Leu Gly Leu Gly Leu Ser Leu Gly Val
                165                 170                 175

Ala Cys Gly Lys Asn His Asn Asn Ser Lys Asn Asn Asn Ser Lys Gln
                180                 185                 190

Ile Pro Arg Phe Leu Thr Ala Lys Asp Leu Asn Ser Ser Asn Lys Ser
                195                 200                 205

Cys Ile Asn Ser Asn Gly Gly Ser Pro Ser Ser Ala Ser Ser Cys Ser
210                 215                 220

Ser Leu Gly Leu Arg Pro Pro Ser Ala Lys Thr Ser Thr Asn Asn
225                 230                 235                 240

Ser Asn Ala Ser Ala Gly Thr Lys Arg Ala Ala Ser Pro Thr Gly Val
                245                 250                 255

Ser Gln Val Val Gly Trp Pro Pro Ile Arg Ala Tyr Arg Met Asn Ser
                260                 265                 270

Met Ala Asn Gln Ala Lys Ser Val Ala Asn Gly Glu Asn Glu Ser Glu
                275                 280                 285

Phe Asn Glu Arg Lys Gly Lys Asp Ala Ile Tyr Gly Ala Asp Glu Lys
                290                 295                 300

Gly Asn Ala Asn Cys Lys Glu Arg Thr Pro His Lys Ser Cys Leu Phe
305                 310                 315                 320

Val Lys Val Asn Met Asp Gly Val Ala Ile Gly Arg Lys Val Asp Leu
                325                 330                 335

Asn Ser His Ser Ser Tyr Glu Ser Leu Ala Gln Ala Leu Glu Glu Met
                340                 345                 350

Phe Thr Asn Arg Ala Val Glu Gln Ser Ser Gly Glu Glu Leu Met Leu
                355                 360                 365

Met Pro Lys Thr Thr Arg Pro Ser Lys Leu Leu Asp Gly Ser Ser Asp
370                 375                 380

Phe Val Leu Thr Tyr Glu Asp Lys Asp Gly Asp Trp Met Leu Val Gly
```

```
                385                 390                 395                 400
Asp Val Pro Trp Gly Met Phe Ile Ser Ser Val Lys Arg Leu Lys Ile
                    405                 410                 415

Met Arg Thr Ser Glu Ala Asn Gly Leu Ala Pro Arg Ser Glu Glu Arg
                420                 425                 430

Ser Ala Lys Gln Arg Ser Arg Pro Ile
                435                 440

<210> SEQ ID NO 283
<211> LENGTH: 364
<212> TYPE: PRT
<213> ORGANISM: Kochia scoparia

<400> SEQUENCE: 283

Met Ser Glu Ser Gly Pro Lys Leu Leu Asp Leu Ile Pro Lys Glu Lys
1               5                   10                  15

Glu Met Met Ile Lys Lys Asp Gly Gly Asn Glu Glu Arg Arg Tyr Val
                20                  25                  30

Cys Cys Ser Ser Ser Ser Asp Glu Asn Asn Lys Leu Glu Leu Arg Leu
                35                  40                  45

Gly Leu Pro Gly Asp Gly Ile Trp Cys Ala Lys Asn Asn Pro Lys Ser
50                  55                  60

Arg Glu Arg Glu Asp Ser Leu Leu Ser Leu Gly Tyr Phe Lys His Asn
65                  70                  75                  80

Pro Ile Asn Gly Gly Gly Gly Ser Gly Ala Ser Cys Cys Ser Gln Gln
                    85                  90                  95

Gln His Gln Gln Pro Gln Gln His Gln Gln Pro Leu Thr Ala Asn Thr
                100                 105                 110

Thr Ser Ser Ser Pro Phe Leu Gln Asn Lys His His Gln Asn Gln Phe
            115                 120                 125

Lys Thr Cys Thr His Gln Gln Asn Lys Gly Val Pro Val Met Ala Lys
130                 135                 140

Asp Ala Ser Gln Pro Cys Cys Thr Arg Ile Val Glu Leu Gln Thr Ala
145                 150                 155                 160

Glu Lys Lys Ala Phe Ser Pro Ser Ser Ala Ala Asn Thr Ala Val Pro
                165                 170                 175

Asn Thr Ser Gln Lys Arg Ala Ala Pro Pro Val Val Gly Trp Pro Pro
                180                 185                 190

Ile Arg Ser Phe Arg Lys Asn Leu Gly Ser Ser Ser Gly Lys Pro
                195                 200                 205

Val Pro Glu Pro Gln Ser Ala Ile Pro Ser Lys Pro Val Val Glu Lys
                210                 215                 220

Pro Ala Asn Asp Asn Lys Val Asn Asn His Lys Gly Gln Phe Val Lys
225                 230                 235                 240

Ile Asn Met Asp Gly Ile Pro Ile Gly Arg Lys Val Asp Leu Ser Ala
                    245                 250                 255

His Asn Asn Tyr Asp Ser Leu Ser Ser Ala Val Asn Glu Leu Phe Arg
                260                 265                 270

Gly Leu Leu Ala Ala Gln Arg Asp Ser Ser Ala Gly Ser Ile Asp Asn
            275                 280                 285

Glu Gln Glu Glu Gln Lys Pro Ile Thr Gly Val Leu Asp Gly Ser Gly
            290                 295                 300

Glu Tyr Thr Leu Val Tyr Glu Asp Asn Glu Gly Asp Arg Met Leu Val
305                 310                 315                 320
```

Gly Asp Val Pro Trp His Met Phe Val Ser Thr Val Lys Arg Leu Arg
            325                 330                 335

Val Leu Lys Ser Ser Asp Leu Ala Ser Val Ser Arg Gly Gly Asn Asn
        340                 345                 350

Arg Glu Gly Lys Val Met Val Glu Ile Pro Ser Lys
        355                 360

<210> SEQ ID NO 284
<211> LENGTH: 254
<212> TYPE: PRT
<213> ORGANISM: Kochia scoparia

<400> SEQUENCE: 284

Met Glu Leu Glu Leu Gly Leu Ala Ile Ser Asn Gly Pro Pro Lys Ile
1               5                   10                  15

Gln Thr Leu Lys Glu Leu Asp Leu Ile Ser Tyr Val Asn Tyr Lys Gly
            20                  25                  30

Lys Gln Ala Asn Glu Asp Glu Asn Tyr Ser Asn Leu Ser Ser Glu Asn
        35                  40                  45

Ser Val Asn Asp Val Asp Cys Ala Asn Gln Glu Ala Asn Cys Gly Gly
    50                  55                  60

Val Tyr Gln Leu Lys Glu Asn Asp Lys Lys Arg Gly Phe Asp Glu
65                  70                  75                  80

Thr Asn Glu Val Glu Ser Cys Val Thr Leu Pro Leu Leu Leu Trp Asp
                85                  90                  95

Lys His Pro Asn Glu Asp Asp Lys Leu Pro Pro Lys Arg Leu Cys Asn
            100                 105                 110

Ser Thr Ser Phe Thr Leu Asn Lys Asn Asp Gly Asp Asn Ile Val Gly
        115                 120                 125

Trp Pro Pro Ile Lys Ser Tyr Arg Lys Lys Leu Asn Asp Glu Gln Gln
    130                 135                 140

Gln Gln Arg Arg Arg His Val Glu Asp Phe Pro Ala Ile Asp Asn
145                 150                 155                 160

Gly Gly Arg Gly Gly Gly Gly Cys Gly Gly Leu Gln Thr Met Phe Val
                165                 170                 175

Lys Val Gln Ile Glu Gly Cys Phe Ile Thr Arg Lys Ile Asp Leu Lys
            180                 185                 190

Leu Tyr His Ser Tyr Lys Thr Leu Val Cys Ser Leu Leu Ser Met Phe
        195                 200                 205

Gly Lys Gly His Asp Cys Met Asp Asp Tyr Lys Leu Thr Tyr Gln Asp
    210                 215                 220

Glu Asp Gly Asp Trp Leu Leu Ala Gly Asp Val Pro Trp Arg Thr Phe
225                 230                 235                 240

Ile Glu Ser Val Gln Arg Leu Lys Leu Arg Lys Lys Asp Asp
                245                 250

<210> SEQ ID NO 285
<211> LENGTH: 613
<212> TYPE: PRT
<213> ORGANISM: Kochia scoparia

<400> SEQUENCE: 285

Met Glu Gln His Gln Pro Gln Leu Lys Thr His Ile Ile Ser Ser Ser
1               5                   10                  15

Ser Ser Ser Ser Ser Ser Ser Thr Ile Ile Thr Pro Ser Ser Ser Ser
            20                  25                  30

-continued

```
Ser Ser Phe Pro Glu Glu Val Leu Glu His Val Leu Ser Phe Ile Asp
         35                  40                  45

Ser His Ser Asp Leu Asn Ser Val Ser Leu Val Cys Lys Thr Trp Tyr
 50                  55                  60

Glu Ile Glu Arg Trp Cys Arg Arg Ser Ile Phe Ile Gly Asn Cys Tyr
65                  70                  75                  80

Ala Ala Ser Pro Ser Ile Val Ile Arg Arg Phe Lys Asp Val Arg Ser
                 85                  90                  95

Val Thr Ile Lys Gly Lys Pro His Phe Ala Asp Phe Asn Leu Val Pro
                100                 105                 110

Asp Gly Trp Gly Ala His Ala Leu Pro Trp Ile Ser Gln Phe Cys Asp
            115                 120                 125

Ala Phe Pro Ala Leu Glu Leu Arg Leu Lys Arg Met Val Val Thr
    130                 135                 140

Asp Glu Ala Leu Glu Leu Ile Ala Lys Lys Leu Lys Ser Phe Lys Val
145                 150                 155                 160

Leu Val Leu Ser Phe Cys Asp Gly Phe Ser Thr Asp Gly Leu Ala Ser
                165                 170                 175

Ile Ala Ala Asn Cys Arg Asn Leu Lys Thr Leu Asp Leu Cys Glu Ser
                180                 185                 190

Glu Val Asp Asp Leu Ser Gly Asn Trp Ile Ser His Phe Pro Asp Thr
            195                 200                 205

Tyr Thr Ser Leu Glu Ser Leu Asn Val Ala Cys Leu Val Ser Glu Leu
    210                 215                 220

Arg Phe Thr Tyr Leu Glu Arg Leu Val Ser Arg Cys Pro Asn Leu Lys
225                 230                 235                 240

Ser Leu Arg Leu Asn Arg Ser Val Pro Leu Glu Lys Leu Ser Val Leu
                245                 250                 255

Leu Glu Lys Ala Pro Gln Leu Val Asp Phe Gly Thr Gly Ser Phe Leu
                260                 265                 270

Thr Glu Leu Asn Ser Glu Ala His Gly Lys Leu Ala Lys Ala Phe Ala
            275                 280                 285

Gly Ser Lys Gly Leu Lys Gly Leu Tyr Gly Leu Tyr Asp Val Val Pro
    290                 295                 300

Thr Tyr Leu Pro Ala Leu Tyr Pro Val Cys Ser Gly Leu Thr Tyr Leu
305                 310                 315                 320

Asn Leu Ser Tyr Ala Thr Ile His Ser Pro Asp Leu Ile Lys Val Leu
                325                 330                 335

Ser Arg Cys Gln Ser Leu Gln Arg Leu Trp Val Leu Asp Tyr Ile Glu
                340                 345                 350

Asp Cys Gly Leu Glu Val Leu Ala Glu Ser Cys Lys Asp Leu Arg Glu
            355                 360                 365

Leu Arg Val Phe Pro Ser Glu Pro Tyr Val Gln Glu Pro Asn Val Cys
    370                 375                 380

Leu Thr Glu Gln Gly Leu Val Ser Val Ala Met Gly Cys Pro Asn Leu
385                 390                 395                 400

Gln Ser Val Leu Tyr Phe Cys Arg Gln Met Ser Asn Glu Ala Leu Phe
                405                 410                 415

Thr Ile Ala Lys Asn Arg Pro Asn Leu Thr Arg Phe Arg Leu Cys Ile
                420                 425                 430

Ile Glu Pro Gln Arg Pro Asp Tyr Val Thr Asn Gln Pro Leu Asp Glu
            435                 440                 445

Gly Phe Gly Ala Ile Val Glu His Cys Lys Asp Leu Arg Arg Leu Ser
```

|       |       |       |       | 450   |       |       |       |       | 455   |       |       |       |       | 460   |       |
|-------|-------|-------|-------|-------|-------|-------|-------|-------|-------|-------|-------|-------|-------|-------|-------|

Leu Ser Gly Leu Leu Thr Asp Arg Val Phe Glu Ile Gly Thr His
465                 470                 475                 480

Ala Lys Lys Leu Glu Met Leu Ser Leu Ala Phe Ala Gly Glu Ser Asp
                485                 490                 495

Leu Gly Leu His Tyr Leu Leu Ser Gly Cys Lys Asn Leu Arg Lys Leu
            500                 505                 510

Glu Ile Arg Asp Cys Pro Phe Gly Gly Lys Ala Leu Leu Val Asn Ala
        515                 520                 525

Ala Lys Leu Asp Thr Met Arg Ser Leu Trp Met Ser Ser Cys Gln Val
    530                 535                 540

Ser Tyr Glu Glu Cys Lys Gln Leu Gly Lys Lys Met Pro Lys Leu Asn
545                 550                 555                 560

Val Glu Val Met Asp Glu Arg Gly His Pro Asp Ser Arg Ala Asn Glu
                565                 570                 575

Cys Pro Val Glu Lys Leu Tyr Ile Tyr Arg Thr Leu Val Gly Pro Arg
            580                 585                 590

Leu Asp Ser Pro Glu Phe Val Cys Thr Met Ser Glu Asp Pro Ala Ser
        595                 600                 605

Pro Leu Cys Thr Glu
    610

```
<210> SEQ ID NO 286
<211> LENGTH: 1842
<212> TYPE: DNA
<213> ORGANISM: Kochia scoparia

<400> SEQUENCE: 286
atggagcaac accaacccca gctcaaaacc cacatcatct catcctcctc ctcctcatca      60
tcctcatcca ccatcatcac cccatcatct tcatcatcat catttccaga ggaagtgctg     120
gagcacgtgc tgtcattcat cgactcacac tccgacctga actccgtctc gctcgtgtgc     180
aaaacatggt acgaaatcga acggtggtgt cgccgcagta tcttcatcgg aaactgctac     240
gctgccagcc cttcgatcgt tatccgacgg tttaaggacg ttagatctgt taccattaaa     300
gggaagcctc attttgctga ctttaatctt gttcctgacg gttgggggcc ccacgctttg     360
ccttggatct cgcagttttg cgacgctttc cctgctcttg aggagctcag gttgaagagg     420
atggttgtta ctgatgaagc tcttgagctg attgctaaga agttgaagtc ttttaaggtc     480
ttggttttga gttttgtgat ggggtttttct actgatggtt tggcttctat tgctgctaat     540
tgtaggaatt tgaaaactct ggacttatgt gagagtgaag ttgatgactt gagcgggaat     600
tggataagcc attttccaga tacttacacc tctcttgaat ctctaaatgt ggcctgcctt     660
gtctctgagt tgcggtttac ctatcttgag cgtttagtga gcagatgccc aaacctaaaa     720
tcactccggc tcaaccgttc agtgcccttg agaagctttc agttctcct ggagaaggct     780 cctcagttag ttgactttgg cacaggttca tttttgaccg agcttaactc tgaagcccat     840
ggaaagcttg cgaaggcatt tgcaggatcc aaagggctta aggtctctca tggtctctac     900
gatgtggtcc ccactatctt cctgccttg tatcctgtct gctcggggct cacttatttg     960
aacctgagtt atgctacaat tcactctcct gatctgatca aagttcttag tcgctgtcag    1020
agtcttcaga gactttgggt acttgattat atagaagatt gtggccttga agtacttgca    1080
gaatcatgca aggatctacg ggagttgcgc gtcttcccctt ctgagcctta tgttcaagaa    1140
ccaaatgttt gcttaactga acaaggtttg gtttcagttg ccatgggctg tcctaatctg    1200
```

-continued

```
caatcagttc tctattttg tcgccaaatg tccaatgaag ctttgtttac cattgcaaaa    1260
aatcgcccca acctaacgcg ttttcgccta tgcatcattg agccccaacg cccagactat    1320
gtaactaatc aaccactaga tgagggtttc ggggccatcg ttgagcattg caaggatctc    1380
cgccgccttt cattgtcggg tctactcact gatcgtgttt ttgagctcat gggacccat     1440 gccaaaaagc ttgagatgtt atctttggca tttgctggag aaagtgattt gggtttgcat    1500 tatctttat cagggtgcaa gaaccttagg aaactcgaga ttagggattg cccatttggt     1560
ggtaaggcac tattggtgaa tgcagctaag ctggacacaa tgcgatccct ttggatgtct    1620
tcatgccaag taagctacga ggagtgtaaa caacttggca agaagatgcc gaagttgaat    1680
gttgaggtca tggatgaaag ggggcaccct gactcgaggg ccaatgaatg cccggttgag    1740
aagctttaca taccggac acttgtggga cccaggttag actctccaga gtttgtttgt      1800
acaatgagtg aagatccagc atcaccgttg tgcactgaat aa                       1842
```

<210> SEQ ID NO 287
<211> LENGTH: 583
<212> TYPE: PRT
<213> ORGANISM: Kochia scoparia

<400> SEQUENCE: 287

```
Met Gly Ser Lys Lys Cys Lys Asn Ser Pro Asn Ser Glu Ser Leu Leu
1               5                   10                  15

Lys Ile Ser Ser Phe Pro Asp Glu Val Leu Glu Lys Val Leu Gly Leu
            20                  25                  30

Leu Glu Ser His Lys Asp Arg Ser Ser Val Ser Leu Val Cys Lys Asp
        35                  40                  45

Trp Tyr Asn Ala Glu Arg Trp Ser Arg Thr His Val Phe Ile Gly Asn
    50                  55                  60

Cys Tyr Ser Val Thr Pro Glu Ile Val Ala Arg Arg Phe Pro Lys Ile
65                  70                  75                  80

Lys Ser Val Ile Ile Lys Gly Lys Pro Arg Phe Ser Asp Phe Asn Leu
                85                  90                  95

Val Pro Glu Asn Trp Gly Ala Asp Ile His Pro Trp Leu Asp Cys Phe
            100                 105                 110

Ala Lys Ala Tyr Pro Ser Leu Glu Glu Leu Arg Leu Lys Arg Met Thr
        115                 120                 125

Ile Ser Asp Glu Ser Leu Glu Phe Leu Ala Met Ser Phe Pro Lys Phe
    130                 135                 140

Lys Arg Ile Ser Leu Leu Ser Cys Asp Gly Phe Ser Thr Asp Gly Leu
145                 150                 155                 160

Ala Ala Ile Ala Thr His Cys Lys Asn Leu Val Glu Leu Asp Ile Gln
                165                 170                 175

Glu Asn Gly Val Asp Asp Arg Ser Gly Ser Trp Leu Ser Cys Phe Pro
            180                 185                 190

Glu Asn Phe Thr Ser Leu Glu Ile Leu Asn Phe Ser Asn Leu Asn Ser
        195                 200                 205

Glu Val Ser Phe Ser Ser Leu Glu Arg Leu Val Ala Arg Cys Lys Ser
    210                 215                 220

Leu Arg Val Leu Lys Val Asn Lys Gly Val Asn Leu Glu Gln Leu Gln
225                 230                 235                 240

Lys Leu Leu Ser Leu Ala Pro Arg Leu Thr Gln Leu Gly Thr Gly Ala
                245                 250                 255
```

Phe Ser Gln Glu Leu Gln Pro Thr Gln Tyr Gly Leu Leu Glu Ser Val
            260                 265                 270

Leu Asn Asn Tyr Arg Ser Leu Gln Thr Ile Ser Gly Leu Trp Glu Ala
        275                 280                 285

Asn Ser Leu Tyr Leu Pro Ile Leu Tyr Pro Ala Cys Ser Gly Leu Thr
    290                 295                 300

Phe Leu Asn Leu Ser Asp Ala Pro Leu Gln Cys Asp Glu Leu Ala Gln
305                 310                 315                 320

Leu Leu Glu Asn Cys Pro Asn Leu Arg Arg Leu Trp Val Leu Asp Thr
                325                 330                 335

Val Gly Asp Lys Gly Leu Glu Ala Val Gly Ser Ser Cys Pro Leu Leu
            340                 345                 350

Glu Glu Leu Arg Val Phe Pro Ala Ser Pro Phe Asp Ala Glu Ile Asp
        355                 360                 365

His Gly Val Thr Glu Thr Gly Phe Val Ala Val Ser Tyr Gly Cys Pro
    370                 375                 380

Lys Leu His Tyr Val Leu Tyr Phe Cys Arg Glu Met Thr Asn Ala Ala
385                 390                 395                 400

Val Ala Thr Ile Val Gln Asn Cys Pro Asp Phe Thr His Phe Arg Leu
                405                 410                 415

Cys Ile Met Asn Pro Gly Gln Pro Asp His Leu Thr Asn Glu Pro Met
            420                 425                 430

Asp Glu Ala Phe Gly Ala Val Val Lys Ser Cys Lys Lys Leu Arg Arg
        435                 440                 445

Leu Ala Leu Ser Gly Leu Leu Thr Asp Leu Thr Phe Glu Tyr Ile Gly
    450                 455                 460

Lys Tyr Ala Lys Asn Leu Glu Thr Leu Ser Val Ala Phe Ala Gly Ser
465                 470                 475                 480

Ser Asp Leu Gly Met Gln Trp Val Leu Ala Gly Cys Pro Lys Leu Arg
                485                 490                 495

Arg Leu Glu Ile Arg Asp Cys Pro Phe Gly Asn Thr Ala Leu Leu Ser
            500                 505                 510

Gly Leu Glu Lys Tyr Glu Ser Met Arg Ser Leu Trp Met Ser Ala Cys
        515                 520                 525

Lys Val Thr Met Ser Ala Cys Arg Gln Leu Ala Lys Glu Met Pro Met
    530                 535                 540

Leu Asn Val Glu Val Ile Lys Asp Glu Asp Ser Asp Glu Cys Asp Ala
545                 550                 555                 560

Asn Lys Val Tyr Val Tyr Arg Thr Val Ala Gly Pro Arg Lys Asp Ala
                565                 570                 575

Pro Pro Phe Val Leu Thr Leu
            580

<210> SEQ ID NO 288
<211> LENGTH: 1752
<212> TYPE: DNA
<213> ORGANISM: Kochia scoparia

<400> SEQUENCE: 288
atgggttcaa aaagtgcaaa aattccccca aattcagaat ctttgctaaa aatctcttca    60
ttcccagatg aggttttgga gaaagttttg ggcttgcttg aatctcacaa agatagaagc   120
tcagtttcat ggtttgcaaa agattggtat aatgctgaaa gatggagtag aacccatgtt   180
tttattggga attgttattc tgtaacacct gaaattgttg ctagaagatt cccaaaaatc   240

```
aagagtgtta tcataaaagg gaaacctaga ttttcagatt tcaatttggt gcctgaaaat    300
tggggtgctg atattcatcc ttggctcgat tgctttgcta aagcttaccc ttctttggag    360
gaattaaggt tgaagaggat gactattagt gatgaaagtt tggagttttt agctatgtct    420
tttcctaaat ttaagaggat ttctcttctt agctgtgatg gattcagtac tgatggtctt    480
gctgctattg ccactcattg caagaactta gttgagcttg acattcaaga aaatggagtt    540
gatgatcgca gtggcagctg gttaagttgc tttcctgaaa attttacgtc actgaaaatt    600
ctaaactttt ccaatcttaa ttcggaagtc agcttttcat cccttgagag acttgtagcc    660
aggtgtaaat cattgagggt tttgaaagtg aacaaaggtg taaacttgga gcaattacag    720
aaattgctta gccttgcacc tcgtctgaca cagctgggca caggtgcctt ctcacaggag    780
ctccagccta ctcagtatgg gcttcttgaa agtgttttaa caactatcg tagtcttcaa    840
actatctctg gtttatggga agccaattca ttatatctac ccatactcta tcctgcttgc    900
tcagggctga cttttctgaa tctgagtgat gcacctttac aatgtgatga acttgctcaa    960
cttctggaaa actgtccaaa ccttcgacga ctttgggtgc tggacactgt tggtgataag   1020
ggtctagaag ctgttggatc aagctgccct ttgcttgagg aactccgggt atttcctgca   1080
agcccatttg atgctgaaat tgaccatgga gttacagaga ctggttttgt cgctgtttct   1140
tatggatgcc ctaagctcca ctatgttctc tacttctgcc gggaaatgac aaatgctgca   1200
gtagcaacca ttgtgcaaaa ctgtcctgat ttcacacatt ccgcctctg cataatgaat   1260
cctggtcagc ccgatcattt gactaatgaa ccaatggatg aggcttttgg cgcggtggta   1320
aaatcttgta agaagctcag aagactcgca ctttctggtc tattgactga cttgacgttc   1380
gaatacattg ggaaatatgc caagaatttg gagactcttt ctgtggcttt tgctggaagc   1440
agtgacttgg gtatgcaatg ggttctcgct ggctgtccta agctgaggcg gctggaaatc   1500
agagattgtc cctttgggaa cactgctctt ctttcagggt tggagaagta cgaatcgatg   1560
aggtctctgt ggatgtctgc atgcaaagtc acaatgagtg cctgtaggca gttggcaaaa   1620
gaaatgccca tgttgaatgt tgaggtcatt aaggatgaag attctgacga gtgtgatgct   1680
aataaagttt atgtctaccg cactgttgca ggacctagaa aagatgctcc tccttttgtt   1740
ctgacgctat ga                                                      1752
```

<210> SEQ ID NO 289
<211> LENGTH: 574
<212> TYPE: PRT
<213> ORGANISM: Kochia scoparia

<400> SEQUENCE: 289

```
Met Asn Tyr Phe Pro Glu Glu Val Leu Glu His Ile Phe Asp Phe Val
1               5                  10                  15

Thr Thr Asn Gln Asp Arg Asn Ser Val Ser Leu Val Cys Lys Thr Trp
            20                  25                  30

Tyr Lys Val Glu Arg Glu Ser Arg Ser Lys Val Phe Ile Gly Asn Cys
        35                  40                  45

Tyr Ala Ile Ser Pro Glu Lys Leu Ile Gly Arg Phe Pro Arg Leu Lys
    50                  55                  60

Ser Leu Thr Leu Lys Gly Lys Pro His Phe Ala Asp Phe Asn Leu Val
65                  70                  75                  80

Pro His Asp Trp Gly Ala Tyr Val Tyr Pro Trp Ile Glu Ala Leu Ala
                85                  90                  95

Lys Gly Cys Pro Ala Phe Glu Glu Leu Lys Leu Lys Arg Met Val Val
```

```
                100             105                110
Thr Asp Glu Gly Leu Glu Leu Leu Ser Lys Ser Phe Leu His Phe Lys
            115                 120             125

Ser Leu Val Leu Val Ser Cys Glu Gly Phe Thr Thr Asp Gly Leu Ala
            130                 135             140

Ala Val Ala Ser Thr Cys Arg Tyr Leu Arg Glu Leu Asp Leu Gln Glu
145                 150                 155                 160

Asn Glu Val Asp Asp Arg Lys Gly His Trp Leu Ser Cys Phe Pro Glu
                165                 170             175

Ser Cys Thr Ser Leu Val Ser Leu Asn Phe Ala Cys Leu Lys Gly Glu
            180                 185             190

Val Asn Leu Gly Ala Leu Glu Arg Leu Val Ala Arg Ser Pro Asn Leu
            195                 200             205

Arg Ser Leu Arg Leu Asn Arg Ala Val Pro Phe Glu Thr Leu Gln Lys
            210                 215             220

Ile Leu Thr Lys Ala Pro Gln Leu Ala Asp Leu Gly Thr Gly Ser Phe
225                 230                 235                 240

Ile His Asp Pro Lys Ser Glu Thr Phe Asn Asn Leu Lys Asn Ala Val
                245                 250             255

Ser Lys Cys Glu Ser Ile Lys Ser Leu Ser Gly Phe Leu Glu Val Ala
            260                 265             270

Ala Arg Cys Leu Pro Ala Ile Tyr Pro Val Cys Ser Asn Leu Thr Ser
            275                 280             285

Leu Asn Leu Ser Tyr Ala Pro Gly Ile Cys Gly Phe Glu Leu Thr Gln
            290                 295             300

Leu Ile Leu His Cys Asn Arg Leu Gln Lys Leu Trp Ile Leu Asp Cys
305                 310                 315                 320

Ile Gly Asp Lys Gly Leu Ala Val Val Ala Asp Thr Cys Lys Glu Leu
                325                 330             335

Glu Glu Leu Arg Val Phe Pro Thr Asp Pro Phe Ala His Gly Asp Ala
            340                 345             350

Ala Ala Val Thr Glu Glu Gly Leu Val Ala Ile Ser Ser Gly Cys Pro
            355                 360             365

Lys Leu Asn Ser Val Leu Tyr Phe Cys His Gln Met Thr Asn Ala Gly
            370                 375             380

Leu Ile Thr Val Ala Lys Asn Cys Pro Asn Phe Thr Arg Phe Arg Leu
385                 390                 395                 400

Cys Ile Leu Asp Pro Ile Lys Pro Asp Ala Val Thr Gly Glu Pro Leu
                405                 410             415

Asp Glu Gly Phe Gly Ala Ile Val Gln Ser Cys Lys Gln Leu Arg Arg
            420                 425             430

Leu Ser Ile Ser Gly Leu Leu Thr Asp Lys Val Phe Leu Tyr Ile Gly
            435                 440             445

Met Tyr Ala Lys Gln Leu Glu Met Leu Ser Val Ala Phe Ala Gly Asp
            450                 455             460

Ser Asp Glu Ala Met Ile His Val Leu Asn Gly Cys Glu Arg Leu Arg
465                 470                 475                 480

Lys Leu Glu Ile Arg Asp Cys Pro Phe Gly Asn Leu Ala Leu Leu Thr
                485                 490             495

Asp Ile Gly Lys Tyr Ala Thr Met Arg Ser Leu Trp Met Ser Ser Cys
            500                 505             510

Glu Val Thr Leu Gly Ala Cys Lys Leu Leu Ala Arg Lys Met Pro Gln
            515                 520             525
```

Leu Asn Val Glu Val Ile Asp Glu Asn Glu Glu Gly Asp Phe Asn Leu
    530                 535                 540

Asp Asp Asp Arg Leu Lys Val Asp Lys Met Tyr Leu Tyr Arg Thr Leu
545                 550                 555                 560

Ala Gly Pro Arg Lys Asp Ala Pro Glu Phe Val Trp Thr Leu
                565                 570

<210> SEQ ID NO 290
<211> LENGTH: 1725
<212> TYPE: DNA
<213> ORGANISM: Kochia scoparia

<400> SEQUENCE: 290

| | | | | |
|---|---|---|---|---|
| atgaattatt tcccagaaga agtactagag cacatatttg actttgtaac aacaaaccaa | | | | 60 |
| gatagaaact cagtatcatt agtatgcaaa acatggtata agtagagag agaaagcaga | | | | 120 |
| tctaaagtat tcataggaaa ctgctatgca ataagcccag aaaaattaat tgggagattt | | | | 180 |
| ccaagattga agtcactaac cctaaaaggg aaacccatt ttgcggattt caatttggtg | | | | 240 |
| cctcatgatt ggggagctta tgtttaccct tggattgagg cccttgcaaa agggtgccct | | | | 300 |
| gcttttgaag agcttaagct gaagagaatg gttgttactg atgaaggtct tgagcttttg | | | | 360 |
| tctaaatctt ttctccattt taagtccttg gttttggtga gttgtgaagg ttttactact | | | | 420 |
| gatggtcttg ctgctgttgc ctctacttgc aggtacttga gagagttgga cttacaggaa | | | | 480 |
| aatgaggtgg atgatcgaaa ggggcattgg ctaagttgct ttcctgagag ttgcacttca | | | | 540 |
| cttgtgtccc tgaattttgc atgcctcaag ggcgaagtaa atttgggggc cttgagagg | | | | 600 |
| ctggtagctc ggagtccaaa tctgaggagt ctcaggctaa accgtgctgt tccatttgag | | | | 660 |
| acacttcaga agattctcac caaggcacct caacttgcag attgggcac tgggtctttc | | | | 720 |
| atacatgacc caaagtctga gactttcaat aacctaaaga atgctgtttc aaagtgtgaa | | | | 780 |
| tcaattaaaa gcttatcggg attcttggag gttgctgctc gctgcctgcc tgcgatatat | | | | 840 |
| cctgtttgct caaaccttac ttctttgaac cttagctatg cacctggaat tgtgggttc | | | | 900 |
| gagcttaccc agctaattct tcattgcaac agactccaaa aactttggat attagactgt | | | | 960 |
| attggagaca aggggcttgc tgttgtggca gacacttgta agaactggaa gagctaaga | | | | 1020 |
| gttttttccaa ctgacccatt tgcccatggg atgcagctg ctgtcaccga ggaaggtctt | | | | 1080 |
| gtagccattt caagtgggtg tccgaagctg aattctgtct tgtacttctg ccaccaaatg | | | | 1140 |
| acaaacgcag ggctgataac agtggcaaag aactgcccaa atttcacccg atttaggttg | | | | 1200 |
| tgtatattag acccaataaa acctgatgct gtcactgggg aacctttaga tgagggtttt | | | | 1260 |
| ggggcaattg ttcaatcatg caagcaattg aggcggcttt caatttcagg ctgctaacc | | | | 1320 |
| gacaaggttt ttctgtacat tggaatgtac gccaagcaat tagagatgct ttctgttgca | | | | 1380 |
| tttgctggag atagtgatga ggcaatgatc catgtttga atgggtgtga gaggcttcga | | | | 1440 |
| aagttggaaa ttcgggattg tccgtttggg aatttggcac ttctgacaga cattgggaag | | | | 1500 |
| tatgcgacaa tgcgatccct ttggatgtcg tcctgtgaag tgaccctagg ggcttgcaag | | | | 1560 |
| ttgcttgcga ggaagatgcc acaactaaac gttgaggtga ttgacgagaa cgaggagggg | | | | 1620 |
| gatttcaatc ttgatgatga ccggctgaaa gtagacaaga tgtacttgta tcgaacgttg | | | | 1680 |
| gctgggccga ggaaagatgc tccagaattc gtatggacct tgtag | | | | 1725 |

<210> SEQ ID NO 291
<211> LENGTH: 608

<212> TYPE: PRT
<213> ORGANISM: Kochia scoparia

<400> SEQUENCE: 291

```
Met Arg Glu Gly Thr Asp Asn Arg Pro Asp Ala Thr Ser Glu Thr Val
1               5                   10                  15

Thr Ile Gly Ser Val Val Gly Gln Gly Val Val Ala Ser Ala Tyr Ile
            20                  25                  30

Pro Pro Cys Pro Asp Gln Val Leu Glu Asn Val Leu Glu Asn Val Leu
        35                  40                  45

His Phe Leu Thr Cys Arg Arg Asp Arg Asn Ala Ala Ser Leu Val Cys
    50                  55                  60

Lys Ala Trp Tyr Arg Ala Glu Ala Leu Thr Arg Ser His Leu Phe Ile
65                  70                  75                  80

Gly Asn Cys Tyr Ala Val Gly Pro Ala Arg Val Thr Glu Arg Phe Arg
                85                  90                  95

Arg Val Arg Ser Val Ile Ile Lys Gly Arg Pro Arg Phe Ala Asp Phe
            100                 105                 110

Gly Leu Met Pro Pro Asn Trp Gly Ala His Ser Tyr Arg Trp Phe Ser
        115                 120                 125

Val Phe Ala Gln Ala Tyr Pro Gly Leu Glu Lys Ile His Leu Lys Arg
    130                 135                 140

Met Cys Val Thr Asp Asp Asp Leu Glu Leu Ile Ser Lys Ser Phe Pro
145                 150                 155                 160

Ser Leu Lys Glu Ile Thr Leu Val Cys Cys Glu Ala Phe Gly Thr Ser
                165                 170                 175

Gly Leu Ala Phe Leu Ala Ser Asn Ser Arg Gln Leu Arg Val Leu Asp
            180                 185                 190

Leu Phe Glu Asp Glu Val Asn Asp Glu Val Asp Trp Ile Ser Cys
        195                 200                 205

Phe Pro Glu Thr Gly Thr Cys Leu Glu Ser Leu Ser Phe Glu Cys Ile
    210                 215                 220

Asp Phe Pro Ile Asn Phe Asn Ala Leu Glu Arg Leu Leu Ala Arg Ser
225                 230                 235                 240

Pro Asn Phe Lys Lys Leu Arg Val Asn Arg Phe Val Ser Leu Asp Leu
                245                 250                 255

Leu His Arg Leu Met Cys Arg Ala Pro Gln Leu Thr His Leu Gly Thr
            260                 265                 270

Gly Ser Phe Gly Leu Asn Glu Val Trp Gln Pro Thr Glu Gln Asp Leu
        275                 280                 285

Asp Tyr Arg Ala Ala Phe Ala Ala Cys Lys Ser Leu Val Cys Leu Ser
    290                 295                 300

Gly Phe Arg Glu Ile Ala Pro Leu Phe Leu Pro Ser Met Tyr Pro Val
305                 310                 315                 320

Cys Ala Asn Leu Thr Ser Leu Asn Phe Ser Tyr Ala Asn Ile Asp Ala
                325                 330                 335

Glu Glu Leu Lys Ser Val Ile Cys His Cys His Asn Leu Arg Thr Phe
            340                 345                 350

Trp Val Leu Asp Ser Val Gly Asp Glu Gly Leu Gln Ala Val Ser Ser
        355                 360                 365

Thr Cys Lys Asp Leu Arg Glu Leu Arg Val Phe Pro Ile Asp Ala Arg
    370                 375                 380

Glu Asp Ser Glu Gly Phe Val Ser Glu Leu Gly Leu Leu Ala Ile Ser
385                 390                 395                 400
```

Glu Gly Cys Arg Lys Leu Glu Ser Ile Leu Tyr Phe Cys Gln Arg Met
            405                 410                 415

Thr Asn Ala Ala Val Val Ala Met Ser Lys Asn Cys Pro Glu Leu Val
            420                 425                 430

Val Phe Arg Leu Cys Ile Met Gly Arg His Arg Pro Asp His Ile Thr
            435                 440                 445

Asn Glu Pro Met Asp Glu Gly Phe Gly Ala Ile Val Met Asn Cys Lys
        450                 455                 460

Lys Leu Thr Arg Leu Ala Val Ser Gly Leu Leu Thr Asp Lys Ala Phe
465                 470                 475                 480

Glu Tyr Ile Gly Arg Tyr Gly Lys Leu Val Arg Thr Leu Ser Val Ala
            485                 490                 495

Phe Ala Gly Asp Thr Asp Met Ala Leu Lys Tyr Val Leu Glu Gly Cys
            500                 505                 510

Pro Lys Leu Leu Lys Leu Glu Val Arg Asp Ser Pro Tyr Gly Asp Ser
        515                 520                 525

Val Leu Arg Ala Gly Leu Pro His Phe Tyr Asn Met Arg Phe Leu Trp
        530                 535                 540

Met Ser Ala Cys Lys Leu Thr Leu Pro Ala Cys Lys Gln Ile Ala Arg
545                 550                 555                 560

Glu Met Pro His Leu Val Val Glu Val Phe Val Ser Gly Ala Glu Glu
            565                 570                 575

Ala Val Asp Asp Lys Asp Glu Phe Val Asp Thr Leu Tyr Met Tyr Arg
            580                 585                 590

Ser Leu Glu Gly Pro Arg Thr Asp Ala Pro Glu His Val Arg Ile Leu
        595                 600                 605

<210> SEQ ID NO 292
<211> LENGTH: 1827
<212> TYPE: DNA
<213> ORGANISM: Kochia scoparia

<400> SEQUENCE: 292
atgagagagg gcaccgataa cagacccgat gctacttccg aaacagttac catcgggtct      60
gttgttggac aaggcgtggt ggcgtcggca tacatcccac cgtgtccgga tcaggtgttg     120
gagaacgtgc tcgagaacgt tctccacttc ctgacgtgcc gccgcgacag gaacgcggct     180
tcgctggtgt gcaaggcgtg gtaccgcgct gaggcgctca cccgatccca cctcttcatt     240
gggaactgct acgcggtggg gcccgcccgt gtgacggagc ggttcaggag ggttagatcg     300
gtgatcataa agggcaggcc tcgtttcgct gatttcgggc ttatgccacc gaactggggt     360
gctcactctt atcgttggtt ttctgtgttt gctcaagctt accctggcct tgagaagatt     420
cacttgaagc gtatgtgtgt cactgatgat gatcttgagc tcatttctaa gtcgtttcct     480
tccttgaagg aaatcactct tgtttgctgt gaagcttttg cacttccgg tcttgctttt     540 cttgcttcca actcaagaca attgagagtg ttggatctgt tgaggatga ggtgaatgat     600 gatgaagtgg attggatatc atgctttcct gaaaccggga catgtcttga atctcttagc     660
tttgaatgca ttgatttccc tattaatttc aatgcgttag agaggctatt agcaagatcc     720
cctaacttca agaagcttag ggtcaatcgc ttcgtctcac tcgatttgtt gcatcgtctc     780
atgtgtcgag ctccgcagct aacccattta ggaactgggt cgtttggtct gaatgaagtt     840
tggcaaccaa ctgagcaaga cttggattat cgagctgcgt tgctgcttg taaatccctt     900 gtttgtttat caggatttag ggagattgca ccgcttttct tgccttccat gtaccctgtt     960

```
tgtgctaacc tcacttcctt gaactttagc tatgctaata tagatgcaga ggaactcaaa    1020
tcagtgattt gtcattgcca caatctccgg accttttggg tgttagattc agttggggat    1080
gaagggcttc aagctgtttc atcaacttgc aaggatctcc gagagcttcg tgttttccca    1140
attgatgctc gggaagacag tgaggggttt gtgtctgagc tgggtttgct tgctatttct    1200
gaagggtgta ggaaattgga atccatatta tatttctgtc agaggatgac aaatgctgct    1260
gtggttgcaa tgtcaaaaaa ttgcccggag cttgtggtgt ttcggctatg tatcatgggt    1320
cgacaccgcc cggatcacat taccaatgag cctatggatg aagggtttgg agccattgtc    1380
atgaattgca agaagctcac ccgtcttgca gtttctgggt tgttaactga caaggcattt    1440
gagtacattg gccgatacgg aaaattggtg cgcaccctat cggttgcttt tgctggggat    1500
acggatatgg ccctgaaata tgttcttgag ggttgcccca aattgctgaa gcttgaggtt    1560
cgggatagcc cgtatggtga ttctgtgtta cgagcaggtt taccccactt ttacaacatg    1620
agatttctgt ggatgtctgc ttgtaaattg actcttcctg cttgcaagca gattgcaaga    1680
gaaatgcctc atttagtagt cgaggtgttt gttagtgggg cggaagaagc tgttgacgac    1740
aaggatgaat ttgtggatac tctatatatg taccgatctc ttgaggggcc aagaactgat    1800 gccctgaac atgtgaggat attgtag                                          1827
```

<210> SEQ ID NO 293
<211> LENGTH: 5
<212> TYPE: PRT
<213> ORGANISM: Artificial Sequence
<220> FEATURE:
<223> OTHER INFORMATION: Degron domain
<220> FEATURE:
<221> NAME/KEY: misc_feature
<222> LOCATION: (1)..(1)
<223> OTHER INFORMATION: Xaa can be Asn, Ile, Leu
<220> FEATURE:
<221> NAME/KEY: misc_feature
<222> LOCATION: (5)..(5)
<223> OTHER INFORMATION: Xaa can be Ile, Val, Leu, Met

<400> SEQUENCE: 293

Xaa Trp Pro Pro Xaa
1               5